US009428528B2

(12) United States Patent
Curtis et al.

(10) Patent No.: US 9,428,528 B2
(45) Date of Patent: *Aug. 30, 2016

(54) PHENICOL ANTIBACTERIALS

(71) Applicant: Zoetis Services LLC, Florham Park, NJ (US)

(72) Inventors: Michael Curtis, Portage, MI (US); Richard A Ewin, Kalamazoo, MI (US); Timothy Allan Johnson, Richland, MI (US); Susan M. K. Sheehan, Galesburg, MI (US)

(73) Assignee: Zoetis Services LLC, Florham Park, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/071,597

(22) Filed: Mar. 16, 2016

(65) Prior Publication Data

US 2016/0194342 A1 Jul. 7, 2016

Related U.S. Application Data

(60) Division of application No. 14/731,650, filed on Jun. 5, 2015, now Pat. No. 9,340,564, which is a continuation of application No. 13/785,422, filed on Mar. 5, 2013, now Pat. No. 9,073,894.

(60) Provisional application No. 61/607,280, filed on Mar. 6, 2012.

(51) Int. Cl.

| | |
|---|---|
| C07D 487/10 | (2006.01) |
| C07D 213/16 | (2006.01) |
| C07D 413/04 | (2006.01) |
| C07D 333/20 | (2006.01) |
| C07D 401/04 | (2006.01) |
| C07D 405/04 | (2006.01) |
| C07D 277/28 | (2006.01) |
| A61K 31/381 | (2006.01) |
| A61K 31/426 | (2006.01) |
| A61K 31/4439 | (2006.01) |
| A61K 31/5377 | (2006.01) |
| C07F 9/58 | (2006.01) |
| C07D 401/06 | (2006.01) |
| C07D 213/40 | (2006.01) |
| C07D 239/26 | (2006.01) |
| C07D 413/06 | (2006.01) |
| C07D 241/12 | (2006.01) |
| C07D 417/06 | (2006.01) |
| C07D 271/06 | (2006.01) |
| C07D 285/12 | (2006.01) |
| C07D 213/38 | (2006.01) |
| C07D 471/04 | (2006.01) |
| C07D 471/10 | (2006.01) |
| C07D 491/107 | (2006.01) |
| C07D 495/10 | (2006.01) |
| C07D 513/04 | (2006.01) |

(52) U.S. Cl.
CPC ............... *C07F 9/58* (2013.01); *C07D 213/16* (2013.01); *C07D 213/38* (2013.01); *C07D 213/40* (2013.01); *C07D 239/26* (2013.01); *C07D 241/12* (2013.01); *C07D 271/06* (2013.01); *C07D 277/28* (2013.01); *C07D 285/12* (2013.01); *C07D 333/20* (2013.01); *C07D 401/04* (2013.01); *C07D 401/06* (2013.01); *C07D 413/06* (2013.01); *C07D 417/06* (2013.01); *C07D 471/04* (2013.01); *C07D 471/10* (2013.01); *C07D 487/10* (2013.01); *C07D 491/107* (2013.01); *C07D 495/10* (2013.01); *C07D 513/04* (2013.01); *C07F 9/582* (2013.01)

(58) Field of Classification Search
None
See application file for complete search history.

(56) References Cited

U.S. PATENT DOCUMENTS

| | | | |
|---|---|---|---|
| 7,041,670 B2 | 5/2006 | Boojamra et al. | |
| 9,073,894 B2 | 7/2015 | Ewin et al. | |
| 9,340,564 B2 * | 5/2016 | Ewin | .......... C07D 333/20 |
| 2007/0155799 A1 | 7/2007 | Glinka et al. | |
| 2013/0237502 A1 | 9/2013 | Curtis et al. | |

FOREIGN PATENT DOCUMENTS

| | | |
|---|---|---|
| WO | 03/077828 | 9/2003 |
| WO | 2012/125832 A2 | 9/2012 |

OTHER PUBLICATIONS

Kerns, Edward et al, Drug-like Properties: Concepts, Structure Design and Methods: from ADME to Toxicity Optimization, (Elsevier, 2008) pp. 92-93.*
Goosen et al., Pharmaceutical Research vol. 19, No. 1, 13-19 (Jan. 2002).*
Fourie, International Journal of Pharmaceutics vol. 279, Issues 1-2, Jul. 26, 2004, pp. 59-66.*
Edwards, J. Med. Chem. 39 (1996), pp. 1112-1124.*
Rautio, Eur. J. Pharm. Sci. 11:157-163 (2000).*
PCT International Search Report, PCT/US2013/028554, mailed Apr. 18, 2013 (4 pages).

(Continued)

*Primary Examiner* — Michael Barker
(74) *Attorney, Agent, or Firm* — Paul M. Misiak

(57) ABSTRACT

The present invention provides novel phenicol derivatives, their use for the treatment of infections in mammals, pharmaceutical composition containing these novel compounds, and methods for the preparation of these compounds.

6 Claims, No Drawings

(56) References Cited

OTHER PUBLICATIONS

Bolton et al., "Detection of Multidrug-Resistant *Salmonella enterica* Serotype typhimurium DT104 Based on a Gene Which Confers Cross-Resistance to Florfenicol and Chloramphenicol", Journal of Clinical Microbiology, 1999, 37 (5):1348-1351.

Keyes et al., "Detection of Florfenicol Resistance Genes in *Escherichia coli* Isolated from Sick Chickens", Antimicrobial Agents and Chemotherapy, 2000, 44(2):421-424.

Cloeckaert et al., "Nonenzymatic Chloramphenicol Resistance Mediated by IncC Plasmid R55 is Encoded by a floR Gene Variant", Antimicrobial Agents and Chemotherapy, 2001, 45(8):2381-2382.

Kim et al., "Sequence Analysis of the Florfenicol Resistance Gene Encoded in the Transferable R-Plasmid of a Fish Pathogen, Pasteurella piscicida", Microbiology and Immunology, 1996, 40(9):665-669.

Cloeckaert et al., "Plasmid-Mediated Florfenicol Resistance Encoded by the floR Gene in *Escherichia coli* Isolated from Cattle", Antimicrobial Agents and Chemotherapy, 2000, 44(10):2858-2860.

* cited by examiner

PHENICOL ANTIBACTERIALS

CROSS-REFERENCE TO RELATED APPLICATIONS

This application is a divisional of U.S. patent application Ser. No. 14/731,650 filed Jun. 5, 2015, recently allowed; which was a continuation of U.S. patent application Ser. No. 13/785,422, filed Mar. 5, 2013, now granted as U.S. Pat. No. 9,073,894; which claims the benefit of priority to U.S. Provisional Application No. 61/607,280 filed Mar. 6, 2012.

FIELD OF THE INVENTION

The present invention provides novel phenicol derivatives, their use for the treatment of infections in mammals, pharmaceutical composition containing these novel compounds, and methods for the preparation of these compounds.

BACKGROUND OF THE INVENTION

There is a growing need for new antibiotic agents for the treatment of bacterial infections in animals, and in particular there is a need for new agents which overcome increasing bacterial resistance to existing antibiotics.

Florfenicol is a broad spectrum phenicol antibiotic used exclusively in veterinary medicine. Phenicol antibiotics as a class are potent inhibitors of bacterial protein biosynthesis. Florfenicol has a broad spectrum of activity against many gram-negative and gram-positive bacteria, and is useful in the prevention and treatment of bacterial infections due to susceptible pathogens in birds, reptiles, fish, shellfish and mammals. An important use of florfenicol is in the treatment of respiratory infections in cattle, such as those caused by, for example, *Mannheimia haemolytica, Pasteurella multocida* and *Haemophilus somnus*. Effective treatment of bovine respiratory disease (BRD) plays a significant role in reducing what is otherwise one of the leading causes of economic loss to both the dairy and beef industries worldwide.

Reports in recent years indicate that bacterial resistance to florfenicol is developing and has been observed across multiple bacterial genera and species, such as *Salmonella* (Bolton, L. F., et al., Clin. Microbiol., 1999, 37, 1348), *E. coli* (Keyes, K., et al., Antimicrob. Agents Chemother., 2000, 44, 421), *Klebsiella pneumoniae* (Cloeckaert, A., et al., Antimicrob. Agents Chemother., 2001, 45, 2381), and in the aquacultural pathogen, *Photobacterium damselae* subsp. *piscicida* (formerly *Pasteurella piscicida*) (Kim, E., et al., Microbiol. Immunol., 1996, 40, 665). In light of the increasing threat of florfenicol resistance and the apparent mobility of the resistance genes across bacterial species and animal hosts (Cloeckaert, A., et al., Antimicrob. Agents Chemother., 2000, 44, 2858), there is an important need for new antibiotics that maintain or surpass the activity of florfenicol, while also overcoming the challenges of florfenicol resistance. The compounds of the present invention represent such an improvement.

SUMMARY OF THE INVENTION

The present invention provides a compound of formula I

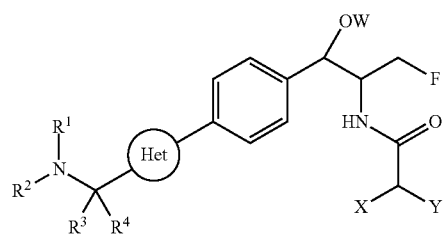

or pharmaceutical acceptable salts or prodrugs thereof wherein:

Het moiety is a 4- to 14-membered cyclic or bicyclic ring system having from one to five hetero atoms selected from N, O, and S, optionally substituted with one to three $R^6$;

$R^1$ and $R^2$ are each independently
 a. H,
 b. —$C_{1-8}$alkyl, optionally substituted with one or more OH, —SH, —CN, —$NO_2$, halo, —$NHR^5$, —$NC_{1-4}$alkyl$R^5$, —$OC_{1-4}$alkyl, —$SC_{1-4}$alkyl, —S(C=O)$C_{1-4}$alkyl, —C(=O)$NR^5R^5$, —$SO_2R^5$, —$SO_2NR^5R^5$, or —$C_{3-6}$cycloalkyl,
 c. —$C_{3-8}$cycloalkyl, optionally substituted with one to three $R^6$,
 d. —$SO_2R^5$, —C(=O)$NR^5R^5$, —$SO_2NR^5R^5$, —C(=O)$OR^5$, or —C(=O)$R^5$,
 e. 4- to 6-membered heterocyclic ring moiety optionally having from one to four hetero atoms selected from the group consisting from N, S and O, wherein the ring or atom is optionally substituted with one to three $R^6$, or
 f. $R^1$ and $R^2$ taken together with the nitrogen to which they are attached form a 4- to 11-membered cyclic or bicyclic ring moiety optionally having an additional one to two hetero atoms selected from the group consisting of N, S and O, wherein the ring or atom is optionally substituted with one to three $R^6$;

$R^3$ and $R^4$ are each independently
 a. —H,
 b. —$C_{1-8}$alkyl optionally substituted with OH, —SH, halo, —$CF_3$, —CN, —$NO_2$, $NH_2$, —$NHR^5$, —$NHR^5$—$OC_{1-4}$alkyl, —$CH_2$—O—$CH_3$, —$SC_{1-4}$alkyl, —S(C=O)$C_{1-4}$alkyl, —C(=O)$NR^5R^5$, —C(=O)OH, —$SO_2NR^5$, or —$SO_2R^5$,
 c. —$C_{3-8}$ cycloalkyl, optionally substituted with one to three $R^6$,
 d. —C(=O)$C_{1-8}$alkyl wherein alkyl is optionally substituted with —S(=$O_2$)$R^5$, —$SO_2NR^5$, or —C(=O)$R^5$,
 e. 4- to 6-membered heterocyclic ring moiety optionally having from one to three hetero atoms selected from the group consisting from N, S and O, wherein the heterocyclic ring is optionally substituted with one to three $R^6$,
 f. $R^3$ and $R^4$ taken together form a $C_{3-8}$cycloalkyl, optionally substituted with one to three $R^6$; or
 g. $R^3$ and $R^4$ taken together with one or two hetero atoms selected from the group consisting from N, S and O to form an oxo group (=O) or to form a 4- to 6-membered heterocyclic ring moiety, wherein the heterocyclic ring is optionally substituted with one to three $R^6$; or $R^1$ and $R^3$, $R^2$ and $R^4$, $R^1$ and $R^4$ or $R^2$ and $R^3$ taken together with the nitrogen atom to which they are attached to form a 4- to 6-membered heterocyclic ring moiety optionally having from one to two hetero atoms selected from the group consisting of N, S and O, wherein the heterocyclic ring is optionally substituted with one to three $R^6$;

at each occurrence, $R^5$ is independently hydrogen, $C_{1-6}$alkyl, —$C_{3-6}$cycloalkyl, $NH_2$ or tetrahydro-2H-pyranyl, wherein said alkyl is optionally substituted with one, two or three $R^6$;

at each occurrence, $R^6$ is H, $C_{1-6}$alkyl, halo, —CN, —$NO_2$, —$CF_3$, —$C_{3-6}$cycloalkyl, oxo (=O), —$NH_2$, —$NHC_{1-4}$alkyl, —$N(C_{1-4}$alkyl$)_2$, —$OC_{1-4}$alkyl, oxo, —SH, —$SC_{1-4}$alkyl, —$S(C=O)C_{1-4}$alkyl, —$SO_2R^5$, —$SONC_{1-4}$alkyl, —$C(=O)C_{1-4}$ alkyl, —$C(=O)NH_2$, —$C(=O)NHC_{1-4}$alkyl, —$C(=O)N(C_{1-4}$alkyl$)_2$, —NC(=O)$NH_2$, —NC(=O)$NHC_{1-4}$alkyl, NC(=O)$N(C_{1-4}$alkyl$)_2$, $CF_3$ or a 4- to 6-membered heterocyclic ring moiety optionally having from one to four hetero atoms selected from the group consisting of N, S and O;

W is —H, —PO(OH)$_2$, —PO(OH)halo, —$CH_2$OPO(OH)$_2$, —$C(=O)C_{1-4}$alkyl, or —$CH_2OC(=O)C_{1-4}$alkyl, wherein $C_{1-4}$alkyl is optionally substituted with —$OCO_2H$, —$OCO_2C_{1-4}$alkyl, or —$OC(=O)NHC_{1-4}$alkyl;

and X, Y and Z are each independently H, halo, $C_{1-4}$alkyl, $C_{3-6}$cycloalkyl, —OH, $CF_3$, —$NH_2$, —CN, $N_3$ or —S—$CF_3$;

provided that when $R^3$ and $R^4$ are taken together to form an oxo group (=O), then $R^1$ and $R^2$ are not both hydrogen.

In another aspect, the present invention also provides:

pharmaceutical compositions which comprise a pharmaceutically acceptable carrier and a compound of formula I, methods for controlling or treating infections in mammals by administering to a mammal in need of a therapeutically effective amount of a compound of formula I or a pharmaceutically acceptable salt thereof, methods for controlling or treating infections in livestock and companion animals by administering to an animal in need thereof a therapeutically effective amount of a compound of formula I or a pharmaceutically acceptable salt thereof, and methods for the preparation of compounds of the present invention.

DETAILED DESCRIPTION

With respect to the above compound, and throughout the application and claims, the following terms have the meanings defined below.

The term "halo" refers to chloro, bromo, fluoro, and iodo.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-4}$ alkyl refers to alkyl of one to four carbon atoms, inclusive; $C_{1-6}$ alkyl refers to alkyl of one to six carbon atoms, inclusive; and $C_{1-8}$ alkyl refers to alkyl of one to eight carbon atoms, inclusive.

The term alkyl refers to straight, branched and a cyclic saturated monovalent hydrocarbon groups, but reference to an individual radical such as "propyl" embraces only the straight chain radical, a branched chain isomer such as "isopropyl" or a cyclic isomer such as cyclopropylmethyl or cyclopentyl being specifically referred to.

The term "cycloalkyl" refers to a mono ring such as cyclopropyl, cyclobutyl, cyclopentyl, or cyclohexyl.

The term "Het" refers to saturated or unsaturated monocyclic or bicyclic heterocyclics, containing at least one heteroatom selected from N, O, and S. Bicyclic heterocyclics rings may be fused, spiro, or bridged ring systems. Monocyclic heterocyclic rings contain from 4- to 10-ring atoms, preferably from 5 to 6 member atoms in the ring. Bicyclic heterocyclics contain from 7 to 14 member atoms, preferably 9 to 12 member atoms in the ring. Examples of heterocyclic groups include, but are not limited to, substituted or unsubstituted tetrahydrofuran, dioxane, pyrrolidine, piperidine, piperazine, tetrahydrotriazine, tetrahydropyrazole, tetrahydrothiophene, dihydro-1,3-dithiol-2-yl, hexahydrothiepin-4-yl, thienyl, furanyl, pyrrolyl, imidazolyl, pyrazolyl, thiazolyl, isothiazolyl, oxazolyl, isoxazolyl, triazolyl, tetrazolyl, pyridinyl, pyrazinyl, pyridazinyl, pyrimidinyl, piperidinyl, pyrrolidinyl, piperazinyl, azetidinyl, aziridinyl, morpholinyl, thietanyl, oxetaryl, thiophenyl, thiadiazolyl, oxadizolyl. Examples of suitable bicyclic heterocyclic groups include, but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 5-4H-imidazo[4,5-d]thiazolyl, 3-, 5-, or 8-pyrazino[2,3-d]pyridazinyl, 2-, 3-, 5-, or 6-imidazo[2,1-b]thiazolyl, imidazo[1,2-a]pyridinyl, thiazolo[5,4-b]pyridinyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]-benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

For heterocyclic groups containing sulfur, the oxidized sulfur such as SO or $SO_2$ groups are also included.

For heterocyclic groups containing nitrogen, nitrogen groups such as N→O or NH are also included.

At each occurrence, Het is optionally substituted with one to three OH, halo, —CN, —$NO_2$, $C_{1-6}$alkyl, —$C_{3-6}$cycloalkyl, oxo (=O), —$NH_2$, —$NHC_{1-4}$alkyl, —$N(C_{1-4}$alkyl$)_2$, —$OC_{1-4}$alkyl, —SH, —$SC_{1-4}$alkyl, —$S(C=O)C_{1-4}$alkyl, —$SONC_{1-4}$alkyl, —$C(=O)C_{1-4}$alkyl, —$C(=O)NH_2$, —$C(=O)NHC_{1-4}$alkyl, —$C(=O)N(C_{1-4}$alkyl$)_2$, —NC(=O)$NH_2$, —NC(=O)$NHC_{1-4}$alkyl, or NC(=O)$N(C_{1-4}$alkyl$)_2$.

The term "mammal" refers to human or animals including livestock and companion animals. The phrase "companion animal" or "companion animals" refers to animals kept as pets. Examples of companion animals include cats, dogs, and horses. The term "livestock" refers to animals reared or raised in an agricultural setting to make products such as food or fiber, or for its labor. In some embodiments, livestock are suitable for consumption by mammals, for example humans. Examples of livestock animals include mammals, such as cattle, goats, horses, pigs, sheep, including lambs, and rabbits, as well as birds, such as chickens, ducks and turkeys. Specifically, livestock animals of the present invention refer to cattle and pigs. The compounds of the present invention may also be useful in aquaculture, such as fish.

The term "controlling", "treating" or "treatment" of a disease includes: (1) preventing the disease, i.e. causing the clinical symptoms or signs of the disease not to develop in a mammal that may be exposed to or predisposed to the disease but does not yet experience or display symptoms/signs of the disease; (2) inhibiting the disease, i.e., arresting or reducing the development of the disease or its clinical symptoms/signs; or (3) relieving the disease, i.e., causing regression of the disease or its clinical symptoms/signs.

The term "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "pharmaceutically acceptable" means suitable for use in mammals, companion animals or livestock animals.

The term "prodrug" refers to a bio-reversible derivative of a molecule, i.e. a compound of formula I of the present invention. Prodrugs can alter the solubility, lipophilicity and in-vivo distribution of drugs. By deliberately altering these key properties, it may be possible to improve absorption, enhance onset time, reduce first pass metabolism, allow development of aqueous IV formulations and achieve targeted delivery. In addition, prodrugs are useful in improving transdermal delivery, masking taste, minimizing pain on injection, improving stability, etc. In situations where the pharmacophore itself leads to poor delivery properties, prodrugs are one of the few strategies that can be used to salvage the highly active compound. Included within the scope of the present invention are all prodrugs of the compounds of formula I that can be prepared by the standard methods known to one skilled in the art. Prodrugs of the compounds of formula I may be prepared following the methods described in "Prodrugs of phosphates, phosphonates, and phosphinates," Krise J P, Stella V J, Advanced Drug Delivery Reviews, 19: (2) 287-310 May 22, 1996; "Targeted Prodrug Design to Optimize Drug Delivery". Hyo-Kyung Han and Gordon Amidon, AAPS Pharm Sci 2000; 2 (1) article 6; "Prodrugs", L. Prokai and K. Prokai-Tatrai, Chapter 12 in *Injectable Drug Development: Techniques to Reduce Pain and Irritation*, Interpharm Press, Buffalo Grove, Ind., 1999; "Improved oral drug delivery: Solubility limitations overcome by the use of prodrugs", Fleisher D, Bong R, Stewart B H, Advanced Drug Delivery Reviews, 19: (2) 115-130 May 22, 1996; or "Preparation and hydrolysis of water soluble, non-irritating prodrugs of pharmaceuticals with oxaalkanoic acids", Crooks, Peter Anthony; Cynkowski, Tadeusz; Cynkowska, Grazyna; Guo, Hong; Ashton, Paul, PCT Int. Appl. (2000), 65 pp. Examples of representative prodrugs include phosphates, phosphonates, phosphinates, carboxylic esters and carbamates.

Compounds that have the same molecular formula but differ in the nature or sequence of bonding of their atoms or the arrangement of their atoms in space are termed "isomers".

Included within the scope of the described compounds are all isomers (e.g. cis-, trans-, enantiomers, or diastereomers) of the compounds described herein alone as well as any mixtures. All of these forms, including enantiomers, diastereomers, cis, trans, syn, anti, solvates (including hydrates), tautomers, and mixtures thereof, are included in the described compounds.

A specific value for W is H, —PO(OH)$_2$, or —CH$_2$OPO(OH)$_2$.

A specific value for W is H.

A specific value for X and Y is chloride; and Z is H.

A specific value for X and Y is fluoride; and Z is H.

A specific value for the Het moiety is a 5- or 6-membered cyclic ring system having from one to three hetero atoms selected from N, O, and S, including hetero atom groups such as S—O, —SO$_2$, N→O and —NH. The Het moiety is optionally substituted with $R^6$.

A specific value for the Het moiety is pyridinyl, thiophenyl, thiazolyl, thiadiazolyl, imidazolyl, oxadiazolyl, pyrimidinyl, pyrazinyl, isoxazole, isothiazole, or pyridazine.

A specific value for the Het moiety is pyridinyl or thiazolyl.

Specific values for $R^1$ and $R^2$ are independently H or $R^1$ and $R^2$ are taken together with the nitrogen to which they are attached form a 4- to 6-membered heterocyclic ring moiety optionally having an additional one to two hetero atoms selected from the group consisting from N, S and O, wherein the heterocyclic ring is optionally substituted with $R^6$.

Specific values for $R^1$ and $R^2$ are each H.

Specific values for $R^3$ and $R^4$ are independently H or $C_{1-4}$alkyl or $R^3$ and $R^4$ are taken together to form a $C_{3-6}$cycloalkyl.

Specific values for $R^3$ and $R^4$ taken together are to form a cyclopropyl.

Specific values for compounds of the present invention include those wherein W is H, —PO(OH)$_2$, or —CH$_2$OPO(OH)$_2$; the Het moiety is a 5- or 6-membered cyclic ring system having from one to three hetero atoms selected from N, O, and S, optionally substituted with $R^6$; $R^1$ and $R^2$ are each H; —$R^3$ and $R^4$ are independently H or $C_{1-4}$alkyl or $R^3$ and $R^4$ are taken together to form a cyclopropyl; and X, Y and Z are independently H, chloride or fluoride.

Specific values for $R^3$ and $R^4$ taken together with one or two hetero atoms selected from the group consisting of N, S and O are to form a 4- to 6-membered heterocyclic ring moiety, wherein the heterocyclic ring is optionally substituted with one to three $R^6$.

Specific values for $R^3$ and $R^4$ are taken together with an oxygen atom to form an oxetanyl.

Specific values for compounds of the present invention include those wherein W is H or —PO(OH)$_2$; the Het moiety is a 5- or 6-membered cyclic ring system having from one to three hetero atoms selected from N, O, and S, optionally substituted with $R^6$; $R^1$ and $R^2$ are each H; $R^3$ and $R^4$ are taken together with an oxygen atom to form an oxetanyl; and X, Y and Z are independently H, chloride or fluoride.

Specific values for $R^2$ and $R^3$ taken together with the nitrogen atom to which they are attached are to form an azetidinyl.

Specific values for compounds of the present invention include those wherein W is H or —PO(OH)$_2$; Het moiety is a 5- or 6-membered cyclic ring system having from one to three hetero atoms selected from N, O, and S, optionally substituted with $R^6$; $R^1$ and $R^4$ are each H; $R^2$ and $R^3$ are taken together with the nitrogen atom to which they are attached to form an azetidinyl; and X, Y and Z are independently H, chloride or fluoride.

Specific values for $R^1$ and $R^3$ taken together with the nitrogen atom to which they are attached are to form a pyrrolidinyl.

Specific values for compounds of the present invention include those wherein W is H or —PO(OH)$_2$; the Het moiety is a 5- or 6-membered cyclic ring system having from one to three hetero atoms selected from N, O, and S, optionally substituted with R$^6$; R$^2$ and R$^4$ are each H; R$^1$ and R$^3$ are taken together with the nitrogen atom to which they are attached to form a pyrrolidinyl; and X, Y and Z are independently H, chloride or fluoride.

Examples of compounds of the present invention include the following:

N-((1R,2S)-1-(4-(2-(1-aminoethyl)thiazol-5-yl)phenyl)-3-fluoro-1-hydroxypropan-2-yl)-2,2-difluoroacetamide;

N-((1R,2S)-1-(4-(2-(1-aminoethyl)thiazol-5-yl)phenyl)-3-fluoro-1-hydroxypropan-2-yl)-2,2-dichloroacetamide;

(1R,2S)-1-(4-(2-(1-aminoethyl)thiazol-5-yl)phenyl)-2-(2,2-dichloroacetamido)-3-fluoropropyl hydrogen phosphate sodium;

(1R,2S)-1-(4-(2-(1-aminoethyl)thiazol-5-yl)phenyl)-2-(2,2-dichloroacetamido)-3-fluoropropyl dihydrogen phosphate;

(1R,2S)-1-(4-(2-(1-aminoethyl)thiazol-5-yl)phenyl)-2-(2,2-difluoroacetamido)-3-fluoropropyl hydrogen phosphate sodium;

(1R,2S)-1-(4-(2-(1-aminoethyl)thiazol-5-yl)phenyl)-2-(2,2-difluoroacetamido)-3-fluoropropyl dihydrogen phosphate;

N-((1R,2S)-1-(4-(6-(1-aminocyclopropyl)pyridin-3-yl)phenyl)-3-fluoro-1-hydroxypropan-2-yl)-2,2-difluoroacetamide;

N-((1R,2S)-1-(4-(6-(1-aminocyclopropyl)pyridin-3-yl)phenyl)-3-fluoro-1-hydroxypropan-2-yl)-2,2-dichloroacetamide;

(1R,2S)-1-(4-(6-(1-aminocyclopropyl)pyridin-3-yl)phenyl)-2-(2,2-dichloroacetamido)-3-fluoropropyl hydrogen phosphate sodium;

(1R,2S)-1-(4-(6-(1-aminocyclopropyl)pyridin-3-yl)phenyl)-2-(2,2-dichloroacetamido)-3-fluoropropyl dihydrogen phosphate;

(1R,2S)-1-(4-(6-(1-aminocyclopropyl)pyridin-3-yl)phenyl)-2-(2,2-difluoroacetamido)-3-fluoropropyl hydrogen phosphate sodium;

(1R,2S)-1-(4-(6-(1-aminocyclopropyl)pyridin-3-yl)phenyl)-2-(2,2-difluoroacetamido)-3-fluoropropyl dihydrogen phosphate;

N-((1R,2S)-1-(4-(6-((RS)-1-aminoethyl)pyridin-3-yl)phenyl)-3-fluoro-1-hydroxypropan-2-yl)-2,2-difluoroacetamide;

N-((1R,2S)-1-(4-(6-(1-aminoethyl)pyridin-3-yl)phenyl)-3-fluoro-1-hydroxypropan-2-yl)-2,2-dichloroacetamide;

(1R,2S)-1-(4-(6-(1-aminoethyl)pyridin-3-yl)phenyl)-2-(2,2-dichloroacetamido)-3-fluoropropyl hydrogen phosphate sodium;

(1R,2S)-1-(4-(6-(1-aminoethyl)pyridin-3-yl)phenyl)-2-(2,2-dichloroacetamido)-3-fluoropropyl dihydrogen phosphate;

(1R,2S)-1-(4-(6-(1-aminoethyl)pyridin-3-yl)phenyl)-2-(2,2-difluoroacetamido)-3-fluoropropyl hydrogen phosphate sodium;

(1R,2S)-1-(4-(6-(1-aminoethyl)pyridin-3-yl)phenyl)-2-(2,2-difluoroacetamido)-3-fluoropropyl dihydrogen phosphate;

N-((1R,2S)-1-(4-(6-(azetidin-2-yl)pyridin-3-yl)phenyl)-3-fluoro-1-hydroxypropan-2-yl)-2,2-difluoroacetamide;

N-((1R,2S)-1-(4-(6-(azetidin-2-yl)pyridin-3-yl)phenyl)-3-fluoro-1-hydroxypropan-2-yl)-2,2-dichloroacetamide;

(1R,2S)-1-(4-(6-(azetidin-2-yl)pyridin-3-yl)phenyl)-2-(2,2-difluoroacetamido)-3-fluoropropyl dihydrogen phosphate;

(1R,2S)-1-(4-(6-(azetidin-2-yl)pyridin-3-yl)phenyl)-2-(2,2-dichloroacetamido)-3-fluoropropyl dihydrogen phosphate;

N-((1R,2S)-1-(4-(6-(3-aminooxetan-3-yl)pyridin-3-yl)phenyl)-3-fluoro-1-hydroxypropan-2-yl)-2,2-difluoroacetamide;

(1R,2S)-1-(4-(6-(3-aminooxetan-3-yl)pyridin-3-yl)phenyl)-2-(2,2-difluoroacetamido)-3-fluoropropyl dihydrogen phosphate;

(1R,2S)-1-(4-(6-(3-aminooxetan-3-yl)pyridin-3-yl)phenyl)-2-(2,2-dichloroacetamido)-3-fluoropropyl dihydrogen phosphate;

N-((1R,2S)-1-(4-(6-(3-aminooxetan-3-yl)pyridin-3-yl)phenyl)-3-fluoro-1-hydroxypropan-2-yl)-2,2-dichloroacetamide;

2,2-dichloro-N-{(1S,2R)-1-(fluoromethyl)-2-hydroxy-2-[4-(6-pyrrolidin-2-ylpyridin-3-yl)phenyl]ethyl}acetamide;

(1R,2S)-2-(2,2-dichloroacetamido)-3-fluoro-1-(4-(6-(pyrrolidin-2-yl)pyridin-3-yl)phenyl)propyl dihydrogen phosphate;

2,2-Difluoro-N-{(1S,2R)-1-fluoromethyl-2-hydroxy-2-[4-(6-pyrrolidin-2-yl-pyridin-3-yl)-phenyl]-ethyl}-acetamide; and (1R,2S)-2-(2,2-difluoroacetamido)-3-fluoro-1-(4-(6-(pyrrolidin-2-yl)pyridin-3-yl)-phenyl)propyl dihydrogen phosphate.

Also an example of a compound of the present invention is N-((1R,2S)-3-fluoro-1-hydroxy-1-(4-(6-(methylsulfonamidomethyl)pyridin-3-yl)phenyl)propan-2-yl)methanesulfonamide.

The following reaction schemes illustrate the general synthetic procedures of the compounds of the present invention. All starting materials are prepared by procedures described in these schemes or by procedures known to one of ordinary skill in the art.

Scheme I

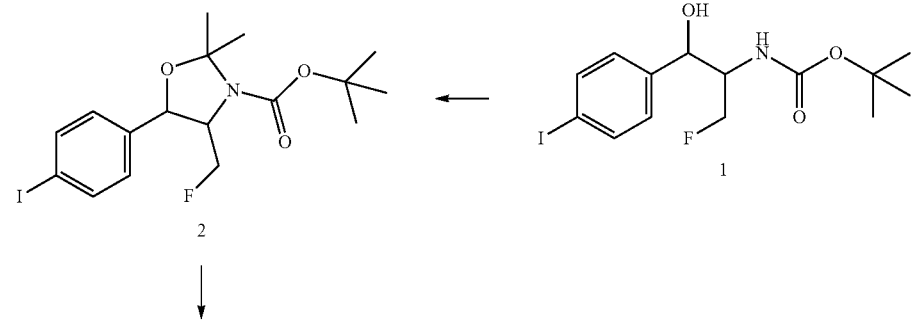

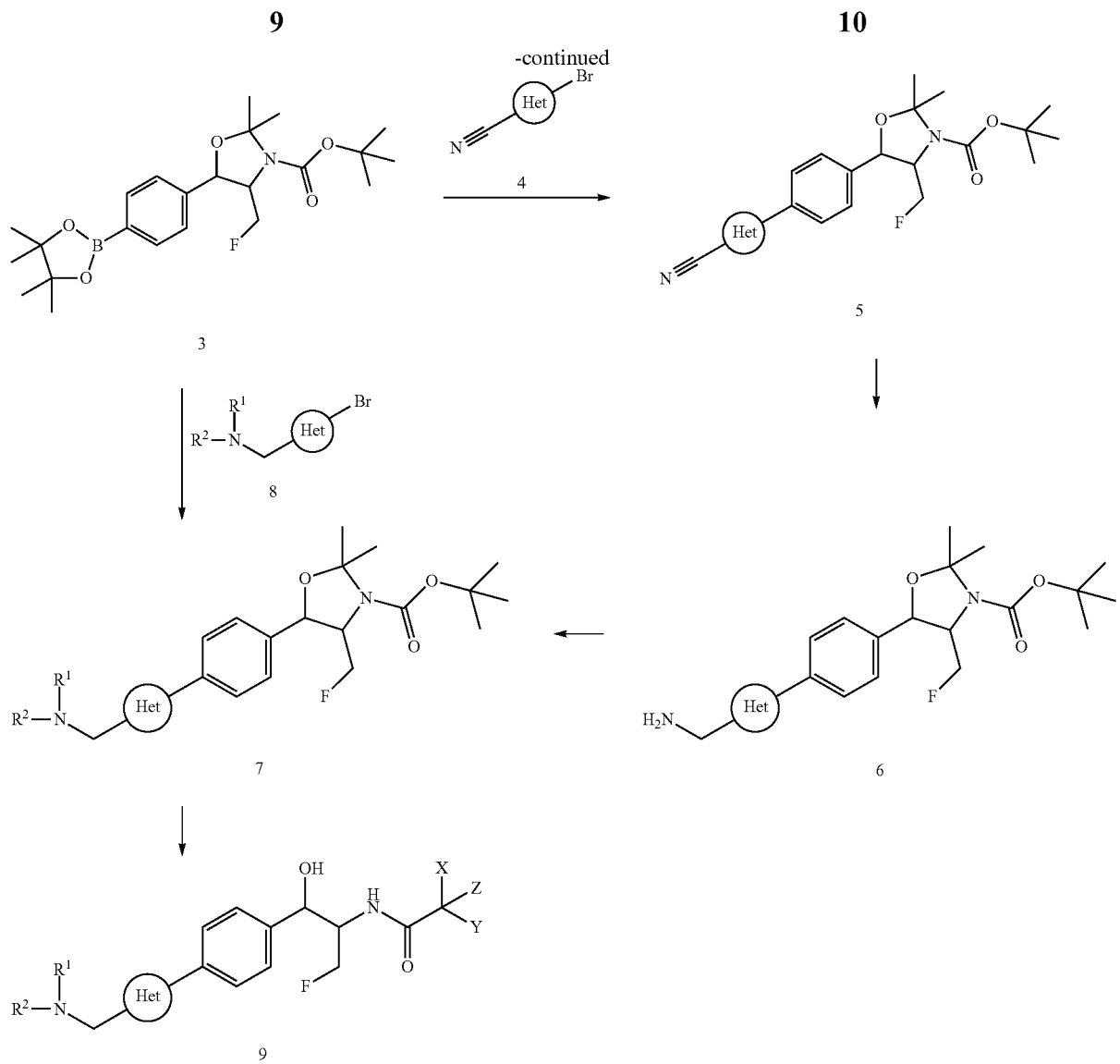

As shown in Scheme I, a compound of structure (2) can be prepared from tert-butyl 3-fluoro-1-hydroxy-1-(4-iodophenyl)propan-2-yl)carbamate (1) in the presence of a suitable ketalization reagent such as 2-methoxypropene and a weak organic acid such as paratoluenesufonic acid at temperature ranging from 0° C. to reflux in polar organic solvents such as dichloromethane. A compound of structure (3) can be obtained by coupling a suitable boronating reagent such as bis(pinacolato)diboron using catalytic amounts of a palladium catalyst such as bis(triphenylphosphine)palladium(ii) chloride or palladium tetrakistriphenylphosphine in the presence of a suitable base such as potassium acetate in polar aprotic solvents such as 1,4-dioxane or THF at temperatures ranging from room temperature to reflux. A compound of structure (5) can be obtained by employing a palladium catalyzed coupling process such as the Suzuki coupling between a suitable heteroarylhalide (4) and boronic ester (3) using a palladium catalyst such as palladium tetrakistriphenylphosphine in the presence of a suitable base such as potassium carbonate or sodium bicarbonate in a suitable biphasic solvent mix such as toluene and water at temperatures ranging from room temperature to reflux. A compound of structure (6) can be prepared from a compound of structure (5) by reaction with a suitable reducing reagent such as palladium on carbon or a mixture of sodium borohydride with nickel chloride in a suitable protic solvent such as methanol or isopropyl alcohol at temperature ranging from 0° C. to reflux. A compound of structure (7) can be prepared by condensation with an appropriate agent such as a sufonylating reagent, for example, mesyl chloride or ethanesulfonyl chloride or methane sulfonic anhydride in the presence of a suitable organic base such as DIPEA or triethylamine in a suitable solvent such as dichloromethane or THF at temperatures ranging from −78° C. to room temperature. Alternatively a compound of structure (7) can be made by directly coupling an appropriate agent such as sulfonamide (8) with a boronic ester of structure (3) using a palladium catalyst such as palladium tetrakistriphenylphosphine in the presence of a suitable base such as potassium carbonate or sodium bicarbonate in a suitable biphasic solvent mix such as toluene and water at temperatures ranging from room temperature to reflux. Utilizing the alternative method also provides a compound of structure (6) where $R^1$ and $R^2$ are independently hydrogen. A compound of structure (9) can be prepared by treatment of a compound of structure (7) with a suitable organic acid such as trifluoroacetic acid in a suitable polar solvent such as dichloromethane or 1,2-dichloroethane at temperatures ranging from 0° C. to room temperature.

Scheme II

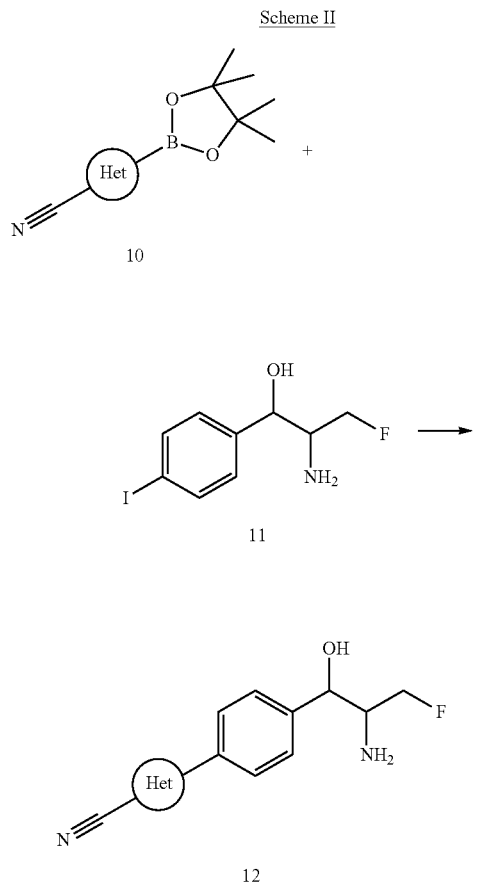

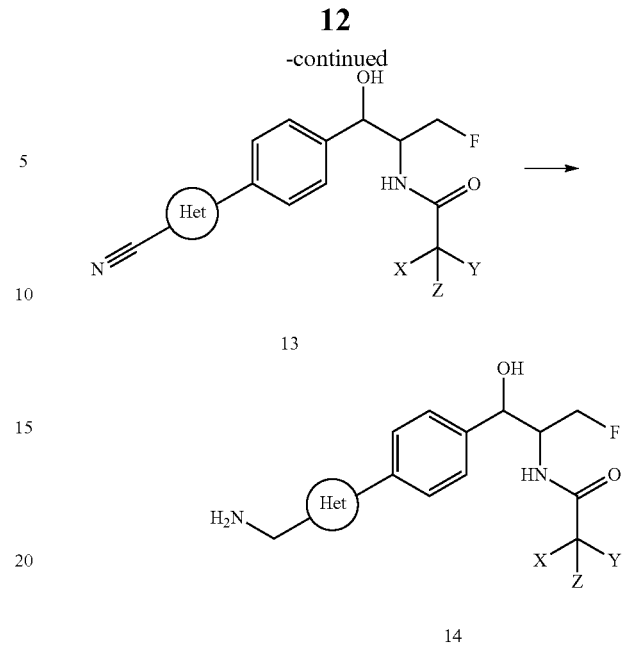

In scheme II, a compound of structure (12) can be prepared from a aryl halide (11) and a suitable boronic ester (10) using a palladium catalyst such as palladium tetrakis-triphenylphosphine in the presence of a suitable base such as potassium carbonate or sodium bicarbonate in a suitable biphasic solvent mix such as toluene and water at temperatures ranging from room temperature to reflux. A compound of structure (13) can be prepared by condensation of an amine (12) with a suitable acylating agent such as dichloroacetyl chloride or ethyldifluoroacetate in the presence of a suitable base such as triethylamine or DIPEA in a suitable polar protic solvent such as methanol or an appropriate polar solvent such as dichloromethane. A compound of structure (14) can be prepared from a compound of structure (13) by reaction with a suitable reducing reagent such as palladium on carbon or a mixture of sodium borohydride with nickel chloride in a suitable protic solvent such as methanol or isopropyl alcohol at a temperature ranging from 0° C. to reflux.

Scheme III

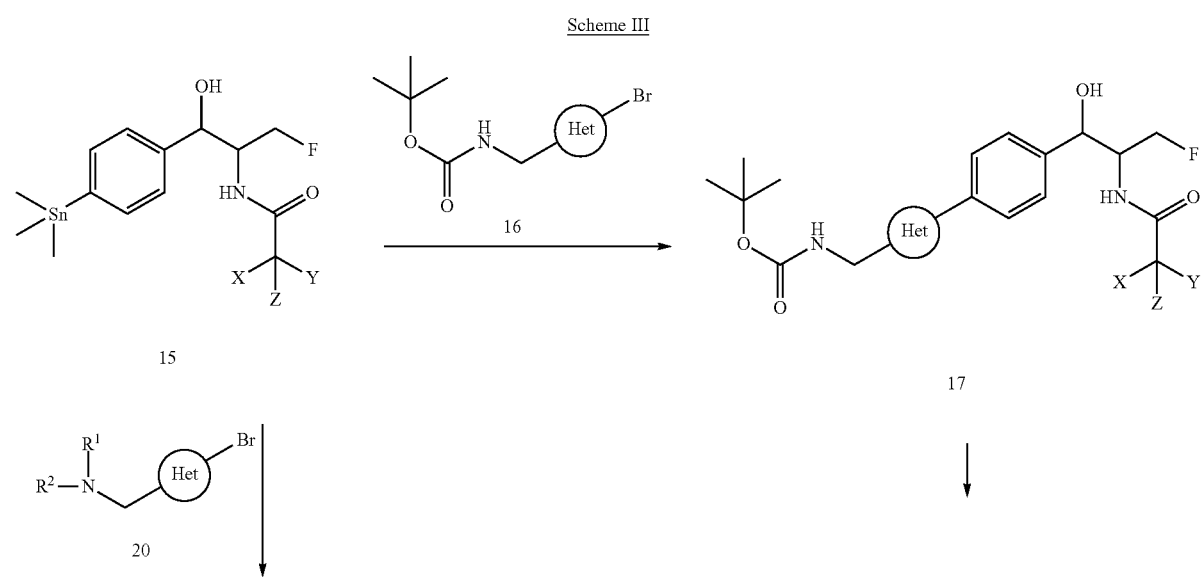

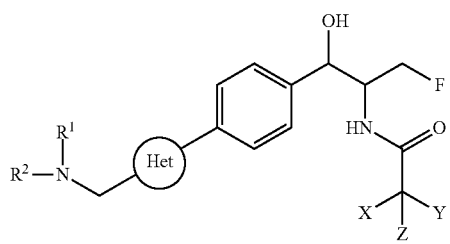

13

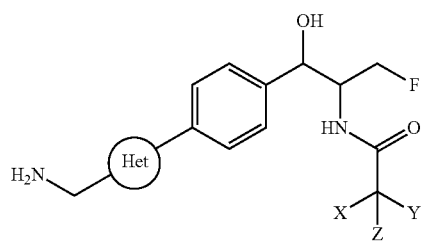

14
-continued 9  18

In Scheme III, a compound of structure (17) can be prepared by Stille coupling of a stannane of structure (15) with an aryl halide of structure (16) using a palladium catalyst such as tris(dibenzylideneacetone)dipalladium or bis(triphenylphosphine)palladium(ii) chloride and optionally with a suitable phosphine ligand such as tris(2-furyl)phosphine along with a suitable metal halide additive such as lithium chloride or cesium fluoride in an appropriate polar aprotic solvent such as NMP or DMF at temperatures ranging from room temperature to 120° C. A compound of structure (18) can be made by treatment of a compound of structure (17) with a suitable organic acid such as trifluoroacetic acid in a suitable solvent such as DCM or 1,2-dichoroethane at temperatures ranging from 0° C. to room temperature. A compound of structure (9) can be prepared from a compound of structure (18) by condensation with an appropriate agent such as a sufonylating reagent, for example, mesyl chloride or ethanesulfonyl chloride or methane sulfonic anhydride in the presence of a suitable organic base such as DIPEA or triethylamine in a suitable solvent such as dichloromethane or THF at temperatures ranging from −78° C. to room temperature. Alternatively, a compound of structure (9) can be made by directly coupling an arylhalide sulfonamide (20) with a boronic ester of stannane (15) a palladium catalyst such as tris(dibenzylideneacetone)dipalladium or bis(triphenylphosphine)palladium(ii)chloride and optionally a suitable phosphine ligand such as tris(2-furyl)phosphine along with a suitable metal halide additive such as lithium chloride or cesium fluoride in an appropriate polar aprotic solvent such as NMP or DMF at temperatures ranging from room temperature to 120° C.

Pharmaceutical Salts

The compound of formula I may be used in its native form or as a salt. In cases where forming a stable nontoxic acid or base salt is desired, administration of the compound as a pharmaceutically acceptable salt may be appropriate. Pharmaceutically acceptable salts of the compounds of formula I include the acetate, ascorbate, aspartate, benzoate, besylate, bicarbonate/carbonate, bisulphate/sulphate, borate, camsylate, citrate, edisylate, etoglutarate, esylate, formate, fumarate, gluceptate, gluconate, glucuronate, glycerophosphate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Composition/Formulation

Pharmaceutical compositions of the present invention may be manufactured by processes well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more pharmaceutically acceptable carriers comprising excipients and auxiliaries, which facilitate processing of the active compound into preparations, which can be used pharmaceutically. Proper formulation is dependent upon the route of administration chosen. Pharmaceutically acceptable excipients and carriers are generally known to those skilled in the art and are thus included in the instant invention. Such excipients and carriers are described, for example, in "Remington's Pharmaceutical Sciences", Mack Pub. Co., New Jersey (1991).

The formulations of the invention can be designed to be short-acting, fast-releasing, long-acting, extended-releasing, or controlled-releasing. Specifically, the formulation of the invention can be an extended release form. Thus, the pharmaceutical formulations can also be formulated for controlled release or for slow release.

Dosage

Pharmaceutical compositions suitable for use in the present invention include compositions wherein the active ingredients are contained in an amount sufficient to achieve the intended purpose, i.e., control or the treatment of infections. More specifically, a therapeutically effective amount means an amount of compound effective to prevent, alleviate or ameliorate symptoms/signs of infections or prolong the survival of the subject being treated.

The quantity of active component, which is the compound of this invention, in the pharmaceutical composition and unit dosage form thereof, may be varied or adjusted widely depending upon the manner of administration, the potency of the particular compound and the desired concentration. Determination of a therapeutically effective amount is well within the capability of those skilled in the art. Generally, the quantity of active component will range between 0.01% to 99% by weight of the composition.

Generally, a therapeutically effective amount of dosage of active component will be in the range of about 0.1 mg to about 100 mg/kg of body weight/day; for example, about 0.1 to about 50 mg/kg of body weight/day; and for example, about 5 to about 50 mg/kg of body weight/day; and, for example, about 20 to about 50 mg/kg of body weight/day. It is to be understood that the dosages may vary depending upon the requirements of each subject and the severity of the infections.

The desired dose may conveniently be presented in a single dose or as divided doses administered at appropriate intervals, for example, as two, three, four or more sub-doses per day. Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

Medical and Veterinary Uses

Compounds of the present invention provides novel phenicol antibacterial agents for the treatment of bovine respiratory disease infections in cattle caused by Gram-negative respiratory pathogens, such as *M. haemolytica, P. multocida, H. somnus*, and *M. bovis*.

Antibacterial Assays

Compounds of the present invention are tested against an assortment of Gram-negative and Gram-positive organisms using the industrial standard techniques described in M31-A3. Performance Standards for Antimicrobial Disk and Dilution Susceptibility Tests for Bacteria Isolated from Animals; Clinical and Laboratory Standards Institute, Approved Standard-Third Edition. The compounds of the present invention demonstrate very good antibacterial activity against BRD pathogens, for example, *M. haemolytica, P. multo., H. somnus* and *M. bovis*.

EXAMPLES

The synthesis of compounds of the present invention is further illustrated by the following examples. The starting materials and various intermediates utilized in the examples may be obtained from commercial sources, or are readily prepared from commercially available organic compounds, using well-known methods to one skilled in the art.

Example 1

Preparation of N-((1R,2S)-1-(4-(6-(aminomethyl) pyridin-3-yl)phenyl)-3-fluoro-1-hydroxypropan-2-yl)-2,2-dichloroacetamide Step 1 Preparation of 5-(4-((1R,2S)-2-amino-3-fluoro-1-hydroxypropyl)-phenyl)picolinonitrile

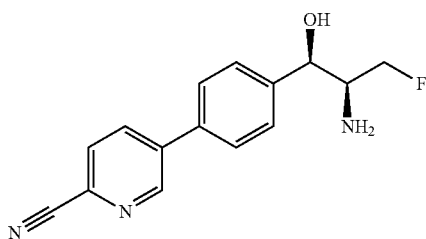 [SMILES: N#Cc1ccc(-c2ccc([C@@H](O)[C@H](N)CF)cc2)cn1]

To a solution of commercially available 5-(4,4,5,5-tetramethyl-1,3,2-dioxaborolan-2-yl)picolinonitrile (0.5 g, 2.17 mmol) in degassed dimethoxyethane (10 mL) and water (3 mL) is added (1R,2S)-2-amino-3-fluoro-1-(4-iodophenyl)-propan-1-ol (0.65 g, 2.20 mmol) and Cs$_2$CO$_3$ (2.15 g, 6.6 mmol). Pd(PPh$_3$)$_4$ (0.25 g, 0.21 mmol) is added and the reaction mixture heated to 90° C. for 1.5 hours. Solvent is evaporated in vacuo and the crude material purified by column chromatography on silica gel eluting in methanol/CHCl$_3$ to afford the title compound (206 mg): 1NMR (400 MHz, CDCl$_3$) δ: 3.09-3.18 (m, 1H), 3.48 (s, 1H), 4.24-4.28 (m, 0.5H), 4.36-4.41 (m, 1H), 4.49-4.52 (m, 0.5H), 4.64 (d, J=6.16 Hz, 1H), 7.53 (d, J=8.16 Hz, 2H), 7.59 (d, J=8.24 Hz, 2H), 7.76 (d, J=8.2, 1H), 8.0 (dd, J1=8.16 Hz, J2=2.32 Hz, 1H), 8.93 (d, J=1.76 Hz, 1H). m/z (CI) 272 [M+H].

Step 2 Preparation of 2,2-dichloro-N-((1R,2S)-1-(4-(6-cyanopyridin-3-yl)phenyl)-3-fluoro-1-hydroxy-propan-2-yl)acetamide

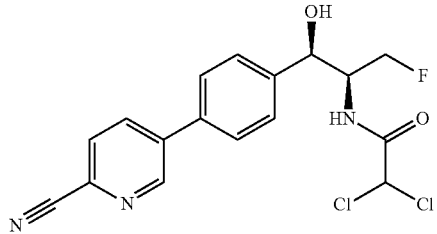 [SMILES: N#Cc1ccc(-c2ccc([C@@H](O)[C@@H](CF)NC(=O)C(Cl)Cl)cc2)cn1]

To the solution of 5-(4-((1R,2S)-2-amino-3-fluoro-1-hydroxypropyl)phenyl)-picolinonitrile (0.5 g, 1.1 mmol) in methanol (5 mL) is added triethylamine (0.22 g, 2.2 mmol) and ethyl dichloro acetate (0.34 g, 2.2 mmol) and reaction mixture is stirred at room temperature for 16 hours. The solvent is evaporated in vacuo and the crude material purified by column chromatography on silica gel using methanol/CH$_2$Cl$_2$ to afford the title compound (264 mg): 1HNMR (400 MHz, CDCl$_3$) δ: 4.26-4.35 (m, 1H), 4.36-4.37 (m, 0.5H), 4.45-4.51 (m, 1H), 4.59-4.63 (m, 0.5H), 5.02 (d, J=3.28 Hz, 1H), 5.84 (s, 1H), 7.47 (d, J=8.2 Hz, 2H), 7.54 (d, J=8.24 Hz, 2H), 7.76 (d, J=8.04 Hz, 1H), 7.96 (dd, J1=8.08 Hz, J2=2.2 Hz, 1H), 8.85 (d, J=1.64 Hz, 1H). m/z (CI) 380 [M+H].

Step 3 Preparation of N-((1R,2S)-1-(4-(6-(aminomethyl)pyridin-3-yl)phenyl)-3-fluoro-1-hydroxypropan-2-yl)-2,2-dichloroacetamide

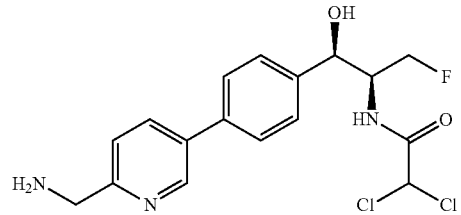 [SMILES: NCc1ccc(-c2ccc([C@@H](O)[C@@H](CF)NC(=O)C(Cl)Cl)cc2)cn1]

To an ice cold solution of lithium aluminum hydride (0.048 g, 1.33 mmol, 4.0 eq) in tetrahydrofuran (10 mL) to −40° C. is added a solution of 2,2-dichloro-N-((1R,2S)-1-(4-(6-cyanopyridin-3-yl)phenyl)-3-fluoro-1-hydroxypropan-2-yl)acetamide (0.13 g, 0.34 mmol) in tetrahydrofuran (5 mL) at −40° C. Further lithium aluminum hydride is added (0.012 g, 0.33 mmol) three times and reaction mixture is stirred at −40° C. for 4 hours. The reaction mixture is quenched with saturated aqueous sodium sulphate and stirred for 15 minutes followed by filtration. The filtrate is evaporated in vacuo and the crude material purified by column chromatography on silica gel using methanol/CH$_2$Cl$_2$ and ammonia. To the solution of the crude in CH$_2$Cl$_2$ (5 mL) is added trifluoroacetic acid (0.5 mL) and stirred reaction mixture at room temperature for 15 min. Distilled out solvent under vacuum and washed the residue with diethyl ether, and the residue is dissolved in 10% methanol in CH$_2$Cl$_2$ and evaporated to dryness. Washed with n-pentane and dried under vacuum to get the title compound (20 mg): 1HNMR (400 MHz, CDCl$_3$) δ:4.24-4.25 (m, 2H), 4.28-4.32 (m, 0.5H), 4.40-4.44 (m, 0.5H), 4.56-4.60 (m, 0.5H), 4.68-4.72 (m, 0.5H), 4.92 (bs, 1H), 6.02 (bs, 1H), 6.52 (s, 1H), 7.48 (d, J=8.28 Hz, 2H), 7.57 (d, J=10.8 Hz, 1H), 7.73 (d, J=8.04 Hz, 2H), 8.17 (dd, J1=2.28 Hz, J2=8.08

Hz 1H), 8.28 (bs, 2H), 8.65 (d, J=8.84 Hz, 1H), 8.93 (d, 1H, J=2.2 Hz). m/z (CI) 386 [M+H].

Example 2

Preparation of N-((1R,2S)-1-(4-(5-(aminomethyl) thiophen-2-yl)phenyl)-3-fluoro-1-hydroxypropan-2-yl)-2,2-dichloroacetamide Step 1 Preparation of tert-butyl ((5-(4-((1R,2S)-2-(2,2-dichloroacetamido)-3-fluoro-1-hydroxypropyl) phenyl)thiophen-2-yl)methyl)carbamate

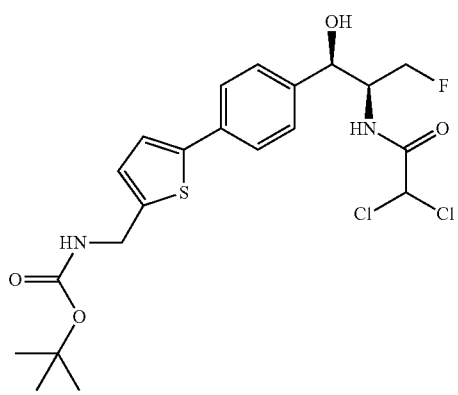 [SMILES: CC(C)(C)OC(=O)NCc1ccc(-c2ccc([C@@H](O)[C@@H](CF)NC(=O)C(Cl)Cl)cc2)s1]

To a solution of tert-butyl ((5-bromothiophen-2-yl) methyl)carbamate (0.508 g, 1.74 mmol) and 2,2-dichloro-N-((1R,2S)-3-fluoro-1-hydroxy-1-(4-(trimethyl-stannyl) phenyl)propan-2-yl)acetamide (0.7 g, 1.58 mmol) in toluene (10 mL) is added cesium fluoride (0.478 g, 3.16 mmol) and copper iodide (30 mg, 0.158 mmol) and degassed with nitrogen for 30 minutes. To this mixture is added Pd(PPh$_3$)$_2$Cl$_2$ (0.11 g, 0.16 mmol) and the mixture is heated to 90° C. for 26 hours. The solvent is evaporated in vacuo to get the crude which is purified by column chromatography on silica gel using methanol in CH$_2$Cl$_2$ to afford the title compound (490 mg): 1HNMR (400 MHz, DMSO-d$_6$) δ:1.39 (s, 9H), 4.17-4.29 (m, 3.5H), 4.37-4.41 (m, 0.5H), 4.54-4.57 (m, 0.5H), 4.65-4.69 (m, 0.5H), 4.84 (t, J=3.56 Hz, 1H), 5.95 (d, J=4.12 Hz, 1H), 6.50 (s, 1H), 6.88 (d, J=3.48 Hz, 1H), 7.29-7.37 (dd, J=8.2 Hz, J=3.6 Hz, 3H), 7.51-7.56 (d, J=8.04 Hz, 3H). m/z (CI) 489[M−H].

Step 2 Preparation of N-((1R,2S)-1-(4-(5-(aminomethyl)thiophen-2-yl)phenyl)-3-fluoro-1-hydroxypropan-2-yl)-2,2-dichloroacetamide

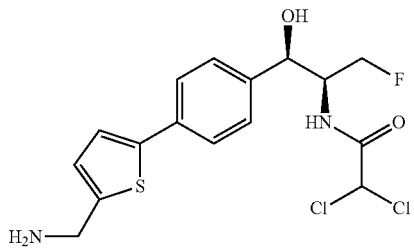 [SMILES: NCc1ccc(-c2ccc([C@@H](O)[C@@H](CF)NC(=O)C(Cl)Cl)cc2)s1]

To a solution of tert-butyl ((5-(4-((1R,2S)-2-(2,2-dichloroacetamido)-3-fluoro-1-hydroxypropyl)phenyl)thiophen-2-yl)methyl)carbamate (140 mg, 0.238 mmol) in CH$_2$Cl$_2$ (10 mL) is added trifluoroacetic acid (1.0 mL) and the reaction mixture stirred at room temperature for 2 hours. The solvent is removed under reduced pressure and the residue washed with diethyl ether, then dissolved in 10% methanol in CH$_2$Cl$_2$ and evaporated to dryness. Washed with n-pentane and dried under vacuum to give the title compound (56 mg): $^1$HNMR (400 MHz, DMSO-d$_6$) δ: 4.19-4.21 (m, 1H), 4.24-4.26 (m, 2H), 4.29-4.31 (m, 0.5H), 4.39-4.43 (m, 0.5H), 4.55-4.59 (m, 0.5H), 4.67-4.70 (m, 0.5H), 4.87 (bs, 1H), 5.90 (bs, 1H) 6.50 (s, 1H), 7.20 (d, J=3.64 Hz, 1H), 7.39 (d, J=8.24 Hz, 2H), 7.43 (d, J=3.68 Hz, 1H), 7.57 (d, J=8.16 Hz, 2H), 8.20 (bs, 3H), 8.59-8.63 (m, 1H). m/z (CI) 388 [M−H].

Example 3

Preparation of 2,2-dichloro-N-((1R,2S)-3-fluoro-1-hydroxy-1-(4-(5-(methylsulfonamidomethyl)thiophen-2-yl)phenyl)propan-2-yl)acetamide

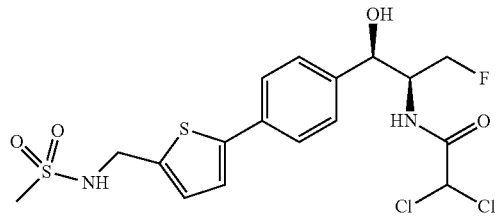 [SMILES: CS(=O)(=O)NCc1ccc(-c2ccc([C@@H](O)[C@@H](CF)NC(=O)C(Cl)Cl)cc2)s1]

To a suspension of N-((1R,2S)-1-(4-(5-(aminomethyl) thiophen-2-yl)phenyl)-3-fluoro-1-hydroxypropan-2-yl)-2,2-dichloroacetamide (150 mg, 0.383 mmol) in dichloromethane is added triethylamine (160 μL, 1.15 mmol) followed by methanesulfonyl chloride (30 μL, 0.383 mmol). Resulting yellow solution is stirred at room temperature for 30 minutes. The reaction is concentrated then purified using HPLC to give the title compound (99 mg): $^1$HNMR (400 MHz, DMSO-d$_6$): δ 8.58 (d, 1H), 7.71 (t, 1H), 7.55 (d, 2H), 7.37 (d, 2H), 7.33 (d, 2H), 7.01 (d, 1H), 6.51 (s, 1H), 5.95 (br s, 1H), 4.85 (d, 1H), 4.71-4.52 (m, 1H), 4.44-4.13 (m, 4H), 2.89 (s, 3H).

Example 4

Preparation of N-((1R,2S)-1-(4-(2-(aminomethyl) thiazol-5-yl)phenyl)-3-fluoro-1-hydroxypropan-2-yl)-2,2-dichloroacetamide Step 1 Preparation of tert-butyl ((5-(4-((1R,2S)-2-(2,2-dichloroacetamido)-3-fluoro-1-hydroxypropyl) phenyl)thiazol-2-yl)methyl)carbamate

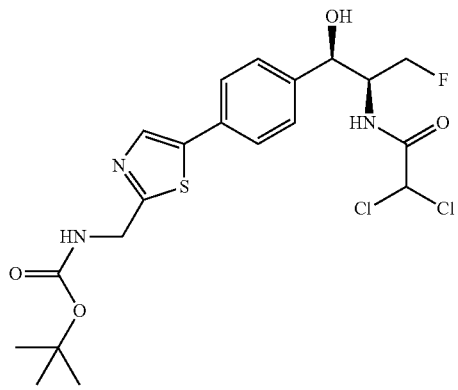 [SMILES: CC(C)(C)OC(=O)NCc1ncc(-c2ccc([C@@H](O)[C@@H](CF)NC(=O)C(Cl)Cl)cc2)s1]

Following the general procedure of Example 2—Step 1 and making non-critical variations but using 2,2-dichloro-N-((1R,2S)-3-fluoro-1-hydroxy-1-(4-(trimethyl-stannyl)phenyl)propan-2-yl)acetamide and tert-butyl ((5-bromothiazol-2-yl)methyl)carbamate as starting materials title compound is obtained (346 mg): $^1$HNMR (400 MHz, DMSO-$d_6$) 1.41 (s, 9H), 4.19-4.22 (m, 1H), 4.26-4.30 (m, 0.5H), 4.36-4.42 (m, 2.5H), 4.54-4.58 (m, 0.5H), 4.66-4.70 (m, 0.5H), 4.86 (t, J=3.4 Hz, 1H), 5.98 (d, J=4.16 Hz, 1H), 6.50 (s, 1H), 7.39 (d, J=8.2 Hz, 2H), 7.60 (d, J=8.0 Hz, 2H), 7.77-7.82 (m, 1H), 8.05 (s, 1H), 8.60 (d, J=8.8 Hz, 1H) m/z (CI) 492 [M+H].

Step 2 Preparation of N-((1R,2S)-1-(4-(2-(aminomethyl)thiazol-5-yl)phenyl)-3-fluoro-1-hydroxypropan-2-yl)-2,2-dichloroacetamide

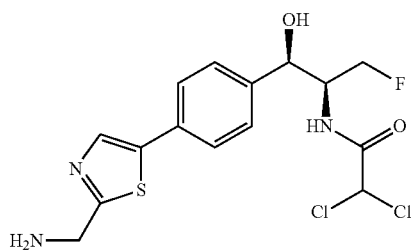 [SMILES: NCc1ncc(-c2ccc([C@@H](O)[C@@H](CF)NC(=O)C(Cl)Cl)cc2)s1]

To a stirred solution of the product of Step 1, Example 4 (0.248 g, 0.50 mmol) in CHCl$_3$ (10 mL) is added trifluoroacetic acid (1.1 mL) and stirred the reaction mixture at room temperature for 2 hours. Reaction mixture is concentrated in vacuo and washed the residue with diethyl ether. Residue is dissolved in 10% methanol in CH$_2$Cl$_2$ and evaporated to dryness then dried under vacuum to give the title compound $^1$H-NMR (400 MHz, DMSO-$d_6$) δ: 4.20-4.22 (m, 1H), 4.28-32 (m, 0.5H), 4.40-4.49 (m, 2.5H), 4.56-4.60 (m, 0.5H), 467-4.71 (m, 0.5H), 4.89 (t, J=3.8 Hz, 1H), 6.02 (d, J=4.28 Hz, 1H), 6.50 (s, 1H), 7.43 (d, J=8.2 Hz, 2H), 7.62 (d, J=8.2 Hz, 2H), 8.28 (s, 1H), 8.48 (bs, 2H), 8.63 (d, J=9 Hz, 1H). m/z (CI) 392 [M−H].

Example 5

Preparation of 2,2-dichloro-N-((1R,2S)-3-fluoro-1-hydroxy-1-(4-(6-(methylsulfonamidomethyl)pyridin-3-yl)phenyl)propan-2-yl)acetamide

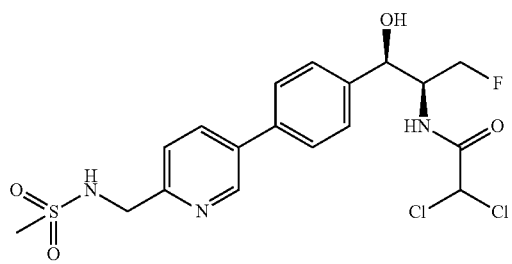 [SMILES: CS(=O)(=O)NCc1ccc(-c2ccc([C@@H](O)[C@@H](CF)NC(=O)C(Cl)Cl)cc2)cn1]

N-((5-bromopyridin-2-yl)methyl)methanesulfonamide (previously described in WO9528400) (240 mg, 0.90 mmol) and 2,2-dichloro-N-((1R,2S)-3-fluoro-1-hydroxy-1-(4-(trimethylstannyl)phenyl)propan-2-yl)acetamide (400 mg, 0.90 mmol) in 2-methylpyrrolidinone (5 mL) are treated with lithium chloride (115 mg, 2.7 mmol) and degassed and purged with nitrogen. Bis(triphenylphosphine)-palladium(ii) chloride is added and the mixture heated at 100° C. for 3 hours. The mixture is cooled, diluted with water and extracted with ethyl acetate, dried over anhydrous sodium sulfate, filtered, concentrated and purified by reverse phase chromatography to give the title compound (324 mg): 1H NMR (400 MHz, CDCl$_3$) δ: 2.96 (s, 3H), 4.2-4.3 (m, 3H), 4.4 (m, 0.5H), 4.57 (m, 0.5H), 4.58 (m, 0.5H), 4.70 (m, 0.5H), 4.90 (bs, 1H), 6.00 (s, 1H), 6.52 (s, 1H), 7.47 (d, 2H), 7.52, (d, 1H), 7.69 (d, 3H), 8.1 (m, 1H), 8.85 (m, 1H), 8.82 (bs, 1H). m/z (CI) 464.

Example 6

Preparation of N-((1R,2S)-1-(4-(5-(aminomethyl)-1,3,4-thiadiazol-2-yl)phenyl)-3-fluoro-1-hydroxypropan-2-yl)-2,2-dichloroacetamide

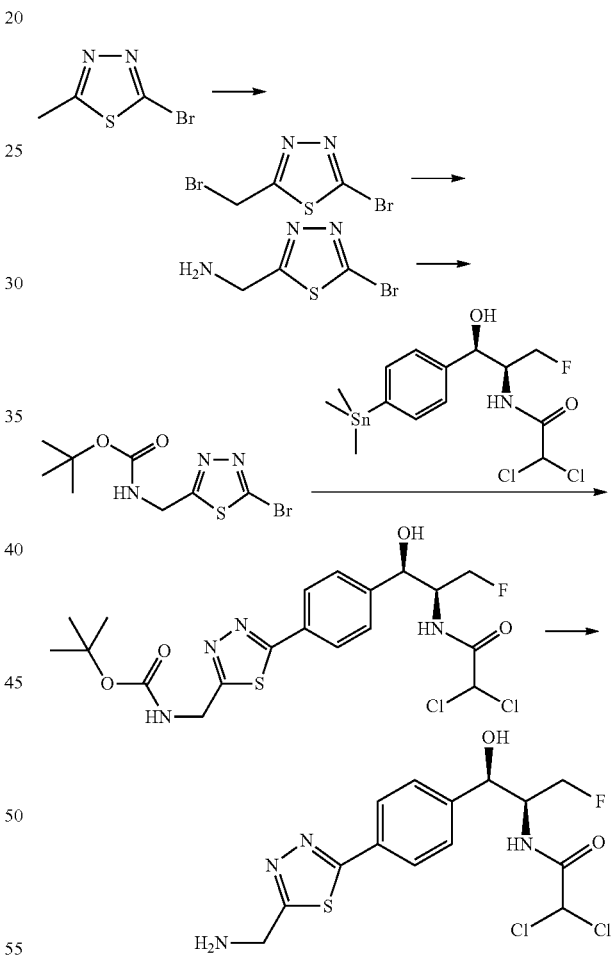

Step 1 Preparation of 2-bromo-5-(bromomethyl)-1,3,4-thiadiazole

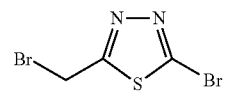

To a solution of 2-bromo-5-methyl-1,3,4-thiadiazole (0.50 g, 2.79 mmol) in CCl$_4$ (8 mL) is added N-bromosuccinamide (0.543 g, 3.067 mmol) and azobisisobutyronitrile (0.022 g, 0.139 mmol) and reaction mixture is heated to 70° C. for 3 hours. Reaction mixture is cooled to 0° C. and the solvent evaporated in vacuo to give the crude material, which is purified by column chromatography eluting in 5% ethylacetate in hexane to afford give the title compound (0.150 g): $^1$H-NMR (400 MHz, CDCl$_3$) δ 4.75 (s, 2H). LC-MS (m/z): [M+H]=260.8.

Step 2 Preparation of (5-bromo-1,3,4-thiadiazol-2-yl)methanamine

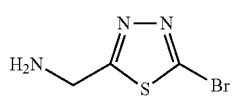

Gaseous ammonia is bubbled through a solution of 2-bromo-5-(bromomethyl)-1,3,4-thiadiazole (0.6 g, 2.352 mmol) in methanol (15 mL) for 15 minutes. The reaction mixture is stirred at room temperature for 5 hours. The reaction mixture is concentrated in vacuo, and dried to afford the title compound (0.47 g). $^1$HNMR (400 MHz, DMSO-d$_6$) δ 5.14 (s, 2H). LC-MS (m/z): [M+H]=193.90.

Step 3 Preparation of tert-butyl ((5-bromo-1,3,4-thiadiazol-2-yl)methyl)carbamate

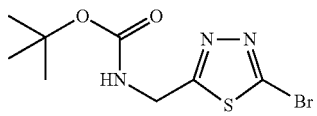

To a stirred solution of (5-bromo-1,3,4-thiadiazol-2-yl)methanamine (0.425 g, 2.19 mmol) in 1,4-dioxane (10 mL) is added 10% aqueous K$_2$CO$_3$ solution (0.392 g, 2.84 mmol). The mixture is cooled to 0° C., and di-tert-butyl dicarbonate (0.525 g, 2.40 mmol) is added. The reaction mixture is stirred for 3 hours. The reaction mixture is concentrated in vacuo. The crude material is diluted with water and extracted with ethyl acetate. Organic layer is dried over sodium sulphate, concentrated and purified by column chromatography on silica gel eluting in 20% ethylacetate in hexane to give the title compound (0.30 g): $^1$H-NMR (400 MHz, CDCl$_3$) δ 1.45 (s, 9H), 4.34-4.40 (bs, 1H), 4.66 (d, J=6.28 Hz, 2H), LC-MS (m/z): [M+H]=294.

Step 4 Preparation of tert-butyl ((5-(4-((1R,2S)-2-(2,2-dichloroacetamido)-3-fluoro-1-hydroxypropyl)phenyl)-1,3,4-thiadiazol-2-yl)methyl)carbamate

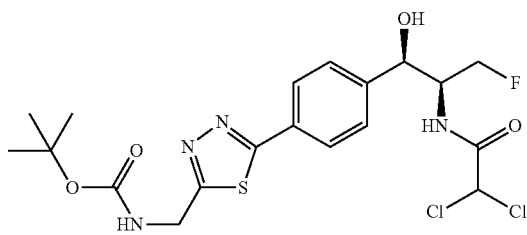 [SMILES: CC(C)(C)OC(=O)NCc1nnc(-c2ccc([C@@H](O)[C@@H](CF)NC(=O)C(Cl)Cl)cc2)s1]

To a stirred solution of tert-butyl ((5-bromo-1,3,4-thiadiazol-2-yl)methyl)-carbamate (0.878 g, 2.98 mmol) and 2,2-dichloro-N-((1R,2S)-3-fluoro-1-hydroxy-1-(4-(trimethyl-stannyl)phenyl)propan-2-yl)acetamide (1.20 g, 2.71 mmol) in dimethylformamide (20 mL) is added CsF (0.818 g, 5.42 mmol) followed by CuI (0.051 g, 0.271 mmol). Resulting reaction mixture is degassed with nitrogen for 30 minutes and Pd(PPh$_3$)$_4$ (0.313 g, 0.271 mmol) added. The reaction mixture is heated to 90° C. for 5 hours. Reaction mixture is concentrated in vacuo to give the crude material, which is purified by column chromatography on silica gel eluting in 1% methanol in CH$_2$Cl$_2$ to give the title compound (100 mg): $^1$H-NMR (400 MHz, DMSO-d$_6$) δ 1.40 (s, 9H), 4.24-4.26 (m, 1H), 4.29-4.33 (m, 0.5H), 4.41-4.45 (m, 0.5H), 4.52 (d, J=5.96 Hz, 2H), 4.57-4.61 (m, 0.5H), 4.69-4.72 (m, 0.5H), 4.93 (t, J=3.76 Hz 1H), 6.08 (d, J=4.28 Hz, 1H), 6.49 (s, 1H), 7.51 (d, J=8.24 Hz, 2H), 7.86-7.90 (m, 3H), 8.63 (d, J=8.96 Hz, 1H). LC-Ms (m/z): [M−H]=490.80.

Step 5 Preparation of N-((1R,2S)-1-(4-(5-(aminomethyl)-1,3,4-thiadiazol-2-yl)phenyl)-3-fluoro-1-hydroxypropan-2-yl)-2,2-dichloroacetamide

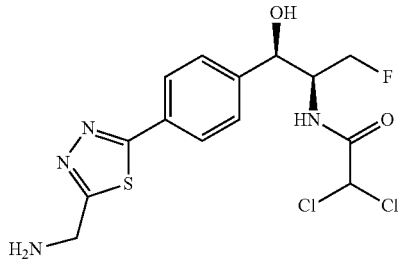 [SMILES: NCc1nnc(-c2ccc([C@@H](O)[C@@H](CF)NC(=O)C(Cl)Cl)cc2)s1]

To a stirred solution of tert-butyl ((5-(4-((1R,2S)-2-(2,2-dichloroacetamido)-3-fluoro-1-hydroxypropyl)phenyl)-1,3,4-thiadiazol-2-yl)methyl)carbamate (100 mg, 0.203 mmol) in CH$_2$Cl$_2$ (10 mL) is added trifluoroacetic acid (1.0 mL). After 2 hours the reaction mixture is concentrated in vacuo and the residue washed with diethyl ether. The residue is dissolved in 10% methanol in CH$_2$Cl$_2$ and evaporated to dryness, washed with n-pentane, dried under vacuum to give the title compound (108 mg): $^1$H-NMR (400 MHz, DMSO-d$_6$) δ 4.27-4.28 (m, 1H), 4.31-4.35 (m, 0.5H), 4.43-4.47 (m, 0.5H), 4.59-4.61 (m, 0.5H), 4.64 (s, 2H), 4.70-4.74 (m, 0.5H), 4.96 (t, J=2.76 Hz, 1H), 6.10 (d, J=4.28 Hz, 1H), 6.48 (s, 1H), 7.54 (d, J=8.32 Hz, 2H), 7.94 (d, J=8.32 Hz, 2H), 8.60 (bs, 2H), 8.64 (d, J=9.12 Hz, 1H). LC-Ms (m/z): [M+H]=393.10.

Example 7

Preparation of N-((1R,2S)-1-(4-(6-((1H-imidazol-1-yl)methyl)-pyridin-3-yl)phenyl)-3-fluoro-1-hydroxypropan-2-yl)-2,2-dichloroacetamide

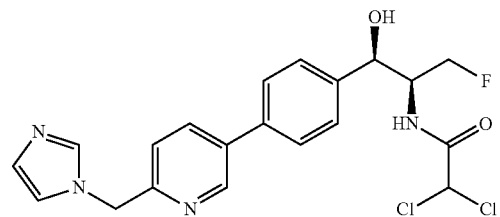 [SMILES: O=C(N[C@H](CF)[C@H](O)c1ccc(-c2ccc(Cn3ccnc3)nc2)cc1)C(Cl)Cl]

Following the general procedure of Example 6—Step 4 and making non-critical variations but using 2,2-dichloro-N-((1R,2S)-3-fluoro-1-hydroxy-1-(4-(trimethyl-stannyl)phenyl)propan-2-yl)acetamide and commercially available 2-((1H-imidazol-1-yl)methyl)-5-bromopyridine the title compound is obtained (20 mg): ¹H-NMR (400 MHz, DMSO-d₆) 4.21-4.24 (m, 1H), 4.27-40.31 (m, 0.5H), 4.38-4.42 (m, 0.5H), 4.55-4.59 (m, 0.5H), 4.67-4.70 (m, 0.5H), 4.89 (t, J=3.6 Hz, 1H), 5.33 (s, 2H), 5.99 (d, J=4.16 Hz, 1H), 6.51 (s, 1H), 6.92 (s, 1H), 7.22 (t, J=3.84 Hz, 2H), 7.46 (d, J=8.2 Hz, 2H), 7.67 (d, J=8.28 Hz, 2H), 7.77 (s, 1H), 8.06-8.08 (d, d J=2.36 Hz, J=8.08 Hz, 1H), 8.63 (d, J=8.84 Hz, 1H), 8.84 (d, J=2.2 Hz, 1H). LC-Ms (m/z): [M+H] =437.1.

Example 8

Preparation of N-((1R,2S)-1-(4-(3-(aminomethyl)-1,2,4-oxadiazol-5-yl)phenyl)-3-fluoro-1-hydroxypropan-2-yl)-2,2-dichloroacetamide Step 1 Preparation of Methyl 4-((4S,5R)-3-(2,2-dichloroacetyl)-4-(fluoromethyl)-2,2-dimethyloxazolidin-5-yl)benzoate

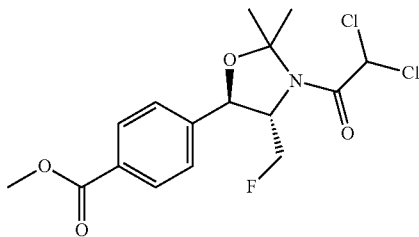 [SMILES: COC(=O)c1ccc([C@H]2OC(C)(C)N(C(=O)C(Cl)Cl)[C@@H]2CF)cc1]

To a flask containing 2,2-dichloro-1-((4S,5R)-4-(fluoromethyl)-5-(4-iodophenyl)-2,2-dimethyloxazolidin-3-yl)ethanone (2.0 g, 4.48 mmol) is added triethylamine (5 mL) and methanol (5 mL). Carbon monoxide gas is bubbled through the solution while stirring for 30 min. Pd(OAc)₂ (51 mg, 0.22 mmol) and Xantphos (132 mg, 0.22 mmol) are next added and a balloon containing carbon monoxide is secured to the flask outlet. The reaction is heated for 2 hours at 60° C. and then cooled to room temperature. Next, the reaction is diluted with water, extracted with ethylacetate, dried over Na₂SO₄, and concentrated under vacuum. The residue is chromatographed on silica gel eluting from 100% hexanes to 50:50 ethylacetate:hexanes to afford the title compound (1.11 g): ¹H NMR (400 MHz, CDCl₃) 8.10 (d, 2H, J=8.0 Hz), 7.55 (d, 2H, J=8.0 Hz), 6.34 (m, 1H), 5.30-4.42 (m, 4H), 3.95 (s, 3H), 1.97-1.53 (m, 6H). m/z (CI) 320 [M-(CH₃)₂CO].

Step 2 Preparation of 4-((4S,5R)-3-(2,2-dichloroacetyl)-4-(fluoromethyl)-2,2-dimethyloxazolidin-5-yl)benzoic acid

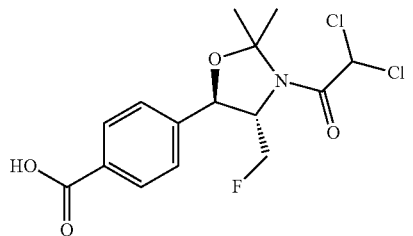 [SMILES: CC1(C)O[C@H](c2ccc(C(=O)O)cc2)[C@@H](CF)N1C(=O)C(Cl)Cl]

To a 5:1 (60 mL) dioxane:water solution of the product of Step 1, Example 8 (1.1 g, 2.9 mmol) is added lithium hydroxide (212 mg, 8.9 mmol) and the resulting mixture is stirred at room temperature for 18 hours. Next, the reaction mixture is cooled to 0° C. and 1N HCl (7.5 mL) is added to neutralize (pH-7). The reaction is partitioned between water (50 mL) and CH₂Cl₂ (150 mL). The organic phase is collected, dried over sodium sulfate and concentrated to give the title compound (979 mg): ¹H NMR (400 MHz, DMSO-d₆) 7.98 (d, 2H, J=8.0 Hz), 7.60 (d, 2H, J=8.0 Hz), 5.28 (m, 1H), 4.96-4.81 (m, 2.5H), 4.75-4.70 (m, 0.5H), 4.67-4.62 (m, 0.5H) 4.55-4.50 (m, 0.5H), 1.61 (s, 3H), 1.46 (s, 3H).

Step 3 Preparation of tert-butyl (5-(4-((4S,5R)-3-(2,2-dichloroacetyl)-4-(fluoromethyl)-2,2-dimethyloxazolidin-5-yl)phenyl)-1,2,4-oxadiazol-3-yl)methylcarbamate

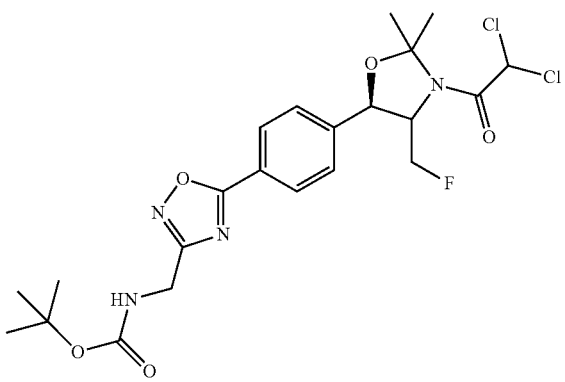

To a solution of the product of Step 2, Example 8 (525 mg, 1.4 mmol) in dimethylformamide (15 mL) is added 1,1'-Carbonyldiimidazole (286 mg, 1.7 mmol). The resulting solution is stirred at room temperature for 30 minutes at which time sodium acetate (140 mg, 1.7 mmol) and commercially available tert-butyl 2-(hydroxyamino)-2-iminoethylcarbamate (325 mg, 1.7 mmol) are added. The reaction is then stirred at room temperature for 72 hours. Next, the reaction is diluted with ethylacetate (75 mL) and washed with water (3×75 mL). The organic phase is dried (Na₂SO₄) and concentrated under vacuum. To the residue is added toluene (15 mL) and sodium acetate (140 mg, 1.7 mmol). The resulting mixture is heated to reflux for 18 hours while stirring, then cooled to room temperature and concentrated under vacuum. The residue is chromatographed on silica gel eluting from 100% hexanes to 50:50 EtOAc:hexanes to afford the title compound (280 mg): ¹H NMR (400 MHz, CDCl₃) 8.19 (d, 2H, J=8.0 Hz), 7.64 (d, 2H, J=8.0 Hz), 6.33 (m, 1H), 5.16 (m, 2H) 4.88-4.52 (m, 4H), 1.75 (s, 3H), 1.59 (s, 3H), 1.50 (s, 9H). m/z (CI) 461 [M-(CH₃)₂CO].

Step 4 Preparation of N-((1R,2S)-1-(4-(3-(aminomethyl)-1,2,4-oxadiazol-5-yl)phenyl)-3-fluoro-1-hydroxypropan-2-yl)-2,2-dichloroacetamide

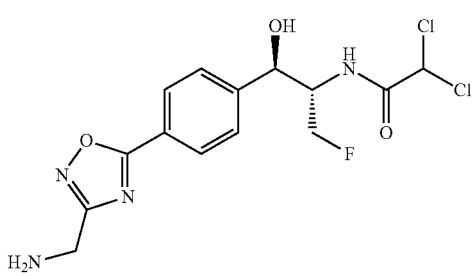 [SMILES: NCc1noc(-c2ccc([C@@H](O)[C@@H](CF)NC(=O)C(Cl)Cl)cc2)n1]

Following the general procedure of Example 2—Step 2 and making non-critical variations but using the product of Step 3—Example 8 the title compound is obtained (280 mg): $^1$H NMR (400 MHz, DMSO-d$_6$) 8.73-8.57 (m, 4H), 8.07 (d, 2H, J=8.0 Hz), 7.65 (d, 2H, J=8.0 Hz), 6.16 (m, 1H), 5.02 (m, 1H) 4.76-4.72 (m, 0.5H), 4.64-4.60 (m, 0.5H), 4.50-4.24 (m, 4H). m/z (CI) 377 [M+H].

Example 9

Preparation of 2,2-dichloro-N-((1R,2S)-3-fluoro-1-hydroxy-1-(4-(6-(1-(methylsulfonyl)pyrrolidin-2-yl)pyridin-3-yl)phenyl)propan-2-yl)acetamide Step 1 Preparation of 5-bromo-2-(1-(methylsulfonyl)pyrrolidin-2-yl)pyridine

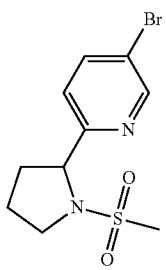 [SMILES: CS(=O)(=O)N1CCCC1c1ccc(Br)cn1]

Following the general procedure of Example 3, and making non-critical variations but using 5-Bromo-2-(pyrrolidin-2-yl)pyridine (previously described in WO200853319) the title compound is obtained (400 mg): $^1$H NMR (400 MHz, CDCl$_3$) 2.0-2.1 (m, 2H), 2.15-2.25 (m, 1H), 2.35-2.45 (m 1H), 2.8 (s, 3H), 3.5-3.6 (m, 1H), 3.6-3.7 (m, 1H), 4.9-5.0 (m, 1H), 7.45 (d, 1H), 7.85 (dd, 1H), 8.6 (d, 1H). m/z (CI) M+H 305+307.

Step 2 Preparation of 2,2-dichloro-N-((1R,2S)-3-fluoro-1-hydroxy-1-(4-(6-(1-(methylsulfonyl)pyrrolidin-2-yl)pyridin-3-yl)phenyl)propan-2-yl)acetamide

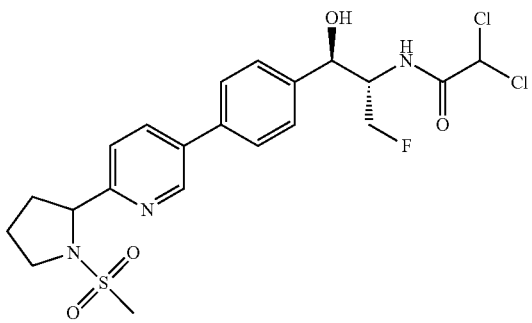 [SMILES: CS(=O)(=O)N1CCCC1c1ccc(-c2ccc([C@@H](O)[C@@H](CF)NC(=O)C(Cl)Cl)cc2)cn1]

A mixture of 5-bromo-2-(1-(methylsulfonyl)pyrrolidin-2-yl)pyridine (100 mg, 0.328 mmol), 2,2-dichloro-N-((1R,2S)-3-fluoro-1-hydroxy-1-(4-(trimethylstannyl)-phenyl)-propan-2-yl)acetamide (145 mg, 0.328 mmol) and tris(2-furyl)phosphine (15.5 mg, 0.066 mmol) is dissolved in N-methylpyrrolidinone (1.6 mL) and deoxygenated. Tris(dibenzyliden-eacetone) dipalladium(0) (30.5 mg, 0.033 mmol) is then added and the mixture is heated to 80° C. overnight. The mixture is then cooled and purified by preparative hplc (Prep HPLC=Waters, Column=Gemini NX C18 21×150 mm 5 um, MP A=0.1% trifluoroacetic acid in water MP B=acetonitrile, Gradient 10% B to 50% in 10 min holding for 2 min, 20 mL/min.) Fractions are dried on rotovap and freeze-dried with 1,4-dioxane to give the title compound (33 mg): $^1$H NMR (400 MHz, DMSO-d$_6$) 1.9-2.0 (m, 2H), 2.0-2.1 (m, 1H), 2.3-2.4 (m, 1H), 3.0 (s, 3H), 3.5-3.6 (m, 2H), 4.15-4.35 (m, 1.5H), 4.45 (t, 0.5H), 4.55-4.65 (m, 0.5H), 4.7-4.75 (m, 0.5H), 4.9-5.0 (m, 2H), 6.5 (s, 1H), 7.5 (d, 2H), 7.65 (d, 1H), 7.75 (d, 2H), 8.2 (dd, 1H), 8.6 (d, 1H), 8.85 (d, 1H). m/z (CI) M+H 504+506.

Example 10

Preparation of 2,2-dichloro-N-((1R,2S)-3-fluoro-1-hydroxy-1-(4-(5-(methylsulfonamidomethyl)-1,3,4-thiadiazol-2-yl)phenyl)propan-2-yl)acetamide

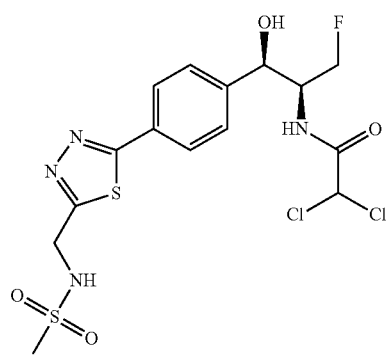 [SMILES: CS(=O)(=O)NCc1nnc(-c2ccc([C@@H](O)[C@@H](CF)NC(=O)C(Cl)Cl)cc2)s1]

Following the general procedure of Example 9—Step 2 and making non-critical variations but using N-((5-bromo-1,3,4-thiadiazol-2-yl)methyl)methanesulfonamide and 2,2-dichloro-N-((1R,2S)-3-fluoro-1-hydroxy-1-(4-(trimethylstannyl)phenyl)-propan-2-yl)acetamide the title compound is obtained (11.8 mg): $^1$H NMR (400 MHz, DMSO-d$_6$) 3.0 (s, 3H), 4.2-4.4 (m, 1.5H), 4.45 (t, 1H), 4.55-4.6 (m, 0.5H), 4.65 (d, 2H), 4.7-4.75 (m, 0.5H), 4.95 (bt, 0.5H), 6.1 (d, 1H), 6.5 (s, 1H), 7.5 (d, 2H), 7.95 (d, 2H), 8.15 (t, 1H), 8.6 (d, 1H). m/z (CI) M+H 471.

Example 11

Preparation of 2,2-dichloro-N-((1R,2S)-3-fluoro-1-hydroxy-1-(4-(6-(1-(methylsulfonamido)ethyl)pyridin-3-yl)phenyl)propan-2-yl)acetamide Step 1 Preparation of (R,S)—N-(1-(5-bromopyridin-2-yl)ethyl)methanesulfonamide

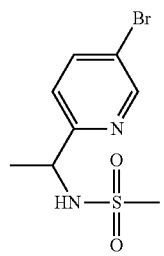

Following the general procedure of Example 3 and making non-critical variations but using commercially available (R,S)-1-(5-Bromopyridin-2-yl) the title compound is obtained (570 mg): $^1$H NMR (400 MHz, DMSO-$d_6$) 1.55 (t, 3H), 2.8 (s, 3H), 4.7 (pent, 1H), 5.6 (d, 1H), 7.2 (d, 1H), 7.85 (dd, 1H), 8.65 (d, 1H). m/z (CI) M+H 279+281.

Step 2 Preparation of 2,2-dichloro-N-((1R,2S)-3-fluoro-1-hydroxy-1-(4-(6-(1-(methylsulfonamido) ethyl)pyridin-3-yl)phenyl)propan-2-yl)acetamide

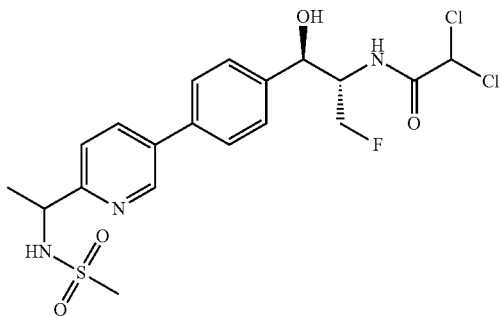 [SMILES: CC(NS(C)(=O)=O)c1ccc(-c2ccc([C@@H](O)[C@@H](CF)NC(=O)C(Cl)Cl)cc2)cn1]

Following the general procedure of Example 9—Step 2 and making non-critical variations but using (R,S)—N-(1-(5-bromopyridin-2-yl)ethyl) and 2,2-dichloro-N-((1R,2S)-3-fluoro-1-hydroxy-1-(4-(trimethylstannyl)phenyl)-propan-2-yl)-acetamide the title compound is obtained (17 mg): $^1$H NMR (400 MHz, DMSO-$d_6$) 1.5 (t, 3H), 2.8 (s, 3H), 4.15-4.35 (m, 1.5H), 4.4 (t, 0.5H), 4.55-4.65 (m, 1.5H), 4.65-4.75 (m, 0.5H), 4.9 (t, 1H), 6.0 (d, 1H), 6.5 (s, 1H), 7.45 (d, 2H), 7.55 (d, 1H), 7.7 (d, 2H), 8.1 (d, 1H), 8.6 (dd, 1H), 8.8 (dd, 1H). m/z (CI) M+H 478+480.

Example 12

Preparation of 2,2-dichloro-N-((1R,2S)-3-fluoro-1-hydroxy-1-(4-(2-(methylsulfonamidomethyl)pyrimidin-5-yl)phenyl)propan-2-yl)acetamide Step 1 Preparation of (4S,5R)-tert-butyl 4-(fluoromethyl)-5-(4-iodophenyl)-2,2-dimethyloxazolidine-3-carboxylate

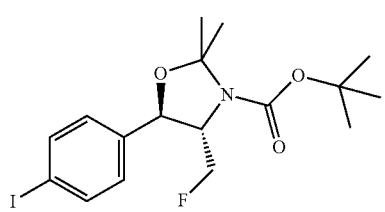 [SMILES: CC(C)(C)OC(=O)N1[C@H](CF)[C@@H](c2ccc(I)cc2)OC1(C)C]

A 1 L round bottom flask containing tert-butyl ((1R,2S)-3-fluoro-1-hydroxy-1-(4-iodophenyl)propan-2-yl)carbamate (24.4 g, 61.8 mmol) is charged with CH$_2$Cl$_2$ (250 mL) followed by 2-methoxypropene (9.0 mL, 92.8 mmol). The solution is cooled via ice bath and para toluene sulfonic acid (59 mg, 0.31 mmol) added. The reaction is stirred for 2 hours at room temperature then quenched with saturated sodium-bicarbonate solution (200 mL). The organics were separated, dried over MgSO$_4$ and concentrated to give the title compound (26.5 g): $^1$H NMR (400 MHz, CDCl$_3$) 7.73 (d, 2H), 7.20 (d, 2H), 5.08 (d, 1H), 5.03-4.69 (m, 1H), 4.54-4.31 (m, 1H), 3.91-3.68 (m, 1H), 1.70 (s, 3H), 1.58 (s, 3H), 1.50 (s, 9H).

Step 2 Preparation of (4S,5R)-tert-butyl 4-(fluoromethyl)-2,2-dimethyl-5-(4-(4,4,5,5-tetramethyl-1,3,2-dioxaborolan-2-yl)phenyl)oxazolidine-3-carboxylate

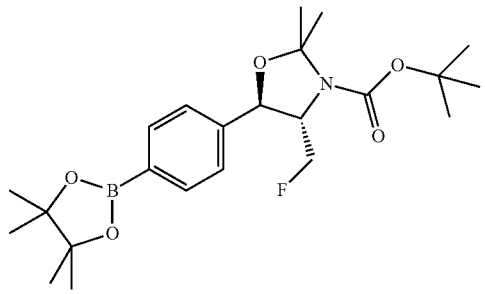 [SMILES: CC(C)(C)OC(=O)N1[C@H](CF)[C@@H](c2ccc(B3OC(C)(C)C(C)(C)O3)cc2)OC1(C)C]

To a solution of the product of Step 1, Example 12 (13.9 g, 32.0 mmol) in dioxane (160 mL) is added bis(pinnacolato)diborane (9.1 g, 35.2 mmol), bis(triphenyl-phosphine)palladium(ii) chloride (454 mg, 0.64 mmol) and potassium acetate (9.6 g, 95.9 mmol) sequentially. The combined mixture is heated to reflux and stirred overnight. After cooling to room temperature the reaction mixture is partitioned between water and ethylacetate. The organics were separated, dried over MgSO$_4$, filtered and evaporated to give a gum, which is purified using column chromatography eluting from neat heptane to neat ethylacetate to give the title compound (8.92 g): $^1$H NMR (400 MHz, CDCl$_3$) 7.85 (d, 2H), 7.45 (d, 2H), 5.15 (d, 1H), 4.52-4.37 (m, 1H), 3.95-3.75 (m, 1H), 1.72 (brs, 3H), 1.60 (brs, 3H), 1.51 (brs, 9H), 1.37 (brs, 12H).

Step 3 Preparation of 5-[4-(2-Cyano-pyrimidin-5-yl)-phenyl]-4-fluoromethyl-2,2-dimethyl-oxazolidine-3-carboxylic acid tert-butyl ester

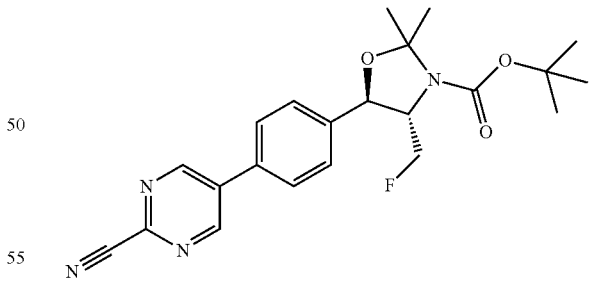

To the solution of 4-Fluoromethyl-2,2-dimethyl-5-[4-(4,4,5,5-tetramethyl-[1,3,2]dioxaborolan-2-yl)-phenyl]oxazolidine-3-carboxylic acid tert-butyl ester (1 g, 2.298 mmol, 1.0 eq) in toluene/water (3:1-24 mL) is added 5-Bromo-pyrimidine-2-carbonitrile (0.42 g, 2.282 mmol, 1.20 eq), Na$_2$CO$_3$ (0.48 g, 4.528 mmol) and degassed with nitrogen for 15 minutes followed by addition of Tetrakis(triphenyl-phosphine)palladium(0) (0.132 g, 0.114 mmol) and heated reaction mixture to 80° C. for 16 hours. Solvent is evaporated in vacuo to get the crude which is purified by column chromatography eluting from 10% ethyl acetate/hexane to give title compound (0.45 g): $^1$H-NMR (400 MHz, DMSO-$d_6$) 1.43 (s, 9H), 1.51 (s, 3H), 1.63 (s, 3H), 3.85-3.92 (m, 1H), 4.47-4.59 (m, 1H), 4.76-4.96 (m, 1H), 5.17 (d, 1H, J=7.16), 7.67 (d, 2H, J=8.24 Hz), 7.96 (d, 2H, J=8.24 Hz), 9.40 (s, 2H).). m/z M−H 410.8.

Step 4 Preparation of 5-[4-(2-Aminomethyl-pyrimidin-5-yl)-phenyl]-4-fluoromethyl-2,2-dimethyl-oxazolidine-3-carboxylic acid tert-butyl ester

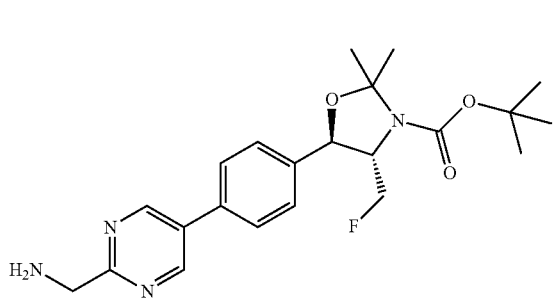 [SMILES: CC(C)(C)OC(=O)N1[C@H](CF)[C@@H](c2ccc(-c3cnc(CN)nc3)cc2)OC1(C)C]

The solution of product of Example 12—Step 3 (0.4 g, 0.97 mmol, 1.0 eq) in methanol (20 mL) is degassed with nitrogen for 15 minutes followed by addition of 10% palladium on carbon (40 mg, 10% w/w) and kept under hydrogen atmosphere (1 atm) at room temperature for 16 hours. Solvent is evaporated in vacuo to get the crude which is purified by column chromatography eluting using 10-13% methanol/CH$_2$Cl$_2$ to give the title compound (0.22 g): $^1$H-NMR (400 MHz, DMSO-$d_6$) 1.43 (s, 9H), 1.51 (s, 3H), 1.63 (s, 3H), 3.85-3.90 (m, 1H), 3.96 (s, 2H), 4.47-4.58 (m, 1H), 4.8-4.9 (m, 2H), 5.14 (d, 1H, J=7.16 Hz), 7.62 (d, 2H, J=8.2 Hz), 7.83 (d, 2H, J=8.08 Hz), 9.11 (s, 2H). m/z M+H 417.1.

Step 5 Preparation of 4-Fluoromethyl-5-{4-[2-(methanesulfonylamino-methyl)-pyrimidin-5-yl]-phenyl}-2,2-dimethyl-oxazolidine-3-carboxylic acid tert-butyl ester

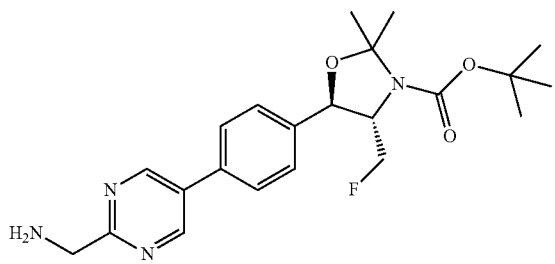 [SMILES: CC(C)(C)OC(=O)N1[C@H](CF)[C@@H](c2ccc(-c3cnc(CN)nc3)cc2)OC1(C)C]

The solution of product of Example 12—Step 4 (0.1 g, 0.240 mmol, 1.0 eq) in CH$_2$Cl$_2$ (10 mL) is cooled to 0° C. and added triethylamine (0.048 g, 0.48 mmol) followed by addition of mesyl chloride (0.041 g, 0.36 mmol) and stirred at room temperature for 2 hours. Solvent is evaporated in vacuo to get the crude which is purified by column chromatography eluting from 30% ethyl acetate/hexane to give title compound (80 mg). m/z M+H 495.1.

Step 6 Preparation of N-{5-[4-(2-Amino-3-fluoro-1-hydroxy-propyl)-phenyl]-pyrimidin-2-ylmethyl}-methanesulfonamide

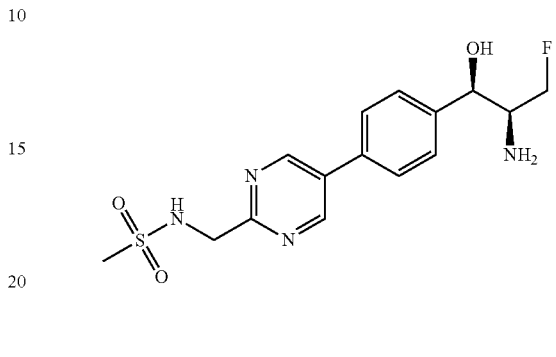

The solution of product of Example 12—Step 5 (0.08 g, 0.16 mmol, 1.0 eq) in CH$_2$Cl$_2$ (2 mL) is added trifluoroacetic acid (0.3 mL, 3.91 mmol) and stirred at room temperature for 2 hours. Solvent is evaporated in vacuo to get the crude as title compound (60 mg). m/z M+H 354.9.

Step 7 Preparation of 2,2-Dichloro-N-(1-fluoromethyl-2-hydroxy-2-{4-[2-(methanesulfonylamino-methyl)-pyrimidin-5-yl]-phenyl}-ethyl)-acetamide

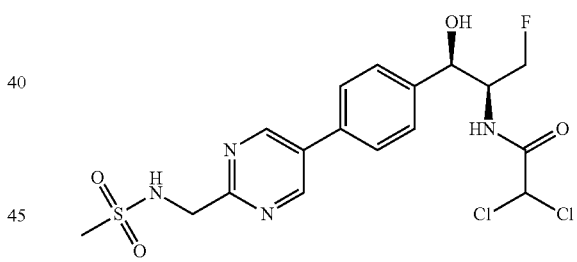

To the solution of product of Example 12—Step 6 (0.06 g, 0.169 mmol, 1.0 eq) in methanol (1.1 mL) is added triethyl amine (0.034 g, 0.33 mmol, 2.0 eq) and ethyl dichloroacetate (0.053 g, 0.33. mmol, 2.0 eq) and stirred the reaction mixture at room temperature for 24 hours. Solvent is evaporated in vacuo to get the crude which is purified by column chromatography eluting from 5% methanol/CH$_2$Cl$_2$ to give the title compound (0.012 g). $^1$H-NMR (400 MHz, DMSO-$d_6$) 2.97 (s, 3H), 4.28-4.30 (m, 1H), 4.32-4.36 (m, 0.5H), 4.43 (s, 2H), 4.56-4.60 (m, 0.5H), 4.68-4.71 (m, 0.5H), 4.92 (m, 1H), 6.03 (d, 1H, J=4.16 Hz), 6.52 (s, 1H), 7.50 (d, 2H, J=8.16 Hz), 7.68 (t, 1H, J=5.76 Hz), 7.78 (d, 2H, J=8.24 Hz), 8.65 (d, 1H, J=8.72 Hz), 9.13 (s, 2H). m/z M+H 464.8.

Example 13

Preparation of 2,2-dichloro-N-((1R,2S)-3-fluoro-1-hydroxy-1-(4-(6-(((R)-5-methyl-2-oxooxazolidin-3-yl)methyl)pyridin-3-yl)phenyl)propan-2-yl)acetamide

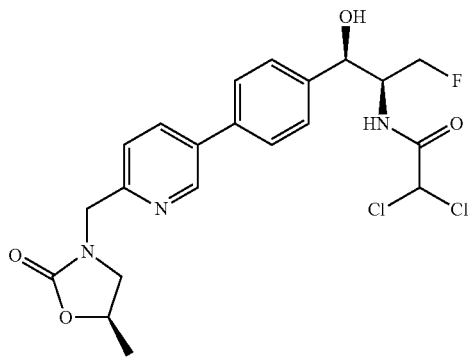 [SMILES: C[C@@H]1CN(Cc2ccc(-c3ccc([C@@H](O)[C@@H](CF)NC(=O)C(Cl)Cl)cc3)cn2)C(=O)O1]

Following the general procedure of Example 9—Step 2 and making non-critical variations but using (R)-3-(5-Bromo-pyridin-2-ylmethyl)-5-methyl-oxazolidin-2-one and 2,2-Dichloro-N-[(1S,2R)-1-fluoromethyl-2-hydroxy-2-(4-trimethyl-stannanyl-phenyl)-ethyl]-acetamide the title compound is obtained (21 mg): $^1$H-NMR (400 MHz, DMSO-d$_6$) 1.33 (d, 3H, J=6.24 Hz), 3.13-3.17 (m, 1H), 3.69 (t, 1H, J=8.4 Hz), 4.21-4.23 (m, 1.5H), 4.27-4.29 (m, 1H), 4.39-4.43 (m, 1H), 4.48 (d, 2H, J=4.96 Hz), 4.56-4.58 (m, 1H), 4.68-4.70 (m, 2H), 4.90 (m, 1H), 6.0 (s, 1H), 6.5 (s, 1H), 7.39 (d, 1H, J=8.04 Hz), 7.47 (d, 2H, J=8.24 Hz), 7.68 (d, 2H, J=8.24 Hz), 8.09 (dd, 1H, J$_1$=2.32 Hz, J$_2$=8.16 Hz), 8.65 (d, 1H, J=8.92 Hz), 8.84 (d, 1H, J=2.12 Hz). LC-Ms (m/z): [M–H] 468.0.

Example 14

Preparation of (1R,2S)-2-(2,2-difluoroacetamido)-3-fluoro-1-(4-(6-(methylsulfonamidomethyl)pyridin-3-yl)phenyl)propyl hydrogen phosphorofluoridate Step 1 Preparation of (1R,2S)-2-(2,2-difluoroacetamido)-3-fluoro-1-(4-(6-(methylsulfonamidomethyl)pyridin-3-yl)phenyl)propyl diphenyl phosphate

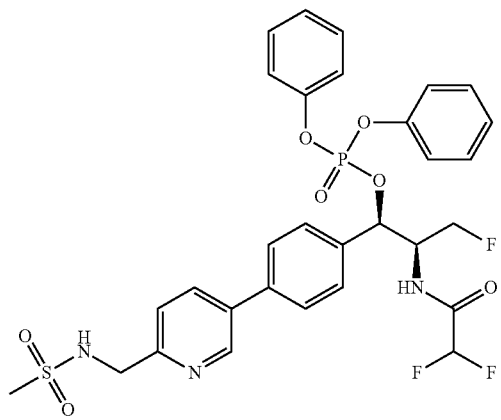 [SMILES: CS(=O)(=O)NCc1ccc(-c2ccc([C@@H](OP(=O)(Oc3ccccc3)Oc3ccccc3)[C@@H](CF)NC(=O)C(F)F)cc2)cn1]

To a slurry of the product of Step 4, Example 16 (1.0 g, 2.3 mmol) in pyridine (2 mL) and CHCl$_3$ (2 mL) is charged dimethylaminopyridine (215 mg, 1.74 mmol). The slurry is cooled using an ice bath, and diphenyl chlorophosphonate (1.04 mL, 4.87 mmol) added dropwise. The reaction is warmed to room temperature, and stirred for 2.5 hours. The reaction is diluted with CH$_2$Cl$_2$ and poured into saturated sodium bicarbonate (10 mL). The organics are separated and the aqueous back-extracted with CH$_2$Cl$_2$. The organics are combined, washed with citric acid, dried over MgSO$_4$, filtered and evaporated to afford the title compound (1.57 g): 1H NMR (600 MHz, CDCl$_3$) δ: 2.95 (3H, s), 4.10-4.30 (1H, dd), 4.38-4.70 (4H, m), 5.62-5.83 (1H, t), 5.76-5.85 (1H, m), 5.95 (1H, bs), 6.97 (2H, d), 7.70-7.26 (7H, m), 7.27-7.33 (1H, m), 7.37 (2H, t), 7.45-7.59 (4H, m), 7.88-8.07 (1H, dd), 8.68-8.83 (1H, m). m/z M+H 664.2.

Step 2 Preparation of (1R,2S)-2-(2,2-difluoroacetamido)-3-fluoro-1-(4-(6-(methylsulfonamidomethyl)pyridin-3-yl)phenyl)propyl hydrogen phosphorofluoridate

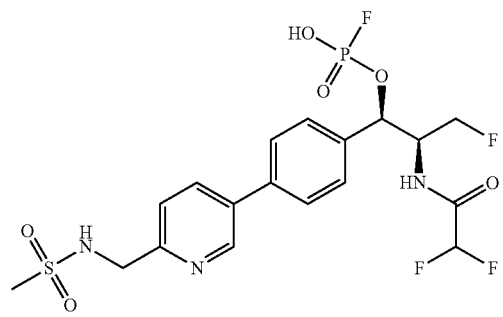 [SMILES: CS(=O)(=O)NCc1ccc(-c2ccc([C@@H](OP(=O)(O)F)[C@@H](CF)NC(=O)C(F)F)cc2)cn1]

To a solution of the product of Step 1, Example 14 (200 mg, 0.3 mmol) in tetrahydrofuran (1.2 mL) is added tetrabutylammonium phosphate (102 mg, 0.39 mmol). The reaction stirs at room temperature for 1.5 hours. The solvent is evaporated and the residue purified by reverse phase chromatography to give the title compound (19 mg): 1H NMR (600 MHz, DMSO-d$_6$) δ: 2.95 (3H, s), 4.25-4.46 (4H, m), 4.58-4.74 (1H, m), 5.34-5.52 (1H, m), 5.97-6.35 (1H, t), 7.43-7.52 (2H, m), 7.54-7.66 (1H, d), 7.69-7.80 (3H, m), 8.10-8.28 (1H, m), 8.83-8.90 (1H, m), 9.15-9.24 (1H, m). m/z M+1 514.1.

Example 15

Preparation of 2,2,2-trifluoro-N-((1R,2S)-3-fluoro-1-hydroxy-1-(4-(6-(methylsulfonamidomethyl)pyridin-3-yl)phenyl)propan-2-yl)acetamide

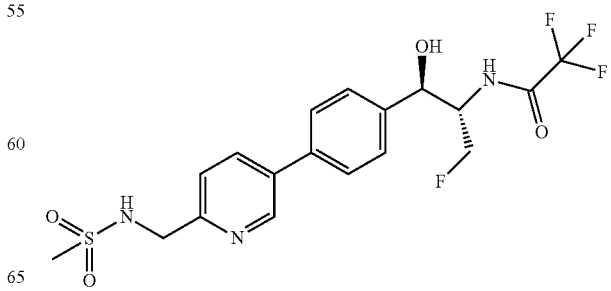

Following the general procedure of Example 14 and making non-critical variations but using trifluoroacetic anhydride in step 2, the title compound is obtained: 1H NMR (400 MHz, DMSO-$d_6$) 2.95 (s, 3H), 4.30-4.45 (m, 1.5H), 4.32 (m, 2H), 4.50-4.60 (m, 1.5H), 4.65-4.70 (m, 1H), 4.89 (m, 1H), 5.85 (m, 1H), 7.46 (d, 2H, J=8.08 Hz), 7.55 (d, 1H, J=8.08 Hz), 7.65-7.75 (m, 3H), 8.11 (m, 1H), 8.84 (s, 1H), 9.48 (m, 1H). m/z (CI) M+H 450.

Example 16

Preparation of 2,2-difluoro-N-((1R,2S)-3-fluoro-1-hydroxy-1-(4-(6-(methylsulfonamidomethyl)pyridin-3-yl)phenyl)propan-2-yl)acetamide Step 1 Preparation of N-((5-bromopyridin-2-yl)methyl)methanesulfonamide

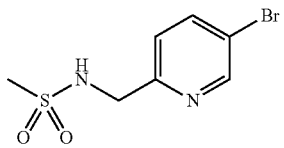

Following the general procedure of Example 3 and making non-critical variations but using commercially available (5-bromopyridin-2-yl)methanamine the title compound is obtained (1.95 g): m/z (CI) M+H 266.

Step 2 Preparation of 2,2-difluoro-N-((1R,2S)-3-fluoro-1-hydroxy-1-(4-iodophenyl)propan-2-yl)acetamide

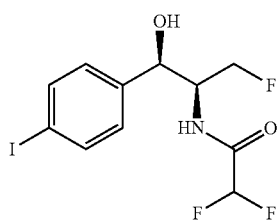 [SMILES: O=C(N[C@H](CF)[C@H](O)c1ccc(I)cc1)C(F)F]

Following the general procedure of Example 1—Step 2 and making non-critical variations but using ethyldifluoroacetane and (1R,2S)-2-amino-3-fluoro-1-(4-iodophenyl)propan-1-ol the title compound is obtained (18.3 g): 1H NMR (400 MHz, CDCl$_3$) 7.72 (2H, d), 7.13 (2H, d), 6.78 (1H, d), 5.85 (1H, t), 5.06 (1H, s), 4.67-4.28 (3H, m), 2.58 (1H, s).

Step 3 Preparation of 2,2-difluoro-N-((1R,2S)-3-fluoro-1-hydroxy-1-(4-(trimethylstannyl)phenyl)propan-2-yl)acetamide

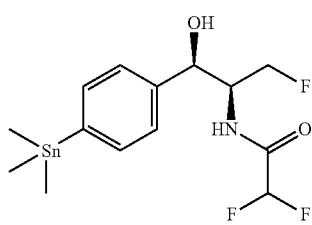 [SMILES: [CH3][Sn]([CH3])([CH3])[c]1ccc([C@@H](O)[C@@H](CF)NC(=O)C(F)F)cc1]

Hexamethylditin (9.9 g, 29.9 mmol) is added to a deoxygenated solution of the product of Example 17—Step 2 (10.6 g, 28.5 mmol), dichlorobis(triphenyl-phosphine)palladium (490 mg, 0.68 mmol) in dioxane (143 mL) and the mixture heated to 80° C. for 1 hour. After cooling to room temperature the mixture is purified using column chromatography eluting from neat heptanes to neat ethylacetate to give the title compound (9.3 g): 1H NMR (400 MHz, CDCl$_3$) 7.27 (2H, d), 7.09 (2H, d), 6.59 (1H, d), 5.62 (1H, t), 4.81-4.79 (1H, t), 4.44-4.08 (3H, m), 2.20 (1H, d), 0.14-0.00 (9H, m).

Step 4 Preparation of 2,2-difluoro-N-((1R,2S)-3-fluoro-1-hydroxy-1-(4-(6-(methylsulfonamidomethyl)pyridin-3-yl)phenyl)propan-2-yl)acetamide

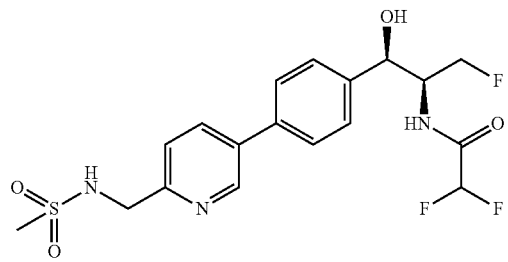 [SMILES: CS(=O)(=O)NCc1ccc(-c2ccc([C@@H](O)[C@@H](CF)NC(=O)C(F)F)cc2)cn1]

Following the general procedure of Example 9—Step 2 and making non-critical variations but using the product of Example 17—Step 1 and Example 17—Step 3 the title compound is obtained (200 mg): 1H NMR (400 MHz, DMSO-$d_6$) 8.86-8.83 (2H, m), 8.13 (1H, d), 7.74-7.69 (3H, m), 7.55 (1H, d), 7.49 (2H, d), 6.23 (1H, t), 5.91 (1H, d), 4.91 (1H, t), 4.70-4.56 (1H, m), 4.47-4.29 (4H, m), 2.97 (3H, s). m/z (CI) M+H 431.

Example 17

Preparation of 2,2-dichloro-N-((1R,2S)-3-fluoro-1-(4-(5-fluoro-6-(methylsulfonamidomethyl)pyridin-3-yl)phenyl)-1-hydroxypropan-2-yl)acetamide Step 1 Preparation of (4S,5R)-tert-butyl 5-(4-(6-cyano-5-fluoropyridin-3-yl)phenyl)-4-(fluoromethyl)-2,2-dimethyloxazolidine-3-carboxylate

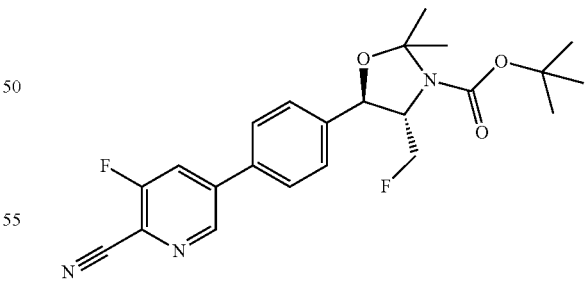

To a solution of commercially available 5-bromo-3-fluoropicolinonitrile (800 mg, 3.98 mmol) in 1,4-dioxane:water (32:8 mL) is added the product of Example 12—Step 2 (1730 mg, 3.98 mmol) and Cs$_2$CO$_3$ (2800 mg, 8.6 mmol) and the resulting solution bubbled with nitrogen gas for 30 minutes. To this reaction mixture is added Pd(PPh$_3$)$_4$ (460 mg, 0.4 mmol) and the resulting reaction mixture heated to 90° C. for 3 hours. The resulting reaction mixture is cooled, diluted with water and extracted with ethyl acetate. The organic layer dried over sodium sulfate and concentrated and purified using column chromatography on silica gel eluting with ethyl acetate in heptane to give the title compound: 1H NMR (400 MHz, CDCl$_3$) 1.52 (s, 9H), 1.63 (s, 3H), 1.75 (s, 3H), 3.80-4.00 (m, 1H), 4.40-4.60 (m, 1H), 4.7-5.2 (m, 1H), 5.22 (d, 1H, J=7.33 Hz), 7.65 (s, 4H), 7.78 (d, 2H, J=9.35 Hz), 8.80 (s, 1H). m/z (CI) M+H 430.

Step 2 Preparation of (4S,5R)-tert-butyl 5-(4-(5-fluoro-6-(methyl-sulfonamido-methyl)pyridin-3-yl)phenyl)-4-(fluoromethyl)-2,2-dimethyl-oxazolidine-3-carboxylate

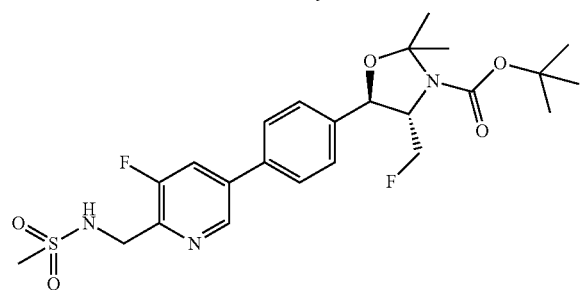

(4S,5R)-tert-butyl-5-(4-(6-cyano-5-fluoropyridin-3-yl)phenyl)-4-(fluoromethyl)-2,2-dimethyloxazolidine-3-carboxylate (1440 mg, 3.4 mmol) in methanol (25 mL) at 5° C. is treated with NiCl$_2$ (80 mg, 0.34 mmol) and then sodium borohydride (380 mg, 10 mmol) is added in portions. The mixture is stirred for 1 hour at room temperature, concentrated to remove the methanol, quenched with aqueous sodium bicarbonate and extracted with ethyl acetate. The organics are dried over anhydrous sodium sulfate, filtered, and concentrated to an oil. The oil is dissolved in dichloromethane (5 mL), cooled to 5° C. and treated with diisopropylethylamine (0.88 mL, 5.0 mmol) and methanesulfonyl chloride (0.30 mL, 3.7 mmol) and stirred for 2 hours at room temperature. The mixture is concentrated and chromatographed on silica eluting with ethyl acetate in heptane to give the title compound. 1H NMR (400 MHz, CDCl$_3$) 1.53 (s, 9H), 1.63 (s, 3H), 1.75 (s, 3H), 3.80-4.00 (m, 1H), 4.40-4.50 (m, 0.5H), 4.55-4.65 (m, 2.5H), 5.22 (d, 1H, J=7.33 Hz), 5.72 (bs, 1H), 7.60-7.70 (m, 5H), 8.63 (s, 1H). m/z (CI) M+H 512.

Step 3 Preparation of 2,2-dichloro-N-((1R,2S)-3-fluoro-1-(4-(5-fluoro-6-(methylsulfonamidomethyl)pyridin-3-yl)phenyl)-1-hydroxypropan-2-yl)acetamide

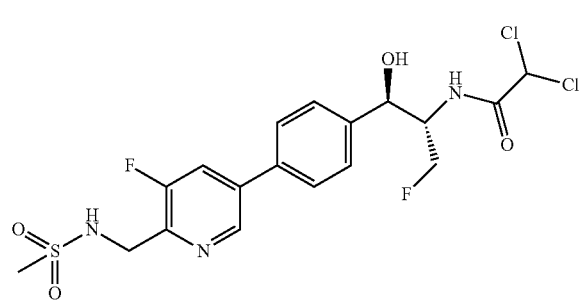 [SMILES: CS(=O)(=O)NCc1ncc(-c2ccc([C@@H](O)[C@@H](CF)NC(=O)C(Cl)Cl)cc2)cc1F]

(4S,5R)-tert-butyl 5-(4-(5-fluoro-6-(methylsulfonamidomethyl)pyridin-3-yl)phenyl)-4-(fluoromethyl)-2,2-dimethyloxazolidine-3-carboxylate (890 mg, 1.74 mmol) is dissolved in CH$_2$Cl$_2$ (20 mL), cooled to 5° C., and treated with trifluoroacetic acid (4 mL), stirred for 1 h at room temperature, diluted with toluene, concentrated to an oil. The oil is basified with aqueous sodium bicarbonate, extracted with ethyl acetate, dried, filtered, concentrated to an oil. The oil is dissolved in methanol (8 mL) and treated with diisopropylethyl amine (0.455 mL, 2.6 mmol) and methyl dichloroacetate (305 mg, 2.1 mmol), stirred at 60° C. for 18 hours, then cooled, and chromatographed on silica eluting with ethyl acetate in heptane to give the title compound. 1H NMR (400 MHz, DMSO-d$_6$) 2.94 (s, 3H), 4.15-4.45 (m, 4H), 4.55-4.75 (m, 1H), 4.92 (t, 1H, J=3.54 Hz), 6.01 (d, 1H, J=4.29 Hz), 6.52 (s, 1H), 7.49 (d, 2H, J=8.08 Hz), 7.59 (t, 1H, J=5.94 Hz), 7.77 (d, 2H, J=8.34 Hz), 8.07 (m, 1H), 8.63 (d, 2H, J=8.84 Hz), 8.77 (s, 1H). m/z (CI) M+H 465.

Example 18

Preparation of 2,2-dichloro-N-((1R,2S)-3-chloro-1-(4-(5-fluoro-6-(methylsulfonamidomethyl)pyridin-3-yl)phenyl)-1-hydroxypropan-2-yl)acetamide Step 1 Preparation of (4S,5R)-tert-butyl 5-(4-(6-cyano-5-chloropyridin-3-yl)phenyl)-4-(fluoromethyl)-2,2-dimethyloxazolidine-3-carboxylate

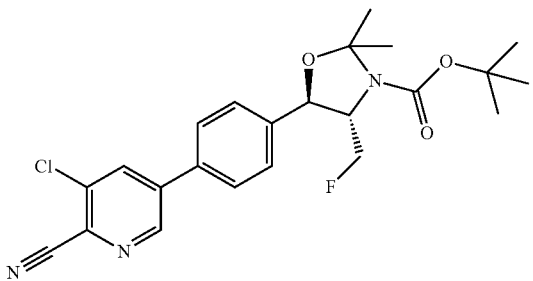 [SMILES: CC(C)(C)OC(=O)N1[C@H](CF)[C@@H](c2ccc(-c3cnc(C#N)c(Cl)c3)cc2)OC1(C)C]

Following the general procedure of Example 17, Step 1 and making non-critical variations but using the product of Example 12—Step 2 and commercially available 5-bromo-3-chloropicolinonitrile the title compound is obtained. 1H NMR (400 MHz, CDCl$_3$) δ: 1.52 (s, 9H), 1.63 (s, 3H), 1.75 (s, 3H), 3.80-4.00 (m, 1H), 4.40-4.60 (m, 1H), 4.7-5.2 (m, 1H), 5.22 (d, 1H, J=7.33 Hz), 7.64 (s, 4H), 8.04 (d, 2H, J=2.02 Hz), 8.84 (d, 2H, J=2.02 Hz). m/z (CI) M+H 446.

Step 2 Preparation of (4S,5R)-tert-butyl-5-(4-(5-chloro-6-(methyl-sulfonamido-methyl)pyridin-3-yl)phenyl)-4-(fluoromethyl)-2,2-dimethyl-oxazolidine-3-carboxylate

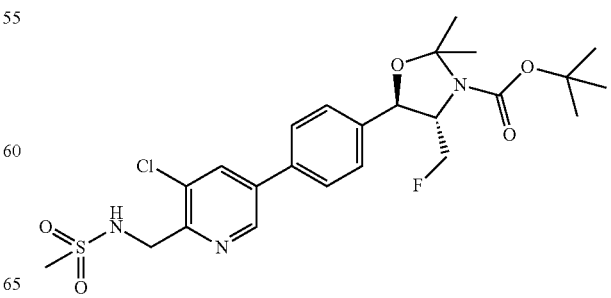

Following the general procedure of Example 17, Step 2 and making non-critical variations but using the product of Step 1—Example 19 title compound is obtained. 1H NMR (400 MHz, CDCl$_3$) δ: 1.53 (s, 9H), 1.63 (s, 3H), 1.75 (s, 3H), 3.02 (s, 3H), 3.80-4.00 (m, 1H), 4.40-4.50 (m, 0.5H), 4.55-4.65 (m, 2.5H), 5.21 (d, 1H, J=7.33 Hz), 5.97 (bs, 1H), 7.61 (s, 5H), 7.61 (s, 1H), 8.70 (s, 1H). m/z (CI) M+H 528.

Step 3 Preparation of 2,2-dichloro-N-((1R,2S)-1-(4-(5-chloro-6-(methylsulfonamidomethyl)pyridin-3-yl)phenyl)-3-fluoro-1-hydroxypropan-2-yl)acetamide

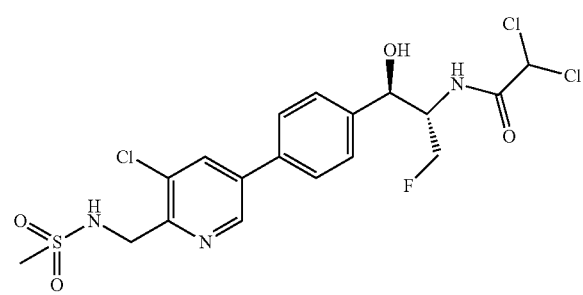 [SMILES: CS(=O)(=O)NCc1ncc(-c2ccc([C@@H](O)[C@@H](CF)NC(=O)C(Cl)Cl)cc2)cc1Cl]

Following the general procedure of Example 17, Step 3 and making non-critical variations but using the product of Step 2—Example 19 the title compound is obtained: 1H NMR (400 MHz, DMSO-d$_6$) 2.96 (s, 3H), 4.15-4.35 (m, 1.5H), 4.35-4.55 (m, 2.5H), 4.55-4.75 (m, 1H), 4.92 (7, 1H, J=3.41 Hz), 6.01 (d, 1H, J=4.04 Hz), 6.52 (m, 1H), 6.53 (s, 1H), 7.45-7.60 (m, 3H), 7.77 (d, 1H, J=8.34 Hz), 8.26 (d, 2H, J=1.77 Hz), 8.63 (d, 2H, J=8.84 Hz), 8.77 (d, 1H, J=1.77 Hz). m/z (CI) M+H 498.

Example 19

Preparation of 2,2-dichloro-N-((1R,2S)-3-fluoro-1-hydroxy-1-(4-(5-(methylsulfonamidomethyl)pyrazin-2-yl)phenyl)propan-2-yl)acetamide Step 1 Preparation of (4S,5R)-tert-butyl 5-(4-(5-cyanopyrazin-2-yl)phenyl)-4-(fluoromethyl)-2,2-dimethyloxazolidine-3-carboxylate

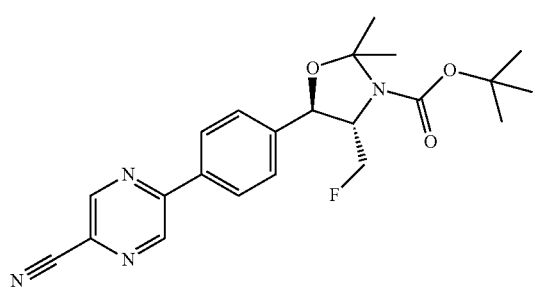 [SMILES: CC(C)(C)OC(=O)N1[C@H](CF)[C@@H](c2ccc(-c3cnc(C#N)cn3)cc2)OC1(C)C]

Following the general procedure of Example 17, Step 1 and making non-critical variations but using the product of Example 12—Step 2 and commercially available 5-bromopyrazine-2-carbonitrile the title compound is obtained $^1$H NMR (400 MHz, CDCl$_3$) 1.52 (s, 9H), 1.63 (s, 3H), 1.75 (s, 3H), 3.80-4.00 (m, 1H), 4.40-4.60 (m, 1H), 5.23 (d, 1H, J=7.33 Hz), 7.66 (d, 2H, J=8.34 Hz), 8.14 (d, 2H, J=8.34 Hz), 8.97 (d, 1H), 9.16 (s, 1H). m/z (CI) M+H 413.

Step 2 Preparation of (4S,5R)-tert-butyl 4-(fluoromethyl)-2,2-dimethyl-5-(4-(5-(methylsulfonamidomethyl)pyrazin-2-yl)phenyl)oxazolidine-3-carboxylate

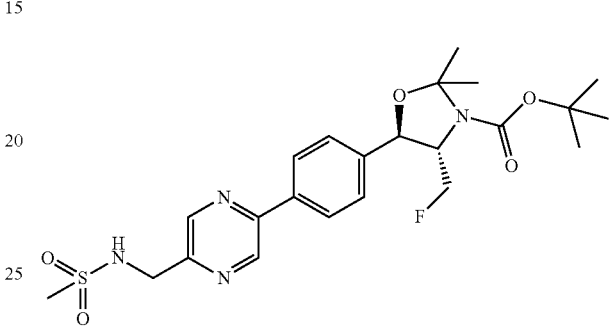

Following the general procedure of Example 17, Step 2 and making non-critical variations but using the product of Step 1—Example 20 the title compound is obtained: $^1$H NMR (400 MHz, CDCl$_3$) 1.52 (s, 9H), 1.63 (s, 3H), 1.75 (s, 3H), 3.01 (s, 3H), 3.80-4.00 (m, 1H), 4.40-4.50 (m, 0.5H), 4.50-4.60 (m, 2.5H), 5.21 (d, 1H, J=7.33 Hz), 5.61 (m, 1H), 7.61 (d, 2H, J=8.34 Hz), 8.05 (d, 2H, J=8.34 Hz), 8.69 (s, 1H), 98.98 (s, 1H). m/z (CI) M+H 495.

Step 3 Preparation of 2,2-dichloro-N-((1R,2S)-3-fluoro-1-hydroxy-1-(4-(5-(methylsulfonamidomethyl)pyrazin-2-yl)phenyl)propan-2-yl)acetamide

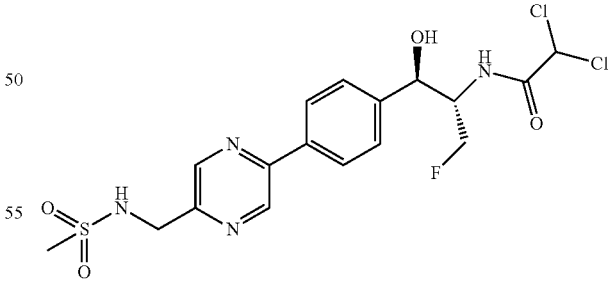

Following the general procedure of Example 17, Step 3 and making non-critical variations but using the product of Example 20—Step 2 the title compound is obtained: $^1$H NMR (400 MHz, DMSO-d$_6$) 2.99 (s, 3H), 4.20-4.50 (m, 4H), 4.50-4.75 (m, 1H), 4.93 (t, 1H, J=3.28 Hz), 6.04 (d, 1H, J=4.29 Hz), 6.52 (s, 1H), 7.51 (d, 1H, J=8.34 Hz), 7.76 (t, 2H, J=6.06 Hz), 8.10 (d, 2H, J=8.34 Hz), 8.62 (d, 2H, J=8.84 Hz), 8.73 (s, 1H), 9.19 (s, 1H). m/z (CI) M−H 483.

Example 20

Preparation of N-((1R,2S)-1-(4-(6-(azetidin-1-ylmethyl)pyridin-3-yl)phenyl)-3-fluoro-1-hydroxypropan-2-yl)-2,2-dichloroacetamide Step 1 Preparation of 2,2-dichloro-1-((4S,5R)-4-(fluoromethyl)-5-(4-(6-(hydroxymethyl)pyridin-3-yl)phenyl)-2,2-dimethyloxazolidin-3-yl)ethanone

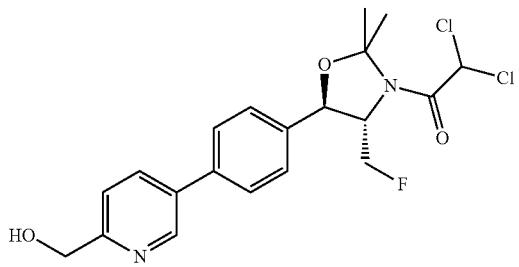 [SMILES: CC1(C)O[C@H](c2ccc(-c3ccc(CO)nc3)cc2)[C@@H](CF)N1C(=O)C(Cl)Cl]

Following the general procedure of Example 1—Step 1 and making non-critical variations but using 2,2-dichloro-1-((4S,5R)-4-(fluoromethyl)-5-(4-iodophenyl)-2,2-dimethyloxazolidin-3-yl)ethanone and (6-(hydroxymethyl)pyridin-3-yl)boronic acid as starting materials the title compound is obtained (800 mg): m/z (CI) M–H 426.1.

Step 2 Preparation of (5-(4-((4S,5R)-3-(2,2-dichloroacetyl)-4-(fluoromethyl)-2,2-dimethyloxazolidin-5-yl)phenyl)pyridin-2-yl)methyl methanesulfonate

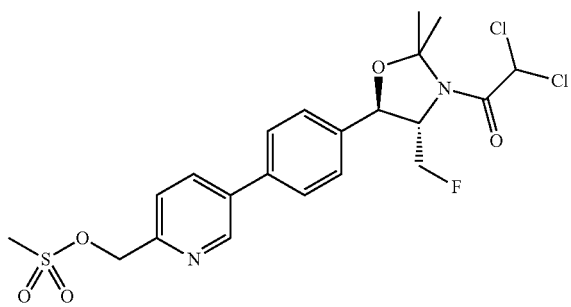 [SMILES: CC1(C)O[C@H](c2ccc(-c3ccc(COS(C)(=O)=O)nc3)cc2)[C@@H](CF)N1C(=O)C(Cl)Cl]

Following the general procedure of Example 3 and making non-critical variations but using the product of Example 21—Step 1 the title compound is obtained (940 mg): m/z (CI) M–H 504.1.

Step 3 Preparation of N-((1R,2S)-1-(4-(6-(azetidin-1-ylmethyl)pyridin-3-yl)phenyl)-3-fluoro-1-hydroxypropan-2-yl)-2,2-dichloroacetamide

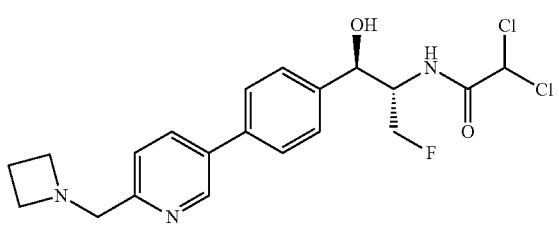 [SMILES: O=C(N[C@H](CF)[C@H](O)c1ccc(-c2ccc(CN3CCC3)nc2)cc1)C(Cl)Cl]

Diisopropylethylamine (296 µL, 1.68 mmol) is added to the product of Example 20, Step 2 (50 mg, 0.11 mmol) and azetidine.HCl salt (146 mg, 1.12 mmol) in dimethylformamide (1 mL) and the mixture heated to 60° C. for 4 hours. The solvent is removed under reduced pressure and the residue dissolved in $CH_2Cl_2$ (2 mL). The mixture is cooled to 0° C. and trifluoroacetic acid (2 mL) added. After 1 hour, the solvent is removed under reduced pressure and the crude product purified using reverse phase HPLC to give the title compound (10 mg): m/z (CI) M–H 425.1.

Example 21

Preparation of 2,2-dichloro-N-((1R,2S)-1-(4-(6-(ethylsulfonamido-methyl)pyridin-3-yl)phenyl)-3-fluoro-1-hydroxypropan-2-yl)acetamide Step 1 Preparation of N-((5-bromopyridin-2-yl)methyl)ethanesulfonamide

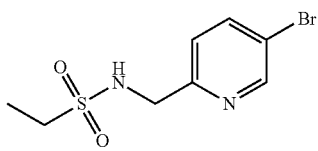

To a solution of (5-bromopyridin-2-yl)methanamine (250 mg, 1.34 mmol) in $CH_2Cl_2$ (3 mL) is added ethyl sulfonyl chloride (95 mg, 0.74 mmol) followed by triethylamine (0.3 mL, 2.0 mmol). The reaction is stirred at room temperature for 1.5 hours. The reaction is directly injected onto a 12 g silica gel column and chromatographed eluting from 100% hexanes to 50:50 ethylacetate:hexanes to afford the title compound (158 mg): m/z (CI) M+H 279+281.

Step 2 Preparation of N-((5-(4-((4S,5R)-3-(2,2-dichloroacetyl)-4-(fluoromethyl)-2,2-dimethyloxazolidin-5-yl)phenyl)pyridin-2-yl)methyl)-ethanesulfonamide

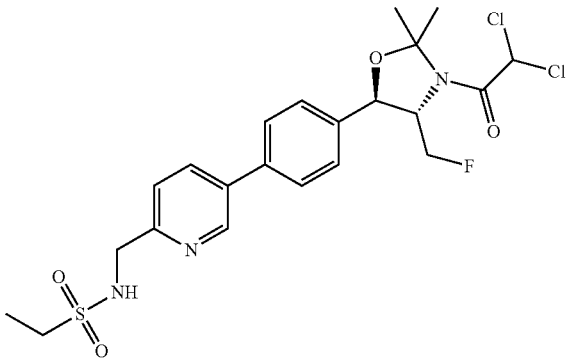 [SMILES: CCS(=O)(=O)NCc1ccc(-c2ccc([C@H]3OC(C)(C)N(C(=O)C(Cl)Cl)[C@@H]3CF)cc2)cn1]

2,2-dichloro-1-((4S,5R)-4-(fluoromethyl)-2,2-dimethyl-5-(4-(trimethylstannyl)-phenyl)-oxazolidin-3-yl)ethanone (281 mg, 0.66 mmol) and N-((5-bromopyridin-2-yl)methyl)ethanesulfonamide (155 mg, 0.56 mmol) are dissolved in N-Methyl-2-pyrrolidone (40 mL) and purged with nitrogen gas. $Pd_2(dba)_3$ (51 mg, 0.055 mmol) and tri-2-furylphosphine (27 mg, 0.11 mmol) are added; the resulting mixture is heated to 80° C. for 18 hours. The reaction mixture is cooled, diluted with ethylacetate, and washed with water. The organic phase is dried ($Na_2SO_4$) and concentrated under vacuum. The crude material is chromatographed (24 g Redi-Sep column) eluting from 100% hexanes to 90:10 ethylacetate:hexanes to afford the title compound (125 mg): m/z (CI) M+H 518.

Step 3 Preparation of 2,2-dichloro-N-((1R,2S)-1-(4-(6-(ethylsulfonamidomethyl)pyridin-3-yl)phenyl)-3-fluoro-1-hydroxypropan-2-yl)acetamide

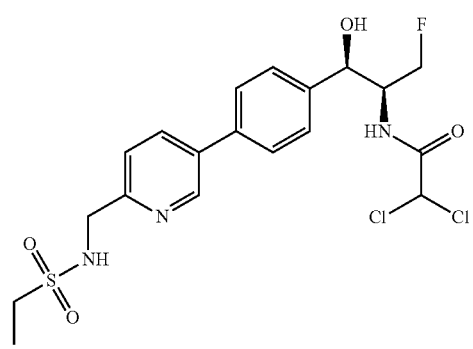 [SMILES: CCS(=O)(=O)NCc1ccc(-c2ccc([C@@H](O)[C@@H](CF)NC(=O)C(Cl)Cl)cc2)cn1]

Following the general procedure of Example 2—Step 2 and making non-critical variations but using the product of Step 2—Example 21 the title compound is obtained (23 mg): $^1$H NMR (400 MHz, DMSO-$d_6$) δ:1.19 (t, 3H), 3.04, (q, 2H), 4.22-4.32 (m, 3.5H), 4.40-4.44 (m, 0.5H), 4.56-4.60 (m, 0.5H), 4.68-4.72 (m, 0.5H), 4.91 (t, 1H), 5.98 (d, 1H), 6.53 (s, 1H), 7.46-7.54 (m, 3H), 7.68-7.73 (m, 3H), 8.10 (dd, 1H), 8.62 (d, 1H), 8.82 (d, 1H); m/z (CI) 478[M+H].

Example 22

2,2-difluoro-N-((1R,2S)-3-fluoro-1-hydroxy-1-(4-(6-((2-methylpropylsulfonamido)methyl)pyridin-3-yl)phenyl)propan-2-yl)acetamide

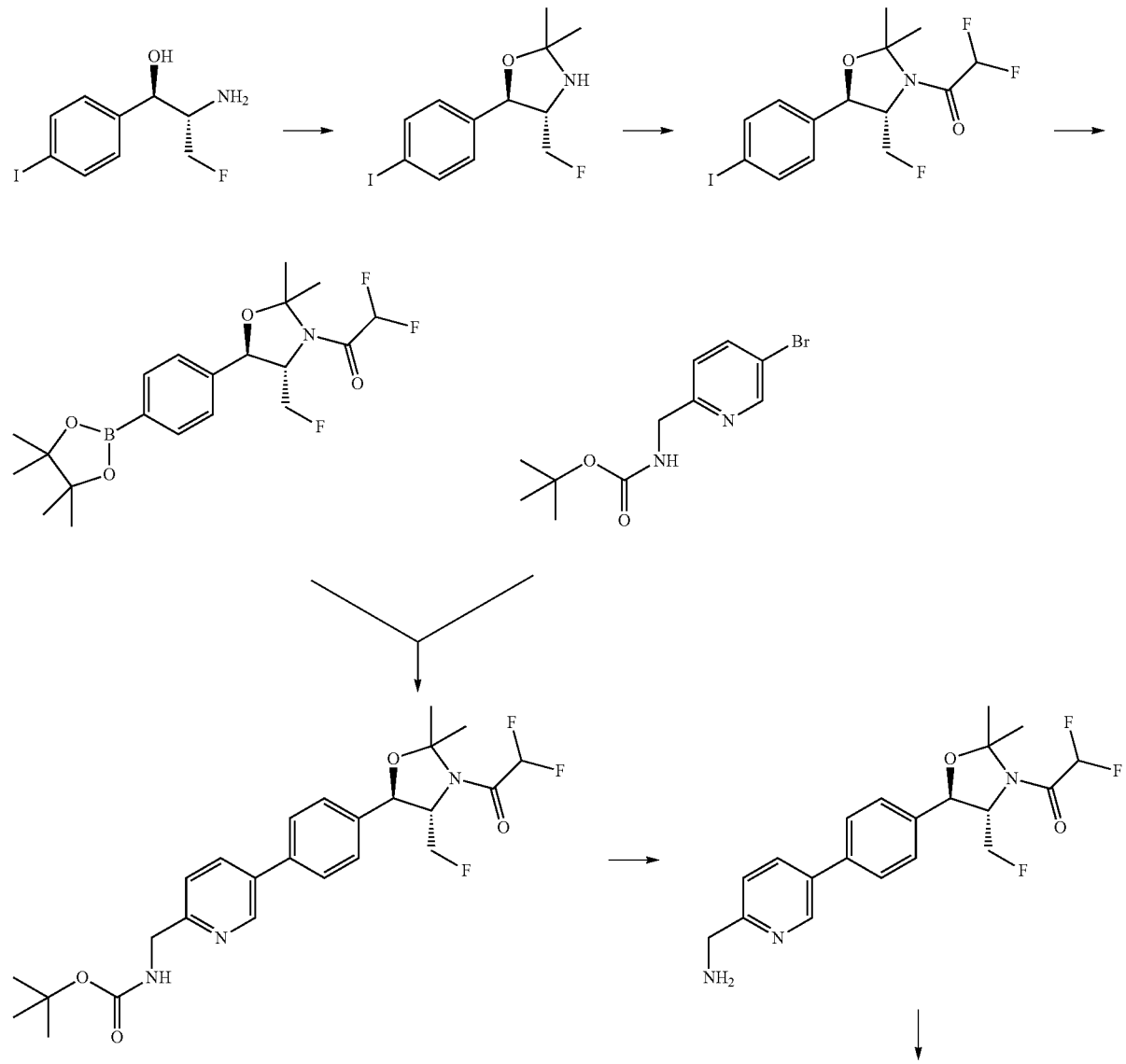

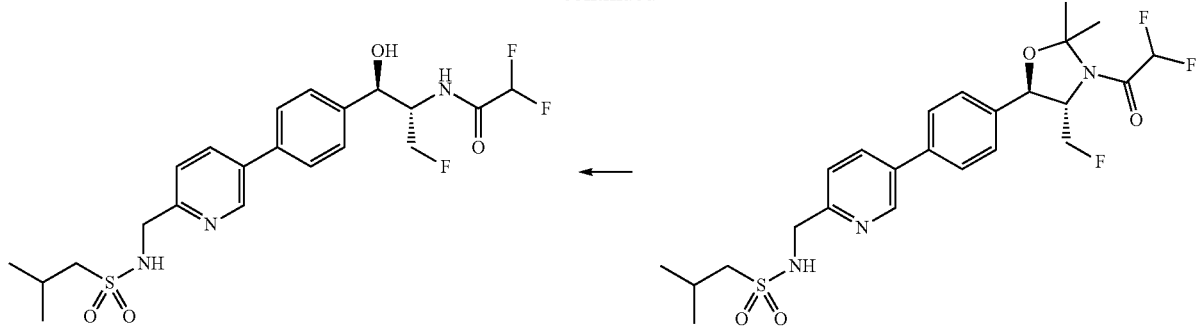

Step 1 Preparation of (4S,5R)-4-(fluoromethyl)-5-(4-iodophenyl)-2,2-dimethyloxazolidine

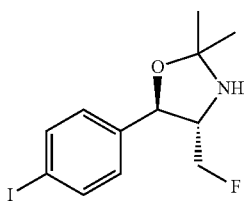 [SMILES: CC1(C)N[C@H](CF)[C@@H](c2ccc(I)cc2)O1]

Acetone (150 mL) is added to commercially available (1R,2S)-2-amino-3-fluoro-1-(4-iodophenyl)propan-1-ol (15.0 g, 50.8 mmol). After stirring overnight at room temperature the solvent is removed under reduced pressure to give the title compound (17.6 g): m/z (CI) M+H 335.

Step 2 Preparation of 2,2-difluoro-1-((4S,5R)-4-(fluoromethyl)-5-(4-iodophenyl)-2,2-dimethyloxazolidin-3-yl)ethanone

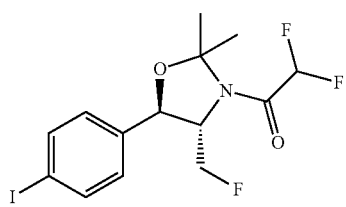 [SMILES: CC1(C)O[C@H](c2ccc(I)cc2)[C@@H](CF)N1C(=O)C(F)F]

To a stirring solution of the product of Step 2—Example 8 (3.0 g, 8.9 mmol) in CH$_2$Cl$_2$ (50 mL) at 0° C. is added triethylamine (6.2 mL, 44.8 mmol) followed by dropwise addition of difluoroacetyl chloride (2.2 mL, 27.0 mmol). The reaction mixture is slowly allowed to warm to room temperature. After 1 hour the reaction mixture is diluted with water (75 mL) and extracted with CH$_2$Cl$_2$ (2×75 mL). The combined organic phase is dried over MgSO$_4$ and concentrated under vacuum. The crude material is chromatographed (80 g Redi-Sep column) eluting from 100% hexanes to 25:75 EtOAc:hexanes to afford the title compound (3.54 g): m/z (CI) M+H 413.0.

Step 3 Preparation of 2,2-difluoro-1-((4S,5R)-4-(fluoromethyl)-2,2-dimethyl-5-(4-(4,4,5,5-tetramethyl-1,3,2-dioxaborolan-2-yl)phenyl)oxazolidin-3-yl)ethanone

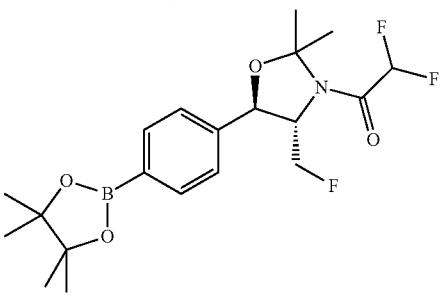 [SMILES: CC1(C)O[C@H](c2ccc(B3OC(C)(C)C(C)(C)O3)cc2)[C@@H](CF)N1C(=O)C(F)F]

To a solution of the product of Step 3—Example 8 (3.5 g, 8.4 mmol) in dioxane (100 mL) is added bis(pinacolato)diboron (2.4 g, 9.3 mmol), potassium acetate (2.5 g, 25.4 mmol), and Pd(PPh$_3$)$_2$Cl$_2$ (300 mg, 0.4 mmol). The reaction is heated to 90° C. under nitrogen for 22 hours. Reaction mixture is cooled to room temperature and concentrated under vacuum to remove dioxane to a volume of ~50 mL. The residue is diluted with water (150 mL) and extracted with CH$_2$Cl$_2$ (2×125 mL). The combined organic phases are dried over Na$_2$SO$_4$ and concentrated under vacuum. The crude material is purified by chromatography (120 g Redi-Sep column) eluting from 100% hexanes to 25:75 EtOAc:hexanes to the title compound (2.06 g): m/z (CI) M+H 413.2.

Step 4 Preparation of tert-butyl (5-(4-((4S,5R)-3-(2,2-difluoroacetyl)-4-(fluoromethyl)-2,2-dimethyloxazolidin-5-yl)phenyl)pyridin-2-yl)methylcarbamate

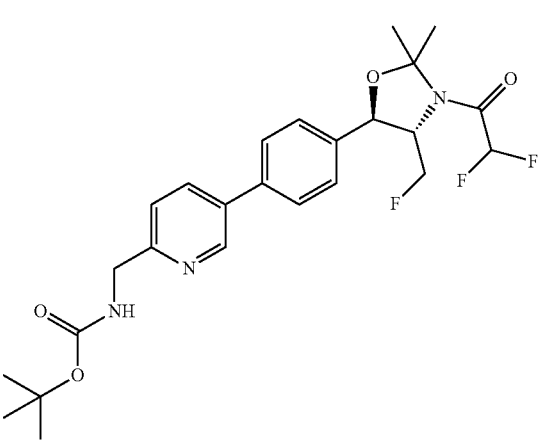 [SMILES: CC(C)(C)OC(=O)NCc1ccc(-c2ccc([C@H]3OC(C)(C)N(C(=O)C(F)F)[C@@H]3CF)cc2)cn1]

To a solution of the product of Step 3, Example 22 (1000 mg, 2.4 mmol) in toluene/ethanol (30:20 mL) is added commercially available tert-butyl (5-bromopyridin-2-yl)methylcarbamate (695 mg, 2.42 mmol), sodium bicarbonate (5 mL of a saturated solution) and Pd(dppf)$_2$Cl$_2$ (90 mg, 0.12 mmol). The reaction mixture is heated to 80° C. while stirring under nitrogen for 4 hours. The reaction mixture is cooled and diluted with water. Contents are extracted with ethylacetate (2×75 mL) and the combined organic phase is dried (Na$_2$SO$_4$) and concentrated under vacuum. Crude material is chromatographed (80 g Redi-Sep column) eluting from 100% hexanes to 90:10 ethylacetate:hexanes to afford the title compound (912 mg): m/z (CI) M+H 494.

Step 5 Preparation of 1-((4S,5R)-5-(4-(6-(aminomethyl)pyridin-3-yl)phenyl)-4-(fluoromethyl)-2,2-dimethyloxazolidin-3-yl)-2,2-difluoroethanone

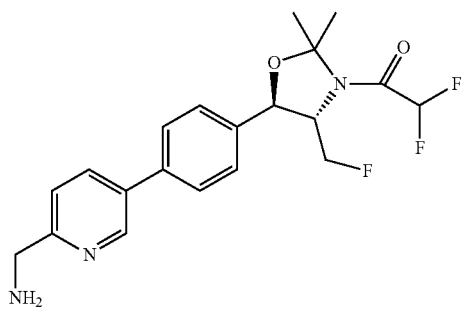 [SMILES: CC1(C)O[C@H](c2ccc(-c3ccc(CN)nc3)cc2)[C@@H](CF)N1C(=O)C(F)F]

To a solution of tert-butyl (5-(4-((4S,5R)-3-(2,2-difluoroacetyl)-4-(fluoromethyl)-2,2-dimethyloxazolidin-5-yl)phenyl)pyridin-2-yl)methylcarbamate (970 mg, 4.5 mmol) in CH$_2$Cl$_2$ (25 mL) at 0° C. is added 2,6-lutidine (460 µL, 3.9 mmol) followed by t-butyldimethylsilyltrifluoromethanesulfonate (700 µL, 2.9 mmol). The reaction is stirred at room temperature for 18 hours. Additional lutidine (230 µL, 1.9 mmol) and t-butyldimethylsilyltrifluoromethanesulfonate (350 µL, 1.4 mmol) is added and contents heated to 35° C. for 1 hour. Saturated NH$_4$Cl is added and the reaction is stirred for 15 minutes. Contents are diluted with CH$_2$Cl$_2$ and separated. The organic phase is washed with saturated NH$_4$Cl, saturated NaHCO$_3$, brine, dried (Na$_2$SO$_4$) and concentrated under vacuum. Crude silyl carbamate is dissolved in tetrahydrofuran (20 mL) and tetrabutylammonium fluoride (0.6 mL, 2.0 mmol) is added and stirred for 20 minutes. Saturated NH$_4$Cl is added and contents are extracted with ethylacetate. The organic phase is washed successively with saturated sodium hydrogen carbonate, brine, dried with Na$_2$SO$_4$ and concentrated under vacuum to afford the title compound (123 mg): m/z (CI) M+H 394.

Step 6 Preparation of 2,2-difluoro-N-((1R,2S)-3-fluoro-1-hydroxy-1-(4-(6-((2-methylpropylsulfonamido)methyl)pyridin-3-yl)phenyl)propan-2-yl)acetamide

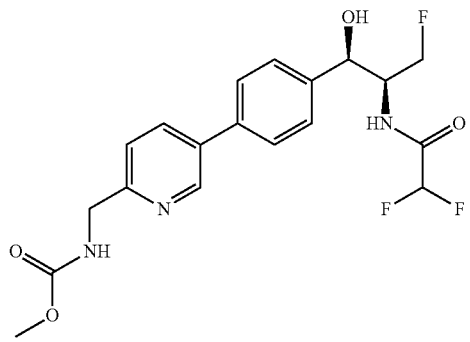 [SMILES: COC(=O)NCc1ccc(-c2ccc([C@@H](O)[C@@H](CF)NC(=O)C(F)F)cc2)cn1]

To a solution of 1-((4S,5R)-5-(4-(6-(aminomethyl)pyridin-3-yl)phenyl)-4-(fluoromethyl)-2,2-dimethyloxazolidin-3-yl)-2,2-difluoroethanone (80 mg, 0.2 mmol) in CH$_2$Cl$_2$ (15 mL) at 0° C. is added triethylamine (80 µL, 0.5 mmol) followed by isobutylsulfonyl chloride (29 mg, 0.2 mmol). The reaction is stirred at room temperature for 1 hour. Next, trifluoroacetic acid (1 mL) is added and the reaction is stirred at room temperature for an additional 1 hour. Toluene (20 mL) is added and the reaction is concentrated under vacuum. The crude reaction is purified using reverse-phase chromatography, free-based with saturated NaHCO$_3$, extracted with ethylacetate, and concentrated under vacuum to afford the title compound (17 mg). $^1$H NMR (400 MHz, DMSO-d$_6$) δ:0.99 (d, 6H), 2.05-2.11 (m, 1H), 2.94 (d, 2H), 4.28-4.36 (m, 3.5H), 4.41-4.45 (m, 0.5H), 4.52-4.58 (m, 0.5H), 4.65-4.68 (m, 0.5H), 4.89 (m, 1H), 5.90 (d, 1H), 6.21 (t, 1H), 7.47 (d, 2H), 7.54 (d, 1H), 7.69-7.74 (m, 3H), 8.12 (dd, 1H), 8.81-8.83 (m, 2H); m/z (CI) 474 [M+H].

Example 23

Preparation of methyl (5-(4-((1R,2S)-2-(2,2-difluoroacetamido)-3-fluoro-1-hydroxypropyl)phenyl)pyridin-2-yl)methylcarbamate Following the general procedure of Example 22—Step 3 and making non-critical variations but using methyl chloroformate the title compound is obtained (21 mg): m/z (CI) M+H 412.

Example 24

Preparation of N-((1R,2S)-1-(4-(6(cyclopropanesulfonamidomethyl)pyridin-3-yl)phenyl)-3-fluoro-1-hydroxypropan-2-yl)-2,2-difluoroacetamide

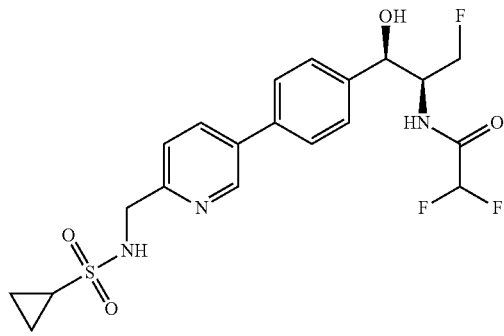 [SMILES: O=C(N[C@H](CF)[C@H](O)c1ccc(-c2ccc(CNS(=O)(=O)C3CC3)nc2)cc1)C(F)F]

Following the general procedure of Example 22—Step 3 and making non-critical variations but using cyclopropanesulfonyl chloride the title compound is obtained (27 mg): m/z (CI) M+H 458.

Example 25

Preparation of 2,2-difluoro-N-((1R,2S)-3-fluoro-1-hydroxy-1-(4-(6-((2-methoxyethylsulfonamido)methyl)pyridin-3-yl)phenyl)propan-2-yl)acetamide

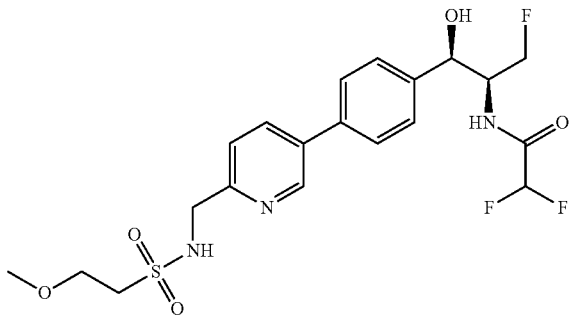 [SMILES: COCCS(=O)(=O)NCc1ccc(-c2ccc([C@@H](O)[C@@H](CF)NC(=O)C(F)F)cc2)cn1]

Following the general procedure of Example 22—Step 3 and making non-critical variations but using 2-methoxyethanesulfonyl chloride the title compound is obtained (27 mg): m/z (CI) M+H 476.

Example 26

Preparation of N-((5-(4-(((1R,2S)-2-(2,2-difluoroacetamido)-3-fluoro-1-hydroxypropyl)phenyl)pyridin-2-yl)methyl)cyclopropanecarboxamide

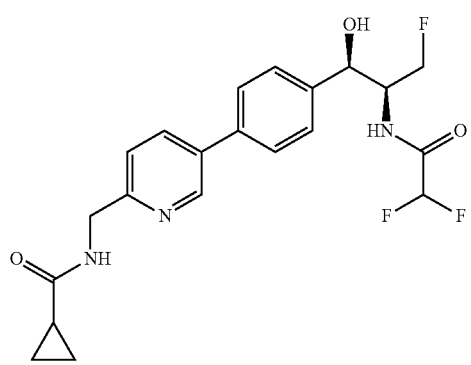 [SMILES: O=C(N[C@H](CF)[C@H](O)c1ccc(-c2ccc(CNC(=O)C3CC3)nc2)cc1)C(F)F]

Following the general procedure of Example 22—Step 3 and making non-critical variations but using cyclopropanecarbonyl chloride the title compound is obtained (21 mg): m/z (CI) M+H 422.

Example 27

Preparation of 2,2-difluoro-N-((1R,2S)-3-fluoro-1-hydroxy-1-(4-(6-((methylsulfonylmethylsulfonamido)methyl)pyridin-3-yl)phenyl)propan-2-yl)acetamide

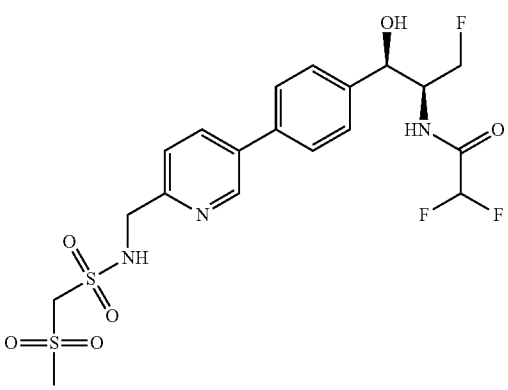 [SMILES: CS(=O)(=O)CS(=O)(=O)NCc1ccc(-c2ccc([C@@H](O)[C@@H](CF)NC(=O)C(F)F)cc2)cn1]

Following the general procedure of Example 22—Step 3 and making non-critical variations but using methylsulfonylmethanesulfonyl chloride the title compound is obtained (14 mg): m/z (CI) M+H 510.

Example 28

Preparation of 2,2-difluoro-N-((1R,2S)-3-fluoro-1-hydroxy-1-(4-(6-((sulfamoylamino)methyl)pyridin-3-yl)phenyl)propan-2-yl)acetamide

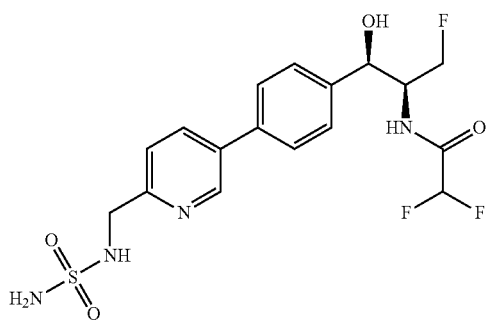 [SMILES: NS(=O)(=O)NCc1ccc(-c2ccc([C@@H](O)[C@@H](CF)NC(=O)C(F)F)cc2)cn1]

Following the general procedure of Example 22—Step 3 and making non-critical variations but using sulfamoyl chloride the title compound is obtained (12 mg): m/z (CI) M+H 433.

Example 29

Preparation of N-((1R,2S)-1-(4-(6-(aminomethyl)pyridin-3-yl)-phenyl)-3-fluoro-1-hydroxypropan-2-yl)-2,2-difluoroacetamide

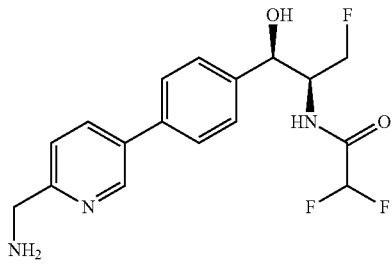 [SMILES: NCc1ccc(-c2ccc([C@@H](O)[C@@H](CF)NC(=O)C(F)F)cc2)cn1]

Following the general procedures of Example 22 and making non-critical variations the title compound is obtained (27 mg): m/z (CI) M+H 354.

Example 30

2,2-difluoro-N-((1R,2S)-3-fluoro-1-hydroxy-1-(4-(6-((2,2,2-trifluoroethylsulfonamido)methyl)pyridin-3-yl)phenyl)propan-2-yl)acetamide

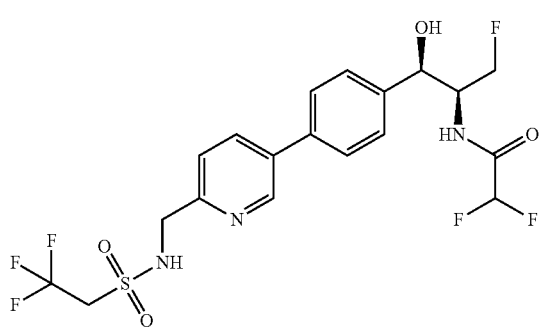

Following the general procedure of Example 22—Step 3 and making non-critical variations but using 2,2,2-trifluoroethanesulfonyl chloride the title compound is obtained (21 mg): m/z (CI) M+H 500.

Example 31

2,2-difluoro-N-((1R,2S)-3-fluoro-1-hydroxy-1-(4-(6-((trifluoromethylsulfonamido)methyl)pyridin-3-yl)phenyl)propan-2-yl)acetamide

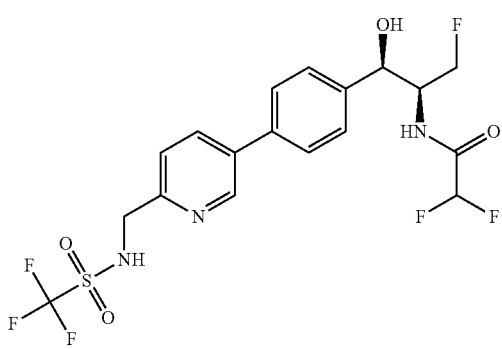 [SMILES: O=C(N[C@H](CF)[C@H](O)c1ccc(-c2ccc(CNS(=O)(=O)C(F)(F)F)nc2)cc1)C(F)F]

Following the general procedure of Example 22—Step 3 and making non-critical variations but using trifluoromethanesulfonyl chloride the title compound is obtained (13 mg): m/z (CI) M+H 486.

Example 32

2,2-difluoro-N-((1R,2S)-3-fluoro-1-hydroxy-1-(4-(6-((tetrahydro-2H-pyran-4-sulfonamido)methyl)pyridin-3-yl)phenyl)propan-2-yl)acetamide

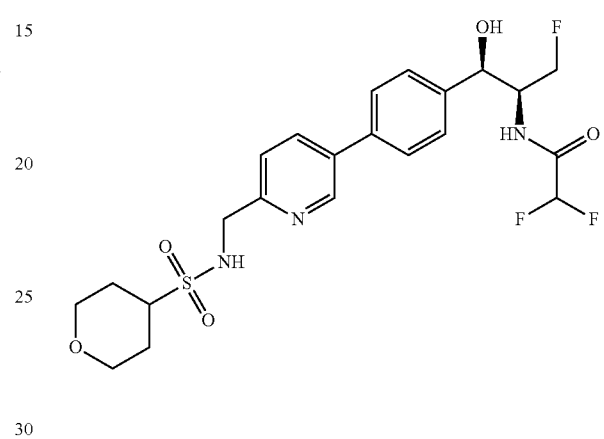

Following the general procedure of Example 22—Step 3 and making non-critical variations but using tetrahydro-2H-pyran-4-sulfonyl chloride the title compound is obtained (43 mg): m/z (CI) M+H 502.

Example 33

2,2-difluoro-N-((1R,2S)-3-fluoro-1-hydroxy-1-(4-(6-((1-methylethylsulfonamido)methyl)pyridin-3-yl)phenyl)propan-2-yl)acetamide

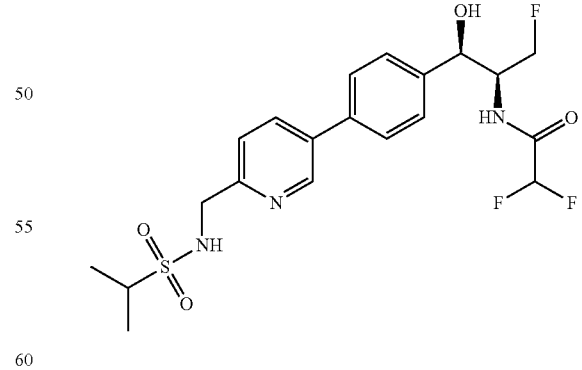

Following the general procedure of Example 22—Step 3 and making non-critical variations but using propane-2-sulfonyl chloride the title compound is obtained (11 mg): m/z (CI) M+H 460.

Example 34

N-((1R,2S)-1-(4-(6-((cyanomethylsulfonamido)methyl)pyridin-3-yl)phenyl)-3-fluoro-1-hydroxypropan-2-yl)-2,2-difluoroacetamide

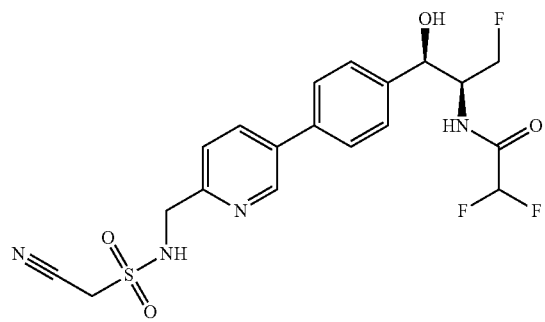 [SMILES: N#CCS(=O)(=O)NCc1ccc(-c2ccc([C@@H](O)[C@@H](CF)NC(=O)C(F)F)cc2)cn1]

Following the general procedure of Example 22—Step 3 and making non-critical variations but using cyanomethanesulfonyl chloride the title compound is obtained (24 mg): m/z (CI) M+H 457.

Example 35

2,2-difluoro-N-((1R,2S)-3-fluoro-1-hydroxy-1-(4-(6-((3-methylureido)methyl)pyridin-3-yl)phenyl)propan-2-yl)acetamide

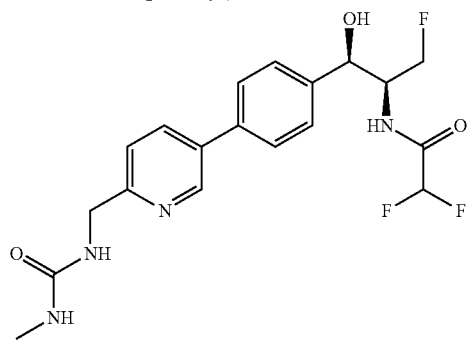

Following the general procedure of Example 22—Step 3 and making non-critical variations but using methyl isocyanate the title compound is obtained (14 mg): m/z (CI) M+H 411.

Example 36

N-((1R,2S)-1-(4-(6-((3-ethylureido)methyl)pyridin-3-yl)phenyl)-3-fluoro-1-hydroxypropan-2-yl)-2,2-difluoroacetamide

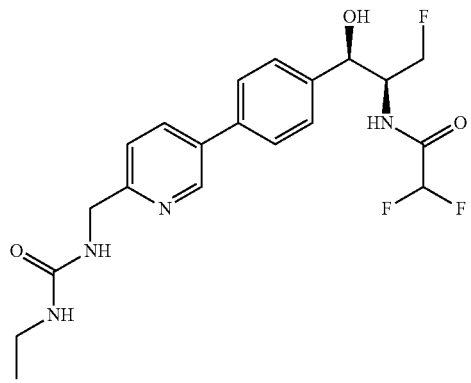 [SMILES: CCNC(=O)NCc1ccc(-c2ccc([C@@H](O)[C@@H](CF)NC(=O)C(F)F)cc2)cn1]

Following the general procedure of Example 22—Step 3 and making non-critical variations but using ethyl isocyanate the title compound is obtained (18 mg): m/z (CI) M+H 425.

Example 37

N-((1R,2S)-1-(4-(6-((difluoromethylsulfonamido)methyl)pyridin-3-yl)phenyl)-3-fluoro-1-hydroxypropan-2-yl)-2,2-difluoroacetamide

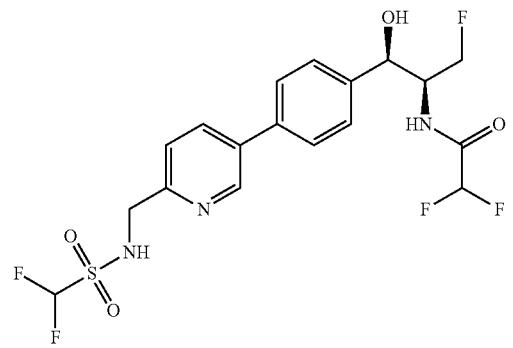 [SMILES: O=C(N[C@H](CF)[C@H](O)c1ccc(-c2ccc(CNS(=O)(=O)C(F)F)nc2)cc1)C(F)F]

Following the general procedure of Example 22—Step 3 and making non-critical variations but using difluoromethanesulfonyl chloride the title compound is obtained (6 mg): m/z (CI) M+H 468.

Example 38

Preparation of N-((1R,2S)-1-(4-(6-(ethylsulfonamidomethyl)pyridin-3-yl)phenyl)-3-fluoro-1-hydroxypropan-2-yl)-2,2-difluoroacetamide Step 1 Preparation of N-((5-(4-((4S,5R)-3-(2,2-difluoroacetyl)-4-(fluoromethyl)-2,2-dimethyloxazolidin-5-yl)phenyl)pyridin-2-yl)methyl)-ethanesulfonamide

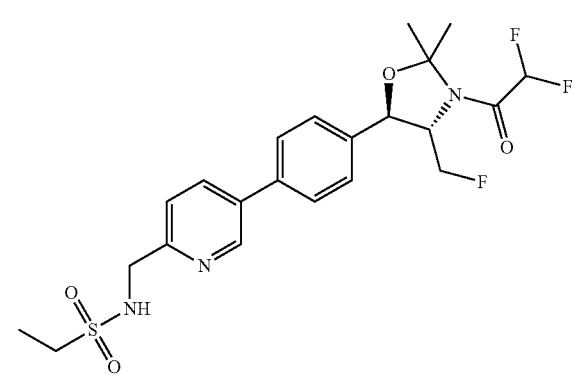 [SMILES: CCS(=O)(=O)NCc1ccc(-c2ccc([C@H]3OC(C)(C)N(C(=O)C(F)F)[C@@H]3CF)cc2)cn1]

Following the general procedure of Example 22—Step 1 and making non-critical variations but using the product of Step 1, Example 21 the title compound is obtained (660 mg): m/z (CI) M+H 486.

Step 2 N-((1R,2S)-1-(4-(6-(ethylsulfonamidomethyl)pyridin-3-yl)phenyl)-3-fluoro-1-hydroxypropan-2-yl)-2,2-difluoroacetamide

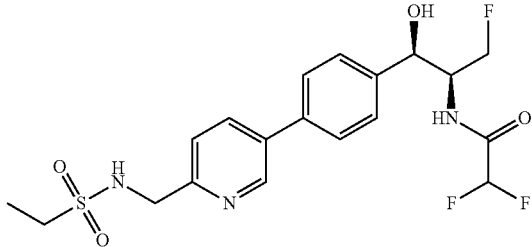 [SMILES: CCS(=O)(=O)NCc1ccc(-c2ccc([C@@H](O)[C@@H](CF)NC(=O)C(F)F)cc2)cn1]

Following the general procedure of Example 2—Step 2 and making non-critical variations but using the product of Step 1—Example 38 the title compound is obtained (157 mg): $^1$H NMR (400 MHz, DMSO-$d_6$) δ: 1.20 (t, 3H), 3.03 (q, 2H), 4.28-4.36 (m, 3.5H), 4.41-4.45 (m, 0.5H), 4.52-4.58 (m, 0.5H), 4.65-4.68 (m, 0.5H), 4.89 (t, 1H), 5.90 (d, 1H), 6.21 (t, 1H), 7.47 (d, 2H), 7.54 (d, 1H), 7.70-7.73 (m, 3H), 8.11 (dd, 1H), 8.81-8.83 (m, 2H); m/z (CI) 446 [M+H].

Example 39

Preparation of 2,2-difluoro-N-((1R,2S)-3-fluoro-1-(4-(6-((fluoro-methylsulfonamido)methyl)pyridin-3-yl)phenyl)-1-hydroxypropan-2-yl)acetamide Step 1 Preparation of N-((5-bromopyridin-2-yl)methyl)-1-fluoromethanesulfonamide

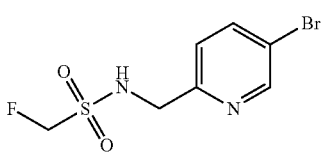 [SMILES: O=S(=O)(CF)NCc1ccc(Br)cn1]

Following the general procedure of Example 21—Step 1 and making non-critical variations but using fluoromethanesulfonyl chloride the title compound is obtained (245 mg): m/z (CI) M+H 283+285.

Step 2 Preparation of N-((5-(4-((4S,5R)-3-(2,2-difluoroacetyl)-4-(fluoromethyl)-2,2-dimethyloxazolidin-5-yl)phenyl)pyridin-2-yl)methyl)-1-fluoromethanesulfonamide

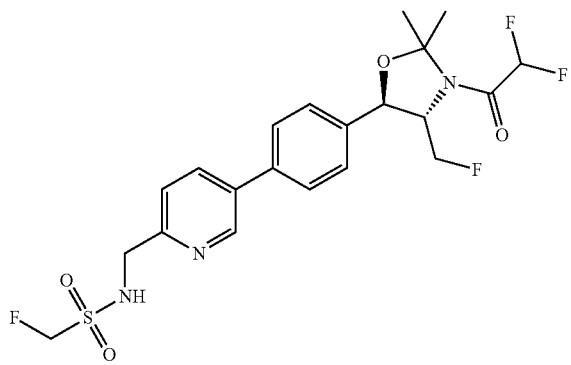 [SMILES: CC1(C)O[C@H](c2ccc(-c3ccc(CNS(=O)(=O)CF)nc3)cc2)[C@@H](CF)N1C(=O)C(F)F]

Following the general procedure of Example 22—Step 1 and making non-critical variations but using N-((5-bromopyridin-2-yl)methyl)-1-fluoromethanesulfonamide the title compound is obtained (175 mg): m/z (CI) M+H 490.

Step 3 2,2-difluoro-N-((1R,2S)-3-fluoro-1-(4-(6-((fluoromethylsulfonamido)methyl)pyridin-3-yl)phenyl)-1-hydroxypropan-2-yl)acetamide

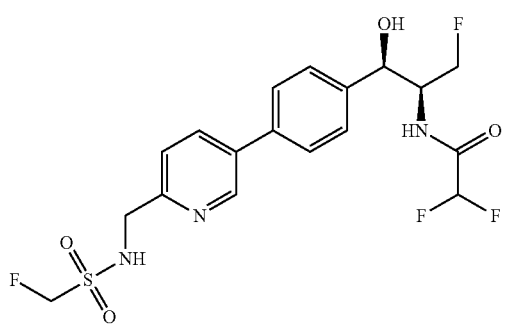 [SMILES: O=C(N[C@H](CF)[C@H](O)c1ccc(-c2ccc(CNS(=O)(=O)CF)nc2)cc1)C(F)F]

Following the general procedure of Example 2—Step 2 and making non-critical variations but using the product of Step 2—Example 39 the title compound is obtained (43 mg): $^1$H NMR (400 MHz, DMSO-$d_6$) δ: 4.29-4.37 (m, 3.5H), 4.41-4.45 (m, 0.5H), 4.52-4.58 (m, 0.5H), 4.65-4.69 (m, 0.5H), 4.89 (t, 1H), 5.43 (d, 2H), 5.90 (d, 1H), 6.21 (t, 1H), 7.47 (d, 2H), 7.52 (d, 1H), 7.71 (d, 2H), 8.12 (dd, 1H) 8.45 (t, 1H), 8.81-8.85 (m, 2H); m/z (CI) 450 [M+H].

Example 40

N-((1R,2S)-1-(4-(6-(2-aminopropan-2-yl)pyridin-3-yl)phenyl)-3-fluoro-1-hydroxypropan-2-yl)-2,2-difluoroacetamide Step 1 Preparation of 2-(5-bromopyridin-2-yl)propan-2-amine

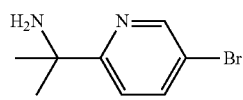

To a 100 mL round bottom flask containing 40 mL anhydrous tetrahydrofuran is added CeCl$_3$ (5 g, 20.28 mmol). The resulting suspension is stirred at room temperature for 18 hours. The mixture is cooled to −78° C. and methyl lithium solution (12.7 mL, 1.6M) is added dropwise and stirred at −78° C. for 30 minutes. A solution of 5-bromo-2-cyanopyridine (1.2 g, 6.8 mmol) in tetrahydrofuran (10 mL) is added and the reaction is stirred at −78° C. for 4 hours before warming to 0° C. Saturated NH$_4$Cl is added and the reaction mixture is allowed to warm to room temperature while stirring. Ethyl acetate (100 mL) is added and the organic phase is separated, dried (Na$_2$SO$_4$), and concentrated under vacuum to afford the title compound (805 mg): m/z (CI) M+H 215+217.

Step 2 Preparation of tert-butyl 2-(5-bromopyridin-2-yl)propan-2-ylcarbamate

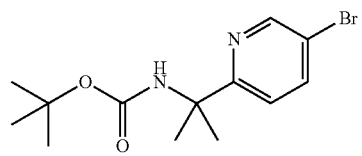 [SMILES: CC(C)(C)OC(=O)NC(C)(C)c1ccc(Br)cn1]

To a solution of 2-(5-bromopyridin-2-yl)propan-2-amine (800 mg, 3.7 mmol) in CH$_2$Cl$_2$ (25 mL) is added di-tert-butyl dicarbonate (830 mg, 3.7 mmol). The reaction is stirred at room temperature for 18 hours. Contents are diluted with NaHCO$_3$ (50 mL) and extracted with CH$_2$Cl$_2$ (50 mL). The organic phase is dried (Na$_2$SO$_4$) and concentrated under vacuum. The crude material is chromatographed eluting from 100% hexanes to 35:65 ethylacetate:hexanes to afford the title compound (635 mg): m/z (CI) M+H 315+317.

Step 3 Preparation of tert-butyl 2-(5-(4-((4S,5R)-3-(2,2-difluoroacetyl)-4-(fluoromethyl)-2,2-dimethyl-oxazolidin-5-yl)phenyl)pyridin-2-yl)propan-2-ylcarbamate

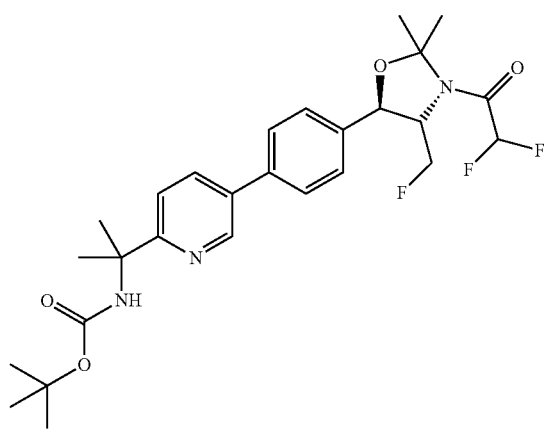

Following the general procedure of Example 22—Step 1 and making non-critical variations but using tert-butyl 2-(5-bromopyridin-2-yl)propan-2-ylcarbamate the title compound is obtained (448 mg): m/z (CI) M+H 522.

Step 4 N-((1R,2S)-1-(4-(6-(2-aminopropan-2-yl)pyridin-3-yl)phenyl)-3-fluoro-1-hydroxypropan-2-yl)-2,2-difluoroacetamide

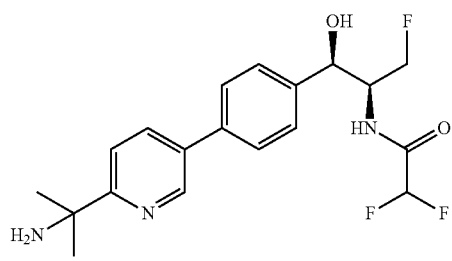 [SMILES: CC(C)(N)c1ccc(-c2ccc([C@@H](O)[C@@H](CF)NC(=O)C(F)F)cc2)cn1]

Following the general procedure of Example 2—Step 2 and making non-critical variations but using the product of Step 3—Example 40 the title compound is obtained (178 mg): $^1$H NMR (400 MHz, DMSO-d$_6$) δ: 1.44 (s, 6H), 4.29-4.37 (m, 1.5H), 4.41-4.45 (m, 0.5H), 4.54-4.58 (m, 0.5H), 4.65-4.68 (m, 0.5H), 4.88 (t, 1H), 5.90 (d, 1H), 6.21 (t, 1H), 7.46 (d, 2H), 7.68-7.73 (m, 3H), 8.04 (dd, 1H), 8.82-8.84 (m, 2H); m/z (CI) 382 [M+H].

Example 41

2,2-difluoro-N-((1R,2S)-3-fluoro-1-hydroxy-1-(4-(2-((methylamino) methyl)thiazol-5-yl)phenyl)propan-2-yl)acetamide

Step 1 Preparation of 5-bromo-2-((triisopropylsilyloxy)methyl)thiazole

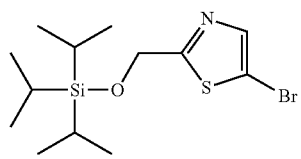 [SMILES: CC(C)[Si](OCc1ncc(Br)s1)(C(C)C)C(C)C]

A 100 mL round bottom flask is charged with (5-bromothiazol-2-yl)methanol (2.5 g, 12.9 mmol), imidazole (1.75 g, 25.8 mmol), dimethylformamide (25 mL), and chlorotriisopropylsilane (3.4 mL, 15.5 mmol). The reaction is stirred at room temperature under nitrogen for 72 hours. Contents are diluted with ethylacetate (150 mL), washed with 0.5M hydrochloric acid (2×100 mL) and brine (100 mL), dried (Na$_2$SO$_4$), and concentrated under vacuum to afford the title compound (4.7 g): m/z (CI) M+H 350+352.

Step 2 Preparation of 2,2-difluoro-1-((4S,5R)-4-(fluoromethyl)-2,2-dimethyl-5-(4-(2-((triisopropylsilyloxy)methyl)thiazol-5-yl)phenyl)oxazolidin-3-yl)ethanone

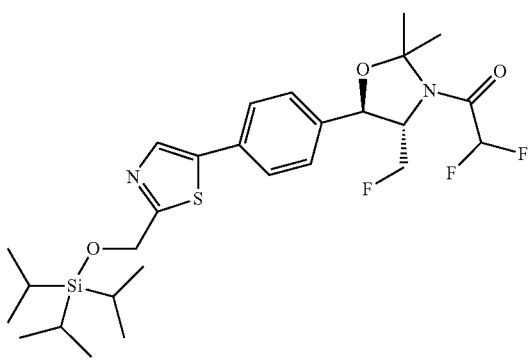 [SMILES: CC(C)[Si](OCc1ncc(-c2ccc([C@H]3OC(C)(C)N(C(=O)C(F)F)[C@@H]3CF)cc2)s1)(C(C)C)C(C)C]

Following the general procedure of Example 22—Step 1 and making non-critical variations but using 5-bromo-2-((triisopropylsilyloxy)methyl)thiazole the title compound is obtained (2.7 g): m/z (CI) M+H 557.

Step 3 Preparation of 2,2-difluoro-1-((4S,5R)-4-(fluoromethyl)-5-(4-(2-(hydroxymethyl)thiazol-5-yl)phenyl)-2,2-dimethyloxazolidin-3-yl)ethanone

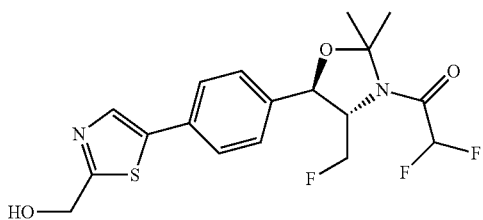 [SMILES: CC1(C)O[C@H](c2ccc(-c3cnc(CO)s3)cc2)[C@@H](CF)N1C(=O)C(F)F]

To a solution of 2,2-difluoro-1-((4S,5R)-4-(fluoromethyl)-2,2-dimethyl-5-(4-(2-((triisopropylsilyloxy)methyl)thiazol-5-yl)phenyl)oxazolidin-3-yl)ethanone (2.6 g, 4.8 mmol) in tetrahydrofuran (50 mL) is added tetrabutylammonium fluoride (5.2 mL of a 1M solution). The reaction is stirred at room temperature for 1 hour. The reaction is diluted with ethylacetate (100 mL) and washed with water and brine. The organic phase is dried ($Na_2SO_4$) and concentrated under vacuum. The crude material is chromatographed eluting from 100% hexanes to 75:25 ethylacetate:hexanes to afford the title compound (1.8 g): m/z (CI) M+H 401.

Step 4 Preparation of 2,2-difluoro-1-((4S,5R)-4-(fluoromethyl)-2,2-dimethyl-5-(4-(2-((methylamino)methyl)thiazol-5-yl)phenyl)oxazolidin-3-yl)ethanone

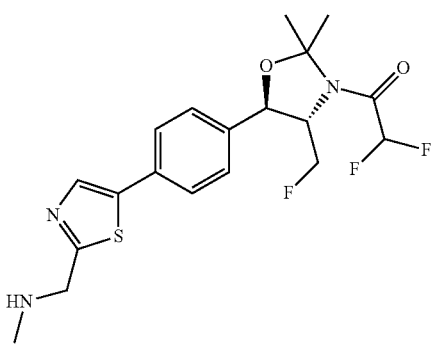 [SMILES: CNCc1ncc(-c2ccc([C@H]3OC(C)(C)N(C(=O)C(F)F)[C@@H]3CF)cc2)s1]

Mesyl anhydride (860 mg, 4.9 mmol) is added to 2,2-difluoro-1-((4S,5R)-4-(fluoromethyl)-5-(4-(2-(hydroxymethyl)thiazol-5-yl)phenyl)-2,2-dimethyl-oxazolidin-3-yl)ethanone (1.4 g, 3.5 mmol) in $CH_2Cl_2$ (35 mL). Pyridine (0.5 mL, 5.9 mmol) is added and stirred at room temperature for 1 hour. The reaction is diluted with $CH_2Cl_2$ (35 mL) and washed with water and brine. The organic phase is dried ($Na_2SO_4$) and concentrated under vacuum. The crude mesylate is dissolved in acetonitrile (10 mL) and transferred to a scintillation vial. Diisopropylethylamine (0.65 mL, 3.7 mmol) and methylamine.HCl (130 mg, 1.9 mmol) are added and the reaction mixture is heated to 55° C. for 18 hours. The reaction mixture is cooled and diluted with saturated $NaHCO_3$ (75 mL). The reaction mixture is extracted with $CH_2Cl_2$ (2×75 mL) and the combined organic phase is dried ($Na_2SO_4$) and concentrated under vacuum to afford the title compound (475 mg): m/z (CI) M+H 414.

Step 5 2,2-difluoro-N-((1R,2S)-3-fluoro-1-hydroxy-1-(4-(2-((methylamino) methyl)thiazol-5-yl)phenyl)propan-2-yl)acetamide

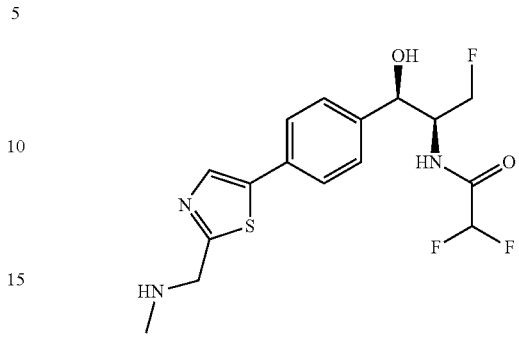

Following the general procedure of Example 2—Step 2 and making non-critical variations but using the product of Step 4—Example 41 the title compound is obtained (64 mg): $^1$H NMR (400 MHz, DMSO-$d_6$) δ: 2.37 (s, 3H), 2.78 (m, 1H), 3.92 (s, 2H), 4.26-4.35 (m, 1.5H), 4.40-4.44 (m, 0.5H), 4.53-4.56 (m, 0.5H), 4.64-4.67 (m, 0.5H), 4.85 (t, 1H), 5.89 (d, 1H), 6.19 (t, 1H), 7.38 (d, 2H), 7.59 (d, 2H), 8.06 (s, 1H), 8.80 (d, 1H); m/z (CI) 374 [M+H].

Example 42

2,2-difluoro-N-((1R,2S)-3-fluoro-1-(4-(2-((3-fluoroazetidin-1-yl)methyl)thiazol-5-yl)phenyl)-1-hydroxypropan-2-yl)acetamide

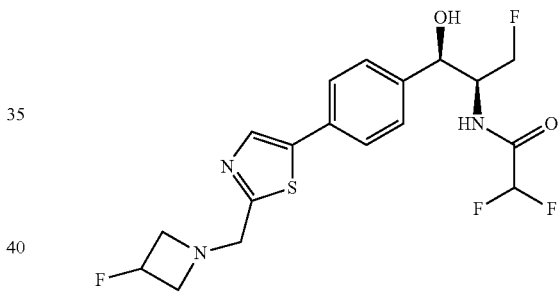

Following the general procedure of Example 41—Steps 4-5 and making non-critical variations but using 3-fluoroazetidine the title compound is obtained (35 mg): m/z (CI) M+H 418.

Example 43

N-((1R,2S)-1-(4-(2-((3-cyanoazetidin-1-yl)methyl)thiazol-5-yl)phenyl)-3-fluoro-1-hydroxypropan-2-yl)-2,2-difluoroacetamide

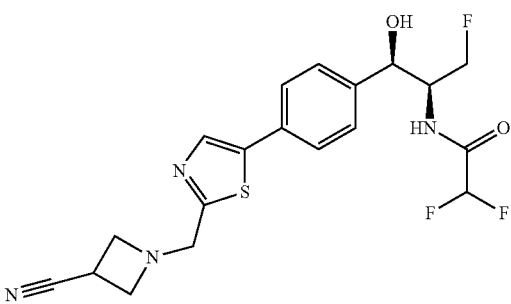 [SMILES: N#CC1CN(Cc2ncc(-c3ccc([C@@H](O)[C@@H](CF)NC(=O)C(F)F)cc3)s2)C1]

Following the general procedure of Example 41—Steps 4-5 and making non-critical variations but using 3-cyanoazetidine the title compound is obtained (22 mg): m/z (CI) M+H 425.

Example 44

2,2-difluoro-N-((1R,2S)-3-fluoro-1-hydroxy-1-(4-(2-((3-hydroxyazetidin-1-yl)methyl)thiazol-5-yl)phenyl)propan-2-yl)acetamide

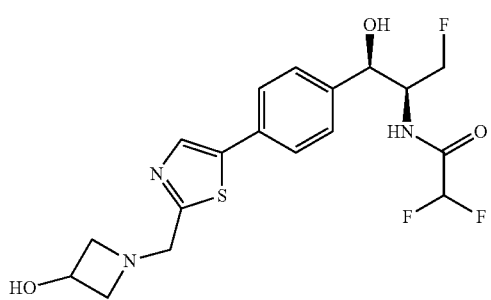 [SMILES: O=C(N[C@H](CF)[C@H](O)c1ccc(-c2cnc(CN3CC(O)C3)s2)cc1)C(F)F]

Following the general procedure of Example 41—Steps 4-5 and making non-critical variations but using 3-hydroxyazetidine the title compound is obtained (18 mg): m/z (CI) M+H 416.

Example 45

N-((1R,2S)-1-(4-(2-((cyclopropylamino)methyl)thiazol-5-yl)phenyl)-3-fluoro-1-hydroxypropan-2-yl)-2,2-difluoroacetamide

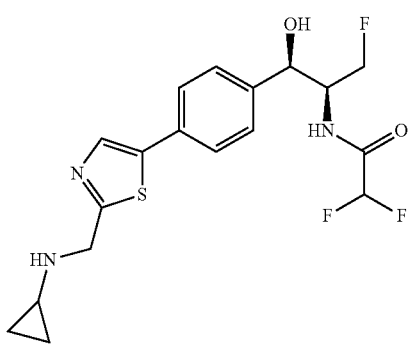 [SMILES: O=C(N[C@H](CF)[C@H](O)c1ccc(-c2cnc(CNC3CC3)s2)cc1)C(F)F]

Following the general procedure of Example 41—Steps 4-5 and making non-critical variations but using cyclopropanamine the title compound is obtained (23 mg): m/z (CI) M+H 400.

Example 46

2,2-difluoro-N-((1R,2S)-3-fluoro-1-hydroxy-1-(4-(2-((2-hydroxyethylamino) methyl)thiazol-5-yl)phenyl)propan-2-yl)acetamide

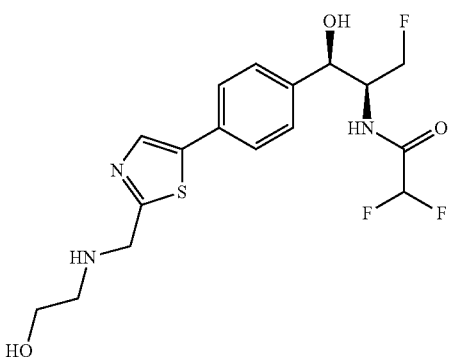 [SMILES: O=C(N[C@H](CF)[C@H](O)c1ccc(-c2cnc(CNCCO)s2)cc1)C(F)F]

Following the general procedure of Example 41—Steps 4-5 and making non-critical variations but using 2-aminoethanol the title compound is obtained (18 mg): m/z (CI) M+H 404.

Example 47

2,2-difluoro-N-((1R,2S)-3-fluoro-1-hydroxy-1-(4-(2-(morpholinomethyl) thiazol-5-yl)phenyl)propan-2-yl)acetamide

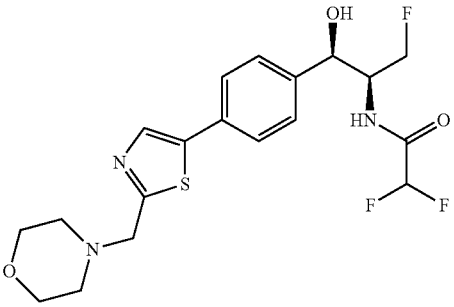 [SMILES: O=C(N[C@H](CF)[C@H](O)c1ccc(-c2cnc(CN3CCOCC3)s2)cc1)C(F)F]

Following the general procedure of Example 41—Steps 4-5 and making non-critical variations but using morpholine the title compound is obtained (37 mg): m/z (CI) M+H 430.

Example 48

2,2-difluoro-N-((1R,2S)-3-fluoro-1-(4-(2-((2-fluoroethylamino)-methyl)thiazol-5-yl)phenyl)-1-hydroxypropan-2-yl)acetamide

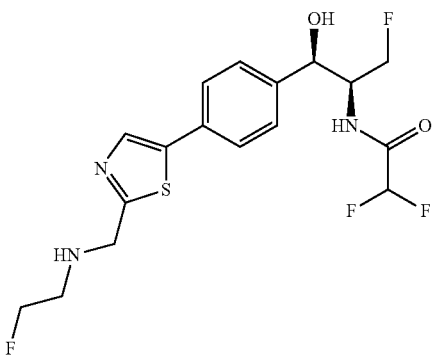 [SMILES: O=C(N[C@H](CF)[C@H](O)c1ccc(-c2cnc(CNCCF)s2)cc1)C(F)F]

Following the general procedure of Example 41—Steps 4-5 and making non-critical variations but using 2-fluoroethanamine the title compound is obtained (28 mg): m/z (CI) M+H 406.

Example 49

N-((1R,2S)-1-(4-(2-(1-aminoethyl)thiazol-5-yl)phenyl)-3-fluoro-1-hydroxypropan-2-yl)-2,2-difluoroacetamide Step 1 N-(1-(5-bromothiazol-2-yl)ethyl)-2-methylpropane-2-sulfinamide

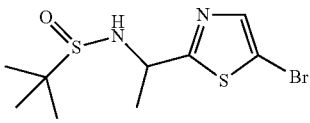

Following the procedure previously described in WO2011053542 (p 47-49), but using racemic 2-methyl-2-propanesulfinamide the title compound is obtained (2.06 g): m/z (CI) M+H 311+313.

Step 2 Preparation of N-(1-(5-(4-((4S,5R)-3-(2,2-difluoroacetyl)-4-(fluoromethyl)-2,2-dimethyloxazolidin-5-yl)phenyl)thiazol-2-yl)ethyl)-2-methylpropane-2-sulfinamide

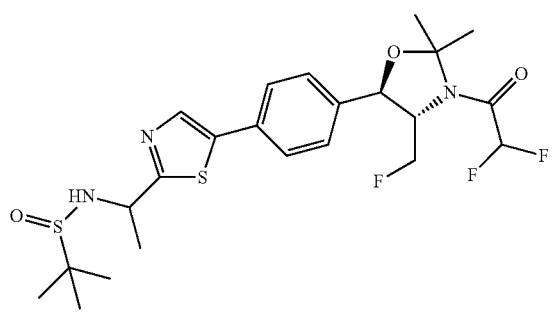 [SMILES: CC(NS(=O)C(C)(C)C)c1ncc(-c2ccc([C@H]3OC(C)(C)N(C(=O)C(F)F)[C@@H]3CF)cc2)s1]

Following the general procedure of Example 22—Step 1 and making non-critical variations but using N-(1-(5-bromothiazol-2-yl)ethyl)-2-methylpropane-2-sulfinamide the title compound is obtained (323 mg): m/z (CI) M+H 518.

Step 3 N-((1R,2S)-1-(4-(2-(1-aminoethyl)thiazol-5-yl)phenyl)-3-fluoro-1-hydroxypropan-2-yl)-2,2-difluoroacetamide

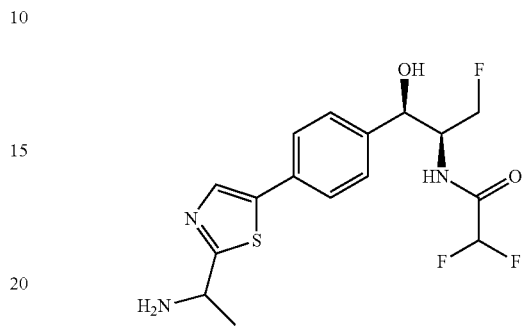

To a solution of N-(1-(5-(4-((4S,5R)-3-(2,2-difluoroacetyl)-4-(fluoromethyl)-2,2-dimethyloxazolidin-5-yl)phenyl)thiazol-2-yl)ethyl)-2-methylpropane-2-sulfinamide (315 mg, 0.6 mmol) in $CH_2Cl_2$ (25 mL) at 0° C. is added trifluoroacetic acid (5 mL) and 5 drops water. The reaction is allowed to warm to room temperature and stir for 1 hour. Toluene (20 mL) is added and contents are concentrated under vacuum. Toluene addition/concentration is repeated and contents are placed under high vacuum for 5 minutes. Methanol (25 mL) is added to the reaction flask and the solution is cooled in an ice bath. HCl in methanol (4 mL of 1.25 mL solution) is added and the reaction is allowed to warm to room temperature while stirring. After 2 hours, the reaction is concentrated under vacuum to ~3 mL of solvent left and purified directly using reverse phase chromatography, eluting from 95:5 water/acetonitrile/0.1% trifluoroacetic acid to 95:5 acetonitrile/water/0.1% trifluoroacetic acid. The purified fractions are concentrated under vacuum to remove acetonitrile. The aqueous phase is diluted with saturated $NaHCO_3$ (100 mL) and extracted with ethylacetate (2×100 mL). The combined organic phase is dried ($Na_2SO_4$) and concentrated under vacuum to afford the title compound (93 mg): $^1$H NMR (400 MHz, DMSO-$d_6$) δ: 1.39 (d, 3H), 2.38 (m, 2H), 4.18-4.33 (m, 2.5H), 4.40-4.44 (m, 0.5H), 4.52-4.56 (m, 0.5H), 4.64-4.67 (m, 0.5H), 4.85 (t, 1H), 5.88 (d, 1H), 6.19 (t, 1H), 7.38 (d, 2H), 7.58 (d, 2H), 8.03 (s, 1H), 8.80 (d, 1H); m/z (CI) 374 [M+H].

The following derivatives of the title compound of Example 49 can be prepared by methods known in the art, including those described in Example 95A below:

N-((1R,2S)-1-(4-(2-(1-aminoethyl)thiazol-5-yl)phenyl)-3-fluoro-1-hydroxypropan-2-yl)-2,2-dichloroacetamide;

(1R,2S)-1-(4-(2-(1-aminoethyl)thiazol-5-yl)phenyl)-2-(2,2-dichloroacetamido)-3-fluoropropyl hydrogen phosphate sodium;

(1R,2S)-1-(4-(2-(1-aminoethyl)thiazol-5-yl)phenyl)-2-(2,2-dichloroacetamido)-3-fluoropropyl dihydrogen phosphate;

(1R,2S)-1-(4-(2-(1-aminoethyl)thiazol-5-yl)phenyl)-2-(2,2-difluoroacetamido)-3-fluoropropyl hydrogen phosphate sodium; and (1R,2S)-1-(4-(2-(1-aminoethyl)thiazol-5-yl)phenyl)-2-(2,2-difluoroacetamido)-3-fluoropropyl dihydrogen phosphate.

Example 50

Preparation of 2,2-Difluoro-N-((1S,2R)-1-fluoromethyl-2-hydroxy-2-{4-[2-(methanesulfonylaminomethyl)-benzothiazol-5-yl]-phenyl}-ethyl)-acetamide

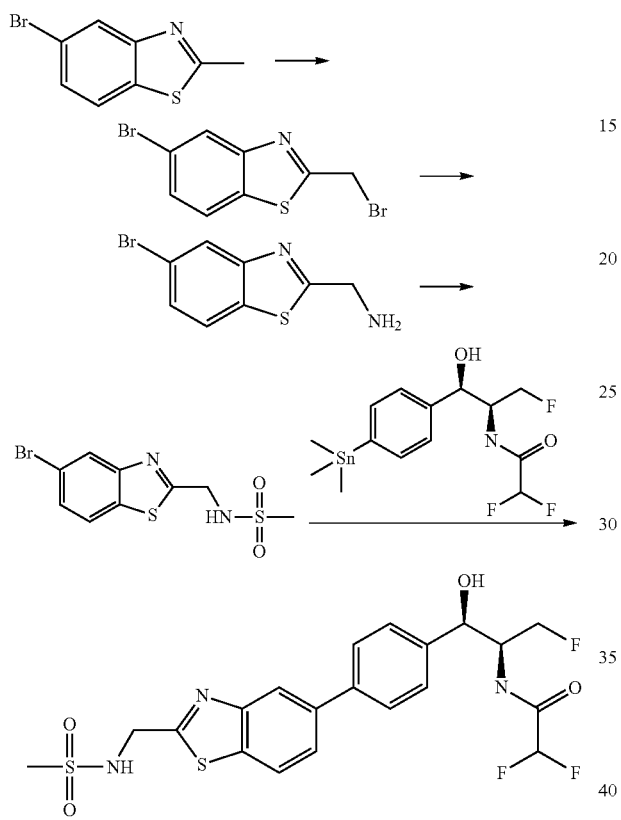

Step 1 Preparation of 5-Bromo-2-bromomethyl-benzothiazole

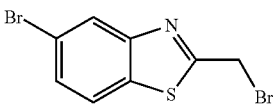

To a solution of 5-Bromo-2-methyl-benzothiazole (1.0 g, 4.385 mmol) in CCl₄ (15 mL) is added N-bromosuccinamide (1.1 g, 6.140 mmol) and azobisisobutyronitrile (0.029 g, 0.175 mmol) at room temperature reaction. The reaction mixture is heated to 75° C. for 16 hours. Reaction mixture is cooled to room temperature, filtered and the solvent evaporated in vacuo to give the crude material, which is then purified by flash chromatography using 3.5% ethyl acetate in hexane as an eluent to afford the title compound (0.85 g). $^1$H NMR (400 MHz, DMSO-d$_6$) δ: 5.12 (s, 2H), 7.68-7.71 (dd, J1=1.92 Hz, J2=8.76 Hz, 1H), 7.95 (d, J=8.6 Hz, 1H), 8.43 (d, J=1.92 Hz, 1H). LC-MS (m/z): [M+H]=308.2.

Step 2 Preparation of C-(5-Bromo-benzothiazol-2-yl)-methylamine

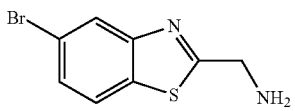

Gaseous ammonia is bubbled through a solution of 5-Bromo-2-bromomethyl-benzothiazole (0.850 g, 2.768 mmol) in methanol (16 mL) for 10 minutes at 0° C. then stirred at room temperature for 3 hours. The reaction mixture is dried over magnesium sulfate, filtered and the solvent is evaporated in vacuo. The crude material is washed with n-pentane and hexane to afford the title compound (0.78 g). $^1$H NMR (400 MHz, DMSO-d$_6$) δ: 4.52 (s, 2H), 7.69-7.72 (dd, J1=1.96 Hz, J2=8.68 Hz, 1H), 7.95 (d, J=8.64 Hz, 1H), 8.46 (d, J=1.96 Hz, 1H). LC-MS (m/z): [M+H]=245.0.

Step 3 Preparation of N-(5-Bromo-benzothiazol-2-ylmethyl)-methanesulfonamide

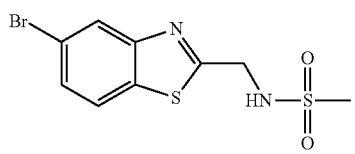 [SMILES: CS(=O)(=O)NCc1nc2cc(Br)ccc2s1]

To a stirred solution of C-(5-Bromo-benzothiazol-2-yl)-methylamine (0.780 g, 3.209 mmol) in CH₂Cl₂ (12 mL) is added triethylamine (1.2 mL, 8.024 mmol). To above solution is added drop wise methane sulfonyl chloride (0.5 mL, 6.419 mmol) at 0° C. then stirred at room temperature for 3 hours. The reaction mixture is concentrated in vacuo and the crude material is diluted with water and extracted with ethyl acetate. The organic layer is dried over sodium sulfate, concentrated and purified by combiflash using 50% ethyl acetate in hexane as an eluent to afford the title compound (0.45 g). $^1$HNMR (400 MHz, DMSO-d$_6$) δ: 3.03 (s, 3H), 4.60 (d, J=5.72 Hz, 2H), 7.64-7.67 (dd, J1=1.88 Hz, J2=8.72 Hz, 1H), 7.88 (d, J=8.68 Hz, 1H), 8.21 (t, J=6 Hz, 1H), 8.40 (d, J=1.88 Hz, 1H). LC-MS (m/z): [M−H]=320.8.

Step 4 Preparation of 2,2-Difluoro-N-((1S,2R)-1-fluoromethyl-2-hydroxy-2-{4-[2-(methanesulfonylamino-methyl)-benzothiazol-5-yl]-phenyl}-ethyl)-acetamide

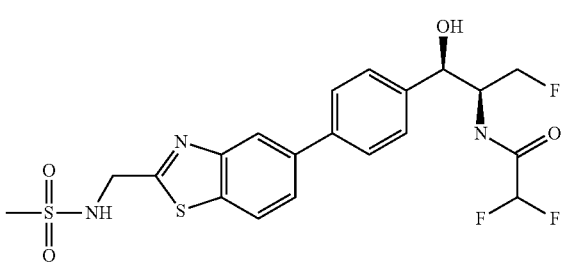 [SMILES: CS(=O)(=O)NCc1nc2cc(-c3ccc([C@@H](O)[C@@H](CF)NC(=O)C(F)F)cc3)ccc2s1]

To a stirred solution of N-(5-Bromo-benzothiazol-2-ylmethyl) methane sulfonamide (0.21 g, 0.656 mmol) and 2,2-Difluoro-N-[(1S,2R)-1-fluoromethyl-2-hydroxy-2-(4-trimethylstannanyl-phenyl)-ethyl]-acetamide (0.404 g, 0.984 mmol) in N-Methyl-2-pyrrolidone (9 mL) is added lithium chloride (0.084 g, 1.968 mmol) at room temperature. Resulting reaction mixture is degassed with nitrogen for 15 minutes then Pd(PPh$_3$)$_2$Cl$_2$ (0.046 g, 0.065 mmol) is added. The reaction mixture heated to 90° C. for 16 hours. Reaction mixture is cooled to room temperature, diluted with water and extracted with ethyl acetate. Organic layer is dried over sodium sulfate, solvent is evaporated in vacuo to give the crude material purified by flash column chromatography using 2.4% methanol in CH$_2$Cl$_2$ as an eluent to give impure compound. The impure compound is again purified by prep-HPLC to give the title compound (5 mg). $^1$HNMR (400 MHz, DMSO) δ: 3.04 (s, 3H), 4.26-4.33 (m, 1H), 4.41-4.43 (m, 0.5H), 4.44-4.50 (m, 0.5H), 4.62 (s, 2H), 4.65-4.68 (m, 0.5H), 4.75-4.79 (m, 0.5H), 4.87-4.88 (m, 1H), 5.9 (d, J=4.56 Hz, 1H), 6.20 (d, J=56.36 Hz, 1H), 7.45 (d, J=8.24 Hz, 2H), 7.63, (d, J=8.16 Hz, 1H), 7.73 (d, J=8.28 Hz, 2H). 7.81 (d, J1=1.8 Hz, J2=8.52 Hz, 1H), 8.42 (d, J=1.6 Hz, 1H), 8.82-8.83 (m, 2H). LC-Ms (m/z): [M−H]=485.8.

Example 51

Preparation of 2,2-Difluoro-N-[(1S,2R)-1-fluoromethyl-2-hydroxy-2-(4-{6-[(methanesulfonyl-methoxy-amino)-methyl]-pyridin-3-yl}-phenyl)-ethyl]-acetamide

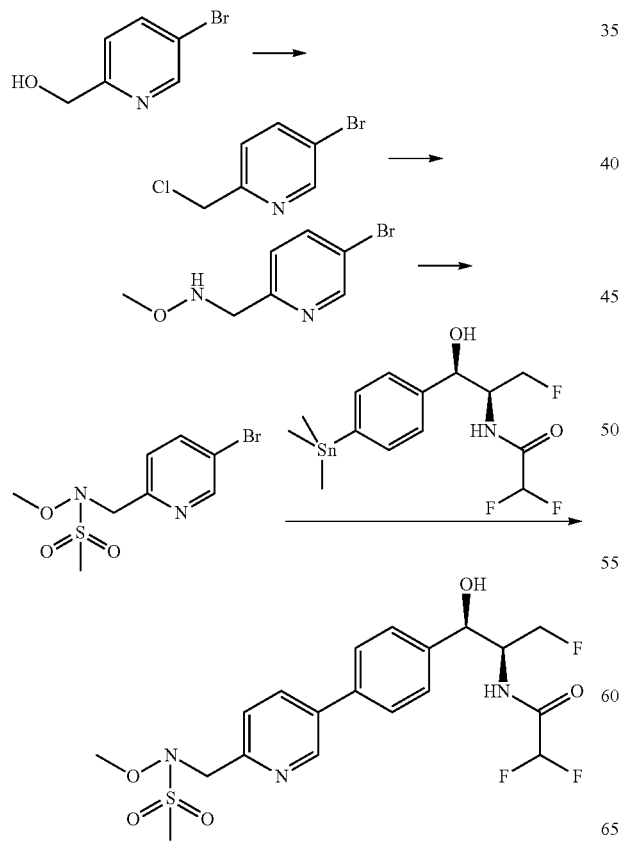

Step 1 Preparation of 5-Bromo-2-chloromethyl-pyridine

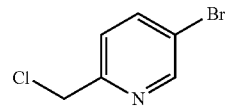

To a stirred solution of (5-Bromo-pyridin-2-yl)-methanol (1 g, 5.319 mmol) in CH$_2$Cl$_2$ (20 mL) is added drop wise thionyl chloride (0.57 mL, 7.979 mmol) at 0° C. then stirred for another 4 hours. Reaction mixture is diluted with saturated sodium bicarbonate solution and extracted with CH$_2$Cl$_2$. Organic layer is dried over sodium sulphate, solvent is evaporated in vacuo and purified by column chromatography using 7% ethyl acetate in hexane as an eluent to afford the title compound (0.8 g). 1HNMR (400 MHz, DMSO-d$_6$) δ: 4.7 (s, 2H), 7.53 (d, 8.36 Hz, 1H), 8.09-8.11 (dd, J1=2.44 Hz, J2=8.23 Hz, 1H), 8.69 (d, J=2.4 Hz, 1H), LC-MS (M/Z): [M+H]=206.0.

Step 2 Preparation of N-(5-Bromo-pyridin-2-ylmethyl)-O-methyl-hydroxylamine

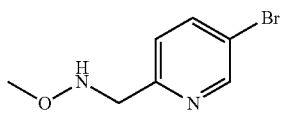

To a stirred solution of 5-Bromo-2-chloromethyl-pyridine (2 g, 9.709 mmol) in dimethylformamide (30 mL) is added methoxy amine hydrochloride salt (0.973 g, 11.65 mmol) and K$_2$CO$_3$ (3.35 g, 24.27 mmol) at room temperature then heated to 60° C. for 16 hours. Reaction mixture diluted with water and extracted with ethyl acetate. Organic layer is dried over sodium sulphate, solvent is evaporated in vacuo and purified by combiflash using 30% ethyl acetate in hexane as an eluent to afford the title compound (0.6 g). 1HNMR (400 MHz, DMSO-d$_6$) δ: 3.36 (s, 3H), 3.99 (d, J=5.88 HZ, 2H), 7.10 (t, 1H), 7.44-7.46 (dd, J1=8.32 Hz, J2=0.32 Hz, 1H), 7.99-8.02 (dd, J1=2.44 Hz, J2=8.4 Hz, 1H), 8.60-8.61 (dd, J1=2.4 Hz, J2=0.4 Hz, 1H). LC-MS (m/z): [M+H]=217.1.

Step 3 Preparation of N-(5-Bromo-pyridin-2-ylmethyl)-N-methoxy-methane sulfonamide

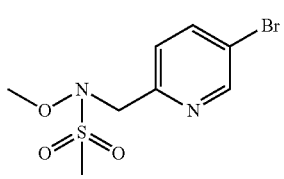

To a stirred solution of N-(5-Bromo-pyridin-2-ylmethyl)-O-methyl-hydroxylamine (0.6 g, 2.765 mmol) in tetrahydrofuran (10 mL) is added sodium bis(trimethylsilyl)amide (0.6 g, 3.318 mmol) and mesyl chloride (0.37 g, 3.318 mmol) at 0° C. The reaction mixture is stirred at room temperature for 16 hours. Reaction mixture diluted with saturated ammonium chloride solution and extracted with ethyl acetate. Organic layer is dried over sodium sulphate, solvent is evaporated in vacuo and purified by flash chromatography using 20% ethyl acetate in hexane as an eluent to afford the title compound (0.3 g). 1HNMR (400 MHz, DMSO-d$_6$) δ: 3.14 (s, 3H), 3.47 (s, 3H), 4.40 (s, 2H), 7.50 (d, J=8.28 Hz, 1H), 8.09-8.12 (dd, J1=2.8 Hz, J2=8.4 Hz, 1H), 8.71 (d, J=2.36 Hz, 1H). LC-MS (m/z): [M+H]=297.1.

Step 4 Preparation of 2,2-Difluoro-N-[(1S,2R)-1-fluoromethyl-2-hydroxy-2-(4-{6-[(methanesulfonyl-methoxy-amino)-methyl]-pyridin-3-yl}-phenyl)-ethyl]-acetamide

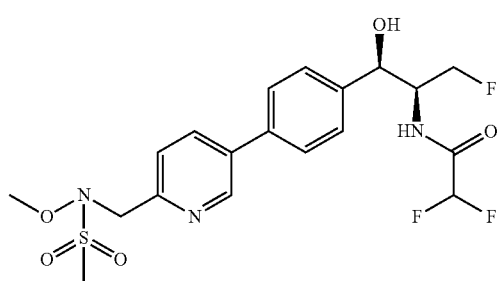 [SMILES: CON(Cc1ccc(-c2ccc([C@@H](O)[C@@H](CF)NC(=O)C(F)F)cc2)cn1)S(C)(=O)=O]

To a stirred solution of N-(5-Bromo-pyridin-2-ylmethyl)-N-methoxy-methane sulfonamide (0.2 g, 0.678 mmol) in N-Methyl-2-pyrrolidone (8 mL) is added and 2,2-Difluoro-N-[(1S,2R)-1-fluoromethyl-2-hydroxy-2-(4-trimethylstannanyl-phenyl)ethyl]-acetamide (0.27 g, 0.678 mmol). Reaction mixture is degassed with nitrogen for 15 minutes then added tris(dibenzylideneacetone)dipalladium(0) (0.06 mg, 0.068 mmol) and Tri-2-furylphosphine (0.03 g, 0.136 mmol) simultaneously. The resulting reaction mixture is stirred at 80° C. for 5 hours. Diluted with water and extracted with ethyl acetate. Organic layer is dried over sodium sulphate, solvent is evaporated in vacuo and purified by combi-flash using 50% ethyl acetate in hexane as an eluent to afford the title compound (0.05 g). 1HNMR (400 MHz, DMSO-d$_6$) δ: 3.16 (s, 3H), 3.49 (s, 3H), 4.30-4.37 (m, 1.5H), 4.41-4.46 (m, 0.5H), 4.46 (s, 2H), 4.54-4.56 (m, 0.5H), 4.65-4.68 (m, 0.5H), 4.89 (m, 1H), 5.94 (d, J=4.2 Hz, 1H), 6.20 (t, J=53.76 Hz, 1H), 7.47 (d, J=8.2 Hz, 2H), 7.59 (d, J=8.16 Hz, 1H), 7.74 (d, J=8.2 Hz, 2H), 8.14-8.16 (dd, J1=2.32 Hz, J2=8.16 Hz, 1H), 8.86 (d, J=8.72 Hz, 1H), 8.91 (d, J=2.08 Hz, 1H). LCMS (m/z): [M+H]=461.9.

Example 52

Preparation of 2,2-Difluoro-N-[(1R,2R)-1-fluoromethyl-2-(4-{6-[(3-fluoro-propylamino)-methyl]-pyridin-3-yl}-phenyl)-2-hydroxy-ethyl]-acetamide

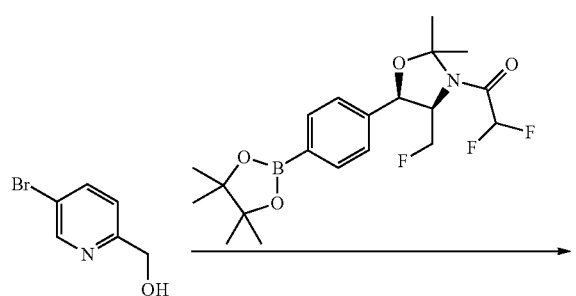

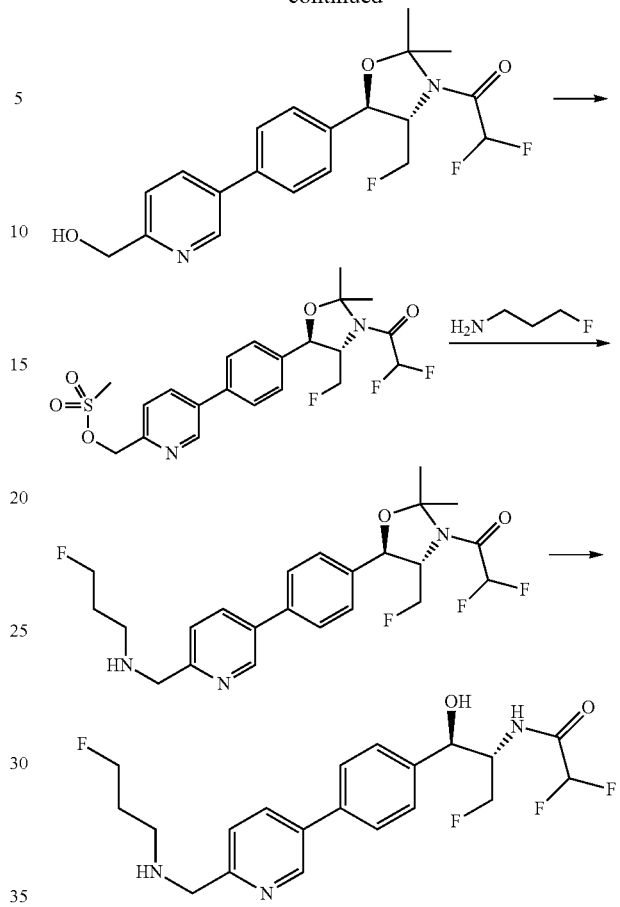

Step 1 Preparation of 2,2-Difluoro-1-{(4S,5R)-4-fluoromethyl-5-[4-(6-hydroxy-methyl-pyridin-3-yl)-phenyl]-2,2-dimethyl-oxazolidin-3-yl}-ethanone

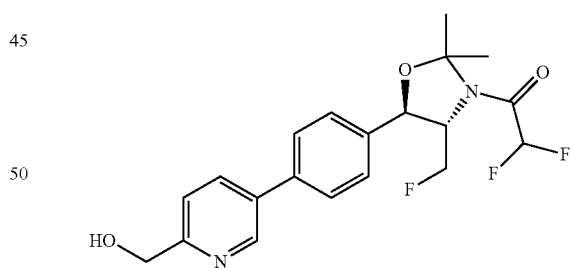

To a stirred solution of 2,2-Difluoro-1-{(4S,5R)-4-fluoromethyl-2,2-dimethyl-5-[4-(4,4,5,5-tetramethyl-[1,3,2]dioxaborolan-2-yl)-phenyl]-oxazolidin-3-yl}-ethanone (2.0 g, 4.843 mmol) in toluene (40 mL), ethanol (10 mL), water (10 mL) and (5-Bromo-pyridin-2-yl)-methanol (0.91 g, 4.843 mmol) is added Na$_2$CO$_3$ (1.54 g, 14.528 mmol) at room temperature. Resulting reaction mixture is degassed with nitrogen for 30 minutes then Pd(PPh$_3$)$_4$ (0.559 g, 0.484 mmol) is added. The reaction mixture is heated to 90° C. for 6 hours. Solvent is evaporated in vacuo then diluted with water and extracted with ethyl acetate. Organic layer is dried over sodium sulphate, solvent is evaporated in vacuo and purified by combi-flash chromatography using 80% ethyl acetate in hexane as an eluent to afford the title compound (0.67 g): $^1$H-NMR (400 MHz, CDCl$_3$) δ: 1.53 (s, 3H), 1.60 (S, 3H), 4.54-4.58 (m, 0.5H), 4.60 (d, J=5.84 Hz, 2H), 4.66-4.72 (m, 1H), 4.81-4.84 (m, 0.5H), 4.90-4.94 (m, 1H), 5.26 (d, J=3.72 Hz, 1H), 5.48 (t, J=5.8 Hz, 1H), 6.64 (t, J=52.4 Hz, 1H), 7.55-7.64 (m, 3H), 7.78 (d, J=8.2 Hz, 2H), 8.09-8.12 (dd, J=2.32 Hz, J=8.16 Hz, 1H), 8.81 (d, 2.04 Hz, 1H). LC-MS (m/z): [M+H]=395.0.

Step 2 Preparation of Methanesulfonic acid 5-{4-[(4S,5R)-3-(2,2-difluoroacetyl)-4-fluoromethyl-2,2-dimethyl-oxazolidin-5-yl]-phenyl}-pyridin-2-ylmethyl ester

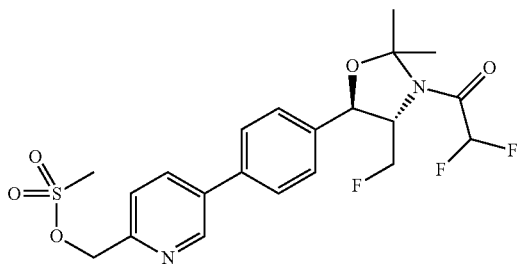 [SMILES: CC1(C)O[C@H](c2ccc(-c3ccc(COS(C)(=O)=O)nc3)cc2)[C@@H](CF)N1C(=O)C(F)F]

To a solution of 2,2-Difluoro-1-{(4S,5R)-4-fluoromethyl-5-[4-(6-hydroxymethyl-pyridin-3-yl)-phenyl]-2,2-dimethyl-oxazolidin-3-yl}-ethanone (1.1 g, 2.792 mmol) in CH$_2$Cl$_2$ (50 mL) is added triethyl amine (0.564 g, 5.584 mmol) followed by methanesulphonyl chloride (0.365 g, 3.071 mmol) at 0° C. then stirred for 30 minutes at 0° C. Reaction mixture is diluted with saturated aqueous bicarbonate solution and extracted with ethyl acetate. Organic layer is dried over sodium sulphate, solvent is evaporated in vacuo and purified by combi-flash chromatography using 30% ethyl acetate in hexane as an eluent to afford the title compound (0.875 g). $^1$H-NMR (400 MHz, DMSO) δ: 1.53 (s, 3H), 1.60 (S, 3H), 3.30 (s, 3H), 4.54-4.58 (m, 0.5H), 4.60-4.70 (m, 1H), 4.82-4.83 (m, 0.5H), 4.90-4.94 (m, 1H), 5.28 (d, J=3.68 Hz, 1H), 5.36 (s, 2H), 6.64 (t, J=52.4 Hz, 1H), 7.61-7.64 (m, 3H), 7.82 (d, J=8.08 Hz, 2H), 8.19-8.21 (dd, J1=2.4 Hz, J2=8.16 Hz, 1H), 8.94 (d, 2.2 Hz, 1H). LC-MS (m/z): [M+H]=473.2.

Step 3 Preparation of 2,2-Difluoro-1-[(4S,5R)-4-fluoromethyl-5-(4-{6-[(3-fluoro-propylamino)-methyl]-pyridin-3-yl}-phenyl)-2,2-dimethyl-oxazolidin-3-yl]-ethanone

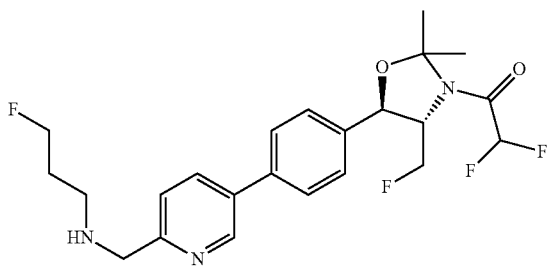 [SMILES: CC1(C)O[C@H](c2ccc(-c3ccc(CNCCCF)nc3)cc2)[C@@H](CF)N1C(=O)C(F)F]

To a solution of 3-Fluoro-propylamine hydrochloride (0.072 g, 0.636 mmol) in acetonitrile (5 mL) is added diisopropylethylamine (0.082 mL, 0.636 mmol) at room temperature. After stirring for 30 minutes methane sulfonic acid 5-{4-[(4S,5R)-3-(2,2-difluoro-acetyl)-4-fluoromethyl-2,2-dimethyl-oxazolidin-5-yl]-phenyl}-pyridin-2-ylmethyl ester (0.1 g, 0.211 mmol) is added then the resulting mixture is stirred at room temperature for overnight. Solvent is evaporated under reduced pressure and the crude material is purified by combi-flash chromatography using 12% methanol in CH$_2$Cl$_2$ as an eluent to afford the title compound (0.093 g). $^1$H-NMR (400 MHz, DMSO-d$_6$) δ: 1.52 (s, 3H), 1.60 (S, 3H), 2.06-2.14 (m, 2H), 3.57-3.60 (m, 2H), 4.35 (s, 2H), 4.49-4.51 (m, 1H), 4.52-4.56 (m, 0.5H), 4.57-4.63 (m, 1H), 4.64-4.70 (m, 1H), 4.83-4.86 (m, 0.5H), 4.93-4.97 (m, 1H), 5.28 (d, J=3.48 Hz, 1H), 6.66 (t, J=52.3 Hz, 1H), 7.61-7.65 (m, 3H), 7.84 (d, J=8.2 Hz, 2H), 8.21-8.23 (dd, J1=3.04 Hz, J2=8.16 Hz, 1H), 8.97 (d, J=1.96 Hz, 1H). LC-MS (m/z): [M+H]=454.1.

Step 4 Preparation of 2,2-Difluoro-N-[(1R,2R)-1-fluoromethyl-2-(4-{6-[(3-fluoro-propylamino)-methyl]-pyridin-3-yl}-phenyl)-2-hydroxy-ethyl]-acetamide

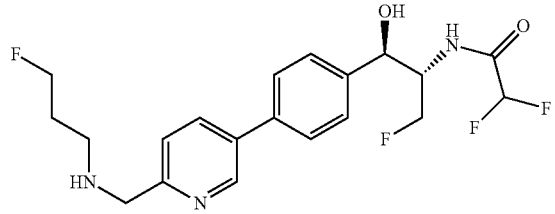 [SMILES: O=C(N[C@H](CF)[C@H](O)c1ccc(-c2ccc(CNCCCF)nc2)cc1)C(F)F]

To a solution of 2,2-Difluoro-1-[(4S,5R)-4-fluoromethyl-5-(4-{6-[(3-fluoro-propylamino)-methyl]-pyridin-3-yl}-phenyl)-2,2-dimethyl-oxazolidin-3-yl]-ethanone (0.113 g, 0.249 mmol) in CH$_2$Cl$_2$ (5 mL) is added trifluoroacetic acid (1.0 mL) at 0° C. The resulting reaction mixture is stirred at room temperature for 5 hours. Solvent is evaporated under reduced pressure and the crude residue is diluted with aqueous bicarbonate solution and extracted with ethyl acetate. Organic layer is dried over sodium sulphate, solvent is evaporated in vacuo and purified by combi-flash chromatography using 15% methanol in CH$_2$Cl$_2$ as eluent. Obtained solid is further washed with n-pentane and diethyl ether to give the title compound (0.034 g). $_1$H NMR (400 MHz, DMSO-d$_6$) δ: 1.84-1.93 (m, 2H), 2.50-2.54 (m, 2H), 2.76 (bs, 1H), 3.99 (bs, 2H), 4.29-4.31 (m, 1.5H), 4.40-4.48 (m, 1.5H), 4.54-4.60 (m, 1.5H), 4.65-4.68 (m, 0.5H), 4.87 (bs, 1H), 5.92 (d, J=4.52 Hz, 1H), 6.20 (t, J=53.64 Hz, 1H), 7.46 (d, J=8.24 Hz, 2H), 7.52 (d, J=8.12 Hz, 1H), 7.70 (d, J=8.24 Hz, 2H), 8.08-8.10 (dd, J1=2.36 Hz, J2=8.2 Hz, 1H), 8.85 (m, 2H). LC-MS (m/z): [M+H]=414.1.

Example 53

Preparation of N-{(1R,2R)-2-[4-(6-Dimethylaminomethyl-pyridin-3-yl)-phenyl]-1-fluoromethyl-2-hydroxy-ethyl}-2,2-difluoroacetamide

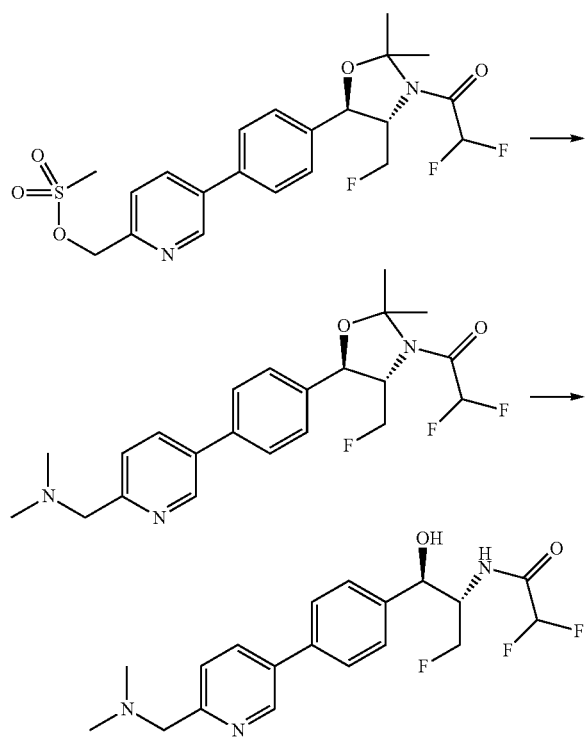

Step 1 Preparation of 1-{(4S,5R)-5-[4-(6-Dimethyl-aminomethyl-pyridin-3-yl)-phenyl]-4-fluoromethyl-2,2-dimethyl-oxazolidin-3-yl}-2,2-difluoro-ethanone To a stirred solution of dimethyl amine (2.0M solution in tetrahydrofuran) (0.31 mL, 0.028 mmol) in tetrahydrofuran (5 mL) is added methanesulfonic acid 5-{4-[(4R,5R)-3-(2,2-difluoro-acetyl)-4-fluoromethyl-2,2-dimethyl-oxazolidin-5-yl]-phenyl}-pyridin-2-ylmethyl ester (0.1 g, 0.212 mmol) and stirred at room temperature overnight. The solvent is evaporated in vacuo and the crude material is purified by combi-flash chromatography using 10% methanol in CH$_2$Cl$_2$ as an eluent to afford the title compound (0.072 g). $^1$H-NMR (400 MHz, DMSO-d$_6$) δ: 1.53 (s, 3H), 1.60 (S, 3H), 2.21 (s, 6H), 3.56 (s, 2H), 4.56-4.58 (m, 0.5H), 4.66-4.72 (m, 1H), 4.80-4.84 (m, 0.5H), 4.90-4.94 (m, 1H), 5.26 (d, J=3.76 Hz, 1H), 6.64 (t, J=52.36 Hz, 1H), 7.50 (d, J=8.08 Hz, 1H), 7.59 (d, J=8.08 Hz, 2H), 7.78 (d, J=8.12 Hz, 2H), 8.07-8.09 (m, 1H), 8.81 (s, 1H). LC-MS (m/z): [M+H]=422.

Step 2 Preparation of N-{(1R,2R)-2-[4-(6-Dimethylaminomethyl-pyridin-3-yl)-phenyl]-1-fluoromethyl-2-hydroxy-ethyl}-2,2-difluoro-acetamide

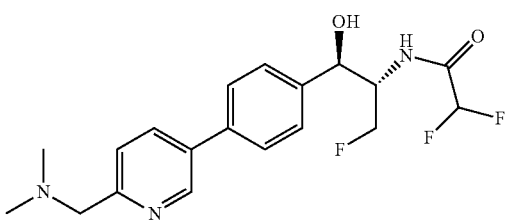 [SMILES: CN(C)Cc1ccc(-c2ccc([C@@H](O)[C@@H](CF)NC(=O)C(F)F)cc2)cn1]

To a solution of 1-{(4S,5R)-5-[4-(6-Dimethylaminomethyl-pyridin-3-yl)-phenyl]-4-fluoromethyl-2,2-dimethyl-oxazolidin-3-yl}-2,2-difluoro-ethanone (0.070 g, 0.166 mmol) in CH$_2$Cl$_2$ (5 mL) is added trifluoroacetic acid (1.0 mL). The resulting reaction mixture is stirred at room temperature for 5 hours. Concentrated to get the crude residue and diluted with aqueous bicarbonate solution and extracted with ethyl acetate. Organic layer is dried over sodium sulphate, solvent is evaporated in vacuo and purified by combi-flash chromatography using 15% methanol in CH$_2$Cl$_2$ as an eluent. Obtained solid is washed with n-pentane and diethyl ether to afford the title compound (0.030 g). $^1$HNMR (400 MHz, DMSO-d$_6$) δ: 2.44 (s, 6H), 3.90 (bs, 2H), 4.28-4.30 (m, 1H), 4.31-4.33 (m, 0.5H), 4.41-4.45 (m, 0.5H), 4.54-4.55 (m, 0.5H), 4.65-4.68 (m, 0.5H), 4.89 (t, J=4.0 Hz, 1H), 5.93 (d, J=4.56 Hz, 1H), 6.20 (t, J=53.76 Hz, 1H), 7.47 (d, J=8.24 Hz, 2H), 7.53 (d, J=8.16 Hz, 1H), 7.72 (d, J=8.24 Hz, 2H), 8.11-8.13 (m, 1H), 8.84-8.87 (m, 2H). LC-MS (m/z): [M+H]=382.1.

Example 54

Preparation of N-{(1R,2R)-2-[4-(6-Ethylaminomethyl-pyridin-3-yl)-phenyl]-1-fluoromethyl-2-hydroxy-ethyl}-2,2-difluoro-acetamide Step 1 Preparation of 1-{(4S,5R)-5-[4-(6-Ethylaminomethyl-pyridin-3-yl)-phenyl]-4-fluoromethyl-2,2-dimethyl-oxazolidin-3-yl}-2,2-difluoro-ethanone

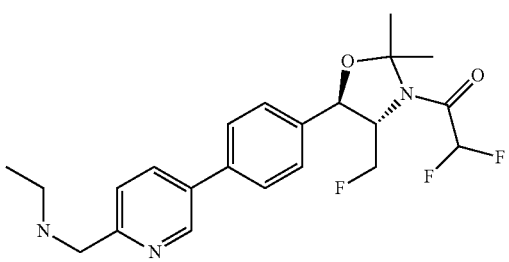 [SMILES: CCNCc1ccc(-c2ccc([C@H]3OC(C)(C)N(C(=O)C(F)F)[C@@H]3CF)cc2)cn1]

To a stirred solution of ethylamine (2.0M solution in tetrahydrofuran; 0.31 mL, 0.027 mmol) in tetrahydrofuran (5 mL) is added methanesulfonic acid 5-{4-[(4S,5R)-3-(2,2-difluoro-acetyl)-4-fluoromethyl-2,2- dimethyl-oxazolidin- 5-yl]-phenyl}-pyridin-2-ylmethyl ester (0.1 g, 0.212 mmol) at room temperature then stirred overnight. Solvent is evaporated in vacuo. The crude material is purified by combi-flash chromatography using 10% methanol in CH$_2$Cl$_2$ as an eluent to afford the title compound (0.062 g). $^1$H-NMR (400 MHz, DMSO-d$_6$) δ: 1.09 (t, J=7.12 Hz, 3H), 1.52 (s, 3H), 1.60 (S, 3H), 2.66-2.71 (q, 2H), 3.96 (s, 2H), 4.51-4.56 (m, 0.5H), 4.57-4.58 (m, 1H), 4.59-4.69 (m, 0.5H), 4.70-4.82 (m, 1H), 5.27 (d, J=3.56 Hz, 1H), 6.64 (t, J=52.4 Hz, 1H), 7.53 (d, J=8.2 Hz, 1H), 7.60 (d, J=8.12 Hz, 2H), 7.79 (d, J=8.2 Hz, 2H), 8.09-8.11 (dd, J1=2.28 Hz, J2=8.08 Hz, 1H), 8.86 (d, J=2.08 Hz, 1H). LC-MS (m/z): [M+H]=422.

Step 2 Preparation of N-{(1R,2R)-2-[4-(6-Ethylaminomethyl-pyridin-3-yl)-phenyl]-1-fluoromethyl-2-hydroxy-ethyl}-2,2-difluoro-acetamide

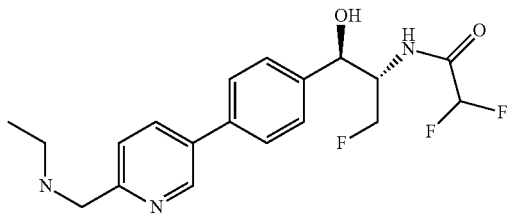 [SMILES: CCNCc1ccc(-c2ccc([C@@H](O)[C@@H](CF)NC(=O)C(F)F)cc2)cn1]

To a solution of 1-{(4S,5R)-5-[4-(6-Ethylaminomethyl-pyridin-3-yl)-phenyl]-4-fluoromethyl-2,2-dimethyl-oxazolidin-3-yl}-2,2-difluoro-ethanone (0.062 g, 0.147 mmol) in CH$_2$Cl$_2$ (5 mL) is added trifluroacetic acid (1.0 mL) at room temperature. The resulting reaction mixture is stirred at room temperature for 5 hours. Solvent is evaporated in vacuo to get the crude residue and diluted with aqueous bicarbonate solution and extracted with ethyl acetate. Organic layer is dried over sodium sulphate, concentrated and purified by combi-flash chromatography using 15% methanol in CH$_2$Cl$_2$ as an eluent. Obtained solid is washed with n-pentane and diethyl ether to afford the title compound (0.035 g) after drying in lypholizer. $^1$H NMR (400 MHz, DMSO-d$_6$) δ: 1.16 (t, J=7.2 Hz, 3H), 2.83-2.88 (q, 2H), 4.14 (s, 2H), 4.30-4.33 (m, 1.5H), 4.41-4.45 (m, 0.5H), 4.55-4.56 (m, 0.5H), 4.65-4.68 (m, 0.5H), 4.89 (t, J=4.08 Hz, 1H), 5.93 (d, J=4.55 Hz, 1H), 6.20 (t, J=53.76 Hz, 1H), 7.47 (d, J=8.24 Hz, 2H), 7.54 (d, J=8.2 Hz, 1H), 7.72 (d, J=8.24 Hz, 2H), 8.12-8.15 (dd, J1=2.32 Hz, J2=8.16 Hz, 1H), 8.85 (d, J=8.8 Hz, 1H), 8.90 (d, J=2.12 Hz, 1H). LC-MS (m/z): [M+H]=382.1.

Example 55

Preparation of N-{(1S,2R)-2-[4-(2-Aminomethyl-oxazol-5-yl)-phenyl]-1-fluoromethyl-2-hydroxy-ethyl}-2,2-dichloro-acetamide

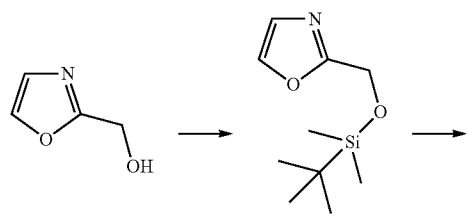

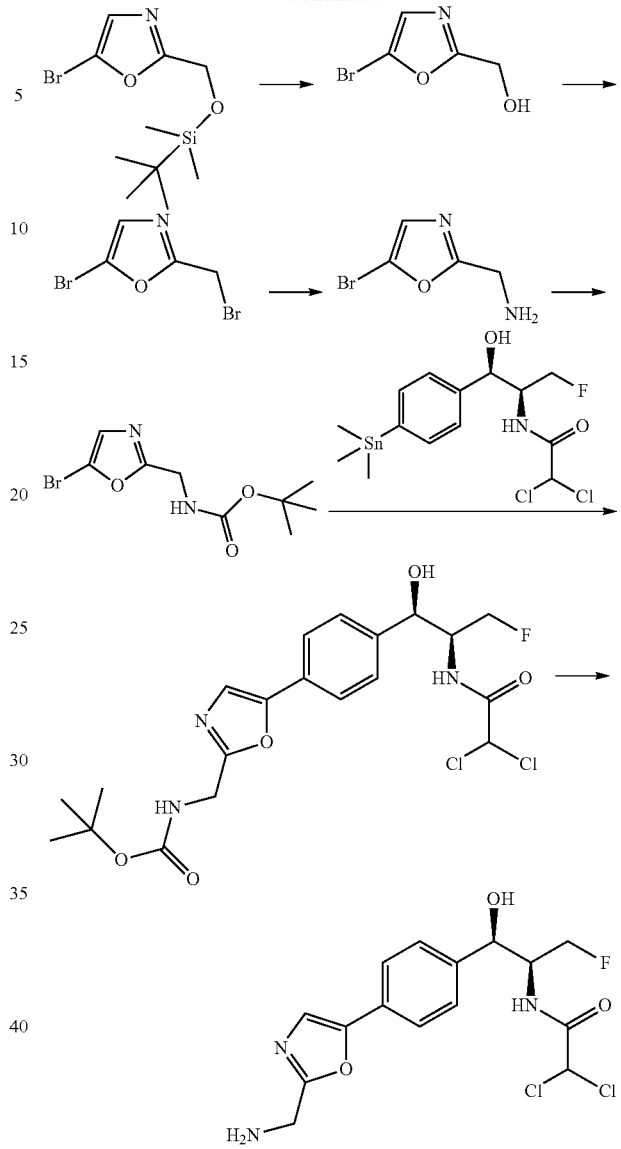

Step 1 Preparation of 2-(tert-Butyl-dimethyl-silanyloxymethyl)-oxazole

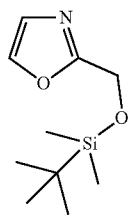

To a solution of oxazol-2-yl-methanol (1.0 g, 0.010 mmol) in dry tetrahydrofuran (15 mL) is added imidazole (1.37 g, 0.020 mmol) and tert-Butyldimethylsilyl chloride (1.97 g, 0.0131 mmol) at 0° C. The reaction mixture is then stirred at room temperature for 4 hours. Reaction mixture is diluted with water and extracted with ethyl acetate. Organic layer is dried over sodium sulphate, solvent is evaporated in vacuo and purified by column chromatography eluting in 5% ethyl acetate in hexane to afford the title compound (0.7 g). $^1$H-NMR (400 MHz, CDCl$_3$) δ: 0.09 (s, 6H), 0.89 (s, 9H), 4.75 (s, 2H), 7.06 (s, 1H), 7.62 (s, 1H). LC-Ms (m/z) [M+H]=214.2.

Step 2 Preparation of 5-Bromo-2-(tert-butyl-dimethyl-silanyloxymethyl)-oxazole

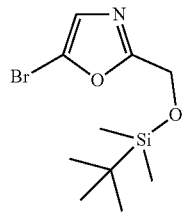

To a solution of 2-(tert-Butyl-dimethyl-silanyloxymethyl)-oxazole) (0.35 g, 1.643 mmol) in dry tetrahydrofuran (8 mL) is added n-Butyl lithium (0.26 g, 4.107 mmol) drop wise under nitrogen atmosphere at −78° C. then stirred at −40° C. for 2 hours. The reaction mixture is again cooled to −78° C. then added carbontetrabromide (1.36 g, 4.107 mmol) and stirred to room temperature for 14 hours. Reaction mixture is diluted with saturated ammonium chloride solution and extracted with ethyl acetate. Organic layer is dried over sodium sulphate, solvent is evaporated in vacuo and purified by column chromatography eluting 2% Ethyl acetate in hexane to afford the crude title compound (0.18 g), which is used in the next step without purification. LC-MS (m/z): [M+H]=294.2.

Step 3 Preparation of (5-Bromo-oxazol-2-yl)-methanol

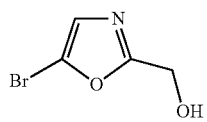

A solution of 5-Bromo-2-(tert-butyl-dimethyl-silanyloxymethyl)-oxazole (0.05 g, 0.171 mmol) in methanol (1.0 mL) is purged with excess of hydrogen chloride gas at 0° C. for 30 minutes. The reaction mixture is stirred to room temperature for 3 hours then concentrated in vacuum to afford title compound (0.03 g), which is used in the next reaction without purification. $^1$H-NMR (400 MHz, DMSO-d$_6$) δ: 3.83 (bs, 1H), 4.47 (s, 2H), 7.26 (s, 1H). LC-MS (m/z): [M+H]=180.1.

Step 4 Preparation of 5-Bromo-2-bromomethyl-oxazole

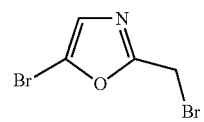

To a stirred solution of (5-Bromo-oxazol-2-yl)-methanol (0.15 g, 0.842 mmol) in dry CH$_2$Cl$_2$ (6.0 mL) added carbon tetrabromide (0.38 g, 1.011 mmol) and triphenyphosphine (0.24 g, 0.962 mmol) at 0° C. then stirred for 2 hours at room temperature. Reaction mixture is concentrated in vacuum and crude material is purified by column chromatography eluting in 5% ethyl acetate in hexane to afford the title compound (0.05 g). $^1$H-NMR (400 MHz, DMSO-d$_6$) δ: 4.42 (s, 2H), 6.99 (s, 1H). LC-Ms (m/z) [M+H] 240.86.

Step 5 Preparation of C-(5-Bromo-oxazol-2-yl)-methylamine

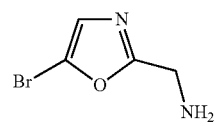

To ammonia solution in methanol (4.0 mL) [Prepared by purging excess ammonia gas in methanol for 15 minutes at room temperature] is added 5-Bromo-2-bromomethyl-oxazole (0.05 g, 0.207 mmol) at room temperature then stir for 14 hours at room temperature. Reaction mixture is concentrated in vacuum to give title compound as hydrochloride salt (0.052 g), which is used in the next step without purification. $^1$H-NMR (400 MHz, DMSO-d$_6$) δ: 4.11 (s, 2H), 7.04 (bs, 3H), 7.36 (s, 1H). LC-Ms (m/z): [M+H]=178.9.

Step 6 Preparation of 5-Bromo-oxazol-2-ylmethyl)-carbamic acid tert-butyl ester

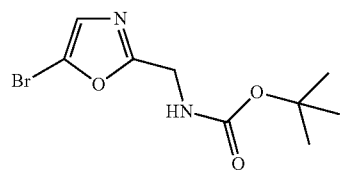

To a stirred solution of C-(5-Bromo-oxazol-2-yl)-methylamine (0.12 g, 0.468 mmol) in Dioxane:water 1:1 (4.0 mL) is added K$_2$CO$_3$ (0.129 g, 0.937 mmol) followed by addition of Di-tert-butyl dicarbonate (0.112 g, 0.515 mmol) at 0° C. then stirred to room temperature for 2 hours. Reaction mixture is diluted with water and extracted with ethyl acetate. Organic layer is dried over sodium sulphate, solvent is evaporated in vacuo and purified by column chromatography eluting in 30% ethyl acetate in hexane to afford the title compound (0.52 g), which is used in the next step without purification. LC-MS (m/z): [M+H]=279.0.

Step 7 Preparation of (5-{4-[(1R,2S)-2-(2,2-Dichloro-acetylamino)-3-fluoro-1-hydroxy-propyl]-phenyl}-oxazol-2-ylmethyl)-carbamic acid tert-butyl ester

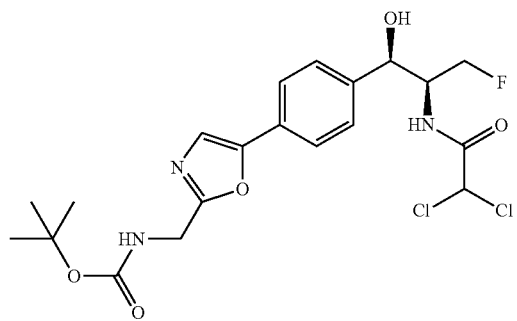 [SMILES: CC(C)(C)OC(=O)NCc1ncc(-c2ccc([C@@H](O)[C@@H](CF)NC(=O)C(Cl)Cl)cc2)o1]

To a stirred solution of 5-Bromo-oxazol-2-ylmethyl)-carbamic acid tert-butyl ester (0.035 g, 0.13 mmol) and 2,2-Dichloro-N-[(1S,2R)-1-fluoromethyl-2-hydroxy-2-(4-trimethylstannanyl-phenyl)-ethyl]-acetamide (0.05 g, 0.11 mmol) in dry toluene (2.0 mL) is added CsF (0.034 g, 0.22 mmol) followed by CuI (0.002 g, 0.011 mmol) at room temperature. The resulting reaction mixture is degassed with nitrogen for 30 minutes then $Pd_2(PPh_3)Cl_2$ (0.008 g, 0.011 mmol) is added and heated in microwave at 100° C. for 30 min. Reaction mixture is diluted with water and extracted with ethyl acetate. Organic layer is dried over sodium sulphate, solvent is evaporated in vacuo and purified by column chromatography eluting in 10% methanol in $CH_2Cl_2$ follow by second purification using preparative HPLC to give the title compound (0.006 g, pure). LC-Ms (m/z): [M−H]=476.0.

Step 8 Preparation of N-{(1S,2R)-2-[4-(2-Aminomethyl-oxazol-5-yl)-phenyl]-1-fluoromethyl-2-hydroxy-ethyl}-2,2-dichloro-acetamide

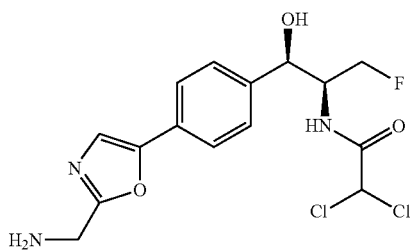

To a stirred solution of (5-{4-[(1R,2S)-2-(2,2-Dichloro-acetylamino)-3-fluoro-1-hydroxy-propyl]-phenyl}-oxazol-2-ylmethyl)-carbamic acid tert-butyl ester (0.006 g, 0.012 mmol) in $CH_2Cl_2$ (1.0 mL) is added trifluoroacetic acid (0.1 mL) at 0° C. and stirred at room temperature for 2 hours. Reaction mixture is concentrated in vacuum and the residue is washed with n-pentane dried under vacuum to give the title compound (0.005 g). $^1$H-NMR (400 MHz, DMSO-$d_6$) δ: 4.22-4.28 (m, 1.5H), 4.31 (s, 2H), 4.40-4.44 (m, 0.5H), 4.56-4.60 (m, 0.5H), 4.68-4.71 (m, 0.5H), 4.89 (m, 1H), 6.02 (d, J=4.28 Hz, 1H), 6.49 (s, 1H), 7.47 (d, J=8.16 Hz, 2H), 7.67 (d, J=8.2 Hz, 2H), 7.72 (s, 1H), 8.21 (bs, 3H), 8.60 (d, J=8.88 Hz, 1H). LC-MS (m/z): [M+H]=376.1.

Example 56

Preparation of 2,2-Dichloro-N-((1S,2R)-1-fluoromethyl-2-hydroxy-2-{4-[6-(isopropylamino-methyl)-pyridin-3-yl]-phenyl}-ethyl)-acetamide

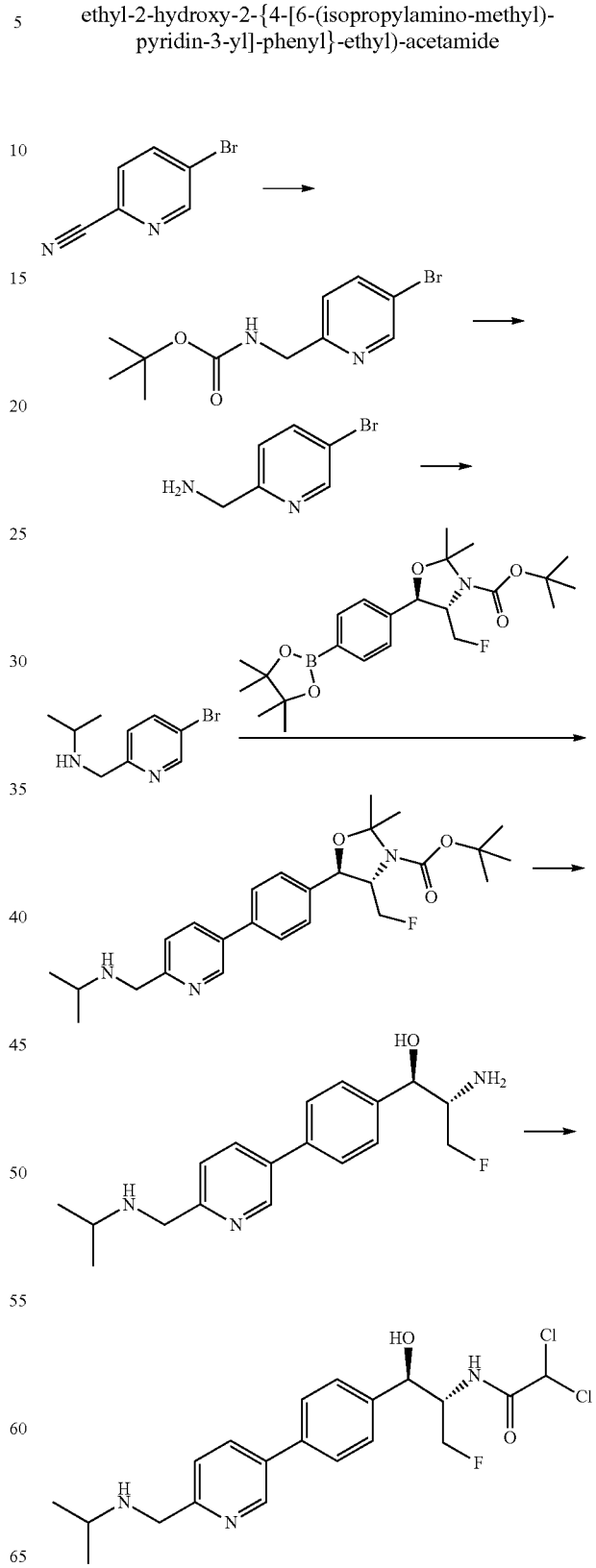

Step 1 Preparation of (5-Bromo-pyridin-2-ylmethyl)-carbamic acid tert-butyl ester

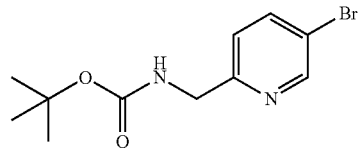 [SMILES: CC(C)(C)OC(=O)NCc1ccc(Br)cn1]

To a solution of 5-Bromo-pyridine-2-carbonitrile (1.0 g, 5.46 mmol) in methanol (10 mL) at 0° C. is added NiCl$_2$.6H$_2$O (0.12 g, 0.54 mmol), Di-tert-butyl dicarbonate (2.38 g, 0.010 mmol) and NaBH$_4$ (0.413 g, 0.010 mmol) at 0° C. then stirred at room temperature for 14 hours. The reaction solvent is removed under reduced pressure and crude is diluted with water and ethyl acetate. The organic layer was separated, dried over sodium sulphate and concentrated in vacuum. The crude is purified by column chromatography eluting with 30% ethyl acetate in hexane to afford the title compound (650 mg). $^1$H-NMR (400 MHz, CDCl$_3$) δ: 1.44 (s, 9H), 4.37 (d, J=5.44 Hz, 2H), 5.41 (bs, 1H), 7.18 (d, J=8.28 Hz, 1H), 7.75-7.78 (dd, J1=8.32 Hz, J2=2.28 Hz, 1H), 8.57 (d, J=2.08 Hz, 1H). LC-MS (m/z): [M+H]=289.0.

Step 2 Preparation of (5-Bromo-pyridin-2-yl)-methylamine

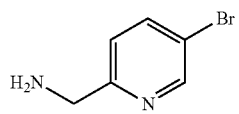

To a solution of (5-Bromo-pyridin-2-ylmethyl)-carbamic acid tert-butyl ester (650 mg, 2.264 mmol) in CH$_2$Cl$_2$ (8.0 mL) is added trifluoroacetic acid (2.0 mL) at 0° C. Reaction mixture is allowed to warm to room temperature and stirred for 4 hours. The volatiles are removed under reduced pressure to afford crude title compound (500 mg). $^1$H-NMR (400 MHz, DMSO-d$_6$) δ: 4.19 (d, J=3.64 Hz, 2H), 7.47 (d, J=8.4 Hz, 1H), 8.14-8.16 (dd, J1=8.36 Hz, J2=2.36 Hz, 1H), 8.32 (bs, 2H), 8.77 (d, J=2.2 Hz, 1H). LC-MS (m/z): [M+H]=189.1.

Step 3 Preparation of (5-Bromo-pyridin-2-ylmethyl)-isopropyl-amine

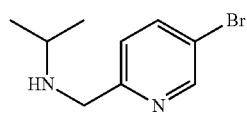

To a solution of (5-Bromo-pyridin-2-yl)-methylamine (0.350 g, 1.871 mmol) in dry acetonitrile (7.0 mL) is added acetone (119 mg, 2.05 mmol) at room temperature.
After stirring for 1 hour at room temperature, sodium Triacetoxy borohydride (595 mg, 2.807 mmol) is added then stir at room temperature for 16 hours. The volatiles are removed under reduced pressure, diluted with saturated aqueous bicarbonate solution and ethyl acetate. The organic layer separated and aqueous layer is extracted with ethyl acetate. Combined organic layer is dried over sodium sulphate, solvent is evaporated in vacuo and crude is purified by column chromatography eluting in 6% methanol in CH$_2$Cl$_2$ to afford the title compound (160 mg). $^1$H-NMR (400 MHz, DMSO-d$_6$) δ: 0.98 (d, J=6.24 Hz, 6H), 2.66-2.73 (m, 1H), 3.76 (s, 2H), 7.44 (d, J=8.36 Hz, 1H), 7.97-7.80 (dd, J1=8.4 Hz, J2=2.4 Hz, 1H), 8.59 (d, J=2.32 Hz, 1H). LC-MS (m/z): [M+H]=230.9.

Step 4 Preparation of (4S,5R)-4-Fluoromethyl-5-{4-[6-(isopropyl amino-methyl)-pyridin-3-yl]-phenyl}-2,2-dimethyl-oxazolidine-3-carboxylic acid tert-butyl ester

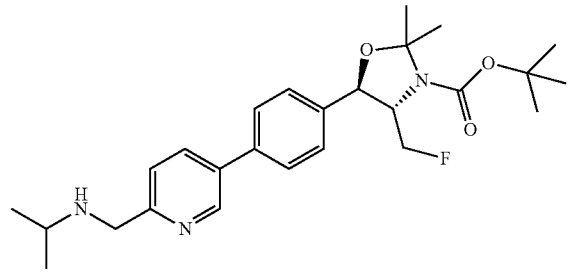 [SMILES: CC(C)NCc1ccc(-c2ccc([C@H]3OC(C)(C)N(C(=O)OC(C)(C)C)[C@@H]3CF)cc2)cn1]

To a solution of (4S,5R)-4-Fluoromethyl-2,2-dimethyl-5-[4-(4,4,5,5-tetramethyl-[1,3,2]dioxaborolan-2-yl)-phenyl]-oxazolidine-3-carboxylic acid tert-butyl ester (270 mg, 0.620 mmol) in dimethoxyethane:water (8:2, 3.6 mL) is added Cs$_2$CO$_3$ (504 mg, 1.55 mmol) and (5-Bromo-pyridin-2-ylmethyl)-isopropyl-amine (156 mg, 0.682 mmol) at room temperature. Reaction mixture is degassed with nitrogen for 30 minutes then Pd(PPh$_3$)$_4$ (71 mg, 0.062 mmol) is added. The resulting reaction mixture is heated to 90° C. for 4 hours. The reaction mixture is diluted with water and ethyl acetate. The organic layer is separated, dried over sodium sulphate and solvent is evaporated in vacuo. The crude is purified by column chromatography eluting in 5% methanol in CH$_2$Cl$_2$ to afford the title compound (100 mg). LC-MS (m/z): [M+H]=458.2.

Step 5 Preparation of (1R,2S)-2-Amino-3-fluoro-1-{4-[6-(isopropyl amino-methyl)-pyridin-3-yl]-phenyl}-propan-1-ol TFA Salt

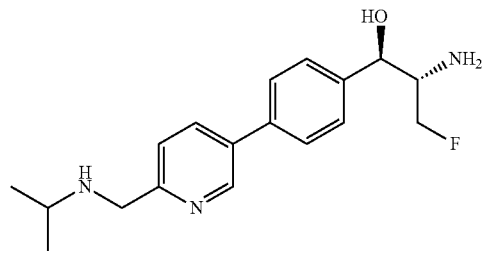 [SMILES: CC(C)NCc1ccc(-c2ccc([C@@H](O)[C@H](N)CF)cc2)cn1]

To a solution of (4R,5R)-4-Fluoromethyl-5-{4-[6-(isopropyl amino-methyl)-pyridin-3-yl]-phenyl}-2,2-dimethyl-oxazolidine-3-carboxylic acid tert-butyl ester (100 mg, 0.218 mmol) in CH₂Cl₂ (0.17 mL) is added trifluoroacetic acid (0.4 mL) at 0° C. Reaction mixture is allowed to stir at room temperature for 2 hours. The volatiles are removed under reduced pressure and crude material is purified by column chromatography over basic alumina using 50% methanol in CH₂Cl₂ as eluent to afford title compound (70 mg, impure). LC-MS (m/z): [M+H]=318.2.

Step 6 Preparation of 2,2-Dichloro-N-((1S,2R)-1-fluoromethyl-2-hydroxy-2-{4-[6-(isopropyl amino-methyl)-pyridin-3-yl]-phenyl}-ethyl)-acetamide

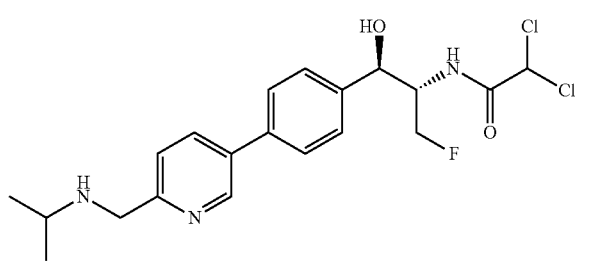 [SMILES: CC(C)NCc1ccc(-c2ccc([C@@H](O)[C@@H](CF)NC(=O)C(Cl)Cl)cc2)cn1]

To a solution of (1R,2S)-2-Amino-3-fluoro-1-{4-[6-(isopropyl amino-methyl)-pyridin-3-yl]-phenyl}-propan-1-ol TFA Salt (70 mg, 0.162 mmol, crude) in dry methanol (0.7 mL) is added ethyl dichloro acetate (51 mg, 0.324 mmol) and triethylamine (32 mg, 0.324 mmol) at room temperature and resulting reaction mixture is stirred for 24 hours. The volatiles are removed under reduced pressure to obtain crude material purified by column chromatography over basic alumina using 5% methanol in CH₂Cl₂ to afford the title compound (21 mg). ¹H-NMR (400 MHz, DMSO-d₆) δ: 1.01 (d, J=6.2 Hz, 6H), 2.70-2.77 (m, 1H), 3.82 (s, 2H), 4.19-4.24 (m, 1H), 4.26-4.31 (m, 0.5H), 4.39-4.43 (m, 0.5H), 4.55-4.59 (m, 0.5H), 4.67-4.71 (m, 0.5H), 4.89 (t, J=3.64 Hz, 1H), 5.99 (d, J=4.16 Hz, 1H), 6.52 (s, 1H), 7.46 (d, J=8.08 Hz, 2H), 7.50 (d, J=7.88 Hz, 1H), 7.66 (d, J=8.2 Hz, 2H), 8.00-8.03 (dd, J1=8.24 Hz, J2=2.4 Hz, 1H), 8.64 (d, J=8.84 Hz, 1H), 8.77 (d, J=2.08 Hz, 1H). LC-MS (m/z): [M+H]=427.9.

Example 57

Preparation of 2,2-Difluoro-N-((1S,2R)-1-fluoromethyl-2-hydroxy-2-{4-[2-(methanesulfonylamino-methyl)-imidazo[1,2-a]pyridin-7-yl]-phenyl}-ethyl)-acetamide

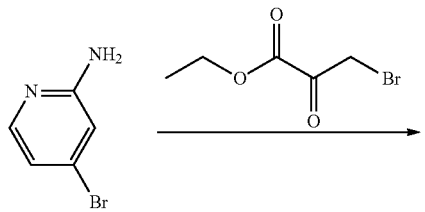

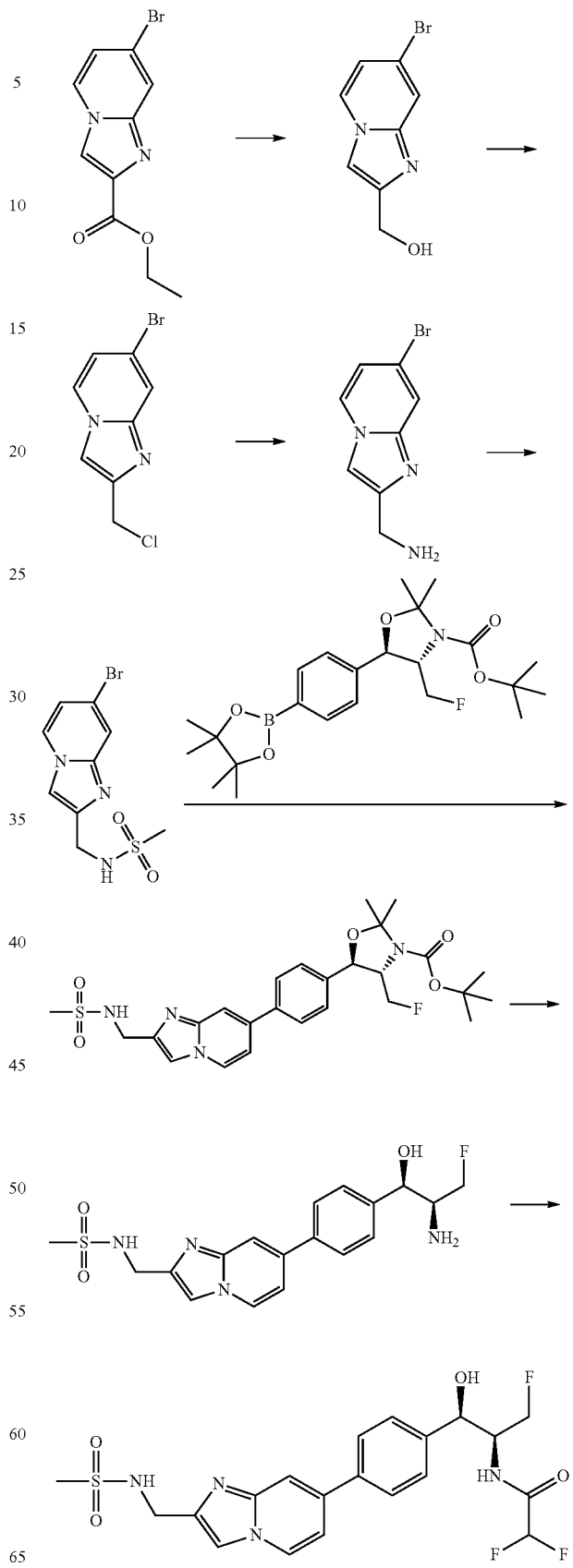

Step 1 Preparation of 7-Bromo-imidazo[1,2-a]pyridine-2-carboxylic acid ethyl ester

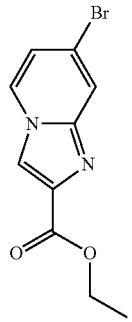

To a stirred solution of 4-Bromo-pyridin-2-ylamine (4 g, 23.12 mmol) in toluene (40 mL) is added 3-Bromo-2-oxo-propionic acid ethyl ester (4.5 g, 23.12 mmol). The reaction mixture is heated at 115° C. for 16 hours. Reaction mixture is cooled to 0° C. then diluted with water and extract with ethyl acetate. Organic layer is dried over sodium sulphate, solvent is evaporated in vacuo to afford the title compound (6.5 g). $^1$H-NMR (400 MHz, DMSO-$d_6$) δ: 1.31 (t, J=7.2 Hz, 3H), 4.26-4.33 (q, J=7.2 Hz, 2H), 7.18-7.20 (dd, J1=1.92 Hz, J2=7.16 Hz, 1H), 7.98 (s, 1H), 8.53 (d, J=7.32 Hz, 1H), 8.57 (s, 1H). LC-MS (m/z): [M+H]=271.0.

Step 2 Preparation of 7-Bromo-imidazo[1,2-a]pyridin-2-yl)-methanol

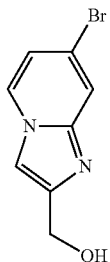 [SMILES: OCc1cn2ccc(Br)cc2n1]

To a stirred solution of 7-Bromo-imidazo[1,2-a]pyridine-2-carboxylic acid ethyl ester (3.3 g, 12.26 mmol) in tetrahydrofuran (30 mL) is added lithium aluminium hydride (2M solution in tetrahydrofuran) (5.8 mL, 12.26 mmol). Reaction mixture is stirred 0° C. for 1 hour. The reaction mixture is diluted with ethyl acetate and the mixture is filtered through Buckner funnel. The residue is dissolved in saturated solution of sodium bicarbonate and extracted with 10% methanol in $CH_2Cl_2$ (30 mL). Organic layer is dried over sodium sulfate, and solvent is evaporated in vacuo to give crude material, purified by column chromatography eluting in 3% MeOH:$CH_2Cl_2$ to afford the title compound (0.340 g). $^1$H-NMR (400 MHz, DMSO-$d_6$) δ: 4.57 (d, J=5.76 Hz, 2H), 5.22 (t, J=5.68 Hz, 1H), 7.00-7.02 (dd, J1=1.96 Hz, J2=7.12 Hz, 1H), 7.76 (d, J=1.64 Hz, 1H), 7.82 (s, 1H), 8.48 (d, J=7.2 Hz, 1H). LC-MS (m/z): [M+H]=227.0.

Step 3 Preparation of 7-Bromo-2-chloromethyl-imidazo[1,2-a]pyridine

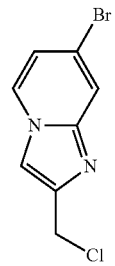 [SMILES: ClCc1cn2ccc(Br)cc2n1]

To a stirred solution of 7-Bromo-imidazo[1,2-a]pyridin-2-yl)-methanol (0.340 g, 1.497 mmol) in $CH_2Cl_2$ (5 mL) is added $SOCl_2$ (0.11 mL, 1.497 mmol) drop wise at 0° C. then stirred at room temperature for 2 hours. The reaction mixture is diluted with saturated sodium bicarbonate and extracted with $CH_2Cl_2$. The organic layer dried over sodium sulfate, and solvent is evaporated under vacuum to afford the title compound (0.325 mg). $^1$H-NMR (400 MHz, DMSO-$d_6$) δ: 4.84 (s, 2H), 7.07-7.09 (dd, J1=1.92 Hz, J2=7.16 Hz), 7.85 (d, J=1.48 Hz, 1H), 8.03 (s, 1H), 8.50 (d, J=7.24 Hz, 1H). LC-MS (m/z): [M+H]=247.0.

Step 4 Preparation of C-(7-Bromo-imidazo[1,2-a]pyridin-2-yl)-methylamine

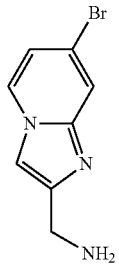 [SMILES: NCc1cn2ccc(Br)cc2n1]

To a stirred solution of 7-Bromo-2-chloromethyl-imidazo[1,2-a]pyridine (0.325 g, 1.326 mmol) in methanol (5 mL), $NH_3$ gas is purged at 0° C. for 30 minutes. The reaction is allowed to stir at room temperature for 16 hours. The solvent is concentrated to afford the title compound (0.315 g). $^1$H-NMR (400 MHz, DMSO-$d_6$) δ: 4.15 (s, 2H), 7.12-7.15 (dd J1=1.96 Hz, J2=7.24 Hz, 1H), 7.90 (s, 1H), 8.03 (s, 1H), 8.32 (bs, 2H), 8.61 (d, J=7.2 Hz, 1H). LC-MS (m/z): [M+H]=225.9.

Step 5 Preparation of N-(7-Bromo-imidazo[1,2-a]pyridin-2-ylmethyl)-methane sulfonamide

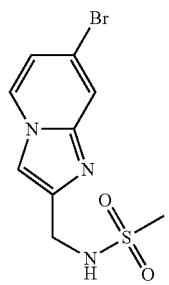 [SMILES: CS(=O)(=O)NCc1cn2ccc(Br)cc2n1]

To a stirred solution of C-(7-Bromo-imidazo[1,2-a]pyridin-2-yl)-methylamine (310 mg, 1.371 mmol) in CH$_2$Cl$_2$ (5 mL) is added triethyl amine (0.23 mL), 1.64 mmol) followed by methane sulfonyl chloride (0.112 mL, 1.371 mmol) at 0° C. then stirred at room temperature for 2 hours. The reaction mixture is diluted with water and extracted with CH$_2$Cl$_2$. Organic layer is dried over sodium sulphate, solvent is evaporated in vacuo and purified by column chromatography eluting in 2% methanol:CH$_2$Cl$_2$ to afford the title compound (130 mg). $^1$H-NMR (400 MHz, DMSO-d$_6$) δ: 2.91 (s, 3H), 4.25 (d, J=6.08 Hz, 2H), 7.04-7.06 (dd, J1=1.88 Hz, J2=7.24 Hz, 1H), 7.58 (t, J=6.12 Hz, 1H), 7.81 (d, J=0.88 Hz, 1H), 7.89 (s, 1H), 8.51 (d, J=7.04 Hz, 1H). LC-MS (m/z): [M+H]=306.0.

Step 6 Preparation of (4S,5R)-4-Fluoromethyl-5-{4-[2-(methanesulfonylamino-methyl)-imidazo[1,2-a]pyridin-7-yl]-phenyl}-2,2-dimethyl-oxazolidine-3-carboxylic acid tert-butyl ester

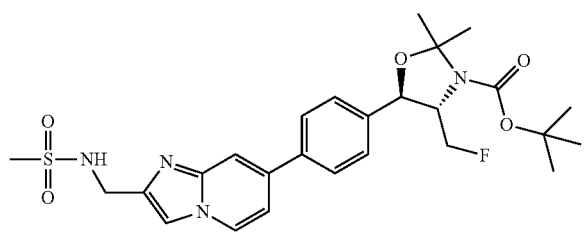 [SMILES: CC(C)(C)OC(=O)N1[C@H](CF)[C@@H](c2ccc(-c3ccn4cc(CNS(C)(=O)=O)nc4c3)cc2)OC1(C)C]

To the solution of N-(7-Bromo-imidazo[1,2-a]pyridin-2-ylmethyl)-methane sulfonamide (71 mg. 0.233 mmol) and (4S,5R)-4-Fluoromethyl-2,2-dimethyl-5-[4-(4,4,5,5-tetramethyl-[1,3,2]dioxaborolan-2-yl)-phenyl]-oxazolidine-3-carboxylic acid tert-butyl ester (111 mg, 0.256 mmol) in dimethoxyethane:water (2.2 mL:0.5 mL) in a microwave tube is added Na$_2$CO$_3$ (62 mg, 0.583 mmol) at room temperature. The resulting reaction mixture is degassed with nitrogen for 30 minutes then added Pd(PPh$_3$)$_2$Cl$_2$ (9 mg, 0.0116 mmol) and heated in microwave at 120° C. for 2 hours. The solvent is evaporated and purified by flash column chromatography eluting in 2% methanol in CH$_2$Cl$_2$ to afford the title compound (75 mg). $^1$H-NMR (400 MHz, DMSO-d$_6$) δ: 1.44 (s, 9H), 1.51 (s, 3H), 1.64 (s, 3H), 2.92 (s, 3H), 3.83-3.89 (m, 1H), 4.28 (d, J=6.12 Hz, 2H), 4.45-4.55 (m, 1H), 4.65-4.75 (m, 1H), 5.13 (d, J=7.2 Hz, 1H), 7.27-7.29 (dd, J1=1.6 Hz, J2=7.20 Hz, 1H), 7.56-7.58 (m, 3H), 7.82-7.88 (m, 4H), 8.61 (d, J=7.2 Hz, 1H). LC-MS (m/z): [M+H]=533.1.

Step 7 Preparation of N-{7-[4-((1R,2S)-2-Amino-3-fluoro-1-hydroxy-propyl)-phenyl]-imidazo[1,2-a]pyridin-2-ylmethyl}-methanesulfonamide

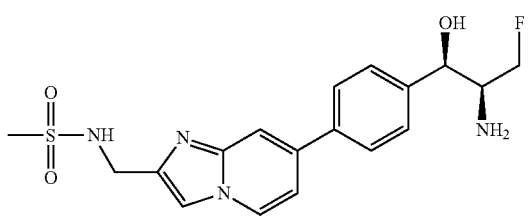 [SMILES: CS(=O)(=O)NCc1cn2ccc(-c3ccc([C@@H](O)[C@H](N)CF)cc3)cc2n1]

To a stirred solution of (4S,5R)-4-Fluoromethyl-5-{4-[2-(methanesulfonylamino-methyl)-imidazo[1,2-a]pyridin-7-yl]-phenyl}-2,2-dimethyl-oxazolidine-3-carboxylic acid tert-butyl ester (75 mg, 0.14 mmol) in CH$_2$Cl$_2$ (1 mL) is added trifluoroacetic acid (0.3 mL) drop wise at 0° C. then stirred at room temperature for 2 hours. The reaction mixture is concentrated and stripped with CH$_2$Cl$_2$ to afford title compound (88 mg, crude) which is used as is in the next step. LC-MS (m/z): [M+H]=393.1.

Step 8 Preparation of 2,2-Difluoro-N-((1S,2R)-1-fluoromethyl-2-hydroxy-2-{4-[2-(methanesulfonylamino-methyl)-imidazo[1,2-a]pyridin-7-yl]-phenyl}-ethyl)-acetamide

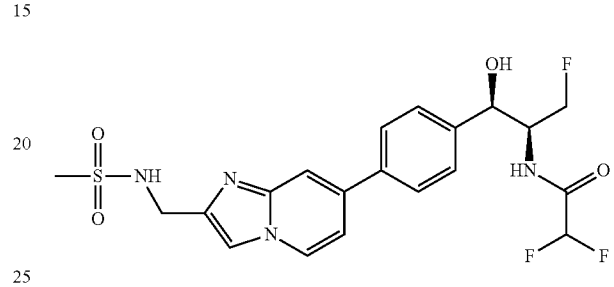

To a stirred solution N-{7-[4-((1R,2S)-2-Amino-3-fluoro-1-hydroxy-propyl)-phenyl]imidazo[1,2-a]pyridin-2-ylmethyl}-methane sulfonamide (88 mg, crude) in methanol (1 mL) is added triethyl amine (0.05 mL, 0.346 mmol) followed by addition of ethyl difluoroacetate (0.02 mL, 0.208 mmol) at 0° C. then stirred at room temperature for 20 h. The reaction mixture is concentrated and purified by flash column chromatography eluting in 2.1% MeOH in CH$_2$Cl$_2$ followed by re-purification by preparative TLC to afford 5 mg and which is re-crystallized in Chloroform: hexane to afford 3 mg of the title compound. $^1$H-NMR (400 MHz, DMSO-d$_6$) δ: 2.94 (s, 3H), 4.31-4.35 (m, 3.5H), 4.41-4.45 (m, 0.5H), 4.54-4.57 (m, 0.5H), 4.65-4.68 (m, 0.5H), 4.89 (t, J=3.96 Hz, 1H), 5.92 (d, J=4.52 Hz, 1H), 6.20 (t, J=53.8 Hz, 1H), 7.34 (d, J=6.16 Hz, 1H), 7.46 (d, J=8.24 Hz, 2H), 7.60 (t, J=6.12, 1H), 7.78-7.83 (m, 3H), 7.90 (s, 1H), 8.63 (d, J=7.16 Hz, 1H), 8.84 (d, J=8.8 Hz, 1H), 8.93 (bs, 1H). LC-MS (m/z): [M+H]=471.2.

Example 58

Preparation of N-((1S,2R)-2-{4-[6-(1-Amino-2,2,2-trifluoro-ethyl)-pyridin-3-yl]-phenyl}-1-fluoromethyl-2-hydroxy-ethyl)-2,2-difluoro-acetamide

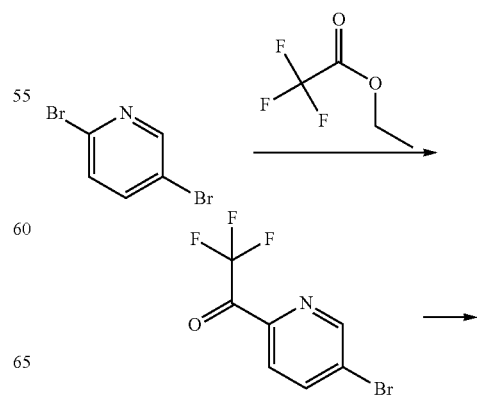

-continued

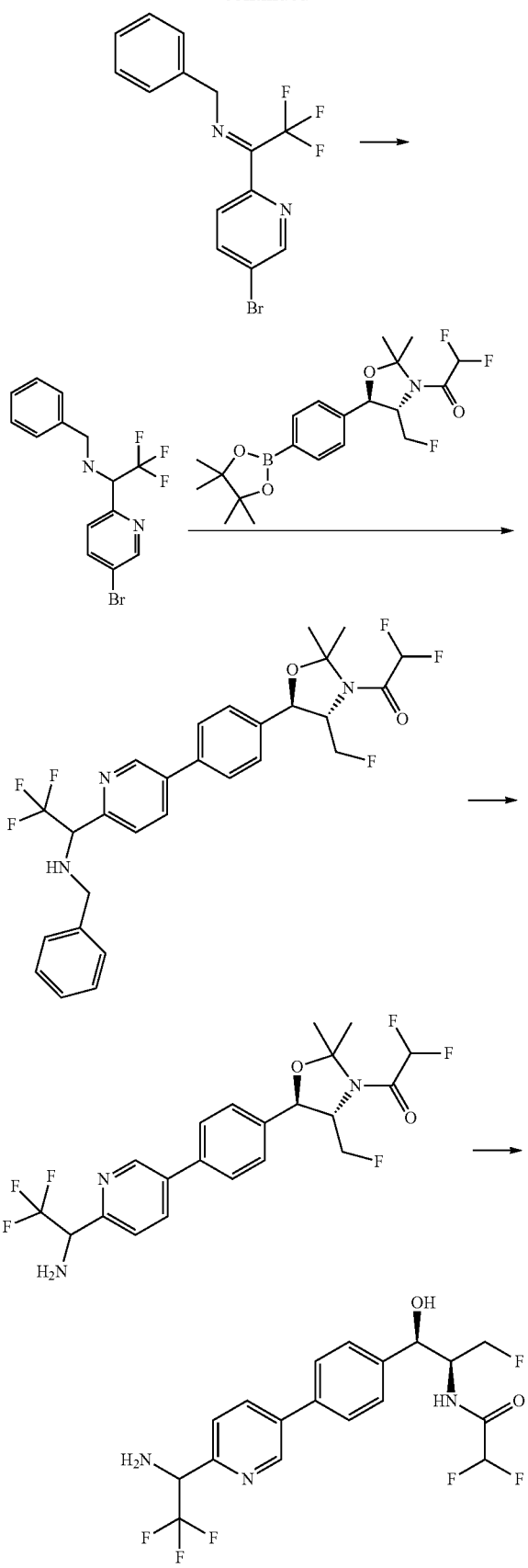

Step 1 Preparation of 1-(5-Bromo-pyridin-2-yl)-2,2,2-trifluoro-ethanone

To a stirred solution of 2, 5-Dibromo-pyridine (4 g, 6.87 mmol) in dry tetrahydrofuran (30 mL) and dry toluene (40 mL) is added drop wise n-Butyl lithium (1.62 g, 25.31 mmol) at −78° C. After stirring for 15-20 minutes, added trifluoro-acetic acid ethyl ester (3.56 g, 25.31 mmol) at −78° C. then stirred at −78° C. for another 30 minutes. The reaction mixture is diluted with saturated ammonium chloride solution and extracted with ethyl acetate. Organic layer is dried over sodium sulphate, solvent is evaporated in vacuo and purified by column chromatography eluting in 20% ethyl acetate in hexane to afford the title compound (1.2 g). $^1$HNMR (400 MHz, DMSO-$d_6$) δ: 7.72 (d, J=8.32 Hz, 1H), 7.85-7.88 (dd, J1=8.32 Hz, J2=2.44 Hz 1H), 8.52 (d, J=2.36 Hz, 1H). LC-MS (m/z): [M+H]=255.8.

Step 2 Preparation of Benzyl-[1-(5-bromo-pyridin-2-yl)-2,2,2-trifluoro-eth-(E)-ylidene]-amine To a solution of 1-(5-Bromo-pyridin-2-yl)-2,2,2-trifluoro-ethanone (7.5 g, 29.52 mmol) in dry toluene (30 mL) is added benzylamine (3.15 g, 29.52 mmol) and titanium ethoxide (7.4 g, 32.48 mmol) at room temperature then stir for 3 hours. Reaction mixture is diluted with saturated sodium bicarbonate solution and extracted with ethyl acetate. Organic layer is dried over sodium sulphate, solvent is evaporated in vacuo and purified by column chromatography eluting in 20% ethyl acetate in hexane to afford the title compound (0.45 g). LC-MS (m/z): [M+H]=345.0.

Step 3 Preparation of Benzyl-[1-(5-bromo-pyridin-2-yl)-2,2,2-trifluoro-ethyl]-amine

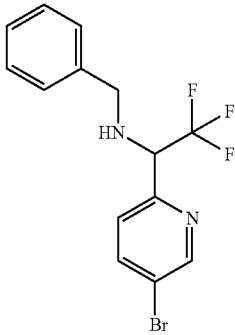 [SMILES: FC(F)(F)C(NCc1ccccc1)c1ccc(Br)cn1]

To a stirred solution of Benzyl-[1-(5-bromo-pyridin-2-yl)-2,2,2-trifluoro-eth-(E)-ylidene]-amine (0.45 g, 1.31 mmol) in methanol (20 mL) is added sodium triacetoxy borohydride (0.55 g, 2.62 mmol) at 0° C. then stir at room temperature for 3 hours. Reaction mixture is diluted with water and extracted with ethyl acetate. Organic layer is dried over sodium sulphate, solvent is evaporated in vacuo and purified by column chromatography eluting in 10% ethyl acetate in hexane to afford the title compound (0.15 g). $^1$H NMR (400 MHz, DMSO-$d_6$) δ: 3.57-3.61 (m, 1H), 3.64-3.73 (m, 2H), 4.50 (m, 1H), 7.22-7.25 (m, 1H), 7.28-7.29 (m, 4H), 7.73 (d, J=8.2 Hz, 1H), 7.91-7.93 (dd, J1=8.2 Hz, J2=2.24 Hz, 1H), 8.48 (d, J=2.08 Hz, 1H). LC-MS (m/z): [M+H]=347.0.

Step 4 Preparation of 1-((4R,5R)-5-{4-[6-(1-Benzylamino-2,2,2-trifluoro-ethyl)-pyridin-3-yl]-phenyl}-4-fluoromethyl-2,2-dimethyl-oxazolidin-3-yl)-2,2-difluoro-ethanone

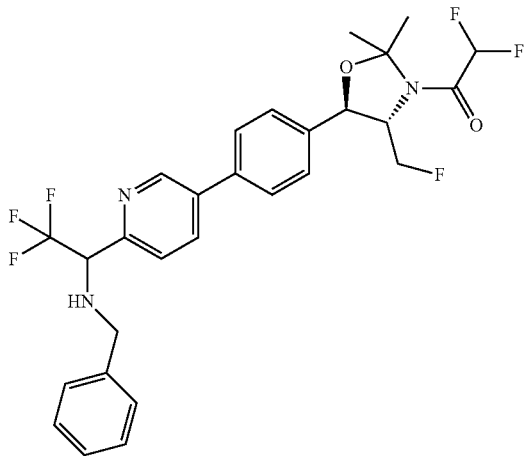 [SMILES: CC1(C)O[C@H](c2ccc(-c3ccc(C(NCc4ccccc4)C(F)(F)F)nc3)cc2)[C@@H](CF)N1C(=O)C(F)F]

To a stirred solution of Benzyl-[1-(5-bromo-pyridin-2-yl)-2,2,2-trifluoro-ethyl]-amine (0.15 g, 0.43 mmol) and 2,2-Difluoro-1-{(4S,5R)-4-fluoromethyl-2,2-dimethyl-5-[4-(4,4,5,5-tetramethyl-[1,3,2]dioxaborolan-2-yl)-phenyl]-oxazolidin-3-yl}-ethanone (0.18 g, 0.43 mmol) in toluene: ethanol:water (1:1:1; 7:7:7 mL) is added Na$_2$CO$_3$ (0.11 g, 1.08 mmol) at room temperature. Resulting reaction mixture is degassed with nitrogen for 30 minutes then added Pd(PPh$_3$)$_4$ (0.05 g, 0.043 mmol) and mixture is heated to 80° C. for 3 hours. Reaction mixture is concentrated in vacuo and crude material is purified by combi-flash eluting in 20% Ethyl acetate in Hexane to afford the title compound (0.22 g). $^1$H NMR (400 MHz, DMSO) δ: 1.52 (s, 3H), 1.60 (s, 3H), 3.59-3.69 (m, 2H), 3.73-3.78 (m, 1H), 4.47-4.51 (m, 0.5H), 4.55-4.59 (m, 0.5H), 4.66-4.72 (m, 1H), 4.75-4.79 (m, 0.5H), 4.80-4.93 (m, 0.5H), 5.28 (d, J=3.68 Hz 1H), 6.65 (t, J=51.92 Hz, 1H) 7.23-7.24 (m, 2H), 7.26-7.31 (m, 3H), 7.56-7.62 (m, 3H), 7.75 (d, J=8.16 Hz, 1H), 8.06 (s, 1H), 8.16 (d, J=8.32 Hz 1H), 8.73 (s, 1H). LC-MS (m/z): [M+H]=552.1.

Step 5 Preparation of 1-((4R,5R)-5-{4-[6-(1-Amino-2,2,2-trifluoro-ethyl)-pyridin-3-yl]-phenyl}-4-fluoromethyl-2,2-dimethyl-oxazolidin-3-yl)-2,2-difluoro-ethanone

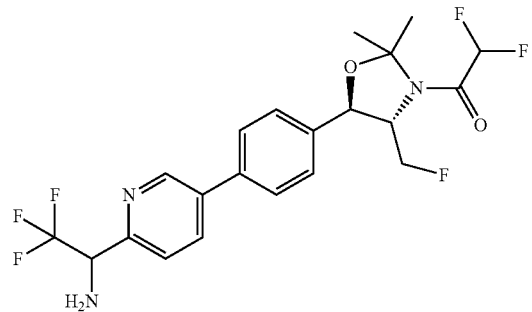 [SMILES: CC1(C)O[C@H](c2ccc(-c3ccc(C(N)C(F)(F)F)nc3)cc2)[C@@H](CF)N1C(=O)C(F)F]

A stirred solution of 1-((4R,5R)-5-{4-[6-(1-Benzylamino-2,2,2-trifluoro-ethyl)-pyridin-3-yl]-phenyl}-4-fluoromethyl-2,2-dimethyl-oxazolidin-3-yl)-2,2-difluoro-ethanone (0.22 g, 0.63 mmol) in methanol (10 mL) at room temperature is degassed with nitrogen for 10 minutes followed by addition of palladium on carbon (0.022 g, 0.0063 mmol). The reaction mixture is stirred at room temperature under hydrogen atmosphere for 16 hours. Reaction mixture is filter through celite, concentrated in vacuo. The crude material is purified by Combi flash eluting in 80% Ethyl acetate in Hexane afford the title compound (0.035 g). 1H-NMR (400 MHz, DMSO-$d_6$) δ: 1.52 (s, 3H), 1.60 (s, 3H), 2.60-2.80 (m, 2H), 4.54-4.58 (m, 0.5H), 4.64-4.73 (m, 2H), 4.81-4.85 (m, 0.5H), 4.91-4.95 (m, 1H), 5.27 (d, J=3.6 Hz, 1H), 6.65 (t, J=52.44 HZ, 1H), 7.60 (d, J=8.28 Hz, 2H), 8.03 (m, 2H), 8.14 (d, J=8.32 Hz, 2H), 8.75 (s, 1H). LC-MS (m/z): [M+H]=462.0.

Step 6 Preparation of N-((1S,2R)-2-{4-[6-(1-Amino-2,2,2-trifluoro-ethyl)-pyridin-3-yl]-phenyl}-1-fluoromethyl-2-hydroxy-ethyl)-2,2-difluoro-acetamide

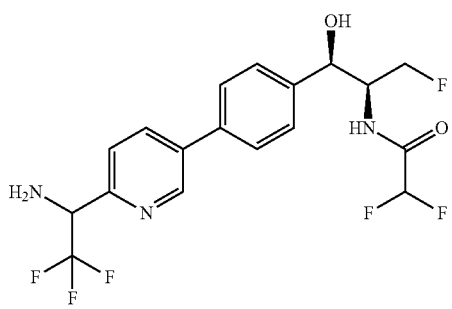 [SMILES: NC(c1ccc(-c2ccc([C@@H](O)[C@@H](CF)NC(=O)C(F)F)cc2)cn1)C(F)(F)F]

To a stirred solution of 1-((4R,5R)-5-{4-[6-(1-Amino-2,2,2-trifluoro-ethyl)-pyridin-3-yl]-phenyl}-4-fluoromethyl-2,2-dimethyl-oxazolidin-3-yl)-2,2-difluoro-ethanone (35 mg, 0.076 mmol) in CH$_2$Cl$_2$ (1 mL) is added trifluoroacetic acid (1 mL) at 0° C. then stirred to room temperature for 3 hours. The solvent evaporated in vacuo and the crude material is diluted with ammonia solution and extract with ethyl acetate. Organic layer is dried over sodium sulphate, solvent is evaporated in vacuo and purified by preparative TLC using in 70% ethyl acetate in hexane to afford the title compound (0.013 g): 1H-NMR (400 MHz, DMSO-d$_6$) δ: 2.66 (d, J=7.28 Hz, 2H), 4.30-4.36 (m, 1.5H), 4.40-4.44 (m, 0.5H), 4.54-4.55 (m, 0.5H), 4.61-4.68 (m, 1.5H), 4.89 (t, J=3.8 Hz, 1H), 5.93 (d, J=4.36 Hz, 1H), 6.19 (t, J=53.8 Hz, 1H), 7.45 (d, J=8.32 Hz, 2H), 8.00 (d, 1.16 Hz, 2H), 8.05 (d, J=8.28 Hz, 2H), 8.73 (s, 1H), 8.84 (d, J=8.56 Hz, 1H). LC-MS (m/z): [M+H]=422.0.

Example 59

Preparation of 2,2-Difluoro-N-((1S,2R)-1-fluoromethyl-2-hydroxy-2-{4-[6-(2,2,2-trifluoro-1-methyl-amino-ethyl)-pyridin-3-yl]-phenyl}-ethyl)-acetamide Step 1 Preparation of [1-(5-Bromo-pyridin-2-yl)-2,2,2-trifluoro-eth-(E)-ylidene]-methyl-amine

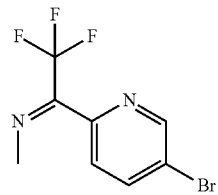

To a stirred solution of 1-(5-Bromo-pyridin-2-yl)-2,2,2-trifluoro-ethanone (1.0 g, 3.93 mol) and methylamine (20 ml, tetrahydrofuran solution) is added titanium ethoxide (0.987 g, 4.33 mmole) at 0° C. then stirred at room temperature for 2 hours. Reaction mixture is diluted with saturated sodium bicarbonate solution and extracted with ethyl acetate. Organic layer is dried over sodium sulphate, concentrated and purified by column chromatography eluting in 20% ethyl acetate in hexane to give the title compound

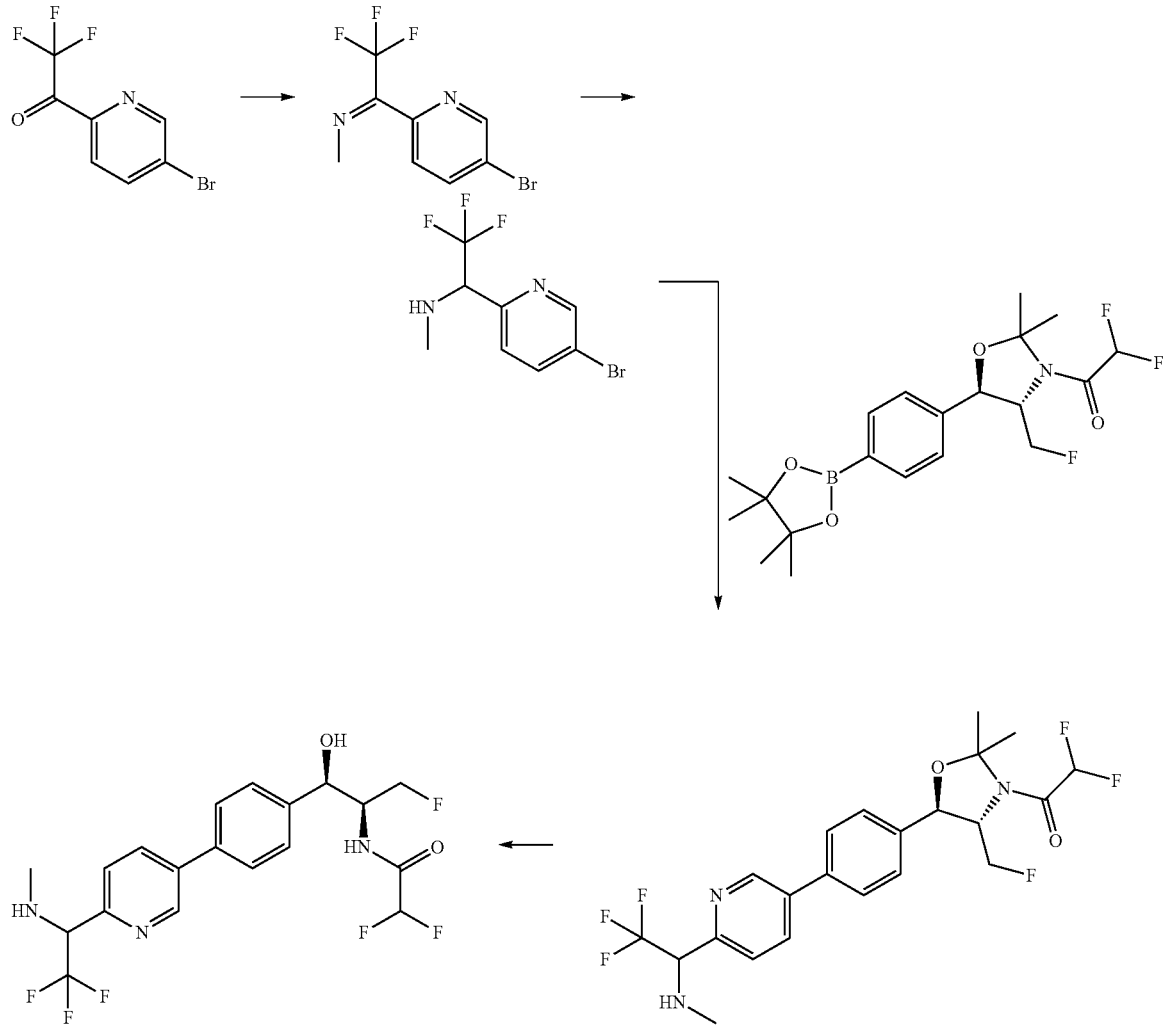

(0.10 g). ¹H-NMR (400 MHz, DMSO) δ: 3.25-3.26 (m, 3H), 7.85-7.90 (m, 2H), 8.49 (s, 1H). LC-MS (m/z): [M+H]=266.8.

Step 2 Preparation of [1-(5-Bromo-pyridin-2-yl)-2,2,2-trifluoro-ethyl]-methyl-amine

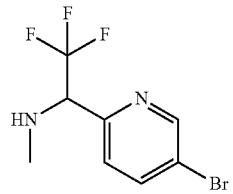

To a stirred solution of [1-(5-Bromo-pyridin-2-yl)-2,2,2-trifluoro-eth-(E)-ylidene]-methyl-amine (0.1 g, 0.375 mmol) in methanol (5 mL) is added sodium cyano borohydride (0.027 g, 0.449 mmol) at 0° C. then stirred room temperature for 2 h. Reaction mixture is diluted with saturated sodium bicarbonate solution and extracted with ethyl acetate. Organic layer is dried over sodium sulphate, solvent is evaporated in vacuo and purified by column chromatography eluting in 10% ethyl acetate in hexane to give the crude title compound (0.075 g, crude). ¹H-NMR (400 MHz, DMSO) δ: 2.21 (d, J=5.32 Hz, 3H), 3.04 (m, 1H), 4.46 (m, 1H), 7.74 (d, J=8.24 Hz, 1H), 8.87 (dd, J1=2.4 Hz, J2=8.28 Hz, 1H), 8.48 (d, J1=2.36 Hz, 1H). LC-MS (m/z): [M+H]=271.2.

Step 3 Preparation of 2,2-Difluoro-1-((4S,5R)-4-fluoromethyl-2,2-dimethyl-5-{4-[6-(2,2,2-trifluoro-1-methylamino-ethyl)-pyridin-3-yl]-phenyl}-oxazolidin-3-yl)ethanone

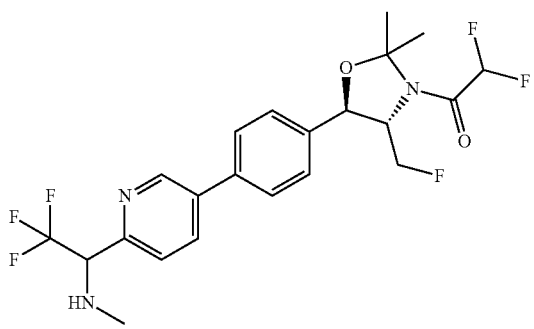 [SMILES: CNC(c1ccc(-c2ccc([C@H]3OC(C)(C)N(C(=O)C(F)F)[C@@H]3CF)cc2)cn1)C(F)(F)F]

To a stirred solution of [1-(5-Bromo-pyridin-2-yl)-2,2,2-trifluoro-ethyl]-methyl-amine (0.075 g, 0.279 mmol) and 2,2-Difluoro-1-{(4S,5R)-4-fluoromethyl-2,2-dimethyl-5-[4-(4,4,5,5-tetramethyl-[1,3,2]dioxaborolan-2-yl)-phenyl]-oxazolidin-3-yl}-ethanone (0.115 g, 0.279 mmol) in toluene:ethanol:water (3:3:3 mL) is added Na₂CO₃ (0.073 g, 0.697 mmol) at room temperature. Resulting reaction mixture is degassed with nitrogen for 30 minutes followed by addition of Pd(PPh₃)₄ (0.032 g, 0.028 mmol) and heated to 80° C. for 3 h. The reaction mixture is concentrated in vacuo then is diluted with water and extracted with ethyl acetate. Organic layer is dried over sodium sulphate and evaporated in vacuum. The crude material is purified by Combi-flash eluting in 20% ethyl acetate in hexane afford the title compound (0.120 g). ¹H-NMR (400 MHz, DMSO) δ: 1.52 (s, 3H), 1.60 (s, 3H), 2.25 (d, J=5.76 Hz, 3H), 3.01-3.05 (m, 1H), 4.44-4.48 (m, 1H), 4.56-4.58 (m, 0.5H), 4.67-4.72 (m, 1H), 4.81-4.88 (m, 0.5H), 4.90-5.00 (m, 1H), 5.27 (d, J=3.68 Hz, 1H), 6.65 (t, J=52.36 Hz, 1H), 7.60 (d, J=8.24 Hz, 2H), 7.98-8.00 (dd, J1=2.04 Hz, J2=8.2 Hz, 1H), 8.06 (d, J=8.24 Hz, 1H), 8.15 (d, J=8.32, 2H), 8.73 (d, J=1.8 Hz, 1H). LC-MS (m/z): [M−H]=476.0.

Step 4 Preparation of 2,2-Difluoro-N-((1S,2R)-1-fluoromethyl-2-hydroxy-2-{4-[6-(2,2,2-trifluoro-1-methylamino-ethyl)-pyridin-3-yl]-phenyl}-ethyl)-acetamide

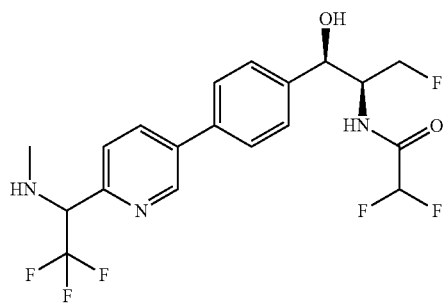 [SMILES: CNC(c1ccc(-c2ccc([C@@H](O)[C@@H](CF)NC(=O)C(F)F)cc2)cn1)C(F)(F)F]

To a solution of 2,2-Difluoro-1-((4S,5R)-4-fluoromethyl-2,2-dimethyl-5-{4-[6-(2,2,2-trifluoro-1-methylamino-ethyl)-pyridin-3-yl]-phenyl}-oxazolidin-3-yl) ethanone (0.12 g, 0.235 mmol) in CH₂Cl₂ (2 mL) is added trifluoroacetic acid (0.5 mL) at 0° C. then is stirred to room temperature for 2 hours. Reaction solvent evaporated in vacuo then diluted with sodium bicarbonate solution and extract with ethyl acetate. Organic layer is dried over sodium sulphate, solvent is evaporated in vacuo and purified by combiflash eluting in 5% Methanol in CH₂Cl₂ to afford the title compound (0.028 g). ¹H-NMR (400 MHz, DMSO) δ: 2.25 (d, J=5.84 Hz, 3H), 3.00-3.04 (m, 1H), 4.31-4.35 (m, 1.5H), 4.41-4.46 (m, 1.5H), 4.55-4.56 (m, 0.5H), 4.65-4.68 (m, 0.5H), 4.90 (m, 1H), 5.93 (d, J=4.36 Hz, 1H), 6.19 (d, J=53.72 Hz, 1H), 7.46 (d, J=8.32 Hz, 2H), 7.95-7.98 (dd, J1=1.96 HzHz, J2=8.32 Hz, 1H), 8.03 (d, J=8.32 Hz, 1H), 8.06 (d, J=8.48 Hz, 2H), 8.71 (d, J=1.88 Hz, 1H), 8.84 (d, J=8.72 Hz, 1H). LC-MS (m/z): [M+H]=436.0.

Example 60

Preparation of 2,2-Difluoro-N-((1S,2R)-1-fluoromethyl-2-hydroxy-2-{4-[6-(1-morpholin-4-yl-ethyl)-pyridin-3-yl]-phenyl}-ethyl)-acetamide

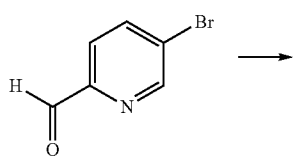

-continued

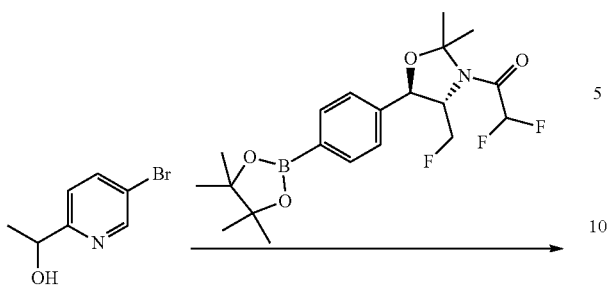

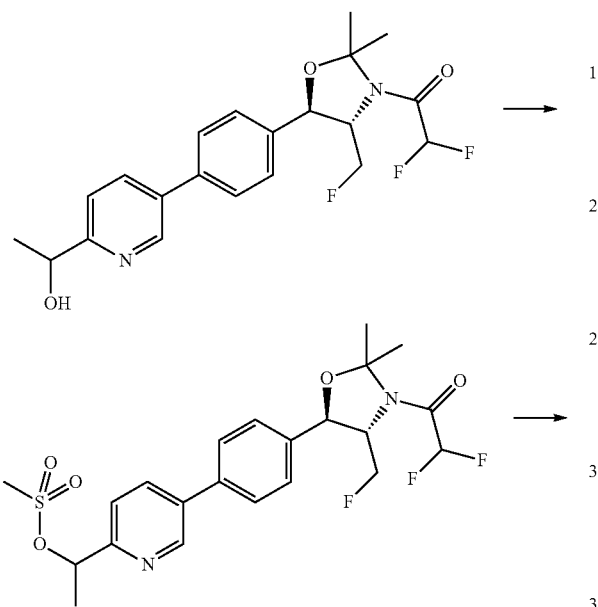

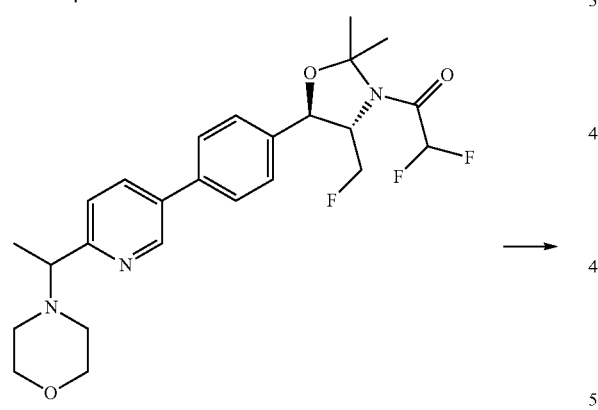

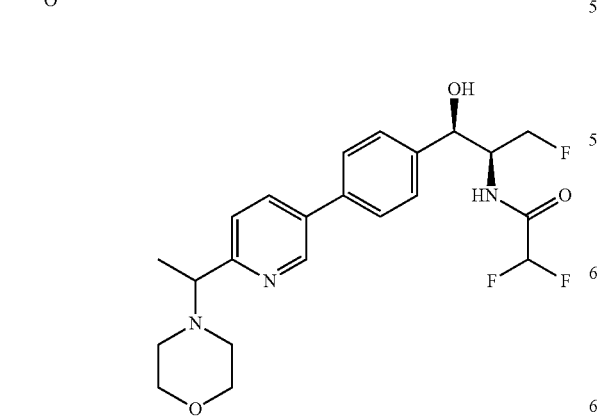

Step 1 Preparation of
1-(5-Bromo-pyridin-2-yl)-ethanol

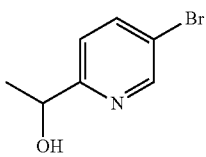

To a stirred solution of 5-Bromo-pyridine-2-carbaldehyde (10 g, 53.76 mmol) in tetrahydrofuran (200 mL) at 0° C. is added drop wise methyl magnesium bromide (45 mL, 64.51 mmol). Reaction mixture is stirred 0° C. for 6 hours and diluted using saturated ammonium chloride solution and extracted with ethyl acetate. Organic layer is dried over sodium sulphate, concentrated and purified by combiflash using 25% ethyl acetate in hexane as an eluent to give the title compound (8 g). 1H NMR (400 MHz, DMSO-d$_6$) δ: 1.34 (d, J=6.52 Hz, 3H), 4.66-4.72 (m, 1H), 5.47 (d, J=4.76 Hz, 1H), 7.48 (d, 8.36 Hz, 1H), 8.021 (dd, J1=2.44 Hz, J2=8.44 Hz 1H), 8.58 (d, J=2.36 Hz, 1H). LC-Ms (m/z): 203.9 [M+H].

Step 2 Preparation of 2,2-Difluoro-1-((4S,5R)-4-fluoromethyl-5-{4-[6-(1-hydroxy-ethyl)-pyridin-3-yl]-phenyl}-2,2-dimethyl-oxazolidin-3-yl)-ethanone

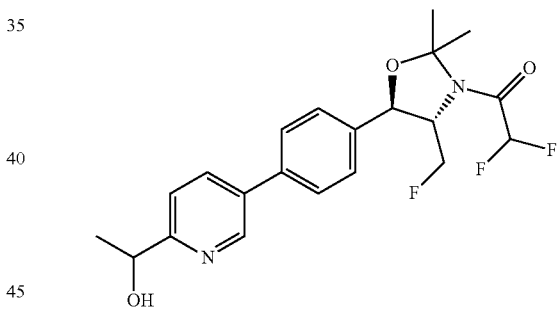

To a stirred solution of 2,2-Difluoro-1-{(4S,5R)-4-fluoromethyl-2,2-dimethyl-5-[4-(4,4,5,5tetramethyl-[1,3,2]dioxaborolan-2-yl)-phenyl]-oxazolidin-3-yl}-ethanone (3 g, 7.26 mmol) and 1-(5-Bromo-pyridin-2-yl)-ethanol (1.46 g, 7.26 mmol) in toluene: ethanol: water (15:15:7 mL) is added Na$_2$CO$_3$ (2.3 g, 21.79 mmol) at room temperature. Resulting reaction mixture is degassed with nitrogen for 30 minutes then Pd(PPh$_3$)$_4$ (0.839 g, 0.726 mmol) is added. The reaction mixture is heated to 100° C. for 16 hours. Solvent is evaporated in vacuo and the crude material is purified by combi-flash using 55% ethyl acetate in hexane as an eluent to afford the title compound (2.2 g). 1H NMR (400 MHz, DMSO-d$_6$) δ: 1.39 (d, J=6.6 Hz, 3H), 1.53 (s, 3H), 1.60 (s, 3H), 4.57-4.58 (m, 0.5H), 4.69-4.70 (m, 1H), 4.75-4.77 (m, 1H), 4.78-7.80 (m, 0.5H), 4.89-4.94 (m, 1H), 5.26 (d, J=3.88 Hz, 1H), 5.41 (d, J=4.6 Hz, 1H), 6.64 (t, J1=52.32 Hz, 1H), 7.57-7.64 (m, 3H), 7.77 (d, J=8.16 Hz, 2H), 8.08 (dd, J1=8.2 Hz, J2=2.32 Hz, 1H), 8.80 (d, J=2.04 Hz, 1H). LC-Ms (m/z): 409 [M+H].

Step 3 Methanesulfonic acid 1-(5-{4-[(4S,5R)-3-(2,2-difluoro-acetyl)-4-fluoromethyl-2,2-dimethyl-oxazolidin-5-yl]-phenyl}-pyridin-2-yl)-ethyl ester

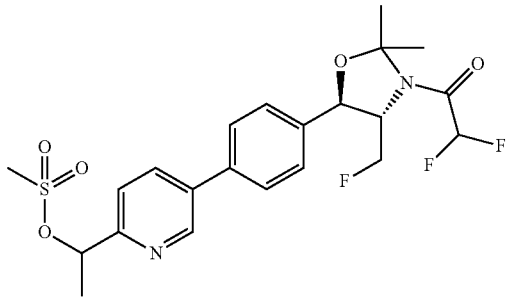 [SMILES: CC(OS(C)(=O)=O)c1ccc(-c2ccc([C@H]3OC(C)(C)N(C(=O)C(F)F)[C@@H]3CF)cc2)cn1]

To a stirred solution of 2,2-Difluoro-1-((4S,5R)-4-fluoromethyl-5-{4-[6-(1-hydroxy-ethyl)-pyridin-3-yl]-phenyl}-2,2-dimethyl-oxazolidin-3-yl)-ethanone (2.2 g, 5.39 mmol) in CH$_2$Cl$_2$ (25 mL) is added triethylamine (1.51 mL, 10.78 mmol) and methane sulfonyl chloride (0.527 mL, 6.47 mmol). Reaction mixture is stirred at 0° C. for 30 minutes then diluted using saturated bicarbonate solution and extracted with CH$_2$Cl$_2$ (30 mL) Organic layer is dried over sodium sulphate, solvent is evaporated in vacuo and purified by combiflash using 45% ethyl acetate in hexane as an eluent to afford the title compound (1.8 g). 1H NMR (400 MHz, DMSO-d$_6$) δ: 1.53 (s, 3H), 1.60 (s, 3H), 1.68 (d, J=6.56 Hz, 3H), 3.21 (s, 3H), 4.54-4.58 (m, 0.5H), 4.66-4.71 (m, 1H), 4.81-4.84 (m, 0.5H), 4.90-4.95 (m, 1H), 5.27 (d, J=3.92 Hz, 1H), 5.79-5.84 (m, 1H), 6.64 (t, J=52.24, 1 H), 7.60-7.63 (m, 3H), 7.81 (d, J=8.2 Hz, 2H), 8.17-8.20 (dd, J1=8.08 Hz, J2=2.24 Hz, 1H), 8.92 (d, J=2.00 Hz, 1H). LC-Ms (m/z): 487.1 [M+H].

Step 4 2,2-Difluoro-1-((4S,5R)-4-fluoromethyl-2,2-dimethyl-5-{4-[6-(1-morpholin-4-yl-ethyl)-pyridin-3-yl]-phenyl}-oxazolidin-3-yl)-ethanone

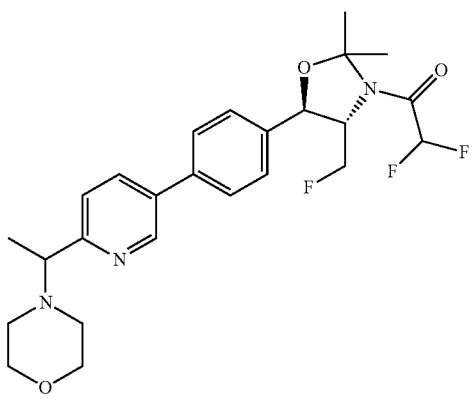 [SMILES: CC(c1ccc(-c2ccc([C@H]3OC(C)(C)N(C(=O)C(F)F)[C@@H]3CF)cc2)cn1)N1CCOCC1]

To a stirred solution of Methanesulfonic acid 1-(5-{4-[(4S,5R)-3-(2,2-difluoro-acetyl)-4-fluoromethyl-2,2-dimethyl-oxazolidin-5-yl]-phenyl}-pyridin-2-yl)-ethyl ester (0.150 g, 0.309 mmol) in acetonitrile (2 mL) is added diisopropylethylamine (0.161 mL, 0.926 mmol) and morphline (0.054 mL, 0.617 mmol). Reaction mixture is stirred at 60° C. for 16 h. The solvent is evaporated in vacuo and the crude material is purified by combiflash using 1% methanol:CH$_2$Cl$_2$ as an eluent to afford the title compound (0.101 g). 1H NMR (400 MHz, CDCl$_3$) δ 1.33 (d, J=6.48 Hz, 3H), 1.53 (s, 3H), 1.60 (s, 3H), 2.32-2.33 (m, 2H), 2.45-2.50 (m, 2H), 3.53-3.58 (m, 4H), 3.60-3.63 (m, 1H), 4.54-4.58 (m, 0.5H), 4.66-4.72 (m, 1H), 4.80-4.84 (m, 0.5H), 4.90-4.94 (m, 1H) 5.26 (d, J=4 Hz, 1H), 6.64 (t, J=52.32, 1H), 7.50 (d, J=8.2 Hz, 2H), 7.59 (d, J=8.12 Hz, 2H), 7.78 (d, J=8.24 Hz, 2H), 8.06-8.10 (dd, J1=8.8 Hz, J2=6.48 Hz, 1H), 8.83 (d, J=2.24 Hz, 1H). LCMS—not ionized.

Step 5 Preparation of 2,2-Difluoro-N-((1S,2R)-1-fluoromethyl-2-hydroxy-2-{4-[6-(1-morpholin-4-yl-ethyl)-pyridin-3-yl]-phenyl}-ethyl)-acetamide

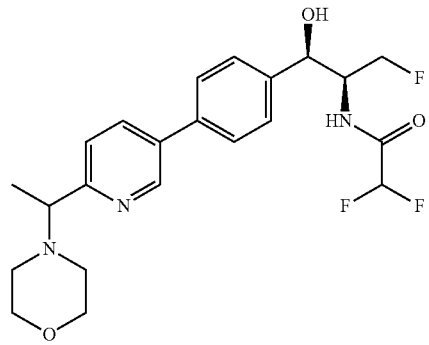 [SMILES: CC(c1ccc(-c2ccc([C@@H](O)[C@@H](CF)NC(=O)C(F)F)cc2)cn1)N1CCOCC1]

To a stirred solution of 2,2-Difluoro-1-((4S,5R)-4-fluoromethyl-2,2-dimethyl-5-{4-[6-(1-morpholin-4-yl-ethyl)-pyridin-3-yl]-phenyl}-oxazolidin-3-yl)-ethanone (0.101 g, 0.309 mmol) in CH$_2$Cl$_2$ (5 mL) is added trifluoroacetic acid (1 mL) at 0° C. Reaction mixture is allowed to stir at room temperature for 4 hours. The solvent evaporated in vacuo and the crude material is diluted with saturated bicarbonate solution and extract with 10% MeOH:DCM. Combined organic layer dried over sodium sulphate, concentrated and purified by combiflash using 5% methanol:CH$_2$Cl$_2$ as eluent to afford desired compound (0.076 g): 1H NMR (400 MHz, CDCl$_3$) δ: 1.33 (d, J=2.52 Hz, 3H), 2.32-2.35 (m, 2H), 2.49-2.50 (m, 2H), 3.55-3.57 (m, 4H), 3.59-3.60 (m, 1H), 4.29-4.30 (m, 1H), 4.32 (m, 0.5H), 4.40-4.44 (m, 0.5H), 4.54-4.55 (m, 0.5H), 4.64-4.66 (m, 0.5H), 4.88 (bs, 1H), 5.92 (d, J=3.96 Hz, 1H), 6.20 (t, J=53.72 Hz, 1H), 7.45 (d, J=8.24 Hz, 2H), 7.49 (d, J=8.24 Hz, 1H), 7.69 (d, J=8.28 Hz, 2H), 8.03-8.06 (dd, J1=8.2 Hz, J2=2.4 Hz, 1H), 8.80 (d, J=2.04 Hz, 1H), 8.86 (d, J=8.56 Hz, 1H). LC-Ms (m/z): 438.1[M+H].

Example 61

Preparation of 2,2-Difluoro-N-((1S,2R)-1-fluoromethyl-2-hydroxy-2-{4-[6-(1-methylamino-ethyl)-pyridin-3-yl]-phenyl}-ethyl)-acetamide This compound is prepared by using procedure same as in Example 60 2,2-Difluoro-1-((4S,5R)-4-fluoromethyl-2,2-dimethyl-5-{4-[6-(1-methylamino-ethyl)-pyridin-3-yl]-phenyl}-oxazolidin-3-yl)-ethanone

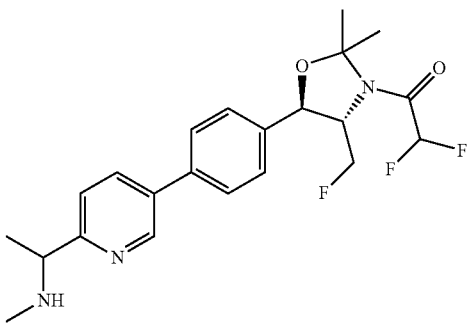 [SMILES: CNC(C)c1ccc(-c2ccc([C@H]3OC(C)(C)N(C(=O)C(F)F)[C@@H]3CF)cc2)cn1]

1H NMR (400 MHz, DMSO-d₆) δ: 1.41 (d, J=6.72 Hz, 3H), 1.52 (s, 3H), 1.60 (s, 3H), 2.36 (s, 3H), 4.14-4.16 (m, 1H), 4.45-4.61 (m, 0.5H), 4.69-4.72 (m, 1H), 4.80-4.90 (m, 0.5H), 4.91-4.96 (m, 1H), 5.28 (d, J=3.68 Hz, 1H), 6.65 (t, J=52.28 Hz, 1H), 7.57 (d, J=8.12 Hz, 1H), 7.61 (d, J=8.12 Hz, 2H), 7.81 (d, J=8.24 Hz, 2H), 8.15-8.18 (dd, J1=8.12 Hz, J2=2.28 Hz, 1H), 8.91 (d, J=2 Hz, 1H). LC-MS (m/z): 422 [M+H].

2,2-Difluoro-N-((1S,2R)-1-fluoromethyl-2-hydroxy-2-{4-[6-(1-methylamino-ethyl)-pyridin-3-yl]-phenyl}-ethyl)-acetamide

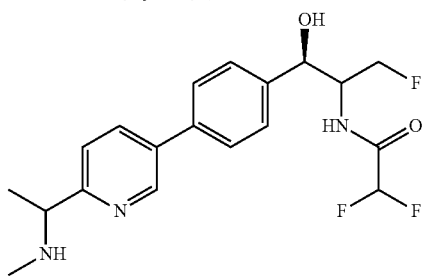

1H NMR (400 MHz, DMSO-d₆) δ: 1.30 (d, J=6.64 Hz, 3H), 2.21 (s, 3H), 3.80 (bs, 1H), 4.29-4.31 (m, 1.5H), 4.40-4.44 (m, 0.5H), 4.54-4.55 (m, 0.5H), 4.64-4.68 (m, 0.5H), 4.87 (bs, 1H), 5.91 (d, J=4.4, 1H), 6.20 (t, J=53.84 Hz, 1H), 7.45 (d, J=8.0 Hz, 2H), 7.50 (d, J=8.16 Hz, 1H), 7.69 (d, J=8.08 Hz, 2H), 8.07 (m, 1H), 8.82-8.86 (m, 2H). LC-MS (m/z): 382.2 [M+H].

Example 62

Preparation of 2,2-Difluoro-N-[(1S,2R)-2-(4-{6-[1-(2-fluoro-ethylamino)-ethyl]-pyridin-3-yl}-phenyl)-1-fluoromethyl-2-hydroxy-ethyl]-acetamide Step 1 Preparation of 2,2-Difluoro-1-[(4S,5R)-5-(4-{6-[1-(2-fluoro-ethylamino)-ethyl]-pyridin-3-yl}-phenyl)-4-fluoromethyl-2,2-dimethyl-oxazolidin-3-yl]-ethanone

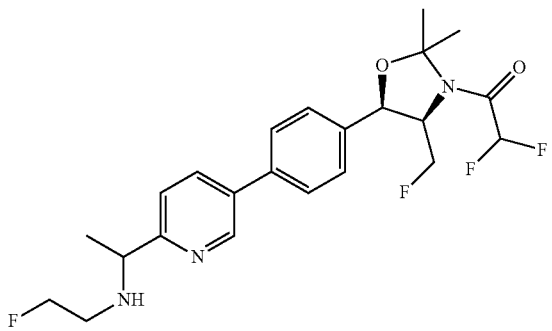 [SMILES: CC(NCCF)c1ccc(-c2ccc([C@H]3OC(C)(C)N(C(=O)C(F)F)[C@H]3CF)cc2)cn1]

This compound is prepared by using procedure same as in Example 60. 1H NMR (400 MHz, DMSO-d₆) δ: 1.30 (d, J=6.68 Hz, 3H), 1.53 (s, 3H), 1.60 (s, 3H), 2.54-2.67 (m, 2H), 3.83-3.86 (m, 1H), 4.36-4.39 (m, 1H), 4.48-4.51 (m, 1H), 4.56-4.58 (m, 0.5H), 4.68-4.70 (m, 1H), 4.80-4.83 (m, 0.5H), 4.89-4.93 (m, 1H), 5.26 (d, J=3.96 Hz, 1H), 6.64 (t, J=52.2 Hz, 1H), 7.53 (d, J=8.12 Hz, 1H), 7.59 (d, J=8.08 Hz, 2H), 7.78 (d, J=8.12 Hz, 2H) 8.05-8.08 (dd, J1=8.04 Hz, J2=2.2 Hz, 1H), 8.2 (d, J=2.12 Hz, 1H). LC-MS (m/z): 454 [M+H].

Step 2 Preparation of 2,2-Difluoro-N-[(1S,2R)-2-(4-{6-[1-(2-fluoro-ethylamino)-ethyl]-pyridin-3-yl}-phenyl)-1-fluoromethyl-2-hydroxy-ethyl]-acetamide

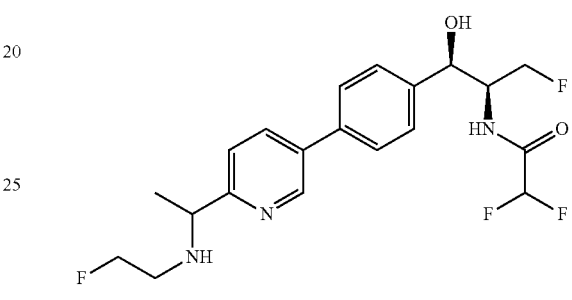

1H NMR (400 MHz, DMSO-d₆) δ 1.29 (d, J=6.72 Hz, 3H), 2.36-2.38 (m, 1H), 2.60-2.61 (m, 1H), 3.84 (bs, 1H), 4.29-4.32 (m, 1.5H), 4.35-4.38 (m, 1H), 4.39-4.42 (m, 0.5H), 4.49-4.50 (m, 1H), 4.55-4.58 (m, 0.5H), 4.65-4.70 (m, 0.5H), 4.88 (bs, 1H), 5.93 (bs, 1H), 6.20 (t, J=53.76 Hz, 1H), 7.45 (d, J=8.24 Hz, 2H), 7.51 (d, J=8.12 Hz, 1H), 7.69 (d, J=8.28 Hz, 2H), 8.03-8.06 (dd, J1=2.4 Hz, J2=8.2 Hz, 1H), 8.80 (d, J=2.2 Hz, 1H), 8.87 (d, J=8.64 Hz, 1H). LC-MS (m/z): [M+H]=414.2.

Example 63

2,2-Difluoro-N-[(1S,2R)-2-(4-{6-[1-(3-fluoro-azetidin-1-yl)-ethyl]-pyridin-3-yl}-phenyl)-1-fluoromethyl-2-hydroxy-ethyl]acetamide

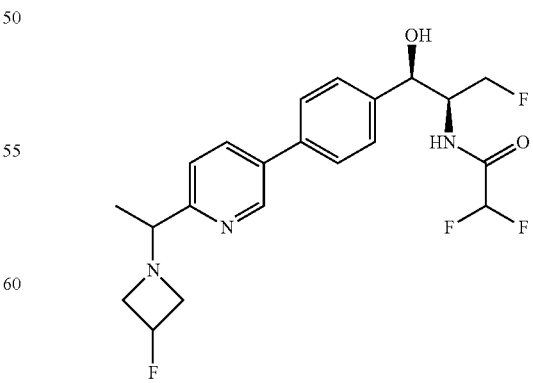

This compound is prepared by using procedure same as in Example 60.

2,2-Difluoro-1-[(4S,5R)-5-(4-{6-[1-(3-fluoro-azetidin-1-yl)-ethyl]-pyridin-3-yl}-phenyl)-4-fluoromethyl-2,2-dimethyl-oxazolidin-3-yl]-ethanone

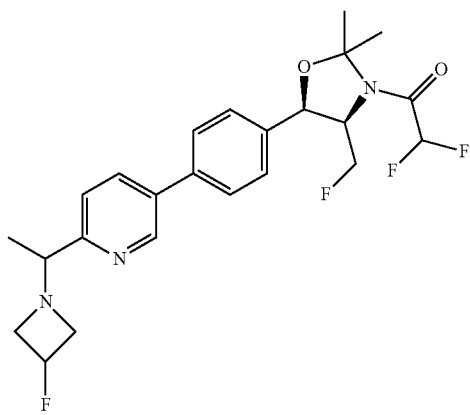 [SMILES: CC(c1ccc(-c2ccc([C@H]3OC(C)(C)N(C(=O)C(F)F)[C@H]3CF)cc2)cn1)N1CC(F)C1]

LC-MS (m/z): 426 [M+H].

2,2-Difluoro-N-[(1S,2R)-2-(4-{6-[1-(3-fluoro-azetidin-1-yl)-ethyl]-pyridin-3-yl}-phenyl)-1-fluoromethyl-2-hydroxy-ethyl]acetamide

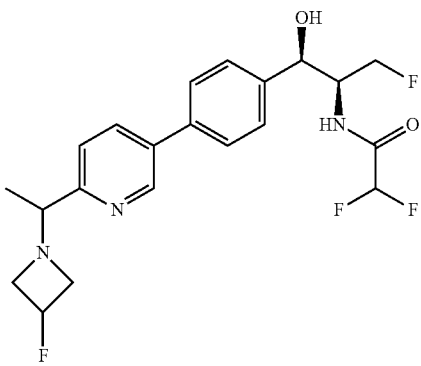 [SMILES: CC(c1ccc(-c2ccc([C@@H](O)[C@@H](CF)NC(=O)C(F)F)cc2)cn1)N1CC(F)C1]

1H NMR (400 MHz, DMSO-$d_6$) δ: 1.19 (d, J=6.52 Hz, 3H), 3.03-3.31 (m, 2H), 3.52-3.60 (m, 2H), 4.28-4.38 (m, 1.5H), 4.40-4.44 (m, 0.5H), 4.54-4.55 (m, 0.5H), 4.64-4.67 (m, 0.5H), 4.87 (m, 1H), 5.08-5.10 (m, 0.5H), 5.22-5.25 (m, 0.5H), 5.93 (bs, 1H), 6.20 (t, J=53.68 Hz, 1H), 7.43-7.46 (m, 3H), 7.68 (d, J=8.24 Hz, 2H), 8.03-8.05 (dd, J1=2.36 Hz, J2=8.12 Hz, 1H), 8.79 (d, J=2.04 Hz, 2H), 8.87 (d, J=8.68 Hz, 1H). LC-MS (m/z): 426.2 [M+H].

Example 64

Preparation of N-((1R,2S)-1-(4-(6-(1-aminocyclopropyl)pyridin-3-yl)phenyl)-3-fluoro-1-hydroxypropan-2-yl)-2,2-difluoroacetamide Step 1 Preparation of tert-butyl (1-(5-(4-((4S,5R)-3-(2,2-difluoroacetyl)-4-(fluoromethyl)-2,2-dimethyloxazolidin-5-yl)phenyl)pyridin-2-yl)cyclopropyl)-carbamate

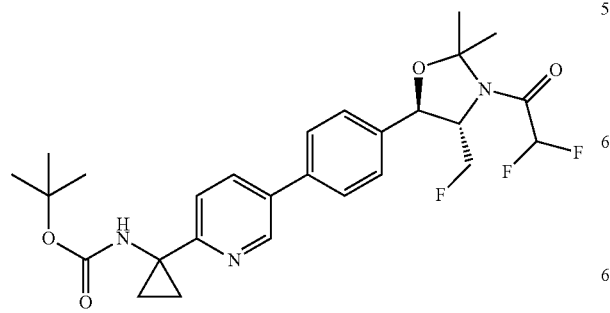

Following the general procedure of Example 22, Step 1 and making non-critical variations but using tert-butyl (1-(5-bromopyridin-2-yl)cyclopropyl)carbamate (Previously described in WO 2012/076063, Description 11, p. 41) the title compound is obtained (535 mg) m/z (CI) 520 [M+H].

Step 2 Preparation of N-((1R,2S)-1-(4-(6-(1-aminocyclopropyl)pyridin-3-yl)phenyl)-3-fluoro-1-hydroxypropan-2-yl)-2,2-difluoroacetamide

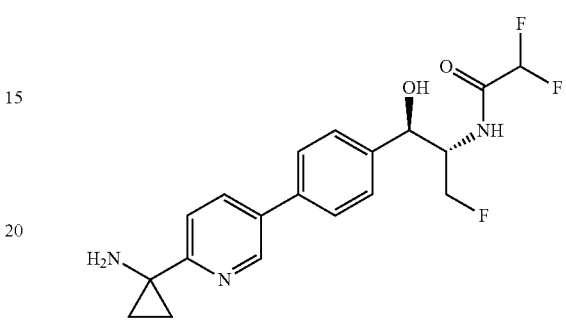

Following the general procedure of Example 2, Step 2 and making non-critical variations but using tert-butyl (1-(5-(4-((4S,5R)-3-(2,2-difluoroacetyl)-4-(fluoromethyl)-2,2-dimethyloxazolidin-5-yl)phenyl)pyridin-2-yl)cyclopropyl)-carbamate the title compound is obtained (323 mg) 1H NMR (300 MHz, DMSO-$d_6$) δ:0.9-1.05 (m, 2H), 1.2-1.3 (m, 2H), 2.45 (s, 2H), 4.2-4.4 (m, 1.5H), 4.4-4.6 (m, 1H), 4.6-4.7 (m, 0.5H), 4.85 (t, 1H), 5.9 (d, 1H), 6.2 (t, 1H), 7.45 (d, 2H), 7.65 (d, 2H), 7.8 (d, 1H), 8.0 (d, 1H), 8.70 (s, 1H), 8.8 (d, 1H). m/z (CI) 380 [M+H].

The following derivatives of the title compound of Example 64 can be prepared by methods known in the art, including those described in Example 95 A below:

N-((1R,2S)-1-(4-(6-(1-aminocyclopropyl)pyridin-3-yl)phenyl)-3-fluoro-1-hydroxypropan-2-yl)-2,2-dichloroacetamide;

(1R,2S)-1-(4-(6-(1-aminocyclopropyl)pyridin-3-yl)phenyl)-2-(2,2-dichloroacetamido)-3-fluoropropyl hydrogen phosphate sodium;

(1R,2S)-1-(4-(6-(1-aminocyclopropyl)pyridin-3-yl)phenyl)-2-(2,2-dichloroacetamido)-3-fluoropropyl dihydrogen phosphate;

(1R,2S)-1-(4-(6-(1-aminocyclopropyl)pyridin-3-yl)phenyl)-2-(2,2-difluoroacetamido)-3-fluoropropyl hydrogen phosphate sodium; and (1R,2S)-1-(4-(6-(1-aminocyclopropyl)pyridin-3-yl)phenyl)-2-(2,2-difluoroacetamido)-3-fluoropropyl dihydrogen phosphate.

Example 65

Preparation of N-((1S,2R)-2-{4-[6-(Acetylaminomethyl)-pyridin-3-yl]-phenyl}-1-fluoromethyl-2-hydroxy-ethyl)-2,2-dichloro-acetamide

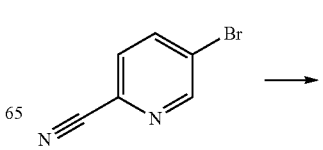

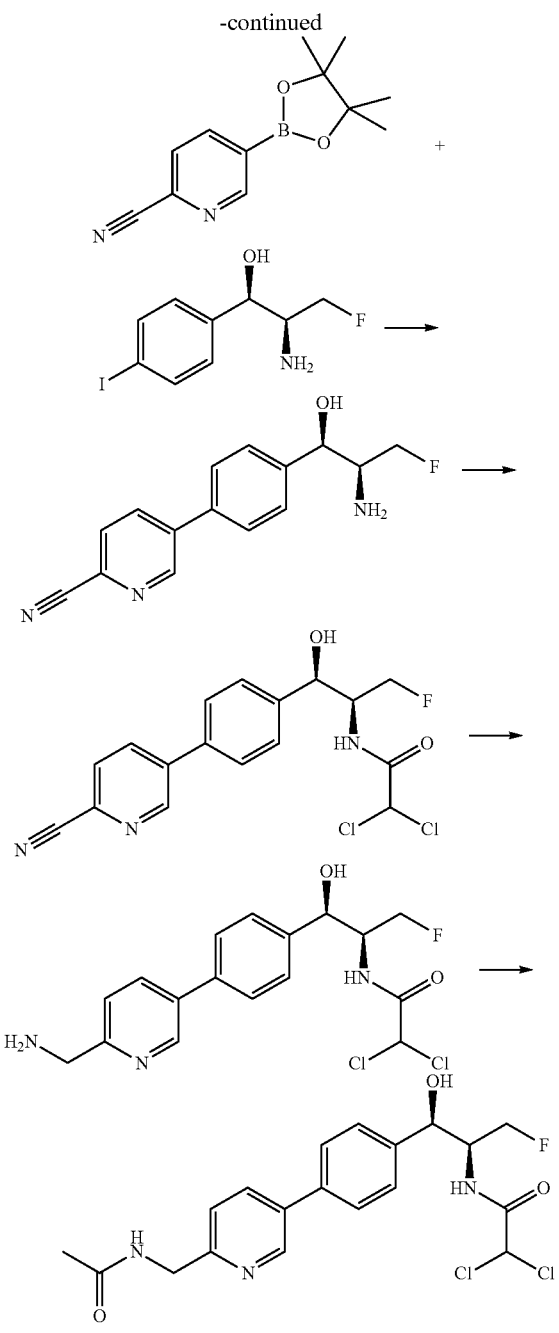

Step 1 Preparation of 5-(4,4,5,5-Tetramethyl-[1,3,2]dioxaborolan-2-yl)-pyridine-2-carbonitrile

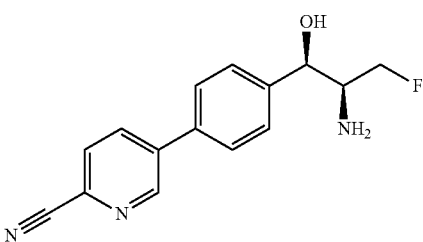

To a solution of 5-Bromo-pyridine-2-carbonitrile (2 g, 10.92 mmol) in Dioxane (60 mL) is added bispinacolato diborane (3.33 g, 13.11 mmol) and Potassium acetate (1.6 g, 16.39 mmol) and reaction mixture is degassed and added tricyclohexyl phosphine (0.4 g, 1.42 mmol), and $Pd_2(dba)_3$ (0.5 g, 0.546 mmol) and heated to 90° C. for overnight. Diluted with water and ethyl acetate. The organic layer was separated, dried over sodium sulphate and solvent is evaporated in vacuo to give crude material, which is purified by column chromatography eluting in 6-8% ethyl acetate in hexane to afford the title compound (1.0 g): $^1$H-NMR (400 MHz, $CDCl_3$) δ: 1.35 (s, 12H), 7.66 (d, J=7.76 Hz, 1H), 8.17 (d, J=8.88 Hz, 1H), 9.00 (s, 1H).

Step 2 Preparation of 5-[4-((1R,2S)-2-Amino-3-fluoro-1-hydroxy-propyl)-phenyl]-pyridine-2-carbonitrile

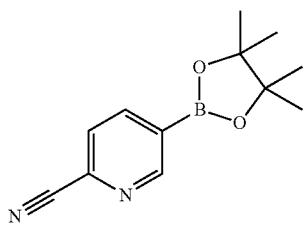 [SMILES: CC1(C)OB(c2ccc(C#N)nc2)OC1(C)C]

To a solution of 5-(4,4,5,5-Tetramethyl-[1,3,2]dioxaborolan-2-yl)-pyridine-2-carbonitrile (0.5 g, 2.17 mmol) in dimethoxyethane (10 mL) and water (3 mL) is added (1R,2S)-2-Amino-3-fluoro-1-(4-iodo-phenyl)-propan-1-ol (0.65 g, 2.20 mmol) and $Cs_2CO_3$ (2.15 g, 6.59 mmol), and degassed with nitrogen followed by addition of $Pd(PPh_3)_4$ (0.25 g, 0.21 mmol) and heated the reaction mixture to 90° C. for 1.5 hours. Solvent is evaporated in vacuo, to get crude material purified by column chromatography eluting in 2.5 to 3% methanol in $CH_2Cl_2$ to afford the title compound (0.3 g) as impure. $^1$H NMR (400 MHz, DMSO-$d_6$) δ: 3.09-3.18 (m, 1H), 3.48 (s, 1H), 4.24-4.28 (m, 0.5H), 4.36-4.41 (m, 1H), 4.49-4.52 (m, 0.5H), 4.64 (d, J=6.16 Hz, 1H), 7.53 (d, J=8.16 Hz, 2H), 7.59 (d, J=8.24 Hz, 2H), 7.76 (d, J=8.2, 1H), 8.0 (dd, J1=8.16 Hz, J2=2.32 Hz, 1H), 8.93 (d, J=1.76 Hz, 1H). LC-MS (m/z): [M+H]=272.00.

Step 3 Preparation of 2,2-Dichloro-N-{(1S,2R)-2-[4-(6-cyano-pyridin-3-yl)-phenyl]-1-fluoromethyl-2-hydroxy-ethyl}-acetamide

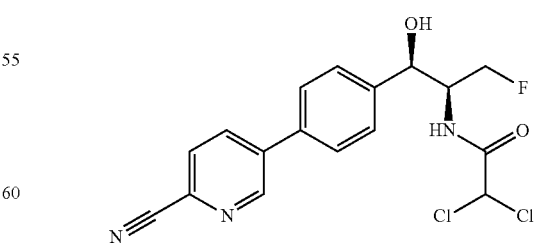

To the solution of 5-(4-((1R,2S)-2-amino-3-fluoro-1-hydroxypropyl)phenyl) pyridine-2-carbonitrile (0.5 g, 1.1 mmol) in methanol (5 mL) is added triethylamine (0.22 g, 2.2 mmol) and ethyl dichloro acetate (0.34 g, 2.2 mmol) and reaction mixture is stirred at room temperature for 16 hours. The solvent is evaporated in vacuo and the crude material purified by column chromatography on silica gel using methanol/CH$_2$Cl$_2$ to afford the title compound (200 mg). $^1$HNMR (400 MHz, DMSO-d$_6$) δ: 4.26-4.35 (m, 1H), 4.36-4.37 (m, 0.5H), 4.45-4.51 (m, 1H), 4.59-4.63 (m, 0.5H), 5.02 (d, J=3.28 Hz, 1H), 5.84 (s, 1H), 7.47 (d, J=8.2 Hz, 2H), 7.54 (d, J=8.24 Hz, 2H), 7.76 (d, J=8.04 Hz, 1H), 7.96 (dd, J1=8.08 Hz, J2=2.2 Hz, 1H), 8.85 (d, J=1.64 Hz, 1H). LC-MS (m/z): [M+H]=379.70.

Step 4 Preparation of N-{(1S,2R)-2-[4-(6-Aminomethyl-pyridin-3-yl)-phenyl]-1-fluoromethyl-2-hydroxy-ethyl}-2,2-dichloro-acetamide

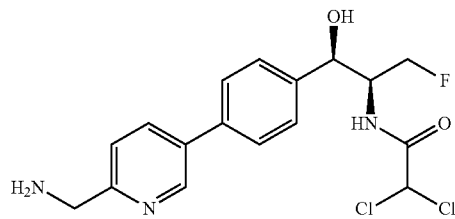 [SMILES: NCc1ccc(-c2ccc([C@@H](O)[C@@H](CF)NC(=O)C(Cl)Cl)cc2)cn1]

To an ice cold solution of lithium aluminum hydride (0.048 g, 1.33 mmol, 4.0 eq) in tetrahydrofuran (10 mL) to −40° C. is added a solution of 2,2-dichloro-N-((1R,2S)-1-(4-(6-cyanopyridin-3-yl)phenyl)-3-fluoro-1-hydroxypropan-2-yl)acetamide (0.13 g, 0.34 mmol) in tetrahydrofuran (5 mL) at −40° C. Further lithium aluminum hydride is added (0.012 g, 0.33 mmol) three times and reaction mixture is stirred at −40° C. for 4 hours. The reaction mixture is quenched with saturated aqueous sodium sulphate and stirred for 15 minutes followed by filtration. The filtrate is evaporated in vacuo and the crude material purified by column chromatography on silica gel using methanol/CH$_2$Cl$_2$ and ammonia to afford title compound (43 mg): 1H NMR (400 MHz, CDCl$_3$) δ: 4.20-4.24 (m, 2H), 4.27-4.29 (m, 0.5H), 4.39-4.43 (m, 0.5H), 4.56-4.59 (m, 1H), 4.67-4.69 (m, 0.5H), 4.89-4.90 (m, 1H), 5.99 (d, J=4.2 Hz, 1H), 6.52 (s, 1H), 7.46-7.48 (m, 3H), 7.64-7.69 (m, 3H), 8.06-8.10 (m, 1H), 8.63 (d, J=8.76 Hz, 1H). LC-MS (m/z): [M+H]=386.10.

Step 5 Preparation of N-((1S,2R)-2-{4-[6-(Acetylamino-methyl)-pyridin-3-yl]-phenyl}-1-fluoromethyl-2-hydroxy-ethyl)-2,2-dichloro-acetamide

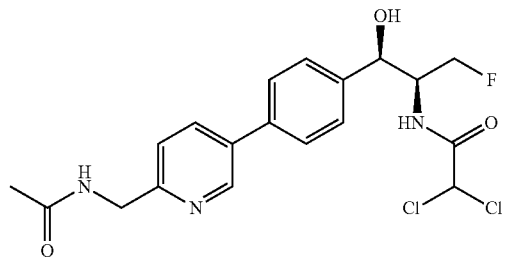 [SMILES: CC(=O)NCc1ccc(-c2ccc([C@@H](O)[C@@H](CF)NC(=O)C(Cl)Cl)cc2)cn1]

To a stirred solution of crude N-{(1S,2R)-2-[4-(6-Aminomethyl-pyridin-3-yl)-phenyl]-1-fluoromethyl-2-hydroxy-ethyl}-2,2-dichloro-acetamide (30 mg, 0.077 mmol) in CH$_2$Cl$_2$ (2 mL) is added triethyl amine (8 mg, 0.078 mmol) and acetic anhydride (20 mg, 0.198) and the reaction mixture was stirred at room temperature for 6 h. Diluted with water and extracted with CH$_2$Cl$_2$ dried over sodium sulphate and solvent is evaporated in vacuo to give crude, which is purified by silica gel prep TLC using the mobile phase 10% methanol in CH$_2$Cl$_2$ to afford title compound (5 mg): $^1$H-NMR (400 MHz, DMSO-d$_6$) δ: (s, 3H), 4.30-4.34 (m, 1H), 4.45 (d, J=5.96 Hz, 2H), 4.48-4.51 (m, 1H), 4.55-4.58 (m, 1H), 5.00 (d, 1H), 5.95 (d, 1H), 6.12 (s, 1H), 6.99 (bs, 1H), 7.34-7.36 (m, 1H), 7.47-7.50 (m, 2H), 7.62-7.67 (m, 2H), 7.96 (dd, J1=8.2 Hz, J2=2.4 Hz, 1H), 8.76 (d, J=2.2 Hz, 1H). LC-Ms (m/z): [M+H]=428.10.

Example 66

Preparation of N-{(1S,2R)-2-[4-(4-Aminomethyl-[1,2,3]triazol-1-yl)-phenyl]-1-fluoromethyl-2-hydroxy-ethyl}-2,2-dichloro-acetamide

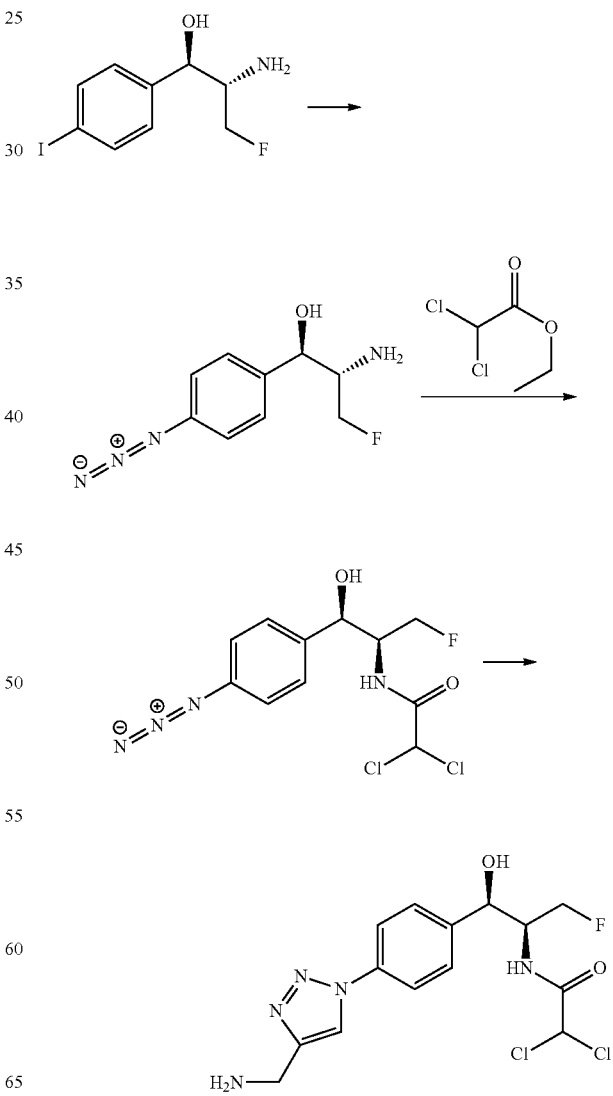

Step 1 Preparation of (1R,2R)-2-Amino-1-(4-azido-phenyl)-3-fluoro-propan-1-ol

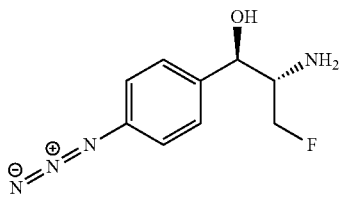 [SMILES: [N-]=[N+]=Nc1ccc([C@@H](O)[C@H](N)CF)cc1]

To the stirred solution of (1R,2R)-2-Amino-3-fluoro-1-(4-iodo-phenyl)-propan-1-ol (1 g, 3.38 mmol) in dimethylsulfoxide: water (9:1, 10 mL) is added NaN3 (0.26 g, 3.99 mmol), Na-ascorbate (0.1 g, 0.50 mmol), CuSO$_4$.5H$_2$O (0.17 g, 0.68 mmol), L-proline (78 mg, 0.67 mmol), K$_2$CO$_3$ (93 mg 0.67 mmol) and resulting reaction mixture heated to 60° C. for 5 hours. Diluted with cold water and extracted with ethylacetate and washed with excess of water and brine. Organic layer dried over sodium sulphate and solvent is evaporated in vacuo to get the crude title compound (0.6 g, crude), used as such in next step. LC-MS (m/z): [M+H]=211.2.

Step 2 Preparation of ((N-[(1S,2R)-2-(4-Azido-phenyl)-1-fluoromethyl-2-hydroxy-ethyl]-2,2-dichloro-acetamide

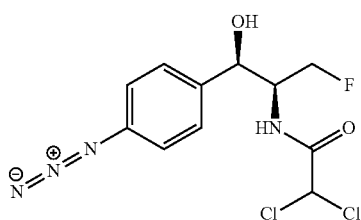 [SMILES: [N-]=[N+]=Nc1ccc([C@@H](O)[C@@H](CF)NC(=O)C(Cl)Cl)cc1]

To the stirred solution of (1R,2R)-2-Amino-1-(4-azido-phenyl)-3-fluoro-propan-1-ol (600 mg, 2.83 mmol) in methanol (6.5 mL) is added triethyl amine (0.57 g, 5.64 mmol) and ethyl dichloroacetate (0.88 g, 5.60 mmol). Resulting reaction mixture is stirred under nitrogen at room temperature for 16 hours. Solvent is evaporated in vacuo to get the crude material purified by column chromatography eluting in 0.5% methanol in dichloromethane to afford the title compound (150 mg). $^1$H-NMR (400 MHz, DMSO-d$_6$) δ: 4.40-4.41 (m, 1H), 4.24-4.26 (m, 0.5H), 4.36-4.38 (m, 0.5H), 4.52-4.54 (m, 0.5H), 4.64-4.66 (m, 0.5H), 4.84 (t, 1H, J=3.64 Hz), 5.96 (d, 1H, J=4.24 Hz), 6.49 (s, 1H), 7.05 (d, 2H, J=8.48 Hz), 7.38 (d, 2H, J=8.44 Hz), 8.58 (d, 1H, J=8.98 Hz). LC-Ms (m/z): [M–H]=318.8.

Step 3 Preparation of (N-{(1S,2R)-2-[4-(4-Aminomethyl-[1,2,3]triazol-1-yl)-phenyl]-1-fluoromethyl-2-hydroxy-ethyl}-2,2-dichloroacetamide

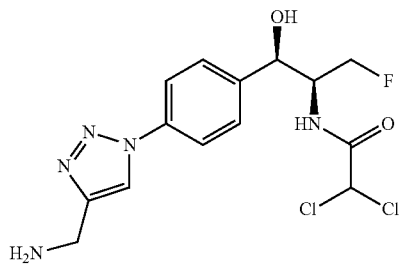 [SMILES: NCc1cn(-c2ccc([C@@H](O)[C@@H](CF)NC(=O)C(Cl)Cl)cc2)nn1]

To the solution of ((N-[(1S,2R)-2-(4-Azido-phenyl)-1-fluoromethyl-2-hydroxy-ethyl]-2,2-dichloro-acetamide (150 mg, 0.465 mmol) in tert-butylalcohol: water (1:1, 3 mL) is added Na-ascorbate (12 mg, 0.060 mmol), CuSO$_4$.5H$_2$O (3 mg, 0.012 mmol), propargyl amine (26 mg, 0.472 mmol) resulting reaction mixture stirred at room temperature for 16 hours. Solvent is evaporated in vacuo to get the crude material purified by column chromatography eluting in 25-40% methanol in dichloromethane and washed with diethyl ether and dried under vacuum to afford the title compound (25 mg). $^1$H-NMR (400 MHz, DMSO-d$_6$) δ: 3.84 (s, 2H), 4.23-4.29 (m, 1H), 4.30-4.34 (m, 0.5H), 4.42-4.46 (m, 0.5H), 4.58-4.61 (m, 0.5H), 4.69-4.73 (m, 0.5H), 4.93 (bs, 1H), 6.07 (d, 1H, J=4.28 Hz), 6.49 (s, 1H), 7.54 (d, 2H, J=8.48 Hz), 7.81 (d, 2H, J=8.52 Hz), 8.57 (s, 1H), 8.61 (d, 1H, J=5.6 Hz). LC-MS (m/z): [M+H]=376.2.

Example 67

Preparation of 2,2-Dichloro-N-((1S,2R)-1-fluoromethyl-2-hydroxy-2-{4-[4-(methanesulfonylamino-methyl)-[1,2,3]triazol-1-yl]-phenyl}-ethyl)-acetamide

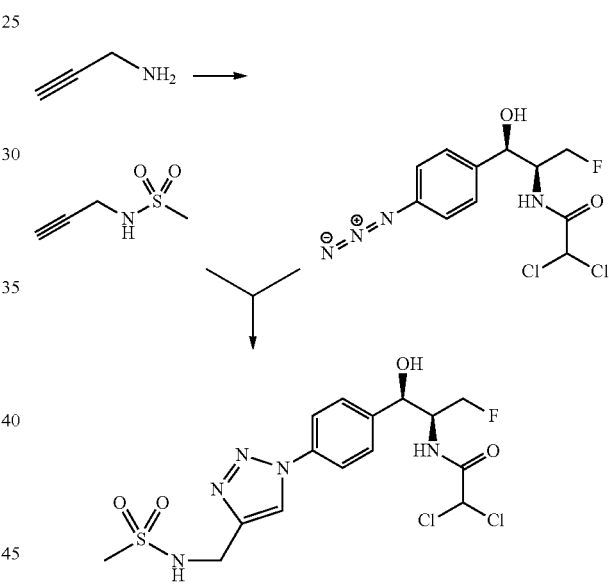

Step 1 Preparation of N-Prop-2-ynyl-methanesulfonamide

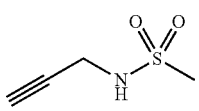

To a stirred solution of prop-2-ynylamine (1 g, 18.18 mmol) in pyridine (1.5 mL) is added mesyl chloride dropwise at 0° C. Resulting reaction mixture stirred at room temperature for 2 hours. Solvent is evaporated in vacuo to get the crude which is washed with pentane and dried completely to afford the crude title compound (3.0 g). $^1$H-NMR (400 MHz, DMSO-d$_6$) δ: 2.36 (s, 1H), 2.95 (s, 3H), 3.32 (t, 1H, J=2.56 Hz), 3.78 (d, J=2.48 Hz, 2H), LC-Ms (m/z): [M–H]=131.7.

Step 2 Preparation of 2,2-dichloro-N-((1R,2S)-3-fluoro-1-hydroxy-1-(4-(4-(methyl sulfonamidomethyl)-1H-1,2,3-triazol-1-yl) phenyl) propan-2-yl) acetamide

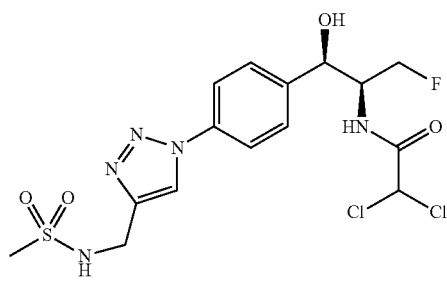 [SMILES: CS(=O)(=O)NCc1cn(-c2ccc([C@@H](O)[C@@H](CF)NC(=O)C(Cl)Cl)cc2)nn1]

Following the general procedure of Example 66, Step 3 and making non-critical variations but using the product of step 1, Example 67 with the product of Example 66, Step 2 the title compound is obtained (45 mg). $^1$H-NMR (400 MHz, DMSO-d$_6$) δ: 2.95 (s, 3H), 4.25-4.26 (m, 1H), 4.30 (s, 2H), 4.33-4.34 (m, 0.5H), 4.42-4.46 (m, 0.5H), 4.58-4.61 (m, 0.5H), 4.69-4.73 (m, 0.5H), 4.95 (t, 1H, J=3.3 Hz), 6.08 (d, 1H, J=3.92 Hz), 6.49 (s, 1H), 7.55 (d, 2H, J=8.56 Hz), 7.84 (d, 2H, J=8.6 Hz), 8.64 (d, 1H, J=9.04 Hz), 8.70 (s, 1H). LC-MS (m/z): [M+H]=453.9.

Example 68

Preparation of 2,2-Dichloro-N-{(1S,2R)-2-[4-(6-ethylaminomethyl-pyridin-3-yl)-phenyl]-1-fluoromethyl-2-hydroxy-ethyl}-acetamide

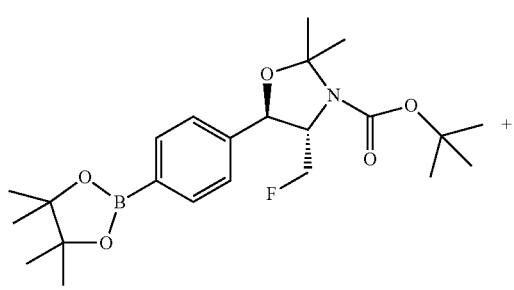

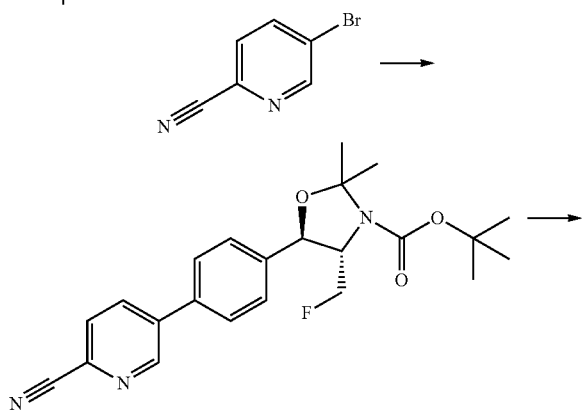

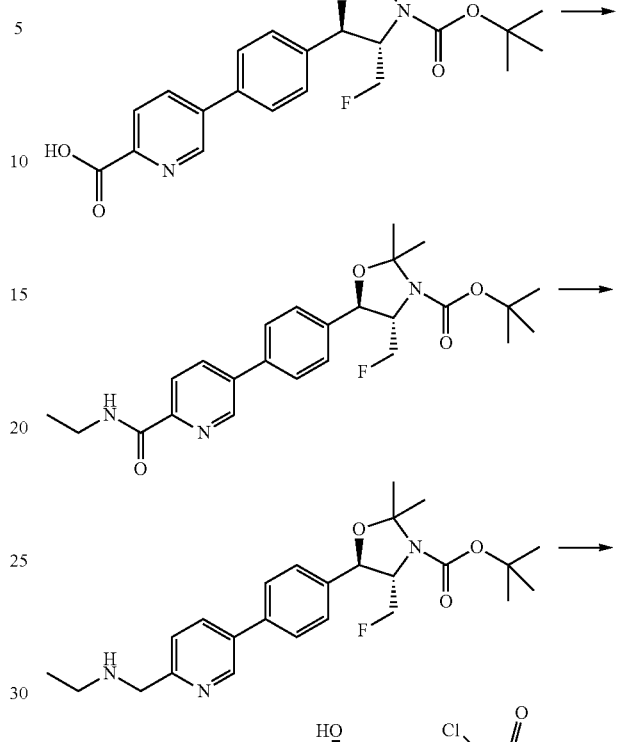

Step 1 (4S,5R)-5-[4-(6-Cyano-pyridin-3-yl)-phenyl]-4-fluoromethyl-2,2-dimethyl-oxazolidine-3-carboxylic acid tert-butyl ester To stirred solution of (4S,5R)-4-Fluoromethyl-2,2-dimethyl-5-[4-(4,4,5,5-tetramethyl-[1,3,2]dioxaborolan-2-yl)-phenyl]-oxazolidine-3-carboxylic acid tert-butyl ester (0.75 g, 1.72 mmol) in dimethoxyethane:water (8:2, 10 mL) is added Cs$_2$CO$_3$ (1.12 g, 3.44 mmol) and 5-Bromo-pyridine- 2-carbonitrile (0.347 g, 1.89 mmol). Reaction mixture is degassed with nitrogen for 30 minutes, followed by addition of Pd(PPh$_3$)$_4$ (0.199 g, 0.172 mmol). The resulting reaction mixture heated to 90° C. for 3 hours. Diluted with water (20 mL) and ethyl acetate (40 mL). The organic layer is separated, dried over sodium sulphate and solvent is evaporated in vacuo to get crude material purified by column chromatography eluting in 15% ethyl acetate in hexane to afford title compound (0.3 g). $^1$H-NMR (400 MHz, DMSO-d$_6$): δ: 1.43 (s, 9H), 1.51 (s, 3H), 1.63 (s, 3H), 3.83-3.90 (m, 1H), 4.47-4.58 (m, 2H), 4.75-4.93 (m, 2H), 5.15 (d, 1H, J=7.2 Hz), 7.64 (d, 2H, J=8.28 Hz), 7.87 (d, 2H, J=8.24 Hz), 8.15 (d, 1H, J=8.16 Hz), 8.36 (dd, 1H, J=8.2 Hz, J=2.2 Hz), 9.12 (d, 1H, J=2.24 Hz), LC-MS (m/z): [M+H]=412.1.

Step 2 Preparation of 5-[4-((4S,5R)-3-tert-Butoxycarbonyl-4-fluoromethyl-2,2-dimethyl-oxazolidin-5-yl)-phenyl]-pyridine-2-carboxylic acid

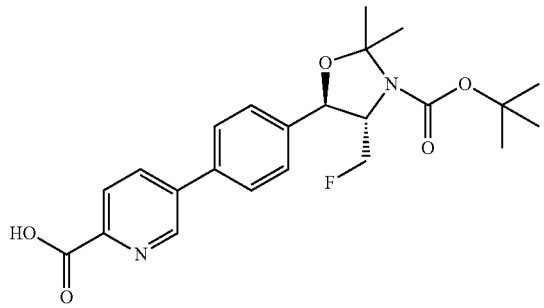 [SMILES: CC(C)(C)OC(=O)N1[C@H](CF)[C@@H](c2ccc(-c3ccc(C(=O)O)nc3)cc2)OC1(C)C]

To the solution of (4S,5R)-5-[4-(6-Cyano-pyridin-3-yl)-phenyl]-4-fluoromethyl-2,2-dimethyl-oxazolidine-3-carboxylic acid tert-butyl ester (0.3 g, 0.729 mmol) in methanol (3 mL) is added KOH (0.409 g, 7.29 mmol) at room temperature. Resulting reaction mixture heated at 65° C. for 48 hours. Solvent is evaporated in vacuo, water (10 mL) is added and aqueous layer is washed with CH$_2$Cl$_2$. Aqueous layer is acidified with saturated citric acid solution and extracted with CH$_2$Cl$_2$. Organic layer dried over sodium sulphate, solvent is evaporated in vacuo to afford title compound (0.22 g): $^1$H-NMR (400 MHz, DMSO-d$_6$): δ: 1.43 (s, 9H), 1.51 (s, 3H), 1.64 (s, 3H), 3.84-3.90 (m, 2H), 4.45-4.58 (m, 2H), 4.77-5.0 (m, 2H), 5.14 (d, 1H, J=7.2 Hz), 7.61 (d, 2H, J=8.08 Hz), 7.83 (d, 2H, J=8.12 Hz), 8.08 (d, 1H, J=8.32 Hz), 8.23 (d, 1H, J=8.68 Hz), 9.0 (s, 1H). LC-MS (m/z): [M+H]=431.2.

Step 3 Preparation of (4S,5R)-5-[4-(6-Ethylcarbamoyl-pyridin-3-yl)-phenyl]-4-fluoromethyl-2,2-dimethyl-oxazolidine-3-carboxylicacid tert-butyl ester

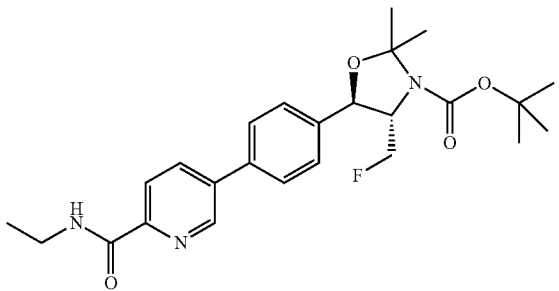 [SMILES: CCNC(=O)c1ccc(-c2ccc([C@H]3OC(C)(C)N(C(=O)OC(C)(C)C)[C@@H]3CF)cc2)cn1]

To a stirred solution of 5-[4-((4S,5R)-3-tert-Butoxycarbonyl-4-fluoromethyl-2,2-dimethyl-oxazolidin-5-yl)-phenyl]-pyridine-2-carboxylic acid (0.3 g, 0.697 mmol) in dry tetrahydrofuran (5 mL) is added ethyl amine (0.038 g, 0.837 mmol), diisopropylamine (0.27 g, 2.092 mmol) and 50% solution of triphenyl phosphine in ethyl acetate (0.332 g, 0.66 mL, 1.046 mmol) and stirred at room temperature for 14 hours. Diluted with water and ethyl acetate, organic layer is separated and aqueous layer is extracted with ethyl acetate. Combined organic layer is dried over sodium sulphate, solvent is evaporated in vacuo to obtained crude material purified by column chromatography eluting in 3% methanol in CH$_2$Cl$_2$ to afford title compound (0.21 g): $^1$H-NMR (400 MHz, DMSO-d$_6$): δ: 1.13 (t, 3H, J=6.98 Hz), 1.44 (s, 9H), 1.51 (s, 3H), 1.64 (s, 3H), 3.34-3.37 (m, 2H), 3.84-3.91 (m, 1H), 4.47-4.59 (m, 1H), 4.76-4.95 (m, 2H), 5.15 (d, 1H, J=7.24 Hz), 7.61 (d, 2H, J=8.28 Hz), 7.83 (d, 2H, J=8.24 Hz), 8.09 (d, 1H, J=8.20 Hz), 8.29 (dd, 1H, J=8.08 Hz, J=2.2 Hz), 8.84 (t, 1H, J=5.68 Hz), 8.93 (d, 1H, J=1.88 Hz) LC-MS (m/z): [M+H]=458.1.

Step 4 Preparation of (4S,5R)-5-[4-(6-Ethylaminomethyl-pyridin-3-yl)-phenyl]-4-fluoromethyl-2,2-dimethyl-oxazolidine-3-carboxylic acid tert-butyl ester

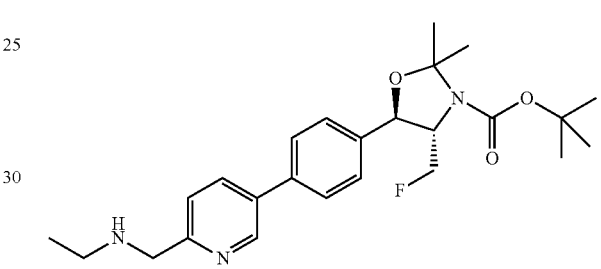

To a stirred solution of (4S,5R)-5-[4-(6-Ethylcarbamoyl-pyridin-3-yl)-phenyl]-4-fluoromethyl-2,2-dimethyl-oxazolidine-3-carboxylicacid tert-butyl ester (0.21 g, 0.459 mmol) in dry tetrahydrofuran (5.25 mL) is added 2 M toluene solution of BH$_3$.dimethylsulfide (0.104 g, 1.378 mmol) at 0° C. Reaction heated to 65° C. for 16 hours. Quenched with Methanol (2 mL). Volatiles were removed under reduced pressure to obtain crude material purified by column chromatography eluting in 6 methanol in CH$_2$Cl$_2$ to afford title compound (0.05 g): $^1$H-NMR (400 MHz, DMSO-d$_6$): δ: 1.09 (t, 3H, J=7.15 Hz), 1.43 (s, 9H), 1.51 (s, 3H), 1.63 (s, 3H), 3.15 (m, 2H), 3.82-3.89 (m, 2H), 3.95 (s, 2H), 4.10 (m, 1H), 4.45-4.55 (m, 2H), 5.12 (d, 1H, J=7.24 Hz), 7.52 (d, 1H, J=8.20 Hz), 7.57 (d, 2H, J=8.20 Hz), 7.75 (d, 2H, J=8.24 Hz), 8.09 (dd, 1H, J=7.88 Hz, J=2.08 Hz), 8.84 (d, 1H, J=1.92 Hz). LC-MS (m/z): [M+H]=444.

Step 5 Preparation of (1S,2S)-2-Amino-1-[4-(6-ethylaminomethyl-pyridin-3-yl)-phenyl]-3-fluoro-propan-1-ol

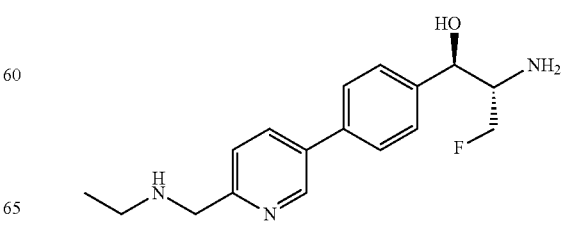

113

To a stirred solution of (4S,5R)-5-[4-(6-Ethylaminomethyl-pyridin-3-yl)-phenyl]-4-fluoromethyl-2,2-dimethyl-oxazolidine-3-carboxylic acid tert-butyl ester (0.05 g, 0.112 mmol) in CH₂Cl₂ (0.2 mL) is added trifluoroacetic acid (0.2 mL) at 0° C. Reaction mixture allowed to warm to room temperature and stirred for 2 hours. The volatiles were removed under reduced pressure to obtain crude material purified by column chromatography eluting in 10% methanol in CH₂Cl₂ to afford crude title compound (0.04 g, crude). LC-MS (m/z): [M+H]=304.2.

Step 6 Preparation of 2,2-Dichloro-N-{(1S,2R)-2-[4-(6-ethylaminomethyl-pyridin-3-yl)-phenyl]-1-fluoromethyl-2-hydroxy-ethyl}-acetamide

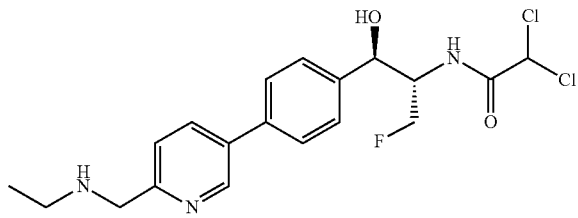 [SMILES: CCNCc1ccc(-c2ccc([C@@H](O)[C@@H](CF)NC(=O)C(Cl)Cl)cc2)cn1]

To a stirred solution of (1S,2S)-2-Amino-1-[4-(6-ethyl-aminomethyl-pyridin-3-yl)-phenyl]-3-fluoro-propan-1-ol (0.04 g, 0.095 mmol, crude) in dry methanol (0.17 mL) is added ethyl dichloro acetate (0.03 g, 0.191 mmol) and triethylamine (0.0194 g, 0.191 mmol) at room temperature and resulting reaction mixture stirred for 16 hours. The volatiles removed under reduced pressure to obtain crude material purified by column chromatography eluting in 7% methanol in CH₂Cl₂ to afford title compound (0.016 g): $^1$H-NMR (400 MHz, DMSO-d₆) δ 1.04 (t, 3H, J=7.09 Hz), 2.54-2.58 (m, 2H), 3.30 (s, 2H), 4.19-4.22 (m, 1H), 4.27-4.31 (m, 0.5H), 4.39-4.43 (m, 0.5H), 4.56-4.59 (m, 0.5H), 4.67-4.71 (m, 0.5H), 4.89-4.90 (m, 1H), 5.99 (d, 1H, J=4.2 Hz), 6.52 (s, 1H), 7.45-7.50 (m, 3H), 7.65 (d, 2H, J=8.2 Hz), 8.02 (dd, 1H, J=8.2 Hz, J=2.4 Hz), 8.62 (d, 1H, J=8.72 Hz), 8.77 (d, 1H, J=2.2 Hz). LC-S (m/z): [M+H]=414.

Example 69

Preparation of N-((1R,2S)-1-(4-(6-(3-aminooxetan-3-yl)pyridin-3-yl)phenyl)-3-fluoro-1-hydroxypropan-2-yl)-2,2-difluoroacetamide

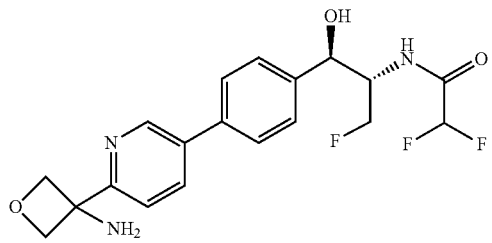 [SMILES: NC1(c2ccc(-c3ccc([C@@H](O)[C@@H](CF)NC(=O)C(F)F)cc3)cn2)COC1]

114

Step 1 Preparation of N-(3-(5-bromopyridin-2-yl)oxetan-3-yl)-2-methylpropane-2-sulfinamide

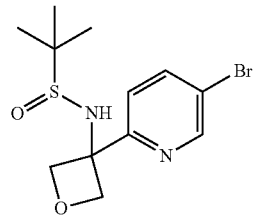 [SMILES: CC(C)(C)S(=O)NC1(c2ccc(Br)cn2)COC1]

To a toluene (20 ml) solution of 2,5-dibromopyridine (1.93 g, 8.16 mmol) that is cooled to −78° C. in an atmosphere of nitrogen is added n-butyllithium (2.5 M in hexanes, 3.6 ml, 8.98 mmol) dropwise via syringe over a period of five minutes. The reaction mixture is stirred at −78° C. for ten minutes more before 2-methyl-N-(oxetan-3-ylidene)propane-2-sulfinamide (1.43 g, 8.16 mmol) is added all at once as a concentrated solution in toluene. The reaction is stirred for 30 minutes at −78° C. and for 20 minutes at 0° C. before it is quenched with saturated aqueous ammonium chloride (5 ml). The volatiles were removed by rotary evaporation at reduced pressure. The residual material is partitioned between water (20 ml) and methylene chloride (50 ml). The aqueous is extracted once more with methylene chloride (30 ml). The combined extracts were concentrated and the residual material is subjected to flash column chromatography using a gradient of acetone in hexanes (20% to 75% over 5 column volumes) to provide N-(3-(5-bromopyridin-2-yl)oxetan-3-yl)-2-methylpropane-2-sulfinamide (850 mg): $^1$H NMR (400 MHz, CDCl₃) 1.32 (s, 9H) 4.91-4.97 (m, 2H) 5.13 (d, 1H) 5.34 (d, 1H) 7.78 (d, 1H) 8.04 (m, 1H) 8.68 (d, 1H); m/z (CI) 333, 335 [m+H]⁺.

Step 2 Preparation of 3-(5-bromopyridin-2-yl)oxetan-3-aminium chloride

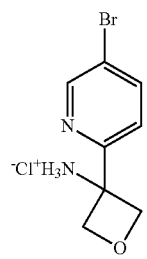

To a methanol (15 ml) solution of N-(3-(5-bromopyridin-2-yl)oxetan-3-yl)-2-methylpropane-2-sulfinamide (850 mg, 2.55 mmol) that had been cooled to 0° C. is added 4N HCl in dioxane (1.3 ml, 5.2 mmol). The solution is stirred for 1 hour at 0° C. The volatiles were removed by rotary evaporation at low pressure. After several evaporation cycles using acetonitrile (3×10 ml) the title product is obtained (584 mg): m/z (CI) 229, 231 [m+H]⁺.

Step 3 Preparation of 1-((4S,5R)-5-(4-(6-(3-aminooxetan-3-yl)pyridin-3-yl)phenyl)-4-(fluoromethyl)-2,2-dimethyloxazolidin-3-yl)-2,2-difluoroethanone

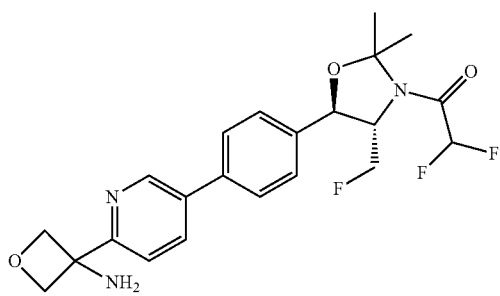 [SMILES: CC1(C)O[C@H](c2ccc(-c3ccc(C4(N)COC4)nc3)cc2)[C@@H](CF)N1C(=O)C(F)F]

To a toluene/ethanol (15 ml toluene, 12 ml ethanol) solution of 2,2-difluoro-1-((4S,5R)-4-(fluoromethyl)-2,2-dimethyl-5-(4-(4,4,5,5-tetramethyl-1,3,2-dioxaborolan-2-yl)phenyl)oxazolidin-3-yl)ethanone (594 mg, 1.44 mmol) is added 3-(5-bromopyridin-2-yl)oxetan-3-aminium chloride (434 mg, 1.44 mmols), sodium bicarbonate (3 mL of a 2M solution) and Pd(dppf)$_2$Cl$_2$ (150 mg, 0.2 mmol)). The reaction mixture is heated to 80° C. while stirring under nitrogen for two hours. The reaction is cooled to room temperature and diluted with ethyl acetate (60 ml). The mixture is washed water (2×10 ml). The organic phase is dried over sodium sulfate and concentrated. The residual material is purified on silica gel (mobile phase 6% methanol in methylene chloride) to give the title compound (436 mg, 70%): m/z (CI) 436 [M+H]$^+$.

Step 4 Preparation of N-((1R,2S)-1-(4-(6-(3-aminooxetan-3-yl)pyridin-3-yl)phenyl)-3-fluoro-1-hydroxypropan-2-yl)-2,2-difluoroacetamide

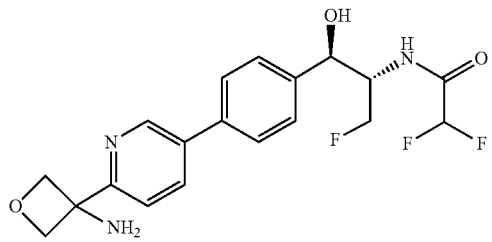 [SMILES: NC1(c2ccc(-c3ccc([C@@H](O)[C@@H](CF)NC(=O)C(F)F)cc3)cn2)COC1]

Following the general procedure of Example 2, Step 2 and making non-critical variations but using the product of Step 3, Example 69 the title compound is obtained (132 mg): $^1$H NMR (400 MHz, methanol-d$_4$) 4.30-4.37 (m, 0.5H) 4.38-4.49 (m, 1.5H) 4.55 (0.5H) 4.62-4.70 (m, 0.5H) 4.82 (d, J=6.57 Hz, 2H) 5.00 (d, J=4.29 Hz, 1H) 5.04 (d, J=6.57 Hz, 2H) 5.86-6.16 (m, 1H) 7.54 (d, J=8.08 Hz, 2H) 7.68 (d, J=8.34 Hz, 2H) 7.78 (d, J=8.84 Hz, 1H) 8.11 (dd, J=8.21, 2.40 Hz, 1H) 8.85 (d, J=1.77 Hz, 1H); m/z (CI) 396 [M+H]$^+$.

The following derivatives of the title compound of Example 69 can be prepared by methods known in the art:
(1R,2S)-1-(4-(6-(3-aminooxetan-3-yl)pyridin-3-yl)phenyl)-2-(2,2-difluoroacetamido)-3-fluoropropyl dihydrogen phosphate;

(1R,2S)-1-(4-(6-(3-aminooxetan-3-yl)pyridin-3-yl)phenyl)-2-(2,2-dichloroacetamido)-3-fluoropropyl dihydrogen phosphate; and N-((1R,2S)-1-(4-(6-(3-aminooxetan-3-yl)pyridin-3-yl)phenyl)-3-fluoro-1-hydroxypropan-2-yl)-2,2-dichloroacetamide.

Example 70

Preparation of 2,2-Dichloro-N-{(1S,2R)-2-[4-(6-dimethylamino-methyl-pyridin-3-yl)-phenyl]-1-fluoromethyl-2-hydroxy-ethyl}-acetamide

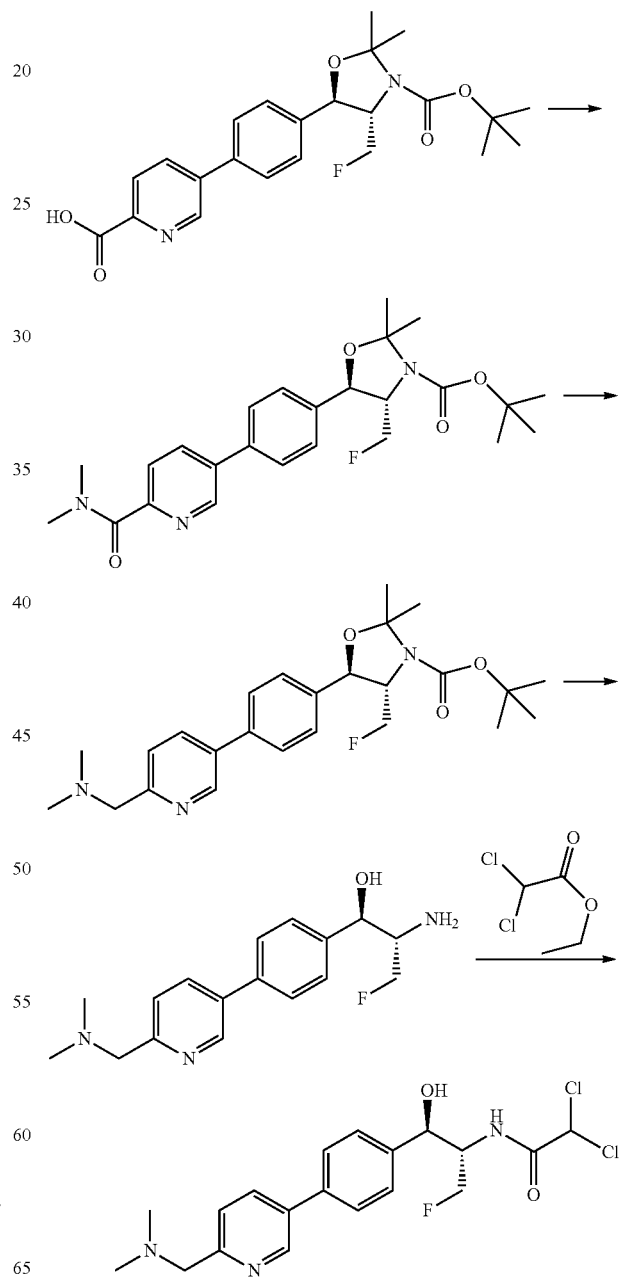

Step 1 Preparation of (4S,5R)-5-[4-(6-Dimethylcarbamoyl-pyridin-3-yl)-phenyl]-4-fluoromethyl-2,2-dimethyl-oxazolidine-3-carboxylic acid tert-butyl ester

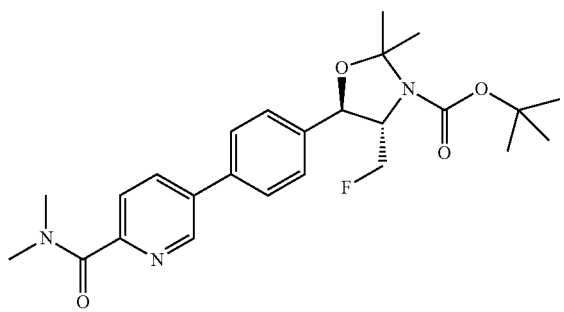 [SMILES: CN(C)C(=O)c1ccc(-c2ccc([C@H]3OC(C)(C)N(C(=O)OC(C)(C)C)[C@@H]3CF)cc2)cn1]

To a stirred solution of 5-[4-((4S,5R)-3-tert-Butoxycarbonyl-4-fluoromethyl-2,2-dimethyl-oxazolidin-5-yl)-phenyl]-pyridine-2-carboxylic acid (220 mg, 0.511 mmol) in dry tetrahydrofuran (6 mL) is added solution of N,N-dimethyl amine, 2 M in tetrahydrofuran (28 mg, 0.31 mL, 0.61 mmol), diisopropylamine (198 mg, 1.534 mmol) and 50% solution of triphenylphosphine in ethyl acetate (244 mg, 0.49 mL, 0.767 mmol) at room temperature. Resulting reaction mixture stirred at same temperature for 14 hours. Diluted with water and ethyl acetate, organic layer is separated and aqueous layer is extracted with ethyl acetate. Combined organic layer is dried over sodium sulphate, solvent is evaporated in vacuo under reduced pressure to obtain crude material purified by column chromatography eluting in 3% methanol in $CH_2Cl_2$ to afford title compound (100 mg): $^1$H-NMR (400 MHz, DMSO-$d_6$) δ: 1.44 (s, 9H), 1.51 (s, 3H), 1.64 (s, 3H), 3.00 (s, 3H), 3.03 (s, 3H), 3.60-3.61 (m, 0.5H), 3.84-3.90 (m, 1.5H), 4.00-4.05 (m, 0.5H), 4.08-4.12 (m, 0.5H), 5.13 (d, 1H, J=7.24 Hz), 7.60 (d, 2H, J=8.24 Hz), 7.64 (d, 1H, J=8.20 Hz), 7.81 (d, 2H, J=8.32 Hz), 8.22 (dd, 1H, J=8.16 Hz, J=2.32 Hz), 8.91 (d, 1H, J=1.88 Hz), LC-MS (m/z): [M+H]=458.2.

Step 2 Preparation of (4S,5R)-5-[4-(6-Dimethylaminomethyl-pyridin-3-yl)-phenyl]-4-fluoromethyl-2,2-dimethyl-oxazolidine-3-carboxylic acid tert-butyl ester

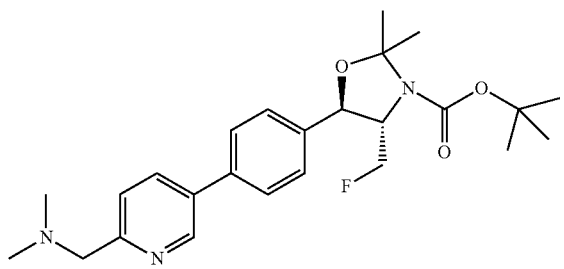 [SMILES: CN(C)Cc1ccc(-c2ccc([C@H]3OC(C)(C)N(C(=O)OC(C)(C)C)[C@@H]3CF)cc2)cn1]

To a stirred solution of (4S,5R)-5-[4-(6-Dimethylcarbamoyl-pyridin-3-yl)-phenyl]-4-fluoromethyl-2,2-dimethyl-oxazolidine-3-carboxylic acid tert-butyl ester (260 mg, 0.569 mmol) in dry tetrahydrofuran (6.5 mL) is added 2M toluene solution $BH_3.DMS$ (130 mg, 1.708 mmol) at 0° C. Reaction heated to 65° C. for 16 hours. Methanol is added to reaction mixture and heated at 65° C. for 2 hours. Volatiles are removed under reduced pressure to obtain crude material purified by column chromatography eluting in 5% methanol in $CH_2Cl_2$ to afford the title compound (50 mg): LC-MS (m/z): [M+H]=444.

Step 3 Preparation of (1S,2S)-2-Amino-1-[4-(6-dimethylaminomethyl-pyridin-3-yl)-phenyl]-3-fluoro-propan-1-ol

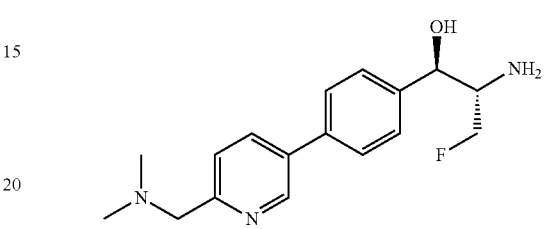

To a stirred solution of (4S,5R)-5-[4-(6-Dimethylaminomethyl-pyridin-3-yl)-phenyl]-4-fluoromethyl-2,2-dimethyl-oxazolidine-3-carboxylic acid tert-butyl ester (80 mg, 0.180 mmol) in $CH_2Cl_2$ (0.32 mL) is added trifluoroacetic acid (0.32 mL). Reaction mixture allowed to warm to room temperature and stirred for 2 hours. The volatiles are removed under reduced pressure to obtain crude material purified by column chromatography eluting in 40% methanol in $CH_2Cl_2$ to afford the title compound (60 mg). LC-MS (m/z): [M+H]=304.1.

Step 4 Preparation of 2,2-Dichloro-N-{(1S,2R)-2-[4-(6-dimethylamino-methyl-pyridin-3-yl)-phenyl]-1-fluoromethyl-2-hydroxy-ethyl}-acetamide

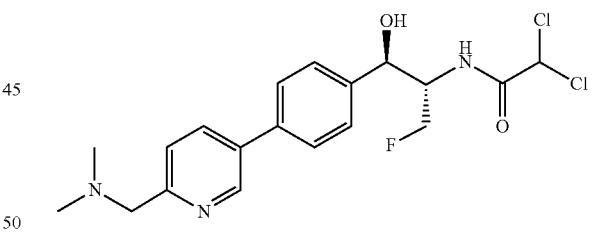

To a stirred solution of (1S,2S)-2-Amino-1-[4-(6-dimethylaminomethyl-pyridin-3-yl)-phenyl]-3-fluoro-propan-1-ol (60 mg, 0.143 mmol) in dry methanol (0.26 mL) is added ethyl dichloroacetate (45 mg, 0.287 mmol) and triethylamine (29 mg, 0.287 mmol) at room temperature and reaction mixture stirred for 24 hours. Solvent is evaporated in vacuo and the crude material purified by column chromatography eluting in 6% methanol in $CH_2Cl_2$ to afford title compound (13 mg): $^1$H-NMR (400 MHz, DMSO-$d_6$) δ: 2.20 (s, 6H), 3.54 (s, 2H), 4.17-4.24 (m, 1H), 4.27-4.31 (m, 0.5H), 4.39-4.41 (m, 0.5H), 4.56-4.58 (m, 0.5H), 4.59-4.71 (m, 0.5H), 4.89 (m, 1H), 4.99 (d, 1H, J=4 Hz), 6.52 (s, 1H), 7.45-7.49 (m, 3H), 7.68 (d, 2H, J=8.24 Hz), 8.03 (dd, 1H, J1=8.08 Hz, J2=2.4 Hz), 8.64 (d, 1H, J=8.8 Hz), 8.77 (d, 1H, J=2.04 Hz). LC-MS (m/z): [M+H]=414.

Example 71

Preparation of 2,2-Dichloro-N-{(1S,2R)-1-fluoromethyl-2-hydroxy-2-[4-(6-ureidomethyl-pyridin-3-yl)-phenyl]-ethyl}-acetamide

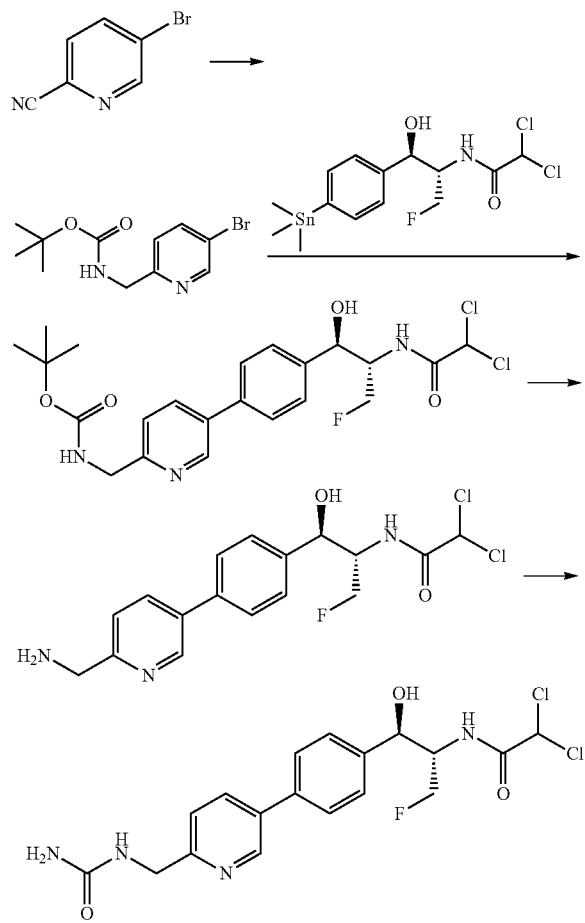

Step 1 Preparation of (5-Bromo-pyridin-2-ylmethyl)-carbamic acid tert-butyl ester

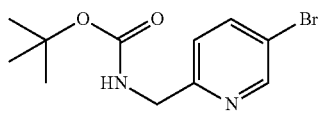 [SMILES: CC(C)(C)OC(=O)NCc1ccc(Br)cn1]

To a solution of 5-Bromo-pyridine-2-carbonitrile (2 g, 10.92 mmol, 1 eq) in methanol (20.0 mL) is added $NiCl_2·6H_2O$ (0.259 g, 1.09 mmol, 0.1 eq) and di-tert-butyldicarbonate (4.76 g, 21.85 mmol, 2 eq). To this resulting mixture is added $NaBH_4$ (0.830 g, 21.57 mmol, 2 eq) at 0° C. ($NaBH_4$ is added in portions). The resulting reaction mixture is stirred at room temperature for 16 hours. Solvent is evaporated in vacuo and the residue diluted with water and extracted with ethyl acetate. The organic layer is dried over $Na_2SO_4$ and solvent is evaporated in vacuo to give crude material which is purified by column chromatography eluting in 10% ethyl acetate/n-Hexane to afford the title compound (1.2 g): $^1$H-NMR (400 MHz, $CDCl_3$) δ: 1.44 (s, 9H), 4.37 (d, 2H, J=5.52 Hz), 5.41-5.44 (bs, 1H), 7.18 (d, 1H, J=8.32 Hz), 7.76 (dd, 1H, $J_1$=2.26 Hz, $J_2$=8.30 Hz), 8.58 (d, 1H, J=4 Hz). LC-Ms (m/z): [M+H]=286.9.

Step 2 Preparation of (5-{4-[(1R,2S)-2-(2,2-Dichloro-acetylamino)-3-fluoro-1-hydroxy-propyl]-phenyl}-pyridin-2-ylmethyl)-carbamic acid tert-butyl ester

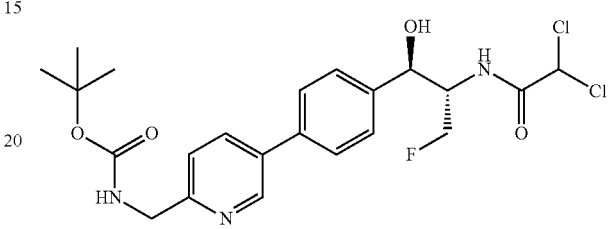

To a solution of the product of Step 1, Example 71 (1.4 g, 3.16 mmol) in N-Methyl-2-pyrrolidone (70.0 mL) is added (5-Bromo-pyridin-2-ylmethyl)-carbamic acid tert-butyl ester (0.905 g, 3.16 mmol) and lithium chloride (0.399 g, 9.501 mmol). The resulting solution bubbled with nitrogen gas for 15 minutes and $Pd(PPh_3)_2Cl_2$ (0.222 g, 0.316 mmol) is added. The resulting reaction mixture heated to 60° C. for 9 hours. The reaction mixture is cooled, diluted with water and extracted with ethyl acetate. Organic layer dried over sodium sulfate and solvent is evaporated in vacuo to give a crude material, which is further purified using column chromatography eluting in 10% methanol in $CH_2Cl_2$ to afford the title compound (220 mg): LC-Ms (m/z): [M+H]=483.8.

Step 3 Preparation of N-{(1S,2R)-2-[4-(6-Aminomethyl-pyridin-3-yl)-phenyl]-1-luoromethyl-2-hydroxy-ethyl}-2,2-dichloro-acetamide trifluoro acetic acid salt

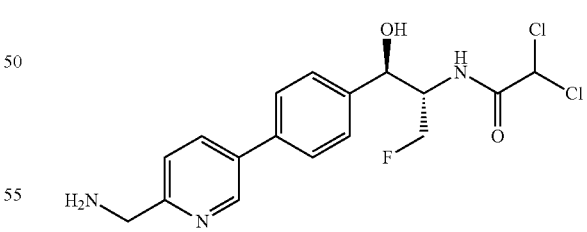

To a solution of (5-{4-[(1R,2S)-2-(2,2-Dichloro-acetylamino)-3-fluoro-1-hydroxy-propyl]-phenyl}-pyridin-2-ylmethyl)-carbamic acid tert-butyl ester (0.212 g, 0.437 mmol) in $CH_2Cl_2$ (2 mL) is added triethylamine (1.0 mL) in drop wise manner at 0° C. The resulting reaction mixture is stirred for 2 hours at room temperature. Solvent is evaporated in vacuo to give a residue, which is stripped with toluene (2×5 mL) to afford title compound (0.250 g): LC-Ms (m/z): M+H=386.1.

Step 4 Preparation of 2,2-Dichloro-N-{(1S,2R)-1-fluoromethyl-2-hydroxy-2-[4-(6-ureidomethyl-pyridin-3-yl)-phenyl]-ethyl}-acetamide

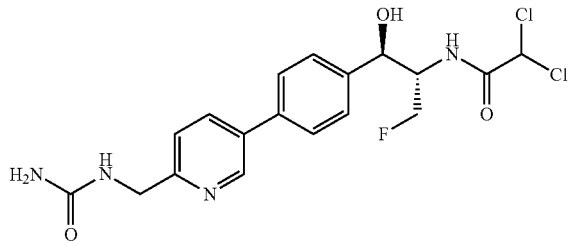 [SMILES: NC(=O)NCc1ccc(-c2ccc([C@@H](O)[C@@H](CF)NC(=O)C(Cl)Cl)cc2)cn1]

To a solution of the product of step 3, Example 71 (0.250 g, 0.649 mmol) in mixture of 1,4-dioxane (16.0 mL) and water (4.0 mL) is added potassium isocyanate (0.057 g, 0.714 mmol). The resulting reaction mixture heated to 90° C. for 2 hours. The reaction mixture is cooled and diluted with water and extracted with ethyl acetate. The organic layer is washed with water and brine, dried over sodium sulfate and solvent is evaporated in vacuo to give a crude material which is purified using column chromatography eluting in 2% methanol in $CH_2Cl_2$ to afford the title compound (0.018 g): $^1$H-NMR (400 MHZ, DMSO-$d_6$) δ: 4.20-4.22 (m, 1H), 4.22-4.24 (m, 0.5H), 4.30 (d, 2H, J=6 Hz), 4.39-4.43 (m, 0.5H), 4.56-4.59 (m, 0.5H), 4.67-4.71 (m, 0.5H), 4.89 (t, 1H, J=3.6 Hz), 5.65 (s, 2H), 6.00 (d, 1H, J=3.1 Hz), 6.52 (s, 1H), 6.56 (t, 1H, J=5.68 Hz), 7.35 (d, 1H, J=8.16 Hz), 7.46 (d, 2H, J=8.2 Hz), 7.66 (d, 2H, J=8.24 Hz), 8.02-8.05 (dd, 1H, $J_1$=2.32 Hz, $J_2$=8.16 Hz), 8.65 (d, 1H, J=8.84 Hz), 8.78 (d, 1H, J=2.08 Hz). LC-Ms (m/z): [M+H]=429.0.

Example 72

Preparation of 2,2-difluoro-N-((1R,2S)-3-fluoro-1-hydroxy-1-(4-(6-(1-(methylsulfonamido)cyclopropyl)pyridin-3-yl)phenyl)propan-2-yl)acetamide

Step 1 Preparation of N-(1-(5-bromopyridin-2-yl)cyclopropyl)methanesulfonamide

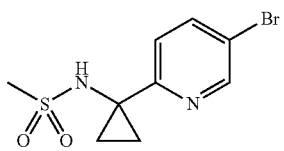

Commercially available 1-(5-bromopyridin-2-yl)cyclopropanamine dihydrochloric acid salt (494 mg, 1.73 mmol) is dissolved in $CH_2Cl_2$ (11.5 mL, 0.15M) and had 3.1 eq. of triethylamine (543 mg, 5.36 mmol) added to it. 1.1 eq. of methanesulfonyl chloride (218 mg, 1.9 mmol) is then added and the mixture stirred for 16 hours. Dichloromethane (20 mL) is added and washed with $NaHCO_3$ (sat, aq). The solvent is evaporated to give the title compound (310 mg): m/z (CI) 293 [M+H].

Step 2 Preparation of 2,2-difluoro-N-((1R,2S)-3-fluoro-1-hydroxy-1-(4-(6-(1-(methylsulfonamido)cyclopropyl)pyridin-3-yl)phenyl)propan-2-yl)acetamide

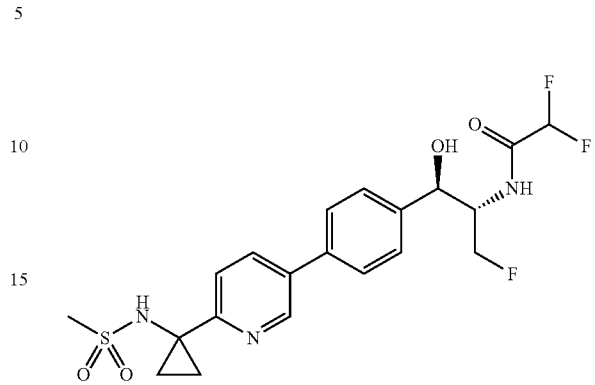

Following the general procedure of Example 9—Step 2 and making non-critical variations but using the product of Example 72—Step 1 and Example 17—Step 3 the title compound is obtained (310 mg): $^1$H NMR (400 MHz, DMSO-$d_6$) δ:1.4-1.45 (m, 2H), 1.45-1.5 (m, 2H), 2.9 (s, 3H), 4.2-4.35 (m, 1.5H), 4.35-4.45 (m, 0.5H), 4.45-4.6 (m, 0.5H), 4.6-4.7 (m, 0.5H), 4.85 (t, 1H), 5.9 (d, 1H), 6.2 (t, 1H), 7.45 (d, 2H), 7.65 (d, 2H), 7.8 (d, 1H), 8.05 (d, 1H), 8.30 (s, 1H), 8.70 (s, 1H), 8.8 (d, 1H). m/z (CI) 458 [M+H].

Example 73

Preparation of 2,2-Dichloro-N-[(1S,2R)-1-fluoromethyl-2-hydroxy-2-(4-{6-[(3-methyl-butylamino)-methyl]-pyridin-3-yl}-phenyl)-ethyl]-acetamide

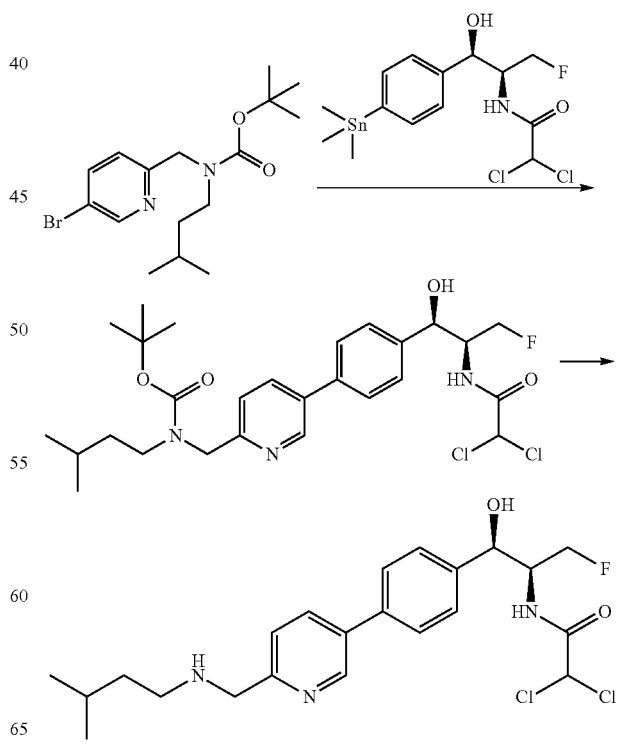

Step 1 Preparation of (5-{4-[(1R,2S)-2-(2,2-Di-chloro-acetylamino)-3-fluoro-1-hydroxy-propyl]-phenyl}-pyridin-2-ylmethyl)-(3-methyl-butyl)-carbamic acid tert-butyl ester

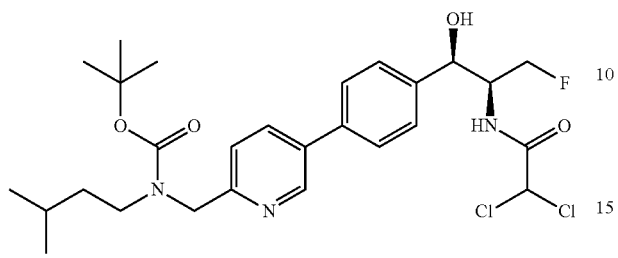

To a solution 2,2-Dichloro-N-[(1S,2R)-1-fluoromethyl-2-hydroxy-2-(4-trimethyl stannanyl-phenyl)-ethyl]-acetamide (100 mg, 0.226 mmol) in N-Methyl-2-pyrrolidone (1.5 mL) is added (5-Bromo-pyridin-2-ylmethyl)-(3-methyl-butyl)-carbamic acid tert-butyl ester (81 mg, 0.226 mmol) and resulting solution bubbled with nitrogen gas for 15 minutes. To this reaction mixture is added $Pd_2(dba)_3$ (21 mg, 0.022 mmol) and P(2-fur)$_3$ (11 mg, 0.045 mmol) under nitrogen atmosphere. The resulting reaction mixture heated to 80° C. for 18 hours. Cooled, diluted with water and extracted with ethyl acetate. The organic layer dried over sodium sulfate and solvent is evaporated in vacuo to give a crude material purified using column chromatography eluting in 2.4% methanol in $CH_2Cl_2$ to afford the title compound (10 mg). LC-MS (m/z): [M+H]=556.1.

Step 2 Preparation of 2,2-Dichloro-N-[(1S,2R)-1-fluoromethyl-2-hydroxy-2-(4-{6-[(3-methyl-buty-lamino)-methyl]-pyridin-3-yl}-phenyl)-ethyl]-acet-amide

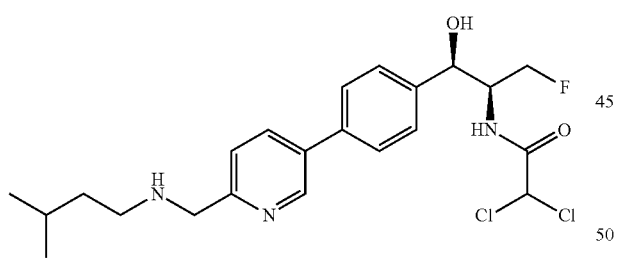

To a solution of (5-{4-[(1R,2S)-2-(2,2-Dichloro-acety-lamino)-3-fluoro-1-hydroxy-propyl]-phenyl}-pyridin-2-yl-methyl)-(3-methyl-butyl)-carbamic acid tert-butyl ester (8 mg, 0.014 mmol) in dry $CH_2Cl_2$ (0.04 mL) is added trifluo-roacetic acid (0.04 mL) and resulting reaction mixture is stirred at room temperature for 2 hours. Solvent is evapo-rated in vacuo to get brown crude, which is washed with diethyl ether:pentane (1:9), to give the title compound (8 mg): $^1$H-NMR (400 MHz, DMSO-d$_6$) δ0.89 (d, 6H, J=6.40 Hz), 1.52-1.58 (m, 2H), 1.60-1.65 (m, 1H), 3.01 (bs, 1H), 4.20-4.23 (m, 2H), 4.29-4.31 (m, 0.5H), 4.36-4.38 (m, 2H), 4.40-4.44 (m, 0.5H), 4.57-4.59 (m, 0.5H), 4.70-4.71 (m, 0.5H), 4.91-4.93 (m, 1H), 6.02 (d, 1H, J=4.28 Hz), 6.52 (s, 1H), 7.49 (d, 2H, J=8.24), 7.57 (d, 1H, J=8.16 Hz), 7.73 (d, 2H, J=8.28 Hz), 8.19 (dd, 1H, J$_1$=8.16 Hz, J$_2$=2.32 Hz), 8.65 (d, 1H, J=8.96 Hz), 8.96 (d, 1H, J=1.96 Hz), 9.00 (bs, 2H). LC-MS (m/z): [M+H]=456.1.

Example 74

Preparation of 2,2-dichloro-N-((1R,2S)-3-fluoro-1-hydroxy-1-(4-(5-(pyrrolidin-2-yl)thiophen-2-yl)phe-nyl)propan-2-yl)acetamide Step 1 Preparation of tert-butyl 2-(5-bromothiophen-2-yl)pyrrolidine-1-carboxylate

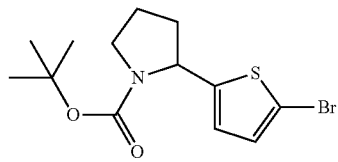 [SMILES: CC(C)(C)OC(=O)N1CCCC1c1ccc(Br)s1]

To a stirred solution of commercially available 2-(5-bromothiophen-2-yl)-pyrrolidine (0.986 g, 4.25 mmol) in 1,4-dioxane (20 mL) is added $K_2CO_3$ (1.21 g, 8.49 mmol) and water (10 mL). The mixture is cooled to 0° C., and di-tert-butyl dicarbonate (1.02 g, 2.40 mmol) is added. The reaction mixture is allowed to warm to ambient and stirred for 16 h. The reaction mixture is concentrated in vacuo. The crude material is diluted with water and extracted with ethyl acetate. Organic layer is filtered through fine silica gel and concentrated to yield the title compound (1.48 g): $^1$H-NMR (400 MHz, CDCl$_3$) δ 1.32-1.52 (m, 9H), 1.86-2.06 (m, 3H), 2.16-2.31 (m, 1H), 3.35-3.58 (m, 2H), 4.91-5.15 (m, 1H), 6.61 (bs, 1H), 6.85 (d, J=3.5 Hz, 1H). m/z (CI) M+H 332.0.

Step 2 Preparation of tert-butyl 2-(5-(4-((1R,2S)-2-(2,2-dichloroacetamido)-3-fluoro-1-hydroxypropyl)phenyl)thiophen-2-yl)pyrrolidine-1-carboxylate

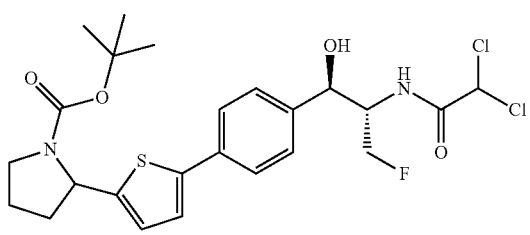 [SMILES: CC(C)(C)OC(=O)N1CCCC1c1ccc(-c2ccc([C@@H](O)[C@@H](CF)NC(=O)C(Cl)Cl)cc2)s1]

To a stirred solution of tert-butyl 2-(5-bromothiophen-2-yl)pyrrolidine-1-carboxylate (0.750 g, 2.26 mmol), 2,2-di-chloro-N-((1R,2S)-3-fluoro-1-hydroxy-1-(4-(trimethylstan-nyl)phenyl)propan-2-yl)acetamide (1.0 g, 2.26 mmol), and tri(furan-2-yl)phosphine (105 mg, 0.452 mmol) in N-Methyl-2-pyrrolidone (10 mL) degassed with nitrogen is added Pd$_2$(dba)$_3$ (207 mg, 0.226 mmol). The reaction mix-ture is heated to 80° C. for 5 hours then left at ambient 70 hours. Reaction mixture partitioned between ethyl acetate (100 mL) and water (100 mL). Organic phase is isolated and concentrated in vacuo to give the crude material, which is purified by column chromatography on silica gel eluting in 0-100% ethyl acetate in heptane to give the title compound (559 mg): $^1$H-NMR (400 MHz, CDCl$_3$) δ 1.32-1.52 (m, 9H), 1.89-2.15 (m, 3H), 2.21-2.37 (m, 1H), 2.59-2.78 (m, 1H), 3.40-3.66 (m, 2H), 4.25-4.38 (m, 1H), 4.43-4.49 (m, 0.5H), 4.54-4.62 (m, 1H), 4.66-4.73 (m, 0.5H), 5.01-5.25 (m, 2H), 5.89 (s, 1H), 6.83 (bs, 1H), 7.06 (d, J=8.6 Hz, 1H), 7.14 (d, J=3.5 Hz, 1H), 7.38 (d, J=8.1 Hz, 2H), 7.56 (d, J=8.1 Hz, 2H). m/z (CI) M-boc+H 431.0.

Step 3 Preparation of 2,2-dichloro-N-((1R,2S)-3-fluoro-1-hydroxy-1-(4-(5-(pyrrolidin-2-yl)thiophen-2-yl)phenyl)propan-2-yl)acetamide

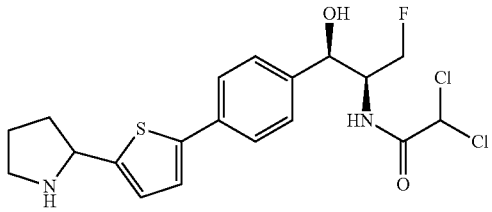 [SMILES: O=C(N[C@H](CF)[C@H](O)c1ccc(-c2ccc(C3CCCN3)s2)cc1)C(Cl)Cl]

Following the general procedure of Example 2, Step 2 and making non-critical variations but using the product of step 3, Example 74 the title compound is obtained (257 mg): $^1$H-NMR (400 MHz, DMSO-d$_6$) δ: 1.60-2.01 (m, 3H), 2.18-2.33 (m, 1H), 2.89-3.21 (m, 2H), 3.31-3.6 (m, 2H), 4.09-4.33 (m, 2H), 4.37-4.44 (m, 0.5H), 4.52-4.62 (m, 1H), 4.64-4.71 (m, 0.5H), 4.83-4.89 (m, 1H), 5.96 (bs, 1H), 6.52 (s, 1H), 6.92-7.12 (m, 1H), 7.26-7.41 (m, 2H), 7.50-7.59 (m, 2H), 8.55-8.62 (m, 1H): m/z (CI) M+H 431.0.

Example 75

Preparation of N-((1R,2S)-1-(4-(5-(1-aminoethyl) thiophen-2-yl)phenyl)-3-fluoro-1-hydroxypropan-2-yl)-2,2-dichloroacetamide Step 1 Preparation of tert-butyl (1-(5-bromothiophen-2-yl)ethyl)carbamate

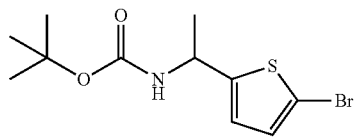 [SMILES: CC(NC(=O)OC(C)(C)C)c1ccc(Br)s1]

The compound is prepared from commercially available 1-(5-bromothiophen-2-yl)ethanamine (992 mg, 4.09 mmol) in a manner analogous to Example 74 Step 1 to give the title compound (1.25 g): $^1$H-NMR (400 MHz, CDCl$_3$) δ: 1.46 (s, 9H), 1.52 (d, J=6.8 Hz, 3H), 4.78 (m, 1H), 4.96 (m, 1H), 6.70 (dd, J=3.8 Hz, 1H), 6.88 (d, J=3.5 Hz, 1H).

Step 2 Preparation of tert-butyl (1-(5-(4-((1R,2S)-2-(2,2-dichloroacetamido)-3-fluoro-1-hydroxypropyl) phenyl)thiophen-2-yl)ethyl)carbamate

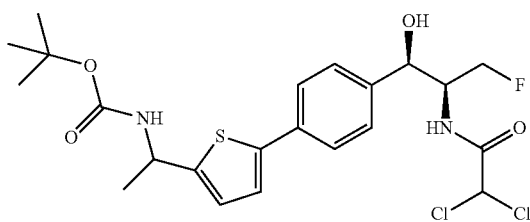 [SMILES: CC(NC(=O)OC(C)(C)C)c1ccc(-c2ccc([C@@H](O)[C@@H](CF)NC(=O)C(Cl)Cl)cc2)s1]

The compound is prepared from tert-butyl (1-(5-bromothiophen-2-yl)ethyl)-carbamate (138 mg, 0.45 mmol) and 2,2-dichloro-N-((1R,2S)-3-fluoro-1-hydroxy-1-(4-(trimethylstannyl)phenyl)propan-2-yl)acetamide (200 mg, 0.45 mmol) in a manner analogous to Example 74, Step 2 to give the title compound (70 mg): $^1$H-NMR (400 MHz, CDCl$_3$) δ: 1.47 (s, 9H), 1.57 (d, J=6.8 Hz, 3H), 2.68 (bs, 1H), 4.25-4.38 (m, 1H), 4.42-4.48 (m, 0.5H), 4.53-4.60 (m, 1H), 4.65-4.72 (m, 0.5H), 4.77-4.89 (m, 1H), 4.98-5.09 (m, 1H) 5.11 (d, J=4.0 Hz, 1H), 5.87 (s, 1H), 6.90 (d, J=3.5 Hz, 1H), 7.04 (d, J=8.6 Hz, 1H), 7.14 (d, J=3.8 Hz, 1H), 7.37 (d, J=8.1 Hz, 2H), 7.55 (m, 2H).

Step 3 Preparation of N-((1R,2S)-1-(4-(5-(1-aminoethyl)thiophen-2-yl)phenyl)-3-fluoro-1-hydroxypropan-2-yl)-2,2-dichloroacetamide

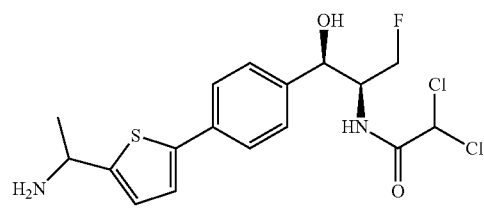 [SMILES: CC(N)c1ccc(-c2ccc([C@@H](O)[C@@H](CF)NC(=O)C(Cl)Cl)cc2)s1]

Following the general procedure of Example 2, Step 2 and making non-critical variations but using the product of step 2, Example 75 the title compound is obtained (8.3 mg): m/z (CI) M+H 406.0.

Example 76

Preparation of 2,2-dichloro-N-((1R,2S)-3-fluoro-1-hydroxy-1-(4-(2-(methylsulfonamidomethyl) thiazol-5-yl)phenyl)propan-2-yl)acetamide

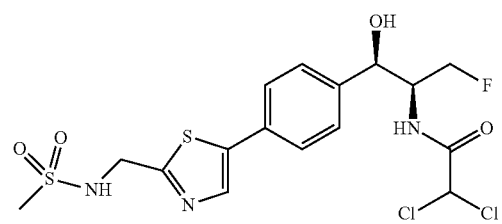 [SMILES: CS(=O)(=O)NCc1ncc(-c2ccc([C@@H](O)[C@@H](CF)NC(=O)C(Cl)Cl)cc2)s1]

The compound is prepared from N-((1R,2S)-1-(4-(2-(aminomethyl)thiazol-5-yl)phenyl)-3-fluoro-1-hydroxypropan-2-yl)-2,2-dichloroacetamide (30 mg, 0.06 mmol) in a manner analogous to Example 3 to give the title compound (6.5 mg): m/z (CI) M+470.

Example 77

Preparation of N-((1R,2S)-1-(4-(5-(aminomethyl)thiophen-3-yl)phenyl)-3-fluoro-1-hydroxypropan-2-yl)-2,2-dichloroacetamide Step 1 Preparation of tert-butyl ((4-(4-((1R,2S)-2-(2,2-dichloroacetamido)-3-fluoro-1-hydroxypropyl)phenyl)thiophen-2-yl)methyl)carbamate

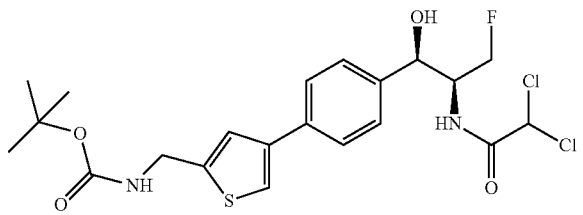 [SMILES: CC(C)(C)OC(=O)NCc1cc(-c2ccc([C@@H](O)[C@@H](CF)NC(=O)C(Cl)Cl)cc2)cs1]

The compound is prepared from tert-butyl ((4-bromothiophen-2-yl)methyl)-carbamate (132 mg, 0.45 mmol) and 2,2-dichloro-N-((1R,2S)-3-fluoro-1-hydroxy-1-(4-(trimethylstannyl)phenyl)propan-2-yl)acetamide (200 mg, 0.45 mmol) in a manner analogous to Example 2 to give the tile compound (45 mg): $^1$H-NMR (400 MHz, CDCl$_3$) 1.47 (s, 9H), 2.73 (bs, 1H), 4.26-4.38 (m, 1H), 4.39-4.52 (m, 2.5H), 4.53-4.61 (m, 1H), 4.65-4.72 (m, 0.5H), 4.87-5.03 (m, 1H), 5.12 (d, J=4.0 Hz, 1H), 5.87 (s, 1H), 7.06 (d, J=8.6 Hz, 1H), 7.20 (s, 1H), 7.32 (d, J=1.5 Hz, 1H), 7.39 (d, J=8.1 Hz, 2H), 7.54 (m, 2H).

Step 2 Preparation of N-((1R,2S)-1-(4-(5-(aminomethyl)thiophen-3-yl)phenyl)-3-fluoro-1-hydroxypropan-2-yl)-2,2-dichloroacetamide

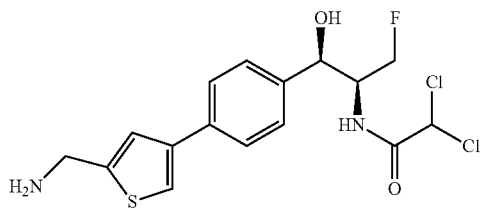 [SMILES: NCc1cc(-c2ccc([C@@H](O)[C@@H](CF)NC(=O)C(Cl)Cl)cc2)cs1]

Following the general procedure of Example 2, Step 2 and making non-critical variations but using the product of Step 1, Example 77, the title compound is obtained (25.8 mg): m/z (CI) M−OH+H 374.0.

Example 78

2,2-dichloro-N-((1R,2S)-3-fluoro-1-hydroxy-1-(4-(5-(morpholino-methyl)thiophen-2-yl)phenyl)propan-2-yl)acetamide

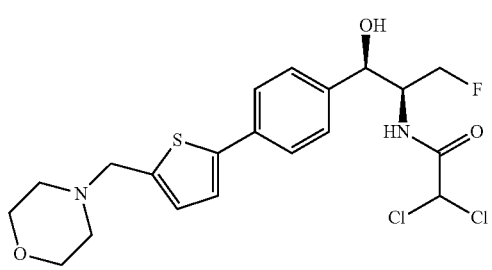 [SMILES: O=C(N[C@H](CF)[C@H](O)c1ccc(-c2ccc(CN3CCOCC3)s2)cc1)C(Cl)Cl]

Following the general procedure of Example 22, Step 1 and making non-critical variations but using 2,2-dichloro-N-((1R,2S)-3-fluoro-1-hydroxy-1-(4-iodophenyl)propan-2-yl)acetamide (150 mg, 0.34 mmol) and 4-((5-(4,4,5,5-tetramethyl-1,3,2-dioxaborolan-2-yl)thiophen-2-yl)methyl)morpholine (114 mg, 0.37 mmol), followed by the general procedure from Example 2, step 2, the title compound is obtained (50 mg): $^1$H NMR (400 MHz, CDCl$_3$) δ: 1.66 (bs, 1H), 2.53 (t, 4H), 3.71 (s, 2H), 3.75 (t, 4H), 4.25-4.38 (m, 1H), 4.42-4.48 (m, 0.5H), 4.53-4.60 (m, 1H), 4.65-4.71 (m, 0.5H), 5.11 (d, 1H), 5.87 (s, 1H), 6.89 (d, J=3.5 Hz, 1H), 7.04 (d, J=8.8 Hz, 1H), 7.16 (d, J=3.5 Hz, 1H), 7.39 (m, 2H), 7.59 (m, 2H).

Example 79

Preparation of N-((1R,2S)-3-fluoro-1-hydroxy-1-(4-(6-(methyl-sulfonamidomethyl)pyridin-3-yl)phenyl)propan-2-yl)cyclopropanecarboxamide Step 1 Preparation of N-((5-(4-((1R,2S)-2-amino-3-fluoro-1-hydroxypropyl) phenyl) pyridin-2-yl)methyl)methanesulfonamide (4S,5R)-tert-butyl4-(fluoromethyl)-2,2-dimethyl-5-(4-(6-(methylsulfonamidomethyl)pyridin-3-yl)phenyl)oxazolidine-3-carboxylate (1800 mg, 3.64 mmol) is dissolved in dichloromethane (20 mL), and treated with trifluoroacetic acid (5.4 mL), for 4 h at room temperature. The reaction mixture is diluted with toluene (30 mL) and concentrated to a syrup. Obtained crude compound is basified with aqueous sodium bicarbonate, extracted with ethyl acetate. Extracts are dried over Na$_2$SO$_4$, filtered, and concentrated to give the title compound (1110 mg): m/z (CI) M+H 354.

Step 2 Preparation of N-((1R,2S)-3-fluoro-1-hydroxy-1-(4-(6-(methyl-sulfonamidomethyl) pyridin-3-yl)phenyl)propan-2-yl)cyclopropanecarboxamide

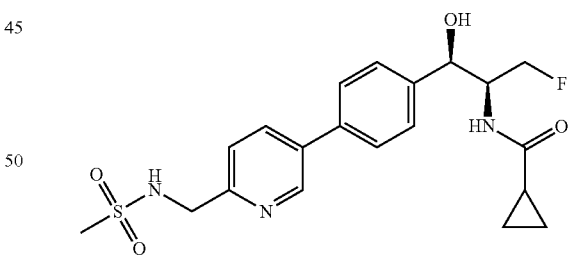

A mixture of amino alcohol (100 mg, 0.28 mmol), cyclopropanecarboxylic acid (25 mg, 0.28 mmol), O-(7-azabenzotriazol-1-yl)-N,N,N',N'-tetramethyluronium hexafluorophosphate (118 mg, 0.31 mmol) and diisopropylethylamine (0.150 mL, 0.85 mmol) in dimethylformamide (1 mL) is stirred at room temperature for 16 hours. Reaction mixture is filtered and purified using HPLC to give the title compound (30 mg): $^1$H NMR (400 MHz, DMSO-d$_6$) (0.5-0.7 (m, 4H), 1.67-1.80 (m, 1H), 2.95 (s, 3H), 4.16-4.41 (m, 4H), 4.45-4.70 (m, 1H), 4.81-4.94 (m, 1H), 5.84 (dd, 1H), 7.43-7.62 (m, 3H), 7.66-7.79 (m, 3H), 8.05-8.19 (m, 2H), 8.85 (d, 1H). m/z (CI) M+H 422.

Example 80

Preparation of 3,3,3-trifluoro-N-((1R,2S)-3-fluoro-1-hydroxy-1-(4-(6-(methylsulfonamidomethyl)pyridin-3-yl)phenyl)propan-2-yl)propanamide

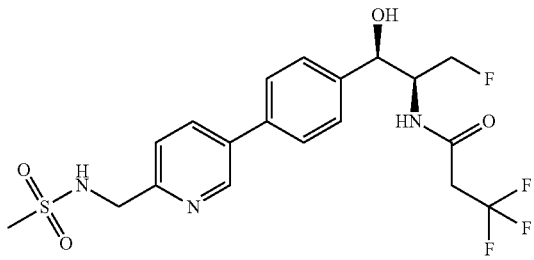 [SMILES: CS(=O)(=O)NCc1ccc(-c2ccc([C@@H](O)[C@@H](CF)NC(=O)CC(F)(F)F)cc2)cn1]

Following the general procedure of Example 1—Step 2 and making non-critical variations but using 3,3,3-trifluoropropanoic acid the title compound is obtained (40 mg). $^1$H NMR (400 MHz, DMSO-d$_6$) 2.95 (s, 3H), 4.19-4.39 (m, 3.5H), 4.49-4.57 9m, 0.5H), 4.60-4.69 (m, 0.5H), 4.82-4.91 (m, 1H), 5.90 (d, 1H), 7.47 (d, 2H), 7.53 (d, 1H), 7.66-7.79 (m, 3H), 8.10 (dd, 1H), 8.34 (d, 1H), 8.82 (d, 1H). m/z (CI) M+H 578.

Example 81

Preparation of 2,2-difluoro-N-((1R,2S)-3-fluoro-1-hydroxy-1-(4-(6-(methylsulfonamidomethyl)pyridin-3-yl)phenyl)propan-2-yl)propanamide

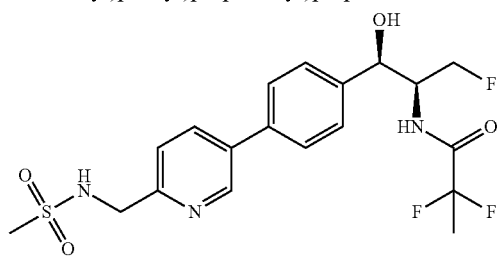

Following the general procedure of Example 1—Step 2 and making non-critical variations but using 2,2-difluoropropanoic acid the title compound is obtained (40 mg). $^1$H NMR (400 MHz, DMSO-d$_6$) 1.63 (t, 3H), 2.95 (s, 3H), 4.27-4.39 (m, 3.5H), 4.44-4.51 (m, 0.5H), 4.52-4.59 9m, 0.5H), 4.64-4.70 (m, 0.5H), 4.86-4.92 (m, 1H), 5.80 (d, 1H), 7.44 (d, 2H), 7.53 (d, 1H), 7.66-7.74 (m, 3H), 8.11 (dd, 1H), 8.42 (d, 1H), 8.83 (d, 1H). m/z (CI) M+H 446.

Example 82

Preparation of 2,2-dichloro-N-((1R,2S)-3-fluoro-1-hydroxy-1-(4-(6-(methylsulfonamidomethyl)pyridin-3-yl)phenyl)propan-2-yl)propanamide

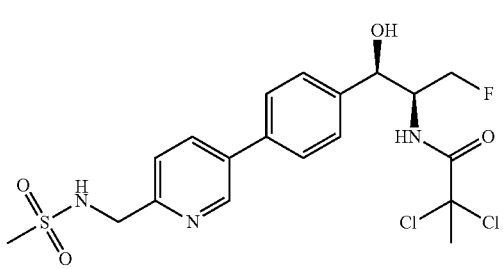 [SMILES: CC(Cl)(Cl)C(=O)N[C@H](CF)[C@H](O)c1ccc(-c2ccc(CNS(C)(=O)=O)nc2)cc1]

Following the general procedure of Example 1—Step 2 and making non-critical variations but using 2,2-dichloropropanoic acid the title compound is obtained (33 mg): $^1$H NMR (400 MHz, DMSO-d$_6$) 2.95 (s, 3H), 4.23-4.36 (m, 3.5H), 4.37-4.44 (m, 0.5H), 4.48-4.63 (m, 1H), 4.67-4.75 (m, 0.5H), 4.90-4.97 (m, 1H), 5.90-5.97 (m, 1H), 7.47 (d, 2H), 7.53 (d, 1H), 7.66-7.74 (m, 3H), 8.06-8.16 (m, 2H), 8.42 (d, 1H), 8.83 (d, 1H). m/z (CI) M+H 478.

Example 83

Preparation of N-((1R,2S)-3-fluoro-1-hydroxy-1-(4-(6-(methyl-sulfonamidomethyl)pyridin-3-yl)phenyl)propan-2-yl)-2-((trifluoromethyl)-thio)acetamide

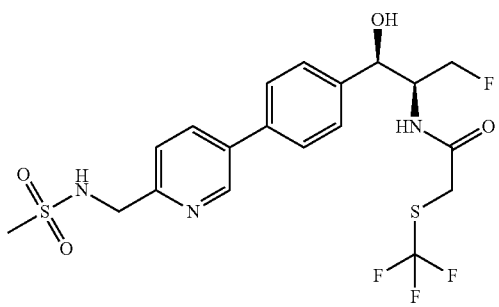 [SMILES: CS(=O)(=O)NCc1ccc(-c2ccc([C@@H](O)[C@@H](CF)NC(=O)CSC(F)(F)F)cc2)cn1]

Following the general procedure of Example 1—Step 2 and making non-critical variations but using 2-((trifluoromethyl)thio)acetic acid the title compound is obtained (35 mg): $^1$H NMR (400 MHz, DMSO-d$_6$) 2.95 (s, 3H), 3.72-3.83 (ABq, 2H), 4.18-4.38 (m, 4H), 4.48-4.55 (m, 0.5H), 4.60-4.67 (m, 0.5H), 4.85-4.92 (m, 1H), 5.90-5.92 (m, 1H), 7.48 (d, 2H), 7.53 (d, 1H), 7.64-7.74 (m, 3H), 8.10 (dd, 1H), 8.37 (d, 1H), 8.82 (d, 1H). m/z (CI) M+H 496.

Example 84

Preparation of 2-azido-N-((1R,2S)-3-fluoro-1-hydroxy-1-(4-(6-(methylsulfonamidomethyl)pyridin-3-yl)phenyl)propan-2-yl)acetamide

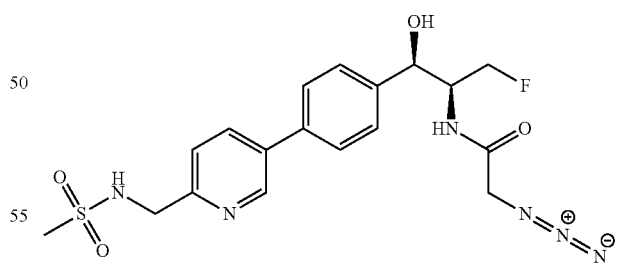

To a slurry of N-((5-(4-((1R,2S)-2-amino-3-fluoro-1-hydroxypropyl) phenyl) pyridin-2-yl) methyl)methanesulfonamide (800 mg, 2.26 mmol) in ethylacetate/aqueous NaHCO$_3$ (1:1) (10 mL) is slowly added bromoacetyl bromide (900 mg, 4.5 mmol) over a period of 20 minutes. Organic layer is separated and aqueous layer extracted with ethyl acetate (3×10 mL). Combined extract is dried over Na$_2$SO$_4$ and concentrated to get crude product. m/z (CI) M+H 474. A mixture of crude bromide (500 mg) and sodium azide (470 mg, 7.0 mmol) in dimethylformamide (6 mL) is heated for 30 min at 50° C. Reaction is cooled, diluted with water (10 mL) and extracted with ethyl acetate (3×15 mL). Combined extract is dried over Na₂SO₄, concentrated under vacuum and then obtained crude product purified on silica gel column using 0 to 5% methanol/CH₂Cl₂ to give the title compound (300 mg): ¹H NMR (400 MHz, DMSO-d₆) 2.95 (s, 3H), 3.71-3.87 (m, 2H), 4.22-4.42 (m, 4H), 4.47-4.58 (m, 0.5H), 4.50-4.70 (m, 0.5H), 4.83-4.93 (m, 1H), 5.83-5.93 (m, 1H), 7.47 (d, 2H), 7.54 (d, 1H), 7.64-7.77 (m, 3H), 8.06-8.20 (m, 2H), 8.83 (d, 1H). m/z (CI) M+H 437.

Example 85

Preparation of N-((1R,2S)-3-fluoro-1-hydroxy-1-(4-(6-(methyl-sulfonamidomethyl)pyridin-3-yl)phenyl)propan-2-yl)methanesulfonamide

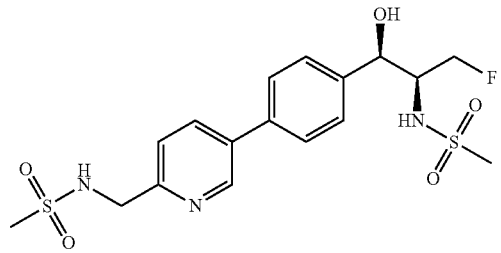

To a slurry of N-((5-(4-((1R,2S)-2-amino-3-fluoro-1-hydroxypropyl) phenyl) pyridin-2-yl) methyl)methanesulfonamide (100 mg, 0.28 mmol) in ethylacetate/aqueous NaHCO₃ (1:1) (2 mL) is slowly added methanesulfonyl chloride (50 mg, 0.42 mmol) over a period of 20 minutes. Reaction is diluted with water (2 mL) and extracted with ethylacetate (3×5 mL). Combined organic solution is dried over Na₂SO₄ and concentrated. Crude product is purified using HPLC to give the title compound (60 mg): ¹H NMR (400 MHz, DMSO-d₆) 2.55 (s, 3H), 2.98 (s, 3H), 3.67-3.80 (m, 1H), 4.18-4.26 (m, 0.5H), 4.31-4.40 (m, 2.5H), 4.48-4.55 (m, 0.5H), 4.60-4.67 (m, 0.5H), 4.80-4.87 (m, 1H), 5.83-5.93 (m, 1H), 7.27 (d, 1H), 7.54 (d, 2H), 7.54 (d, 1H), 7.62 (d, 1H), 7.70-7.79 (m, 3H), 8.20-8.26 (m, 1H), 8.90 (d, 1H). m/z (CI) M+H 432.

Example 86

Preparation of N-((1R,2S)-1-(4-(2-(aminomethyl)thiazolo[5,4-b]pyridin-6-yl)phenyl)-3-fluoro-1-hydroxypropan-2-yl)-2,2-dichloroacetamide

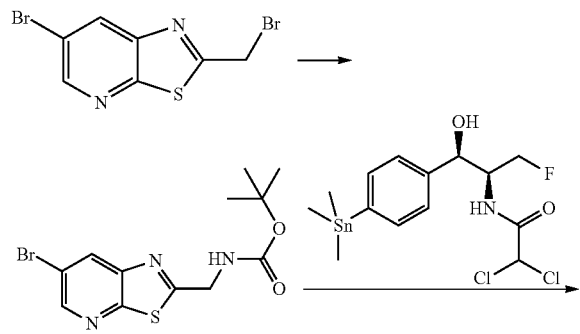

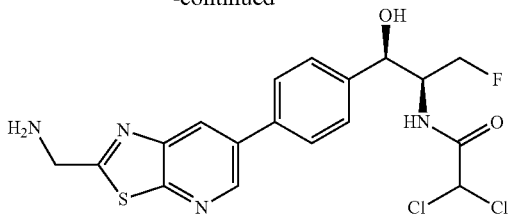

Step 1 Preparation of tert-butyl ((6-bromothiazolo[5,4-b]pyridin-2-yl)methyl)carbamate

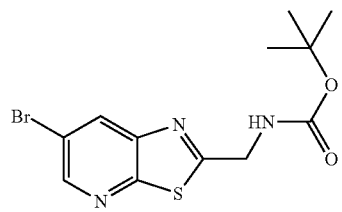 [SMILES: CC(C)(C)OC(=O)NCc1nc2cc(Br)cnc2s1]

To a solution 6-bromo-2-(bromomethyl)thiazolo[5,4-b]pyridine (800 mg, 2.60 mmol) (Journal of Medicinal Chemistry, 53(10), 3927-3936; 2010) in tetrahydrofuran (10 mL) is added ammonium hydroxide (2 mL) and stirred at room temperature for 16 hours. Reaction is concentrated, diluted with water (5 mL) and extracted using ethyl acetate (3×10 ml). Extracts are dried over Na₂SO₄ and concentrated to get crude product (650 mg). m/z (CI) M+244. To a solution of crude amine (350 mg, 1.43 mmol) in tetrahydrofuran (10 mL) and aqueous NaHCO₃ (2 mL) is added boc anhydride and resulting mixture stirred at room temperature for over night. Organic solution is separated and aqueous layer extracted with ethyl acetate (5 mL). Combined organic solution is dried over Na₂SO₄ and concentrated under vacuum to give the title compound (400 mg): ¹H NMR (400 MHz, CDCl₃) 1.50 (s, 9H), 4.74 (d, 2H), 8.36 (s, 1H), 8.62 (s, 1H). m/z (CI) M+2 346.

Step 2 Preparation of tert-butyl ((6-(4-((1R,2S)-2-(2,2-dichloroacetamido)-3-fluoro-1-hydroxypropyl)phenyl)thiazolo[5,4-b]pyridin-2-yl)methyl)carbamate

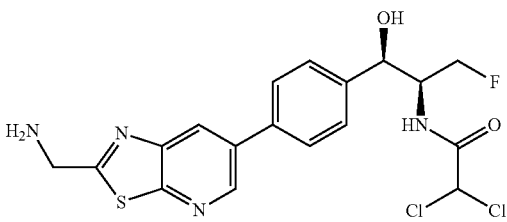 [SMILES: NCc1nc2cc(-c3ccc([C@@H](O)[C@@H](CF)NC(=O)C(Cl)Cl)cc3)cnc2s1]

A mixture of tert-butyl ((6-bromothiazolo[5,4-b]pyridin-2-yl)methyl)carbamate (156 mg, 0.45 mmol), 2,2-dichloro-N-((1R,2S)-3-fluoro-1-hydroxy-1-(4-(trimethylstannyl)phenyl)-propan-2-yl)acetamide (200 mg, 0.45 mmol) and tris (2-furyl)phosphine (21 mg, 0.090 mmol) Tris (dibenzylideneacetone) dipalladium(0) (41 mg, 0.045 mmol) in dimethylformamide (2.5 mL) is heated at 65° C.

for 3 hours under nitrogen. The mixture is then cooled, diluted with water (10 mL) and extracted with ethyl acetate (3×10 mL). Extracts are dried over $Na_2SO_4$ and concentrated to get crude title compound. m/z (CI) M+1 543. To a solution of crude tert-butylcarbamate (200 mg, 0.452 mmol) in DCM (3 mL) is added trifluoroacetic acid (0.5 mL) and stirred at room temperature for 3 hours. Reaction is diluted with toluene (10 mL), concentrated under vacuum, basified with saturated aq $NaHCO_3$ and extracted using ethyl acetate (3×10 mL). Extracts are dried over $Na_2SO_4$, concentrated and crude compound adsorbed on celite and purified on silica gel column using 0 to 20% methanol in ethyl acetate to give the title compound (40 mg). $^1$HNMR (DMSO-$d_6$): 4.17 (m, 2H). 4.27 (m, 1.5H), 4.43 (m, 0.5H), 4.59 (m, 0.5H), 4.70 (m, 0.5H), 4.93 (m, 1H), 6.01 (m, 1H), 6.54 (1H), 7.50 (d, 2H), 7.80 (d, 2H), 8.51 (m, 1H), 8.64 (d, 1H), 8.87 (d, 1H), m/z (CI) M+H 443.

Example 87

Preparation of 2,2-difluoro-N-((1R,2S)-3-fluoro-1-hydroxy-1-(4-(2-(methylsulfonamidomethyl)thiazolo[5,4-b]pyridin-6-yl)phenyl)propan-2-yl)acetamide

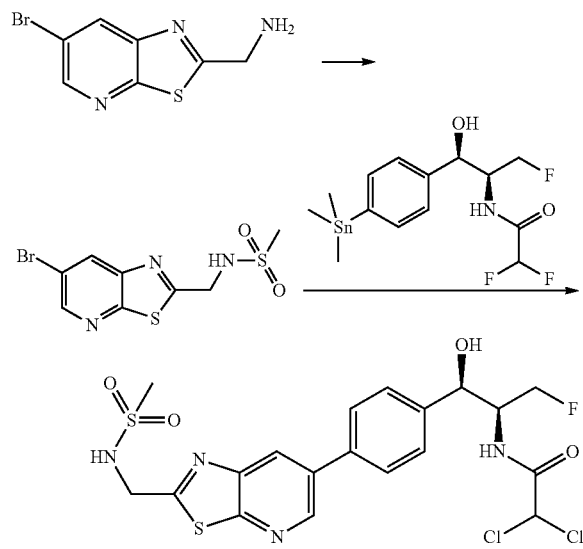

Step 1 Preparation of N-((6-bromothiazolo[5,4-b]pyridin-2-yl)methyl)-methanesulfonamide

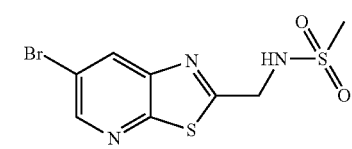 [SMILES: CS(=O)(=O)NCc1nc2cc(Br)cnc2s1]

To a cooled (ice-water) solution of (6-bromothiazolo[5,4-b]pyridin-2-yl)methanamine (800 mg, 3.28 mmol) and pyridine (800 mg, 9.85 mmol) in $CH_2Cl_2$ (10 mL) is slowly added methanesulfonyl chloride (380 mg, 3.28) and stirred at room temperature for 3 hours. Reaction mixture is washed with water (2×10 mL) dried over $Na_2SO_4$ and concentrated.

Obtained crude product purified on silica gel column using 0 to 5% methanol/$CH_2Cl_2$ to give the title compound (800 mg): m/z (CI) M+2 324.

Step 2 Preparation of 2,2-difluoro-N-((1R,2S)-3-fluoro-1-hydroxy-1-(4-(2-(methylsulfonamidomethyl)thiazolo[5,4-b]pyridin-6-yl)phenyl)propan-2-yl)-acetamide

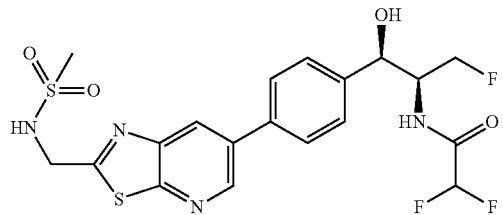 [SMILES: CS(=O)(=O)NCc1nc2cc(-c3ccc([C@@H](O)[C@@H](CF)NC(=O)C(F)F)cc3)cnc2s1]

A mixture of N-((6-bromothiazolo[5,4-b]pyridin-2-yl)methyl)methanesulfonamide (236 mg, 0.732 mmol), 2,2-difluoro-N-((1R,2S)-3-fluoro-1-hydroxy-1-(4-(trimethylstannyl)phenyl)propan-2-yl)acetamide (300 mg, 0.0.732 mmol) and tris(2-furyl)phosphine (34 mg, 0.146 mmol) and Tris(dibenzylideneacetone) dipalladium(0) (68 mg, 0.0732 mmol) in dimethylformamide (3 mL) is heated at 70° C. for 5 hours under nitrogen. The mixture is then cooled, diluted with water (10 mL) and extracted with ethyl acetate (3×15 mL). Extracts are dried over $Na_2SO_4$ and concentrated to get crude product. Obtained product purified by HPLC to give the title compound (90 mg): $^1$H NMR (DMSO-$d_6$): 3.07 (s, 3H), 4.27-4.39 (m, 1.5H), 4.40-4.48 (m, 0.5H), 4.52-4.60 (m, 0.5H), 4.64-4.71 (m, 2.5H) 4.88-4.94 (m, 1H), 6.22 (t, 1H), 7.50 (d, 2H), 7.83 (d, 2H), 8.22-8.33 (m, 1H), 8.62 (bs, 1H), 8.85 (d, 1H), 8.94 (s, 1H). m/z (CI) M+H 489.

Example 88

Preparation of 2,2-dichloro-N-((1R,2S)-3-fluoro-1-(4-(6-((3-fluoroazetidin-1-yl)methyl)pyridin-3-yl)phenyl)-1-hydroxypropan-2-yl)acetamide

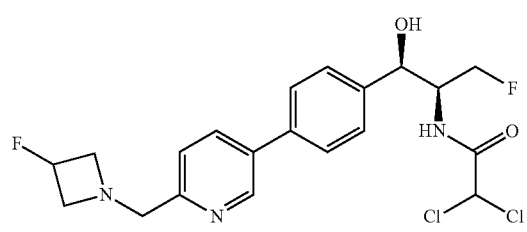 [SMILES: O=C(N[C@H](CF)[C@H](O)c1ccc(-c2ccc(CN3CC(F)C3)nc2)cc1)C(Cl)Cl]

Following the general procedure of Example 20—Step 2 and 3 and making non-critical variations but using 3-fluoroazetidine the HCl salt title compound is obtained (5 mg). m/z (CI) M+H 444.

Example 89

Preparation of N-((1R,2S)-1-(4-(6-((3-aminoazetidin-1-yl)methyl)-pyridin-3-yl)phenyl)-3-fluoro-1-hydroxypropan-2-yl)-2,2-dichloroacetamide

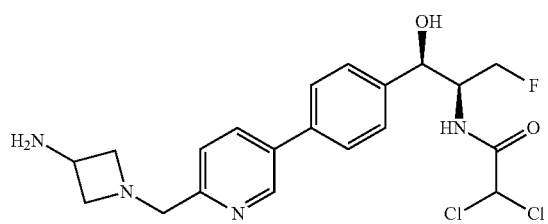 [SMILES: NC1CN(Cc2ccc(-c3ccc([C@@H](O)[C@@H](CF)NC(=O)C(Cl)Cl)cc3)cn2)C1]

Following the general procedure of Example 20—Step 2 and 3 and making non-critical variations but using tert-butyl azetidin-3-ylcarbamate the title compound is obtained (24 mg): m/z (CI) M+H 441.

Example 90

Preparation of 2,2-dichloro-N-((1R,2S)-3-fluoro-1-hydroxy-1-(4-(6-((3-hydroxyazetidin-1-yl)methyl)pyridin-3-yl)phenyl)propan-2-yl)acetamide

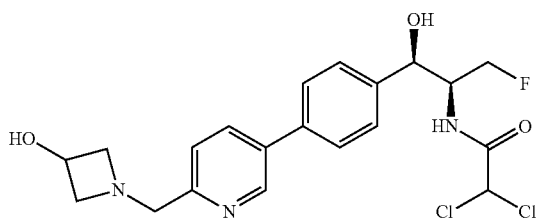 [SMILES: O=C(N[C@H](CF)[C@H](O)c1ccc(-c2ccc(CN3CC(O)C3)nc2)cc1)C(Cl)Cl]

Following the general procedure of Example 20—Step 2 and 3 and making non-critical variations but using azetidin-3-ol HCl salt the title compound is obtained (15 mg): m/z (CI) M+H 442.

Example 91

Preparation of 2-cyano-N-((1R,2S)-3-fluoro-1-hydroxy-1-(4-(6-(methylsulfonamidomethyl)pyridin-3-yl)phenyl)propan-2-yl)acetamide Step 1 Preparation of 3-((4S,5R)-4-(fluoromethyl)-5-(4-iodophenyl)-2,2-dimethyloxazolidin-3-yl)-3-oxopropanenitrile

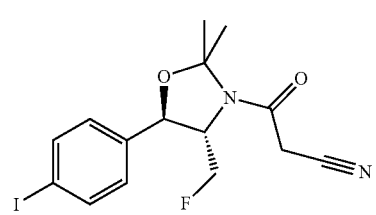 [SMILES: CC1(C)O[C@H](c2ccc(I)cc2)[C@@H](CF)N1C(=O)CC#N]

To a mixture of (4S,5R)-4-(fluoromethyl)-5-(4-iodophenyl)-2,2-dimethyl-oxazolidine (3.5 g, 10.50 mmol), 2-cyanoacetic acid (1.34 g, 15.8 mmol) and O-(7-azabenzotriazol-1-yl)-N,N,N',N'-tetramethyluronium hexafluorophosphate (6.11 g, 15.8 mmol) in dimethylformamide (21 mL) is added triethylamine (2.12 g, 21 mmol) and stirred at room temperature for overnight. The mixture is partitioned between ethylacetate and brine. The organic solution is separated, dried over MgSO$_4$, filtered and evaporated to give a yellow residue, which is purified on silica gel column using heptane to neat ethylacetate to give the title compound (2.75 g): $^1$HNMR (DMSO-d$_6$): 1.48 (s, 3H), 1.53 (s, 3H), 3.96-4.24 (m, 2H), 4.47-4.84 (m, 3H), 5.11 (d, 1H), 7.31 (d, 2H), 7.77 (d, 2H).

Step 2 Preparation of 3-((4S,5R)-4-(fluoromethyl)-2,2-dimethyl-5-(4-(trimethylstannyl) phenyl) oxazolidin-3-yl)-3-oxopropanenitrile

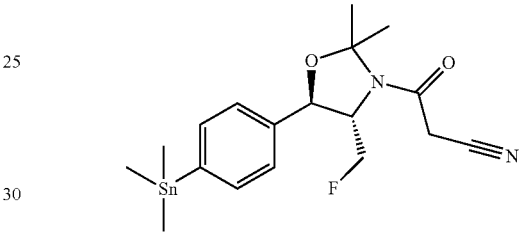

To a solution of 3-((4S,5R)-4-(fluoromethyl)-5-(4-iodophenyl)-2,2-dimethyl-oxazolidin-3-yl)-3-oxopropanenitrile (2.57 g, 6.39 mmol) in dioxane is added hexamethylditin (2.24 g, 6.84 mmol) and then the mixture purged with nitrogen. Palladium (II) bis(tripheylphosphine) dichloride (90 mg, 0.128 mmol)) is added and then content of the reaction mass heated to 80° C. under nitrogen. After 1.5 hours, reaction is cooled, solvent removed and the black oil filtered through silica (eluting with ethylacetate) and evaporated. Crude compound purified on silica gel column using 0-100% ethylacetate in heptane to give the title compound (2.48 g): $^1$HNMR (DMSO-d$_6$): 0.7 (s, 9H), 1.31 (s, 3H), 1.33 (s, 3H), 3.78-4.05 (m, 2H), 4.30-4.60 (m, 3H), 5.11 (d, 1H), 7.31 (d, 2H), 7.77 (d, 2H).

Step 3 Preparation of 2-cyano-N-((1R,2S)-3-fluoro-1-hydroxy-1-(4-(6-(methylsulfonamidomethyl)pyridin-3-yl)phenyl)propan-2-yl)acetamide

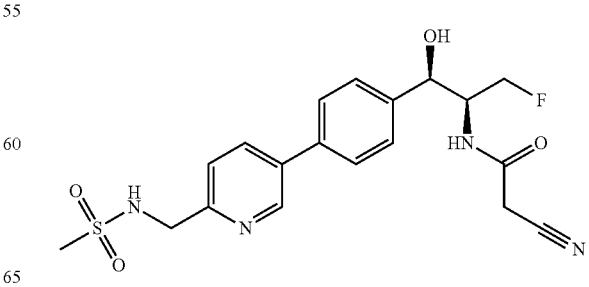

A mixture of 3-((4S,5R)-4-(fluoromethyl)-2,2-dimethyl-5-(4-(trimethylstannyl)-phenyl)oxazolidin-3-yl)-3-oxopropanenitrile (150 mg, 0.342 mmol), N-((5-bromopyridin-2-yl)methyl) methanesulfonamide (90 mg, 0.342 mmol), tris(2-furyl)phosphine (16 mg, 0.068 mmol) and tris(dibenzylideneacetone) dipalladium(0) (32 mg, 0.034 mmol) in dimethylformamide (3 mL) is heated at 70° C. for 4 h under nitrogen. The mixture is then cooled, diluted with water (10 mL) and extracted with ethyl acetate (3×15 mL). Extracts are dried over Na$_2$SO$_4$ and concentrated to get crude product m/z (CI) M+H 461. Obtained product is dissolved in CH$_2$Cl$_2$ (3 mL) and treated with trifluoroacetic acid (0.5 mL) for 3 hours at room temperature. Reaction is diluted with toluene (10 mL) and concentrated to syrup. Obtained crude product dissolved in dimethylformamide (2 mL) and purified using HPLC to give the title product (4 mg): m/z (CI) M+H 421.

Example 92

Preparation of 2,2-dichloro-N-((1R,2S)-3-fluoro-1-hydroxy-1-(4-(3-(methylsulfonamidomethyl)isoxazol-5-yl)phenyl)propan-2-yl)acetamide Step 1 Preparation of (4S,5R)-tert-butyl 4-(fluoromethyl)-2,2-dimethyl-5-(4-((trimethylsilyl)ethynyl)phenyl)oxazolidine-3-carboxylate

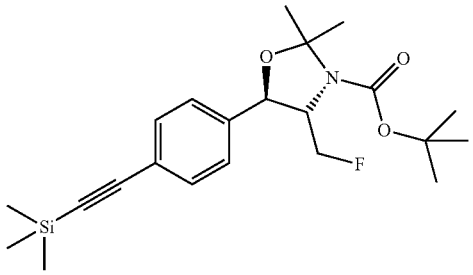

To a toluene (40 ml) solution of (4S,5R)-tert-butyl 4-(fluoromethyl)-5-(4-iodophenyl)-2,2-dimethyloxazolidine-3-carboxylate (2.0 g, 4.6 mmols) is added ethynyltrimethylsilane (451 mg, 4.6 mmols), copper (I)iodide (88 mg, 0.46 mmols, 0.1 equivs), Bis(triphenylphosphine)palladium (II) dichloride (165 mg, 0.23 mmols, 0.05 equivs) and

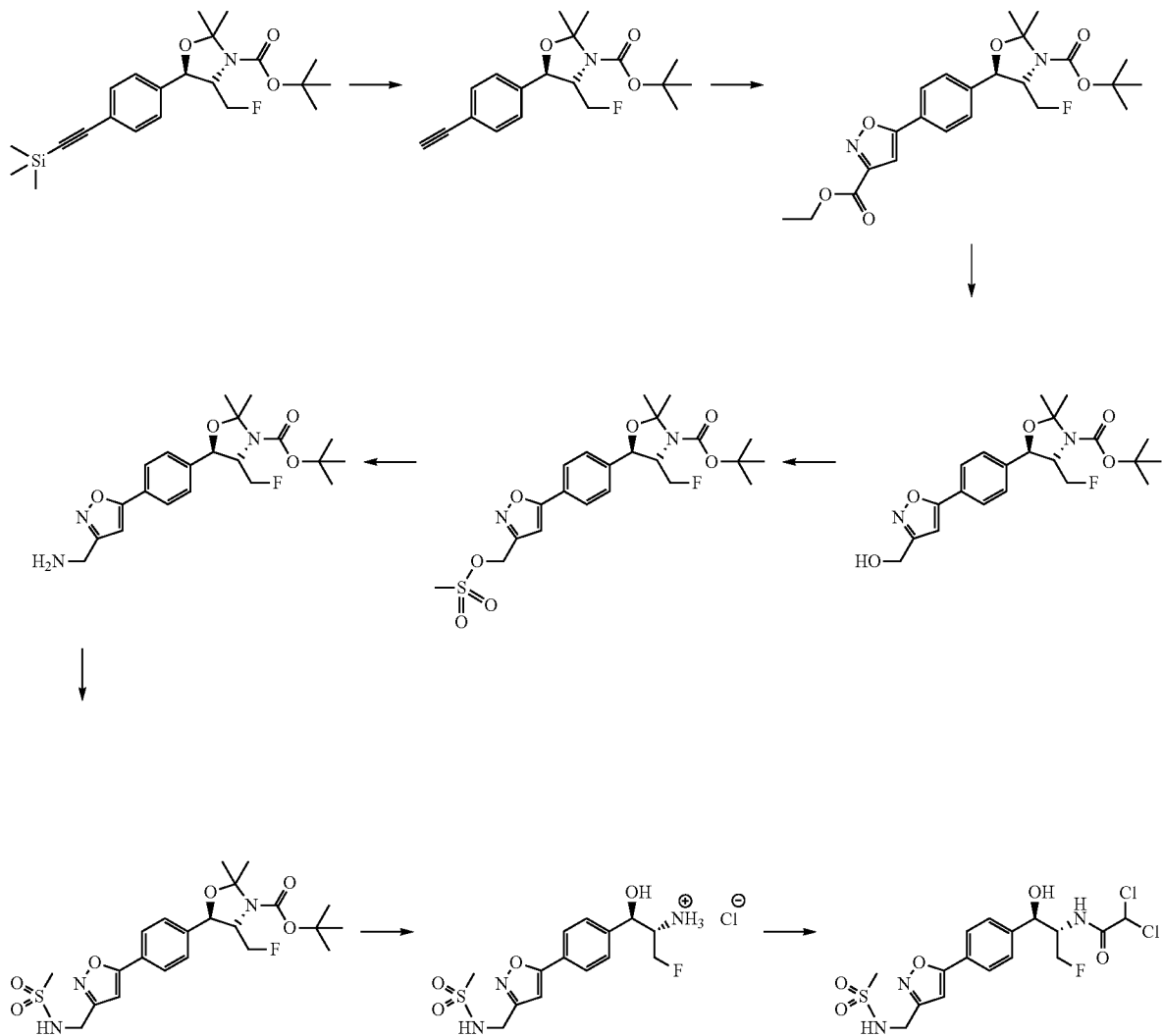

piperidine (782 mg, 9.2 mmols, 2 equivs). The mixture is heated in an atmosphere of nitrogen at 35° C. for six hours. The mixture is filtered through a pad of Celite. The pad of Celite is washed with ethylacetate (2×15 ml). The combined organic filtrates were concentrated using rotary evaporation at reduced pressure to give a crude viscous oil. The oil is purified by flash column chromatography (grading from 100% hexanes to 15% EtOAc) to give the title compound (1.65 g): m/z (CI) 306 ([M+H]+−Boc).

Step 2 Preparation of (4S,5R)-tert-butyl 5-(4-ethynyl phenyl)-4-(fluoromethyl)-2,2-dimethyloxazolidine-3-carboxylate

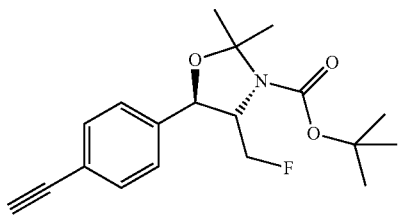

To a THF (20 ml) solution of (4S,5R)-tert-butyl 4-(fluoromethyl)-2,2-dimethyl-5-(4-((trimethylsilyl)ethynyl)phenyl)oxazolidine-3-carboxylate (1.65 g, 4.1 mmol) that had been cooled to −78° C. (dry ice/acetone) is added tetra-n-butyl-ammonium fluoride (5 ml of 1M solution in tetrahydrofuran, 5 mmol). The reaction is stirred at −78° C. for 1 hour. The reaction mixture is quenched (while at −78° C.) by the addition of saturated aqueous ammonium chloride solution (2 ml). The reaction mixture is warmed to room temperature and diluted with ethyl acetate (50 ml). The organic phase is washed with water (3×25 ml), dried over sodium sulfate and the volatiles removed by evaporation to give the title product (1.35 g).

Step 3 Preparation of ethyl 5-(4-((4S,5R)-3-(tert-butoxycarbonyl)-4-(fluoromethyl)-2,2-dimethyloxazolidin-5-yl)phenyl)isoxazole-3-carboxylate

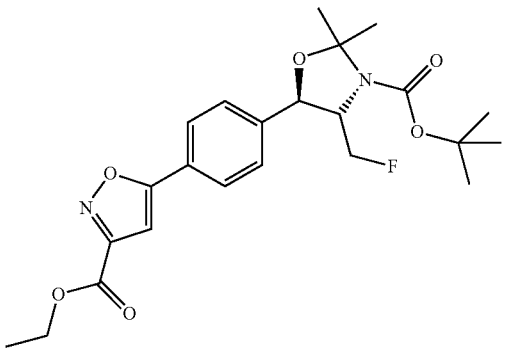

To an ethyl acetate (20 ml) solution of (4S,5R)-tert-butyl 5-(4-ethynylphenyl)-4-(fluoromethyl)-2,2-dimethyloxazolidine-3-carboxylate (1.35 g, 4.0 mmol) is added a dimethylformamide solution of (E)-ethyl 2-chloro-2-(hydroxyimino)-acetate (12.5 ml, 1.5 g, 2.5 equiv). Sodium hydrogen carbonate (3.5 g) is added to the solution and it is allowed to stir overnight at room temperature. The mixture is filtered and diluted with ethyl acetate (100 ml). After washing with water (4×25 ml) the organic phase is concentrated to give the crude product, which is purified on silica gel using a gradient of ethyl acetate in hexanes (0% to 20% ethyl acetate) to give the title compound (567 mg): $^1$H NMR (400 MHz, CDCl$_3$) 1.43-1.56 (m, 14H) 1.62 (s, 3H) 1.74 (br. s., 3H) 4.50 (q, J=7.24 Hz, 3H) 5.20 (d, J=7.33 Hz, 1H) 6.96 (s, 1H) 7.60 (d, J=8.34 Hz, 2H) 7.86 (d, J=8.59 Hz, 2H), m/z (CI) 449 ([M+H]$^+$.

Step 4 Preparation of (4S,5R)-tert-butyl 4-(fluoromethyl)-5-(4-(3-(hydroxymethyl)isoxazol-5-yl)phenyl)-2,2-dimethyloxazolidine-3-carboxylate

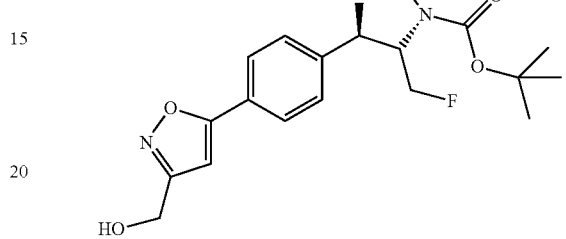

To a cooled (0° C.) THF (25 ml) solution of ethyl 5-(4-((4S,5R)-3-(tert-butoxycarbonyl)-4-(fluoromethyl)-2,2-dimethyloxazolidin-5-yl)phenyl)isoxazole-3-carboxylate (1.0 g, 2.2 mmol) is added sodium borohydride (0.25 g, 6.7 mmol) followed by methanol (3 ml added slowly). The reaction is stirred for 30 minutes at 0° C. and for one hour at room temperature. The excess sodium borohydride is quenched by the addition of saturated aqueous ammonium chloride (5 ml). The reaction mixture is diluted with ethyl acetate (50 ml) and water (25 ml). The layers were mixed and allowed to separate. The organic phase is collected, dried over sodium sulfate and concentrated to give the product, (4S,5R)-tert-butyl 4-(fluoromethyl)-5-(4-(3-(hydroxymethyl)isoxazol-5-yl)phenyl)-2,2-dimethyl-oxazolidine-3-carboxylate (875 mg, 96%), as a viscous oil. $^1$H NMR (400 MHz, CDCl$_3$) 1.52 (s, 9H) 1.59 (s, 3H) 1.74 (br. s., 3H) 2.03-2.08 (m, 1H) 3.83-3.96 (m, 1H) 4.40-4.60 (m, 2H) 4.85 (d, J=6.06 Hz, 2H) 5.19 (d, J=7.58 Hz, 1H) 6.63 (s, 1H) 7.57 (d, J=8.34 Hz, 2H) 7.82 (d, J=8.34 Hz, 2H); m/z (CI) 407 ([M+H]$^+$.

Step 5 Preparation of (4S,5R)-tert-butyl 4-(fluoromethyl)-2,2-dimethyl-5-(4-(3-((methylsulfonyloxy)methyl)isoxazol-5-yl)phenyl)oxazolidine-3-carboxylate

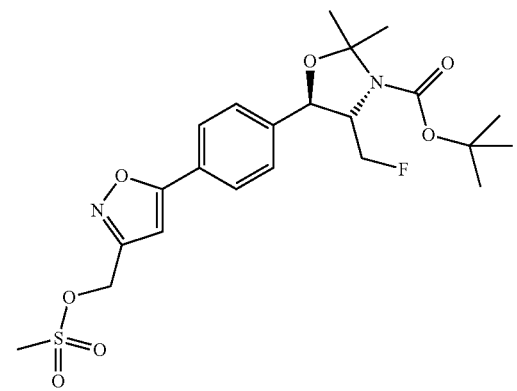

A methylene chloride solution (20 ml) of (4S,5R)-tert-butyl 4-(fluoromethyl)-5-(4-(3-(hydroxymethyl)isoxazol-5-yl)phenyl)-2,2-dimethyloxazolidine-3-carboxylate (876 mg, 2.16 mmol) is cooled to 0° C. and methanesulfonyl chloride (250 mg, 2.16 mmol) is added followed by diisopropylethylamine (278 mg, 2.16 mmol). The reaction is stirred for one hour at 0° C. The reaction is diluted with methylene chloride (20 ml) and washed with water (2×10 ml). The organic phase is dried over sodium sulfate and concentrated to give the title compound (987 mg): m/z (CI) 485 ([M+H]+.

Step 6 Preparation of (4S,5R)-tert-butyl 5-(4-(3-(aminomethyl)isoxazol-5-yl)phenyl)-4-(fluoromethyl)-2,2-dimethyloxazolidine-3-carboxylate

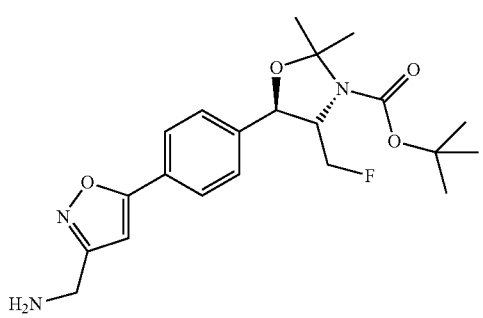

To a dioxane (10 ml) solution of (4S,5R)-tert-butyl 4-(fluoromethyl)-2,2-dimethyl-5-(4-(3-((methylsulfonyloxy)methyl)isoxazol-5-yl)phenyl)oxazolidine-3-carboxylate (1.0 g, 2.1 mmol) is added 30% aqueous ammonium hydroxide solution (5 ml). The mixture is stirred at 35° C. for 12 hours. The product is partitioned between water (50 ml) and methylene chloride (25 ml). The organic phase is dried (sodium sulfate) and concentrated to give the title compound (685 mg): m/z (CI) 406 ([M+H]+.

Step 7 Preparation of (4S,5R)-tert-butyl 4-(fluoromethyl)-2,2-dimethyl-5-(4-(3-(methylsulfonamidomethyl)isoxazol-5-yl)phenyl)oxazolidine-3-carboxylate

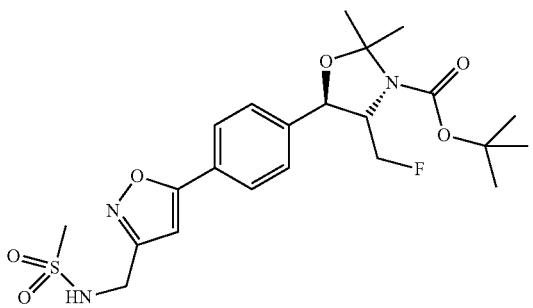

To a methylene chloride (10 ml) solution of (4S,5R)-tert-butyl 5-(4-(3-(aminomethyl)isoxazol-5-yl)phenyl)-4-(fluoromethyl)-2,2-dimethyloxazolidine-3-carboxylate (270 mg, 0.66 mmol) that had been cooled to 0° C. is added mesyl chloride (83 mg, 0.73 mmol) and diisopropylethylamine (94 mg, 0.73 mmol) sequentially. The reaction is stirred at 0° C. for thirty minutes then quenched with water (2 ml). The quenched reaction is stirred for thirty minutes at room temperature. The organic phase is dried over sodium sulfate and concentrated to give the title compound (310 mg): m/z (CI) 484 ([M+H]+.

Step 8 Preparation of (1R,2S)-3-fluoro-1-hydroxy-1-(4-(3-(methylsulfonamidomethyl)isoxazol-5-yl)phenyl)propan-2-aminium chloride

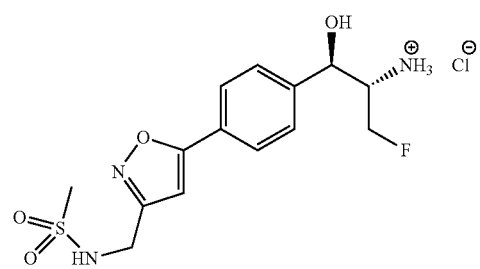 [SMILES: CS(=O)(=O)NCc1cc(-c2ccc([C@@H](O)[C@H]([NH3+])CF)cc2)on1 ; [Cl-]]

To (4S,5R)-tert-butyl 4-(fluoromethyl)-2,2-dimethyl-5-(4-(3-(methylsulfonamido-methyl)isoxazol-5-yl)phenyl)oxazolidine-3-carboxylate (300 mg, 0.62 mmol) is added 4N HCl in dioxane (4 ml) at room temperature. The solution is then cooled to 0° C. and water (0.5 ml) is added. The ice bath is removed after ten minutes and the reaction is stirred at room temperature for one hour. The volatiles were then removed by rotary evaporation. Several evaporation cycles were performed using acetonitrile to ensure complete removal of water and excess HCl gave the title compound (234 mg): m/z (CI) 344 ([M+H]+.

Step 9 Preparation of 2,2-dichloro-N-((1R,2S)-3-fluoro-1-hydroxy-1-(4-(3-(methylsulfonamidomethyl)isoxazol-5-yl)phenyl)propan-2-yl)acetamide

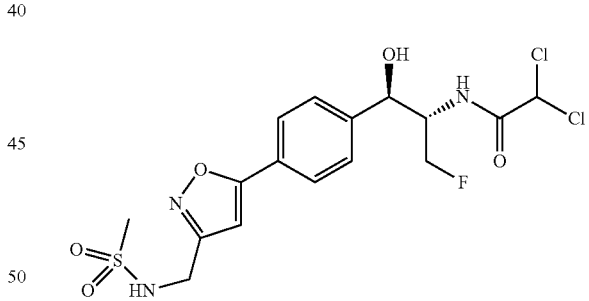

To a dimethylformamide (3 ml) solution of (1R,2S)-3-fluoro-1-hydroxy-1-(4-(3-(methylsulfonamidomethyl)isoxazol-5-yl)phenyl)propan-2-aminium chloride (150 mg, 0.40 mmol) is added diisopropylethylamine (0.255 g, 2 mmol). After cooling the reaction mixture to 0° C. dichloroacetyl chloride (62 mg, 0.42 mmol) is added. The reaction is stirred at 0° C. for twenty minutes then quenched by the addition of water (1 ml). The reaction mixture is concentrated to a volume of approximately two milliliters and subjected to reverse phase HPLC purification to give the title compound (95 mg): $^1$H NMR (400 MHz, CDCl$_3$) 3.06 (s, 3H) 4.30-4.43 (m, 1H) 4.49 (d, J=6.32 Hz, 2H) 4.56-4.67 (m, 2H) 4.93 (m, br, 1H) 5.19-5.24 (m, 1H) 5.87 (s, 1H) 6.61 (s, 1H) 7.03 (d, J=9.09 Hz, 1H) 7.52 (d, J=8.08 Hz, 2H) 7.79 (d, J=8.59 Hz, 2H); m/z (CI) 454, 456, 458 ([M+H]+.

Example 93

Preparation of 2,2-difluoro-N-((1R,2S)-3-fluoro-1-hydroxy-1-(4-(3-(methylsulfonamidomethyl)isoxazol-5-yl)phenyl)propan-2-yl)acetamide

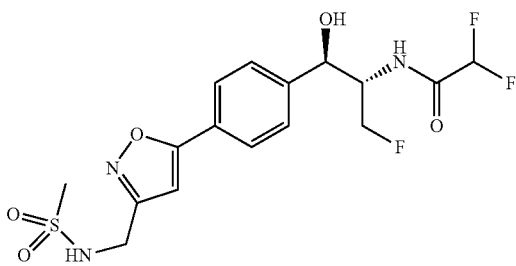 [SMILES: CS(=O)(=O)NCc1cc(-c2ccc([C@@H](O)[C@@H](CF)NC(=O)C(F)F)cc2)on1]

Prepared as described in Step 9, Example 92 but using difluoroacetyl chloride. $^1$H NMR (400 MHz, CDCl$_3$) 3.06 (s, 3H) 4.35-4.75 (m, 6H) 4.93 (m, br, 1H) 5.20 (d, 1H) 5.87 (t, 1H) 6.61 (s, 1H) 7.52 (d, 2H) 7.79 (d, 2H); m/z (CI) 422 [M+H]$^+$.

Example 94

Preparation of 2,2-difluoro-N-((1R,2S)-3-fluoro-1-hydroxy-1-(4-(6-((RS)-1-(methylsulfonamido)ethyl)pyridin-3-yl)phenyl)propan-2-yl)acetamide Step 1 Preparation of N-(1-(5-(4-((4S,5R)-3-(2,2-difluoroacetyl)-4-(fluoromethyl)-2,2-dimethyloxazolidin-5-yl)phenyl)pyridin-2-yl)ethyl)(RS)-methanesulfonamide

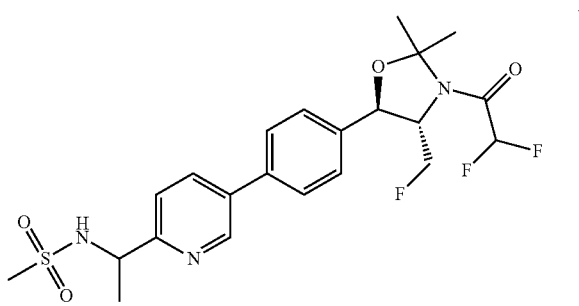

Following the general procedure of Example 11 and making non-critical variations but using the product of Step 1—Example 11 and 2,2-difluoro-1-((4S,5R)-4-(fluoromethyl)-2,2-dimethyl-5-(4-(4,4,5,5-tetramethyl-1,3,2-dioxaborolan-2-yl)phenyl)oxazolidin-3-yl)ethanone, the title compound is obtained (919 mg): $^1$H NMR (400 MHz, CDCl$_3$) δ:1.6-1.9 (m, 9H), 2.8 (s, 3H), 4.5-4.9 (m, 3H), 5.2-5.3 (m, 1H), 5.8-5.9 (m, 1H), 6.15 (t, 1H), 7.4 (d, 1H), 7.55 (d, 2H), 7.65 (d, 2H), 7.9 (d, 1H), 8.8 (s, 1H).

Step 2 Preparation of 2,2-difluoro-N-((1R,2S)-3-fluoro-1-hydroxy-1-(4-(6-((RS)-1-(methylsulfonamido)ethyl)pyridin-3-yl)phenyl)propan-2-yl)acetamide

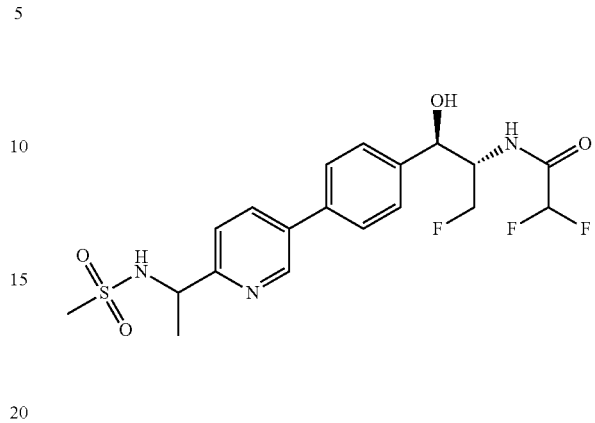

Following the general procedure of Example 2, Step 2 and using the product of Step 1, Example 94, the title compound is obtained (782 mg): $^1$HNMR (400 MHz, DMSO-d$_6$) δ:1.45 (d, 3H), 2.8 (s, 3H), 4.25-4.35 (m, 1.5H), 4.4-4.5 (m, 0.5H), 4.5-4.7 (m, 2H), 4.9 (m, 1H), 5.9 (s, 1H), 6.2 (t, 1H), 7.45 (d, 2H), 7.55 (d, 1H), 7.65-7.75 (m, 3H), 8.1 (d, 1H), 8.8 (s, 2H). m/z (CI) 446 [M+H].

Example 95

Preparation of N-((1R,2S)-1-(4-(6-((RS)-1-aminoethyl)pyridin-3-yl)phenyl)-3-fluoro-1-hydroxypropan-2-yl)-2,2-difluoroacetamide Step 1 Preparation of tert-butyl (1-(5-(4-((4S,5R)-3-(2,2-difluoroacetyl)-4-(fluoromethyl)-2,2-dimethyloxazolidin-5-yl)phenyl)pyridin-2-yl)ethyl)carbamate

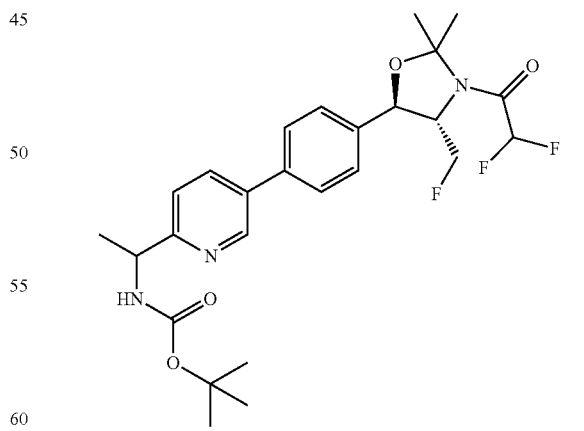

Following the general procedure of Example 22 and making non-critical variations but using tert-butyl (1-(5-bromopyridin-2-yl)ethyl)carbamate (Previously described in WO 2011/138751) the title compound is obtained (910 mg): m/z (CI) 508 [M+H].

Step 2 Preparation of N-((1R,2S)-1-(4-(6-((RS)-1-aminoethyl)pyridin-3-yl)phenyl)-3-fluoro-1-hydroxypropan-2-yl)-2,2-difluoroacetamide

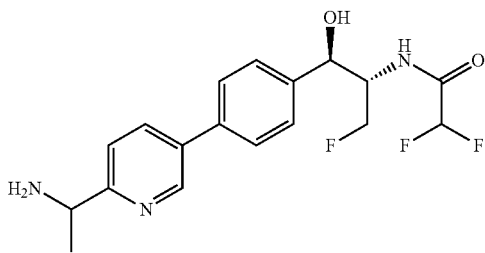 [SMILES: CC(N)c1ccc(-c2ccc([C@@H](O)[C@@H](CF)NC(=O)C(F)F)cc2)cn1]

Following the general procedure of Example 2, Step 2 and using the product of Step 1, Example 95, the title compound is obtained (970 mg): $^1$H NMR (300 MHz, DMSO-d$_6$) δ:1.3 (d, 3H), 4.0-4.15 (m, 1H), 4.25-4.4 (m, 1.5H), 4.4-4.6 (m, 1H), 4.65-4.75 (m, 0.5H), 4.9 (t, 1H), 5.9 (d, 1H), 6.2 (t, 1H), 7.45 (d, 2H), 7.5-7.6 (m, 1H), 7.70 (d, 2H), 8.05 (d, 1H), 8.80 (d, 2H). m/z (CI) 368 [M+H].

The following derivatives of the title compound of Example 95 can be prepared by methods known in the art:
N-((1R,2S)-1-(4-(6-(1-aminoethyl)pyridin-3-yl)phenyl)-3-fluoro-1-hydroxypropan-2-yl)-2,2-dichloroacetamide;
(1R,2S)-1-(4-(6-(1-aminoethyl)pyridin-3-yl)phenyl)-2-(2,2-dichloroacetamido)-3-fluoropropyl hydrogen phosphate sodium;
(1R,2S)-1-(4-(6-(1-aminoethyl)pyridin-3-yl)phenyl)-2-(2,2-dichloroacetamido)-3-fluoropropyl dihydrogen phosphate;
(1R,2S)-1-(4-(6-(1-aminoethyl)pyridin-3-yl)phenyl)-2-(2,2-difluoroacetamido)-3-fluoropropyl hydrogen phosphate sodium; and
(1R,2S)-1-(4-(6-(1-aminoethyl)pyridin-3-yl)phenyl)-2-(2,2-difluoroacetamido)-3-fluoropropyl dihydrogen phosphate. This derivative has been prepared as described below:

Example 95A

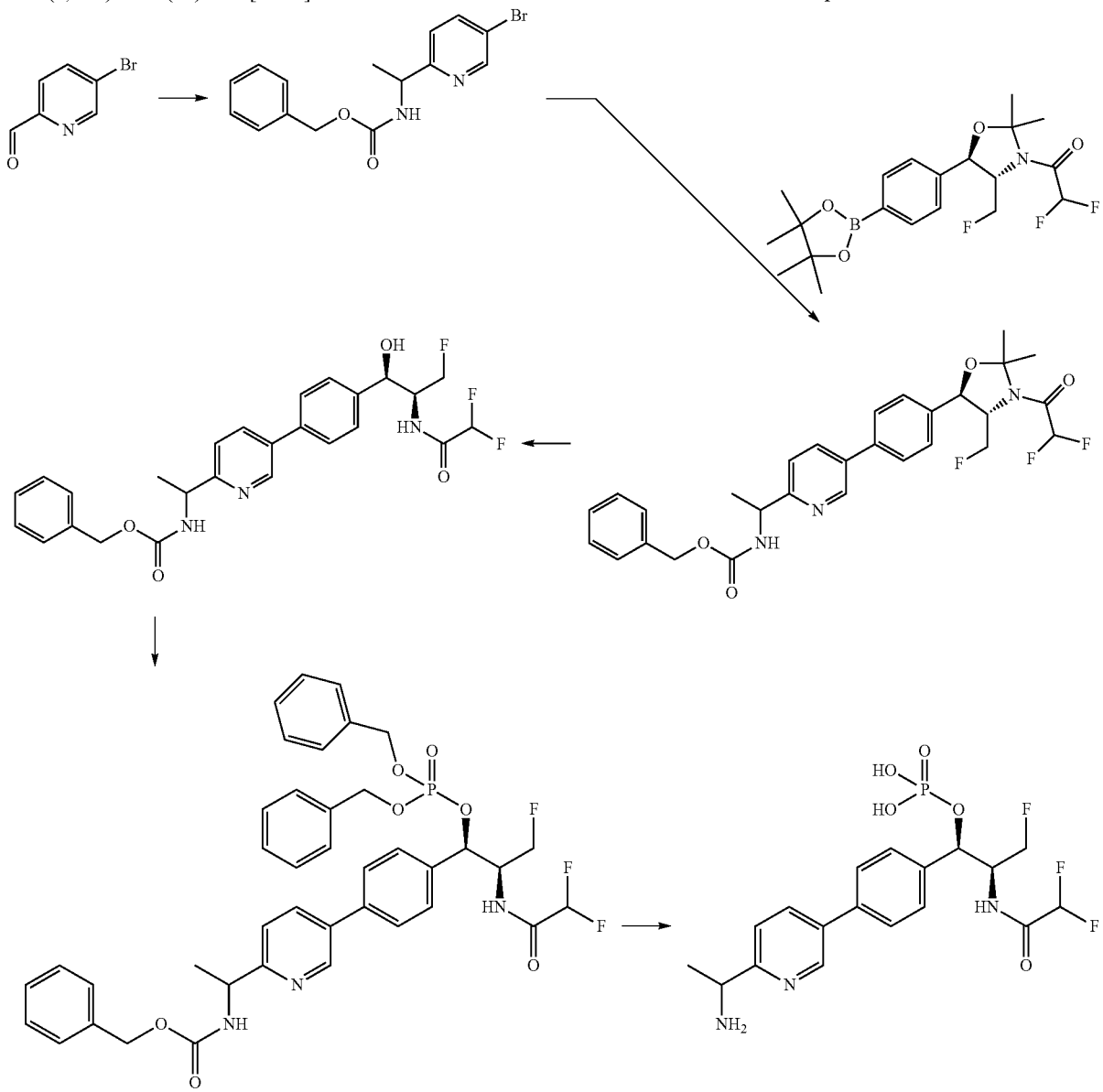

Step 1 Preparation of benzyl (1-(5-bromopyridin-2-yl)ethyl)carbamate

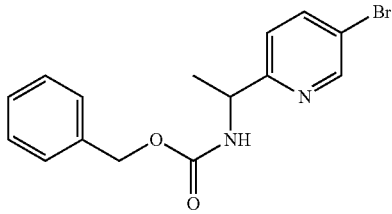 [SMILES: CC(NC(=O)OCc1ccccc1)c1ccc(Br)cn1]

Lithium hexamethyldisilazide is added to commercially available 5-bromo-pyridine-2-carbaldehyde (2.00 g, 10.8 mmol) in THF (20 mL) at −20° C. After 30 minutes the mixture is cooled to −70° C. and methylmagnesium bromide (4.8 mL, 14.5 mmol) is added. The mixture is warmed to room temperature and quenched with saturated aqueous ammonium chloride (15 mL). The mixture is partitioned between water and ethylacetate. The organic layer is separated, washed with brine, dried over MgSO₄, filtered and evaporated to give an intermediate residue (1.90 g). The residue is dissolved in CH₂Cl₂ (40 mL) and 1.0M sodium hydroxide (24 mL, 24 mmol) added. The mixture is cooled to 0° C. and benzyl chloroformate added (1.69 mL, 11.8 mmol) dropwise. After stirring for 4 hours the organic phased is separated, washed with water (30 mL), followed by brine (20 mL), dried over sodium sulfate and the solvent removed under reduced pressure to give the crude product, which is purified by silica chromatography eluting with 20% ethylacetate/heptanes to give the title product (1.17 g): m/z: 334.03.

Step 2 Preparation of benzyl (1-(5-(4-((4S,5R)-3-(2,2-difluoroacetyl)-4-(fluoromethyl)-2,2-dimethyloxazolidin-5-yl)phenyl)pyridin-2-yl)ethyl)carbamate

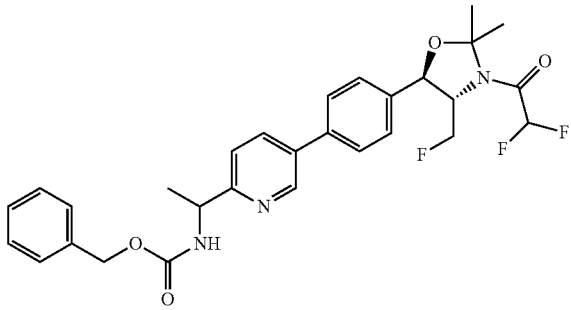 [SMILES: CC(NC(=O)OCc1ccccc1)c1ccc(-c2ccc([C@H]3OC(C)(C)N(C(=O)C(F)F)[C@@H]3CF)cc2)cn1]

A mixture of the product of Example 22, Step 3, benzyl (1-(5-bromopyridin-2-yl)ethyl)carbamate, 2.0M sodium carbonate in water (3.1 mL, 6.2 mmol) in dioxane is degassed with nitrogen. 1,1'-bis(diphenylphosphino)ferrocene dichloropalladium(ii) complex with dichloromethane (169 mg, 0.21 mmol) is added and the mixture heated to 80° C. overnight. After cooling to room temperature the reaction mixture is diluted with water (25 mL) and extracted with ethylacetate. The organic phase is separated, dried over MgSO₄, and concentrated under reduced pressure. The crude material is purified using silica chromatography eluting from 25% ethylacetate/heptane to 35% ethylacetate/heptane to give the title product (1.00 g): m/z: 541.22.

Step 3 Preparation of benzyl (1-(5-(4-((1R,2S)-2-(2,2-difluoroacetamido)-3-fluoro-1-hydroxypropyl)phenyl)pyridin-2-yl)ethyl)carbamate

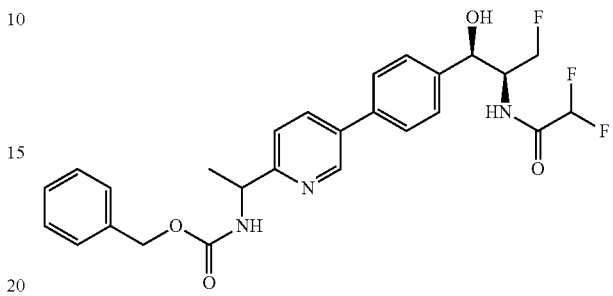

Trifluoroacetic acid (2.2 mL) is added to the product of step 2, Example 95A (1.05 g, 1.94 mmol) in CH₂Cl₂ (39 mL) at 0° C. After 30 minutes the ice bath is removed and the mixture stirred at room temperature for 8 hours. Saturated NaHCO₃ (60 mL) is added and the mixture extracted with CH₂Cl₂ (40 mL). The combined organics are dried over MgSO₄, filtered and evaporated to give the title product (850 mg): m/z: 501.19.

Step 4 Preparation of benzyl (1-(5-(4-((1R,2S)-1-((bis(benzyloxy)-phosphoryl)oxy)-2-(2,2-difluoroacetamido)-3-fluoropropyl)phenyl)pyridin-2-yl)ethyl)carbamate

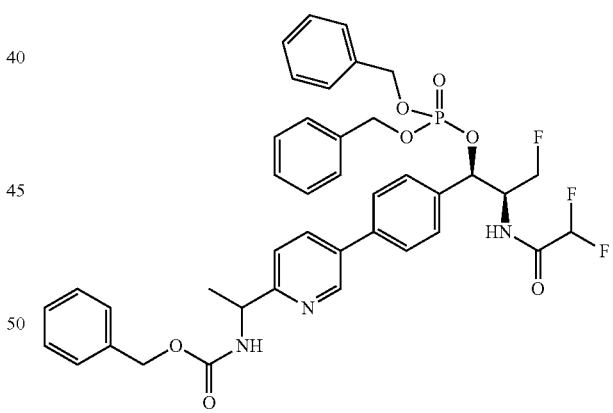

Trifluoroacetic acid (51.6 μL) is added to the product of step 3, Example 95A (0.168 g, 0.335 mmol) and pyridine (54.2 μL, 0.67 mmol) in THF (4.4 mL, 54 mmol) at 0° C. After 5 minutes, bis(benzyloxy)(diisopropylamino)phosphine (0.219 mL, 0.586 mmol) is added. After allowing to warm to room temperature the mixture is stirred for 1 hour. 30% hydrogen peroxide/water (30:70, 60 μL, 0.586 mmol) is added. After 1 hour sodium bisulfate (4 mL) is added and water (10 mL) is added. The reaction mixture is extracted with ethylacetate (2×15 mL). The combined organics are dried over MgSO₄, filtered and evaporated to give the crude product, which is purified by silica chromatography eluting from 25% ethylacetate/heptanes to neat ethylacetate to give the title product (241 mg): m/z: 761.25.

Step 5 Preparation of (1R,2S)-1-(4-(6-(1-aminoethyl)pyridin-3-yl)phenyl)-2-(2,2-difluoroacetamido)-3-fluoropropyl dihydrogen phosphate

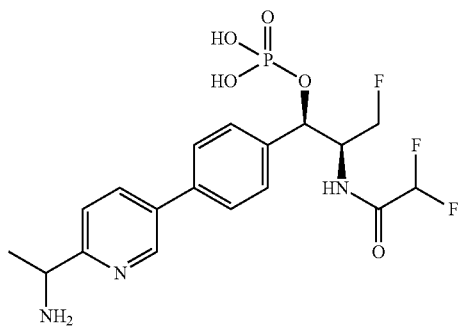 [SMILES: CC(N)c1ccc(-c2ccc([C@@H](OP(=O)(O)O)[C@@H](CF)NC(=O)C(F)F)cc2)cn1]

Palladium on carbon (1:9, 23 mg, 0.022 mmol) is added to the product of step 4, Example 95A (235 mg, 0.308 mmol) in ethanol (5 mL) and water (1 mL). The mixture is evacuated with nitrogen three times and stirred under hydrogen for 5 hours. The reaction mixture is filtered through a 4 mL pad of solka flok and rinsed with alternating 4 mL rinses of ethanol and water ten times. The solvent is removed under reduced pressure to give the crude product, which is taken up in water (5 mL) and filtered through a 0.45 um filter disk, rinsing with water (2 mL). The filtrate is freeze dried to give the title product (126 mg): 1H NMR δ 8.75 (1H, s), 8.07 (1H, d), 7.63 (2H, d), 7.52-7.48 (4H, m), 6.00 (1H, t), 5.42 (1H, d), 4.82 (1H, dd), 4.64-4.43 (4H, m), 1.62 (3H, d); m/z: 447.12.

Example 96

Preparation of 2,2-Difluoro-N-{(1S,2R)-1-fluoromethyl-2-hydroxy-2-[4-(6-pyrrolidin-2-yl-pyridin-3-yl)-phenyl]-ethyl}-acetamide Step 1 Preparation of 2-(5-Bromo-pyridin-2-yl)-pyrrolidine-1-carboxylic acid tert-butyl ester

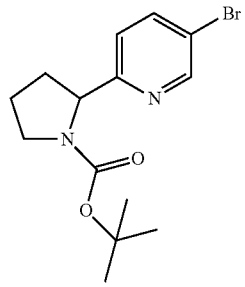 [SMILES: CC(C)(C)OC(=O)N1CCCC1c1ccc(Br)cn1]

A solution of 5-Bromo-2-pyrrolidin-2-yl-pyridine (611 mg, 2.69 mmol) (previously described in WO200853319) in CH₂Cl₂ (20 ml) is treated with di-tert-butyl dicarbonate (881 mg, 4.04 mmol) and triethylamine (0.562 ml, 4.04 mmol), and stirred at ambient temperature for 16 hours. The reaction mixture is washed with 10% aqueous citric acid solution (25 ml). The organic phase is concentrated on to silica gel (5 g) and purified by column chromatography (40 g silica gel, ethyl acetate/heptane 0-50%) to afford the title compound (500 mg): ¹H NMR (400 MHz, CDCl₃) 1.23 (s, 5H), 1.45 (s, 4H), 1.82-2.09 (m, 3H), 2.24-2.43 (m, 1H), 3.47-3.74 (m, 2H), 4.67-4.99 (m, 1H), 7.05-7.14 (m, 1H), 7.71-7.78 (m, 1H), 8.59 (dd, 1H). m/z M+H 327.

Step 2 Preparation of: 2-(5-{4-[(4S,5R)-3-(2,2-Difluoro-acetyl)-4-fluoromethyl-2,2-dimethyl-oxazolidin-5-yl]-phenyl}-pyridin-2-yl)-pyrrolidine-1-carboxylic acid tert-butyl ester

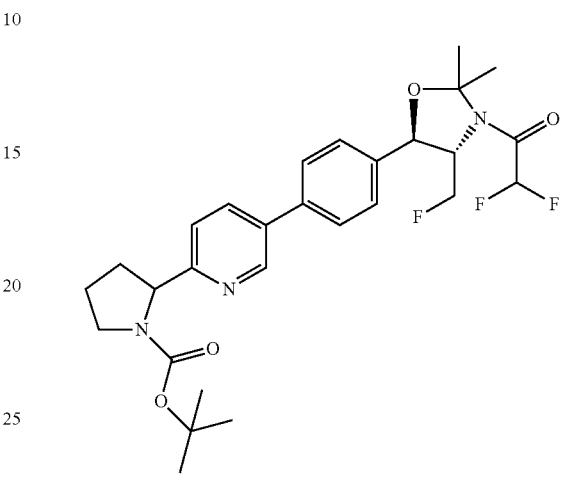

To a solution of 2,2-Difluoro-1-{(4S,5R)-4-fluoromethyl-2,2-dimethyl-5-[4-(4,4,5,5-tetramethyl-[1,3,2]dioxaborolan-2-yl)-phenyl]-oxazolidin-3-yl}-ethanone (634 mg, 1.53 mmol) in a mixture of toluene (12 ml) and ethanol (9 ml) is added 2-(5-Bromo-pyridin-2-yl)-pyrrolidine-1-carboxylic acid tert-butyl ester (500 mg, 1.53 mmol), aqueous sodium bicarbonate solution (2M, 6 mmol, 3 ml), and 1,1'Bis(diphenylphosphino)ferrocene]dichloropalladium (II) (57 mg, 0.08 mmol). The stirred reaction mixture is heated at 80° C. under a blanket of nitrogen for 1 hour. The reaction is concentrated to ⅓ its volume and partitioned between ethyl acetate (25 ml) and water (25 ml). The organic phase is washed with saturated brine (25 ml) and concentrated on to silica gel (3 g). Purification by column chromatography (40 g silica gel, ethyl acetate/heptane 0-100%) affords the title compound (500 mg): ¹H NMR (400 MHz, CDCl₃) 1.25 (s, 5H) 1.48 (s, 4H), 1.64 (s, 3H), 1.70 (s, 3H), 1.85-1.98 (m, 2H), 1.99-2.1 (1H), 2.3-2.48 (m, 1H), 3.5-3.74 (m, 2H), 4.54-5.1 (m, 4H), 5.23-5.33 (m, 1H), 6.13 (t, 1H), 7.23-7.31 (m, 1H) 7.5-7.57 (m, 2H), 7.57-7.67 (m, 2H), 7.78-7.87 (m, 1H), 8.77 (s, 1H). m/z M+H 534.2.

Step 3 2,2-Difluoro-N-{(1S,2R)-1-fluoromethyl-2-hydroxy-2-[4-(6-pyrrolidin-2-yl-pyridin-3-yl)-phenyl]ethyl}-acetamide

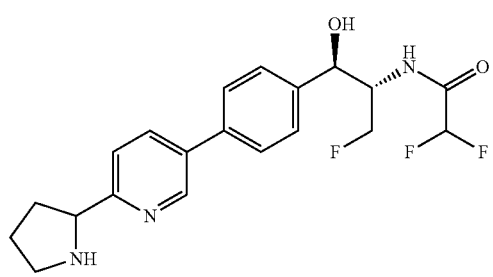 [SMILES: O=C(N[C@H](CF)[C@H](O)c1ccc(-c2ccc(C3CCCN3)nc2)cc1)C(F)F]

To a stirred solution of 2-(5-{4-[(4S,5R)-3-(2,2-Difluoro-acetyl)-4-fluoromethyl-2,2-dimethyl-oxazolidin-5-yl]-phenyl}-pyridin-2-yl)-pyrrolidine-1-carboxylic acid tert-butyl ester (500 mg, 0.94 mmol) and CH$_2$Cl$_2$ (20 mL), cooled to 0° C., is added trifluoroacetic acid (3 mL) and water (100 ul). The reaction is allowed to warm to ambient temperature, and is stirred for a further 2 hours. Toluene (20 mL) is added and the reaction mixture concentrated under vacuum to give the crude product. Purification by preparative HPLC gave the title compound (217 mg): $^1$H NMR (400 MHz, CDCl$_3$), 1.88-2.06 (m, 3H), 2.38-2.48 (m, 1H), 3.22-3.40 (m, 3H), 4.25-4.37 (m, 1.5H), 4.4-4.47 (m, 0.5H), 4.52-4.59 (m, 0.5H), 4.63-4.70 (m, 0.5H), 4.71-4.78 (m, 1H), 4.86-4.94 (m, 1H), 5.89-6.01 (m, 1H), 6.20 (t, 1H), 7.43-7.53 (m, 2H), 7.58-7.63 (1H, m), 7.71-7.77 (m, 2H), 8.15-8.24 (m, 1H), 8.82-8.88 (m, 1H), 8.9-8.94 (m, 1H). m/z M+H 394.

The following derivative of the title compound of Example 96 can be prepared by methods known in the art:
(1R,2S)-2-(2,2-difluoroacetamido)-3-fluoro-1-(4-(6-(pyrrolidin-2-yl)pyridin-3-yl)phenyl)propyl dihydrogen phosphate.

Example 97

Preparation of 2,2-difluoro-N-((1R,2S)-3-fluoro-1-hydroxy-1-(4-(6-(morpholin-3-yl)pyridin-3-yl)phenyl)propan-2-yl)acetamide Step 1 Preparation of tert-butyl 3-(5-bromopyridin-2-yl)morpholine-4-carboxylate

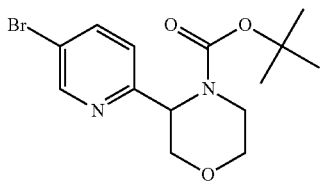 [SMILES: CC(C)(C)OC(=O)N1CCOCC1c1ccc(Br)cn1]

To a stirred suspension of commercially available 3-(5-bromopyridin-2-yl)-morpholine di-hydrochloride salt (615 mg, 1.95 mmol) in 1,4-dioxane (10 mL, 0.2M) is added 10% K$_2$CO$_3$ aqueous solution (11.1 mL, 7.78 mol, 4 eq.). Di-tert-butyl dicarbonate (637 mg, 2.92 mmol, 1.5 eq.) is added and allowed to stir at room temperature overnight. The reaction mixture is left for a further 3 hours before it is diluted with water and extracted with DCM (50 mL). The organic layer is separated and concentrated to give a light yellow oil (580 mg, 87%). m/z (CI) 343 [M+H].

Step 2 Preparation of tert-butyl 3-(5-(4-((4S,5R)-3-(2,2-difluoroacetyl)-4-(fluoromethyl)-2,2-dimethyl-oxazolidin-5-yl)phenyl)pyridin-2-yl)morpholine-4-carboxylate

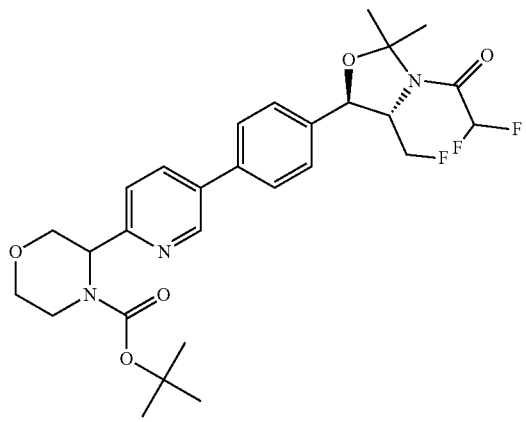 [SMILES: CC(C)(C)OC(=O)N1CCOCC1c1ccc(-c2ccc([C@H]3OC(C)(C)N(C(=O)C(F)F)[C@@H]3CF)cc2)cn1]

Following the general procedure of Example 22, Step 1 and making non-critical variations but using tert-butyl 3-(5-bromopyridin-2-yl)morpholine-4-carboxylate the title compound is obtained (510 mg): m/z (CI) 550 [M+H].

Step 3 Preparation of 2,2-difluoro-N-((1R,2S)-3-fluoro-1-hydroxy-1-(4-(6-(morpholin-3-yl)pyridin-3-yl)phenyl)propan-2-yl)acetamide

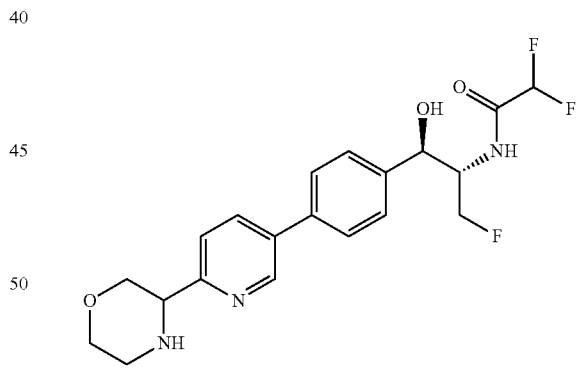

Following the general procedure of Example 2, Step 2 and making non-critical variations but using the product of Step 2, Example 97 the title compound is obtained (251 mg): $^1$H NMR (400 MHz, DMSO-d$_6$) δ 2.95 (d, 2H), 3.35 (d, 2H), 3.4-3.6 (m, 1H), 3.8 (d, 1H), 4.0 (dd, 1H), 4.05 (dd, 1H), 4.25-4.4 (m, 1.5H), 4.4-4.5 (t, 0.5H), 4.5-4.6 (m, 0.5H), 4.6-4.7 (m, 0.5H), 4.9 (t, 1H), 5.9 (d, 1H), 6.2 (t, 1H), 7.45 (d, 2H), 7.55 (d, 1H), 7.65 (d, 2H), 8.1 (dd, 1H), 8.8-8.9 (m, 2H). m/z (CI) 410 [M+H].

Example 98

Preparation of N-((1R,2S)-1-(4-(6-(1-amino-2-methoxyethyl)pyridin-3-yl)phenyl)-3-fluoro-1-hydroxypropan-2-yl)-2,2-difluoroacetamide Step 1 Preparation of 1-((4S,5R)-5-(4-(6-(1-amino-2-methoxyethyl)pyridin-3-yl)phenyl)-4-(fluoromethyl)-2,2-dimethyloxazolidin-3-yl)-2,2-difluoroethanone

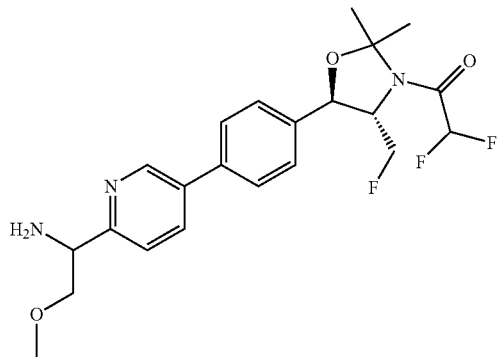 [SMILES: COCC(N)c1ccc(-c2ccc([C@H]3OC(C)(C)N(C(=O)C(F)F)[C@@H]3CF)cc2)cn1]

To a solution of toluene/ethanol (8 ml:6 ml, respectively) is added sequentially 2,2-difluoro-1-((4S,5R)-4-(fluoromethyl)-2,2-dimethyl-5-(4-(4,4,5,5-tetramethyl-1,3,2-dioxaborolan-2-yl)phenyl)oxazolidin-3-yl)ethanone (300 mg, 0.73 mmols), 1-(5-bromopyridin-2-yl)-2-methoxyethanamine (168 mg, 0.73 mmols), 1,1'-BisS(diphenylphosphino) ferrocenedichloro palladium (11) (53 mg, 0.07 mmols), and sodium hydrogen carbonate (2 ml, 2.0M (aq), 4 mmols). The reaction is heated with stirring in an atmosphere of nitrogen for two hours. The deep red reaction mixture is concentrated to dryness using rotary evaporation at low pressure. The residual material is slurried using ethanol (2×20 ml). The ethanol is decanted each time. The decanted solutions are combined and concentrated using rotary evaporation at low pressure to provide the crude product. The crude product, 1-((4S,5R)-5-(4-(6-(1-amino-2-methoxyethyl)pyridin-3-yl)phenyl)-4-(fluoromethyl)-2,2-dimethyloxazolidin-3-yl)-2,2-difluoroethanone, a 1:1 mixture of diasteromers was taken directly to the next step.

Step 2 Preparation of N-((1R,2S)-1-(4-(6-(1-amino-2-methoxyethyl)pyridin-3-yl)phenyl)-3-fluoro-1-hydroxypropan-2-yl)-2,2-difluoroacetamide

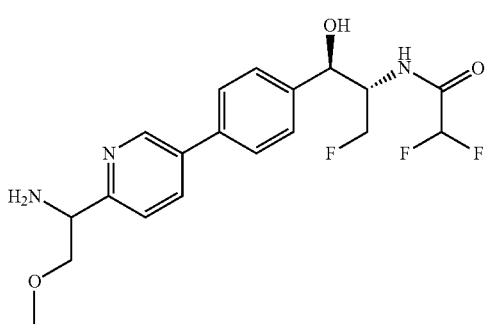 [SMILES: COCC(N)c1ccc(-c2ccc([C@@H](O)[C@@H](CF)NC(=O)C(F)F)cc2)cn1]

A solution 7:3 $CH_2Cl_2$/trifluoroacetic acid (total volume 10 ml), respectively, is added to neat 1-((4S,5R)-5-(4-(6-(1-amino-2-methoxyethyl)pyridin-3-yl)phenyl)-4-(fluoromethyl)-2,2-dimethyloxazolidin-3-yl)-2,2-difluoroethanone. Water (0.2 ml) is added to the reaction mixture. The solution is stirred for two hours at room temperature. The volatiles are removed using rotary evaporation at low pressure to give the crude product that is purified by reverse phase HPLC (water with 0.1% TFA/acetonitrile) to give the TFA salt of N-((1R,2S)-1-(4-(6-(1-amino-2-methoxyethyl)pyridin-3-yl)phenyl)-3-fluoro-1-hydroxypropan-2-yl)-2,2-difluoroacetamide (17 mg) after lyophilization: (m/z (CI) 398 [M+H]$^+$.

Example 99

Preparation of N-[(1S,2R)-2-{4-[6-(1-aminoethyl)pyridin-3-yl]phenyl}-1-(fluoromethyl)-2-hydroxyethyl]-2,2-dichloroacetamide

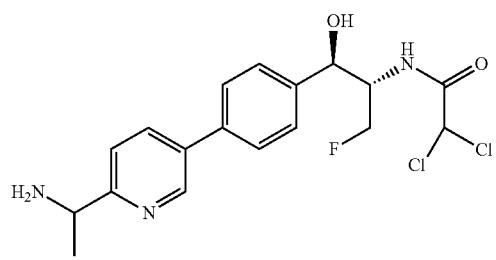 [SMILES: CC(N)c1ccc(-c2ccc([C@@H](O)[C@@H](CF)NC(=O)C(Cl)Cl)cc2)cn1]

Following the general procedures of Example 22 and Example 2 and making non-critical variations but using tert-butyl [1-(5-bromopyridin-2-yl)ethyl]carbamate the title compound is obtained (140 mg): $^1$H NMR (300 MHz, DMSOd-$_6$) δ 1.31 (d, 3H), 2.16 (s, br, 2H), 4.02 (q, 1H), 4.20-4.28 (m, 1.5H), 4.41-4.46 (m, 0.5H), 4.54-4.57 (m, 0.5H), 4.69-4.72 (m, 0.5H), 4.72-4.91 (m, 1H), 6.00 (d, 1H), 6.53 (s, 1H), 7.46 (d, 2H), 7.54 (d, 1H), 7.67 (d, 2H), 8.00-8.03 (dd, 1H), 8.65 (d, 1H), 8.77 (m, 1H). MS (ESI+) m/z 400.1/402.0 [M+H].

Example 100

Preparation of N-[(1S,2R)-2-{4-[6-(1-aminocyclopropyl)pyridin-3-yl]phenyl}-1-(fluoromethyl)-2-hydroxyethyl]-2,2-dichloroacetamide

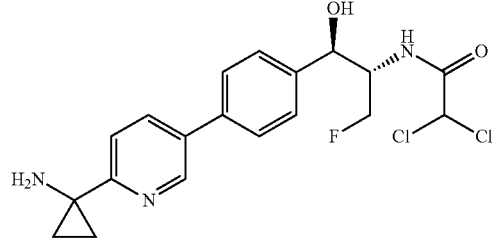 [SMILES: NC1(c2ccc(-c3ccc([C@@H](O)[C@@H](CF)NC(=O)C(Cl)Cl)cc3)cn2)CC1]

Following the general procedures of Example 22 and Example 2 and making non-critical variations but using tert-butyl [1-(5-bromopyridin-2-yl)ethyl]carbamate the title compound is obtained (60 mg): $^1$H NMR (400 MHz, DMSO-d$_6$) δ 0.99 (m, 2H), 1.25 (m, 2H), 4.25 (m, 1.5H), 4.41 (m, 0.5H), 4.58 (m, 0.5H), 4.70 (m, 0.5H), 4.90 (m, 1H), 6.00 (d, 1H), 6.54 (s, 1H), 7.45 (d, 2H), 7.65 (d, 2H), 7.81 (d, 1H), 8.01 (d, 1H), 8.67 (bd, 1H), 8.71 (m, 1H). MS (ESI+) m/z 412 [M+H].

Example 101

Preparation of 4-({(1R,2S)-2-[(difluoroacetyl)amino]-3-fluoro-1-[4-(6-{[(methylsulfonyl)amino]methyl}pyridin-3-yl)phenyl]propyl}oxy)-N,N,N-trimethyl-4-oxobutan-1-aminium bromide Step 1 Preparation of (1R,2S)-2-[(difluoroacetyl)amino]-3-fluoro-1-[4-(6-{[(methylsulfonyl)amino]methyl}pyridin-3-yl)phenyl]propyl 4-bromobutanoate

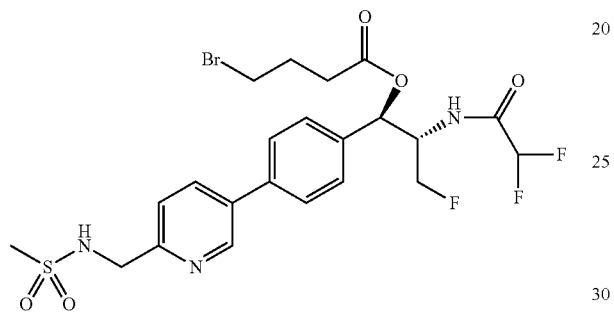

4-Bromobutanoyl chloride (29.6 µL, 0.255 mmol) is added dropwise to a stirred solution of 2,2-difluoro-N-{(1S,2R)-1-(fluoromethyl)-2-hydroxy-2-[4-(6-{[(methylsulfonyl)amino]methyl}pyridin-3-yl)phenyl]ethyl}acetamide (100.0 mg, 0.232 mmol), N,N-diisopropylethylamine (48.4 µL, 0.278 mmol), and 4-dimethylaminopyridine (11.3 mg, 0.093 mmol) in N,N-dimethylformamide (1.00 mL) at rt. The reaction mixture is stirred for 1 hour before being concentrated. The residue was purified by CombiFlash (4 g column) eluting with 0-100% ethyl acetate to yield the title compound (80.0 mg, 59%) as a yellow foam. MS (ESI+) m/z 581.7 [M+H].

Step 2 Preparation of 4-({(1R,2S)-2-[(difluoroacetyl)amino]-3-fluoro-1-[4-(6-{[(methylsulfonyl)amino]methyl}pyridin-3-yl)phenyl]propyl}oxy)-N,N,N-trimethyl-4-oxobutan-1-aminium bromide

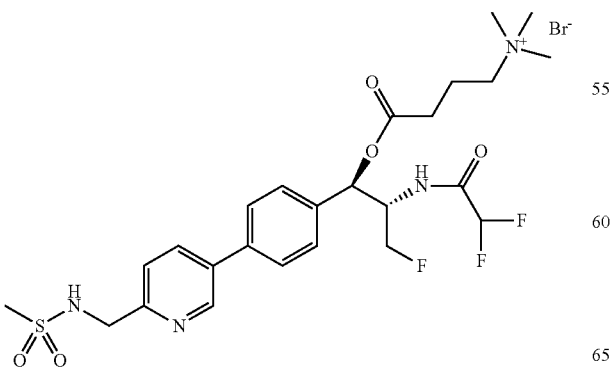

In a sealed tube 4.2 M trimethylamine in ethanol (1.42 mL, 5.98 mmol) is added to a stirred solution of (1R,2S)-2-[(difluoroacetyl)amino]-3-fluoro-1-[4-(6-{[(methylsulfonyl)amino]methyl}pyridin-3-yl)phenyl]propyl 4-bromobutanoate (Step 1, 570.0 mg, 0.982 mmol) in tetrahydrofuran (11.0 mL) at room temperature and the reaction mixture was heated at 50° C. overnight. After stirring overnight the reaction mixture was concentrated and the residue was taken up in water. The aqueous layer was extracted with methylene chloride (3×) to remove all the impurities. The aqueous layer was then lyophilized overnight to afford the title compound (375 mg): $^1$H NMR (300 MHz, DMSO-$d_6$) δ 1.94-1.97 (m, 2H), 2.73-2.77 (t, 2H), 3.05 (s, 9H), 3.23-3.31 (m, 2H), 3.48 (s, 3H), 4.27-4.33 (m, 1.5H), 4.43-4.53 (m, 1H), 4.67-4.71 (m, 0.5H), 4.89-4.91 (m, 1H), 5.13 (s, 2H), 5.91 (d, 1H), 6.20 (t, 1H), 7.45-7.48 (m, 3H), 7.71 (d, 2H), 8.10-8.14 (dd, 1H), 8.82 (d, 1H), 8.86 (d, 1H). MS (ESI+) m/z 559.1 [M].

Example 102

Preparation of 2,2-dichloro-N-{(1S,2R)-1-(fluoromethyl)-2-hydroxy-2-[4-(6-pyrrolidin-2-ylpyridin-3-yl)phenyl]ethyl}acetamide

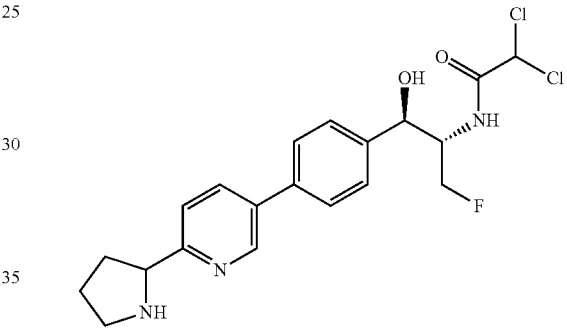

Following the general procedure of Example 96 but using tert-butyl 2-(5-bromopyridin-2-yl)pyrrolidine-1-carboxylate the title compound is obtained (380 mg): $^1$H NMR (300 MHz, DMSO-$d_6$) δ 1.66-1.79 (m, 3H), 2.12-2.18 (m, 1H), 2.86-2.92 (m, 1H), 3.00-3.05 (m, 1H), 3.32 (s, br, 1H), 4.17-4.28 (m, 2.5H), 4.42-4.44 (m, 0.5H), 4.54-4.57 (m, 0.5H), 4.69-4.74 (m, 0.5H), 4.89-4.91 (m, 1H), 6.00 (d, 1H), 6.53 (s, 1H), 7.46 (d, 2H), 7.54 (d, 1H), 7.67 (d, 2H), 7.99-8.02 (dd, 1H), 8.65 (d, 1H), 8.77 (d, 1H). MS (ESI+) m/z 426.0, 428.0 (M+H).

The following derivative of the title compound of Example 102 can be prepared by methods known in the art: (1R,2S)-2-(2,2-dichloroacetamido)-3-fluoro-1-(4-(6-(pyrrolidin-2-yl)pyridin-3-yl)phenyl)propyl dihydrogen phosphate.

Example 103

Preparation of N-{(1S,2R)-2-[4-(2-Aminomethyl-pyrimidin-5-yl)-phenyl]-1-fluoromethyl-2-hydroxy-ethyl}-2,2-difluoro-acetamide trifluoroacetic acid salt

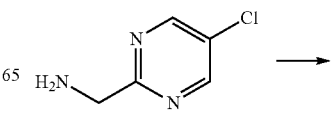

158

Step 2 Preparation of (5-{4-[(4S,5R)-3-(2,2-Difluoro-acetyl)-4-fluoromethyl-2,2-dimethyl-oxazolidin-5-yl]-phenyl}-pyrimidin-2-ylmethyl)-carbamic acid tert-butyl ester

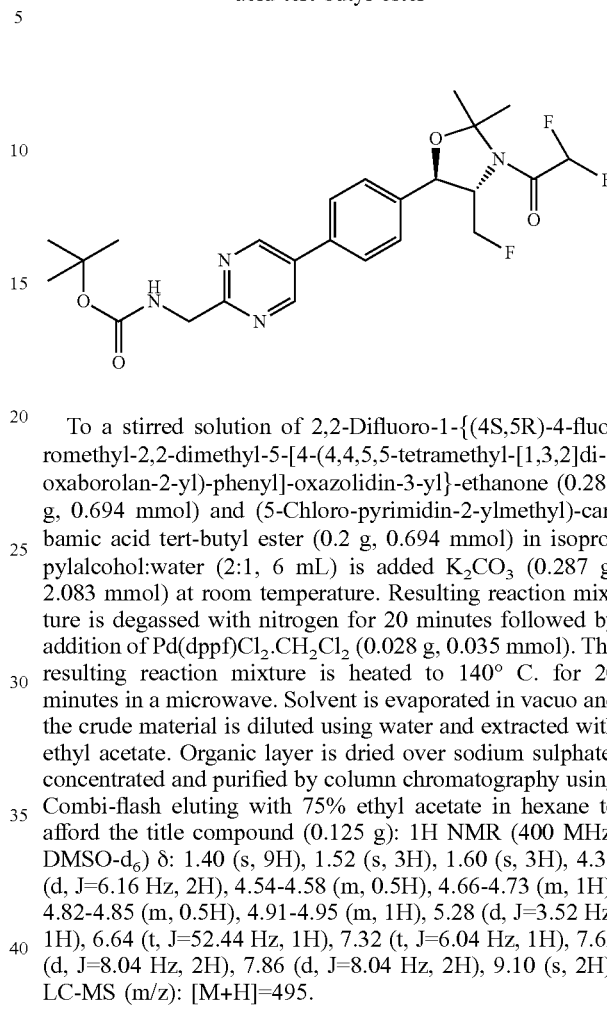

To a stirred solution of 2,2-Difluoro-1-{(4S,5R)-4-fluoromethyl-2,2-dimethyl-5-[4-(4,4,5,5-tetramethyl-[1,3,2]dioxaborolan-2-yl)-phenyl]-oxazolidin-3-yl}-ethanone (0.286 g, 0.694 mmol) and (5-Chloro-pyrimidin-2-ylmethyl)-carbamic acid tert-butyl ester (0.2 g, 0.694 mmol) in isopropylalcohol:water (2:1, 6 mL) is added $K_2CO_3$ (0.287 g, 2.083 mmol) at room temperature. Resulting reaction mixture is degassed with nitrogen for 20 minutes followed by addition of Pd(dppf)Cl$_2$·CH$_2$Cl$_2$ (0.028 g, 0.035 mmol). The resulting reaction mixture is heated to 140° C. for 20 minutes in a microwave. Solvent is evaporated in vacuo and the crude material is diluted using water and extracted with ethyl acetate. Organic layer is dried over sodium sulphate, concentrated and purified by column chromatography using Combi-flash eluting with 75% ethyl acetate in hexane to afford the title compound (0.125 g): 1H NMR (400 MHz, DMSO-d$_6$) δ: 1.40 (s, 9H), 1.52 (s, 3H), 1.60 (s, 3H), 4.36 (d, J=6.16 Hz, 2H), 4.54-4.58 (m, 0.5H), 4.66-4.73 (m, 1H), 4.82-4.85 (m, 0.5H), 4.91-4.95 (m, 1H), 5.28 (d, J=3.52 Hz, 1H), 6.64 (t, J=52.44 Hz, 1H), 7.32 (t, J=6.04 Hz, 1H), 7.62 (d, J=8.04 Hz, 2H), 7.86 (d, J=8.04 Hz, 2H), 9.10 (s, 2H). LC-MS (m/z): [M+H]=495.

Step 3 Preparation of N-{(1S,2R)-2-[4-(2-Aminomethyl-pyrimidin-5-yl)-phenyl]-1-fluoromethyl-2-hydroxy-ethyl}-2,2-difluoro-acetamide trifluoroacetic acid salt

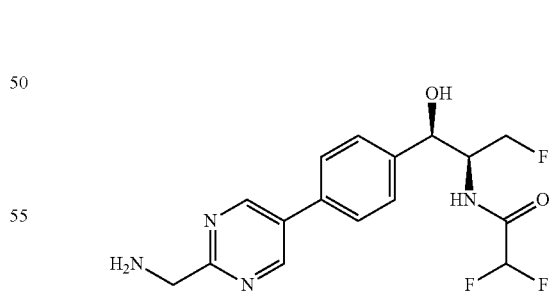

To a stirred solution of (5-{4-[(4S,5R)-3-(2,2-Difluoro-acetyl)-4-fluoromethyl-2,2-dimethyl-oxazolidin-5-yl]-phenyl}-pyrimidin-2-ylmethyl)-carbamic acid tert-butyl ester (0.125 g, 0.253 mmol) in CH$_2$Cl$_2$ (10 mL) is added trifluoroacetic acid (1.0 mL) at room temperature. Resulting reaction mixture is allowed to stir at room temperature for 5 hours. The solvent evaporated in vacuo and the crude material is striped out with CH$_2$Cl$_2$ followed by washing

157

-continued

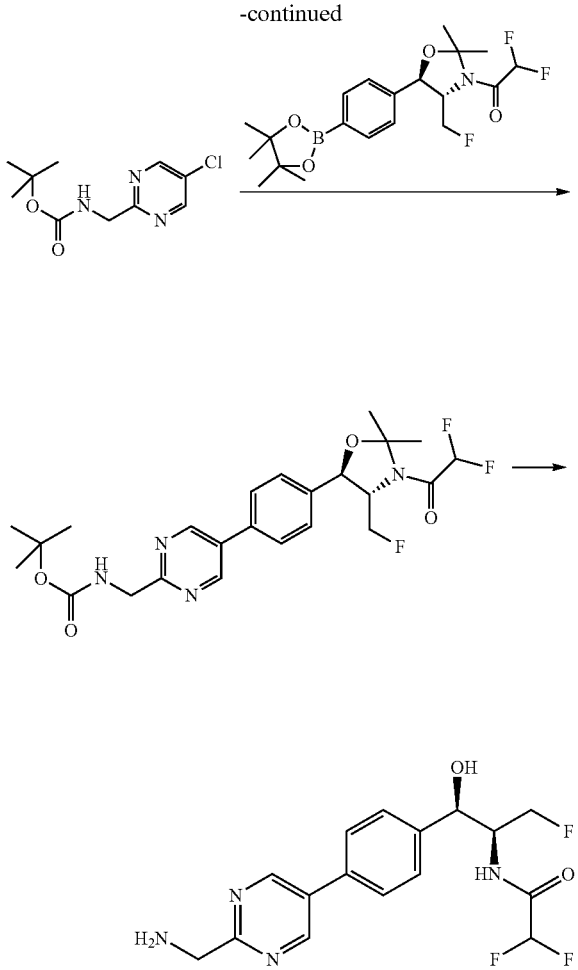

Step 1 Preparation of (5-Chloro-pyrimidin-2-ylmethyl)-carbamic acid tert-butyl ester

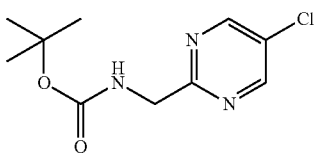 [SMILES: CC(C)(C)OC(=O)NCc1ncc(Cl)cn1]

To a stirred solution of C-(5-Chloro-pyrimidin-2-yl)-methylamine (0.1 g, 0.532 mmol) in CH$_2$Cl$_2$ (2 mL) is added triethyl amine (0.153 mL, 1.064 mmol) at room temperature followed by addition of di-tert-butyl dicarbonate (0.134 mL, 84.50 mmol). Reaction mixture is stirred at room temperature for 2 hours. Solvent is evaporated, and the crude material is purified by combi-flash eluting with 12% methanol in CH$_2$Cl$_2$ to afford the title compound (0.1 g): 1H NMR (400 MHz, DMSO-d$_6$) δ: 1.37 (s, 9H), 4.27 (d, 6.16 Hz, 2H), 7.33 (t, J1=5.92 Hz, 1H), 8.94 (s, 2H). LC-MS (m/z): [M+H]=288.2.

with diethyl ether and dried in lipholiser to afford title compound (0.1 g): 1H NMR (400 MHz, DMSO-$d_6$) δ: 4.31-4.33 (m, 1.5H), 4.36 (d, J=8.84 Hz, 2H), 4.42-4.46 (m, 0.5H), 4.56-4.57 (m, 0.5H), 4.66-4.70 (m, 0.5H), 4.92 (t, J=3.76 Hz, 1H), 5.98 (d, J=4.6 Hz, 1H), 6.20 (t, J=53.72 Hz, 1H), 7.52 (d, J=8.24 Hz, 2H), 7.84 (d, J=8.24 Hz, 2H), 8.36 (bs, 2H), 7.86 (d, J=8.84 Hz, 1H), 9.24 (s, 2H). LC-MS (m/z): [M+H]=354.9.

Example 104

Preparation of N-((1S,2R)-2-{4-[6-(1-Amino-2-cyano-ethyl)-pyridin-3-yl]-phenyl}-1-fluoromethyl-2-hydroxy-ethyl)-2,2-difluoro-acetamide

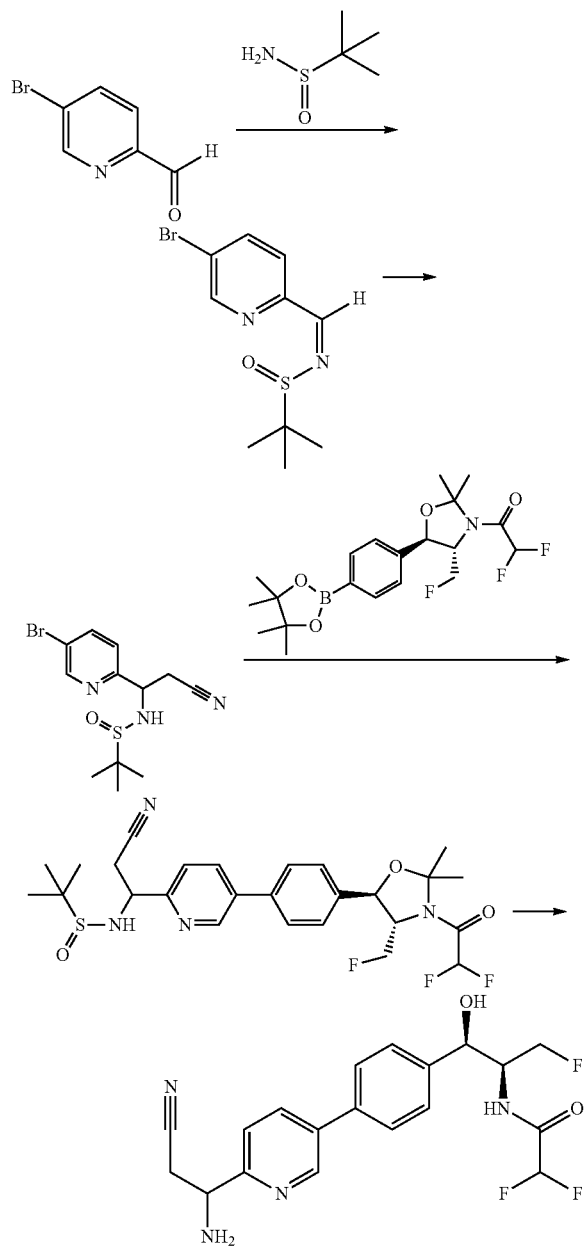

Step 1 Preparation of 2-Methyl-propane-2-sulfinic acid 5-bromo-pyridin-2-ylmethyleneamide

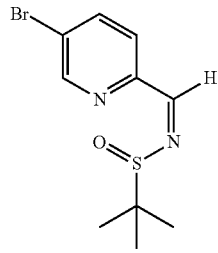

To a stirred solution of 5-Bromo-pyridine-2-carbaldehyde (2.0 g, 10.753 mmol) in $CH_2Cl_2$ (20 mL) and 2-Methyl-propane-2-sulfinic acid amide (2.602 g, 21.505 mmol) is added $CuSO_4$ (5.589 g, 21.505 mmol) at room temperature. Resulting reaction mixture is stirred at room temperature for 3 hours. Reaction mixture is filter through celite. Diluted with water and extracted with $CH_2Cl_2$. Organic layer is dried over sodium sulphate, solvent is evaporated in vacuo and purified by combi-flash chromatography using 5% ethyl acetate in hexane to afford the title compound (2.5 g): $^1$H-NMR (400 MHz, DMSO-$d_6$) δ: 1.19 (s, 9H), 8.03 (d, J=8.52 Hz, 1H), 8.25-8.27 (dd, J=2.32 Hz, J=8.32 Hz, 1H), 8.44 (s, 1H), 8.90 (d, J=1.84 Hz, 1H). LC-MS (m/z): [M+H]=291.1.

Step 2 Preparation of 2-Methyl-propane-2-sulfinic acid [1-(5-bromo-pyridin-2-yl)-2-cyano-ethyl]-amide

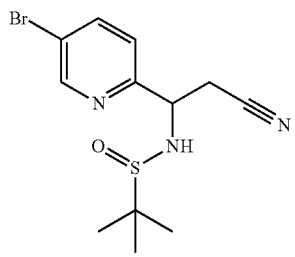

To a solution of Acetonitrile (0.142 g, 3.472 mmol) in dry tetrahydrofuran (10 mL) is added n-butyl lithium (0.222 g, 3.472 mmol) at −78° C. and stir for 30 minutes at same temperature followed by drop wise addition of solution of 2-Methyl-propane-2-sulfinic acid 5-bromo-pyridin-2-ylmethyleneamide (0.5 g, 1.736 mmol) in dry tetrahydrofuran (10 mL) and stirred the reaction at −78° C. for 1 h. Reaction mixture is diluted with aqueous ammonium chloride solution and extracted with ethyl acetate. Organic layer is dried over sodium sulphate, solvent is evaporated in vacuo and purified by combi-flash chromatography using 80% ethyl acetate in hexane to afford the title compound (0.25 g): $^1$H-NMR (400 MHz, DMSO-$d_6$) δ: 1.17 (s, 9H), 2.93-2.99 (m, 1H), 3.11-3.16 (m, 1H), 4.72-4.78 (m, 1H), 6.09 (d, J=9.24, 1H), 7.64 (d, J=8.44 Hz, 1H), 8.12-8.14 (dd, J1=2.36 Hz, J2=8.4 Hz, 1H), 8.674 (d, 2.24 Hz, 1H). LC-MS (m/z): [M+H]=330.0.

Step 3 Preparation of 2-Methyl-propane-2-sulfinic acid [2-cyano-1-(5-{4-[(4S,5R)-3-(2,2-difluoro-acetyl)-4-fluoromethyl-2,2-dimethyl-oxazolidin-5-yl]-phenyl}-pyridin-2-yl)-ethyl]-amide

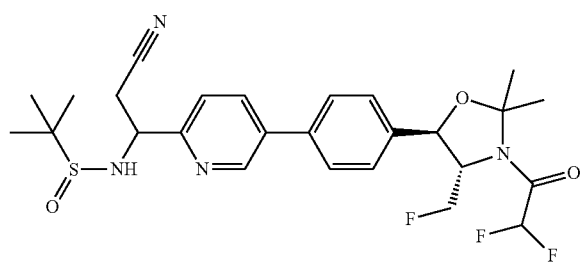 [SMILES: CC1(C)O[C@H](c2ccc(-c3ccc(C(CC#N)NS(=O)C(C)(C)C)nc3)cc2)[C@@H](CF)N1C(=O)C(F)F]

To a stirred solution of 2,2-Difluoro-1-{(4S,5R)-4-fluoromethyl-2,2-dimethyl-5-[4-(4,4,5,5-tetramethyl-[1,3,2]dioxaborolan-2-yl)-phenyl]-oxazolidin-3-yl}-ethanone (0.312 g, 0.758 mmol) and 2-Methyl-propane-2-sulfinic acid [1-(5-bromo-pyridin-2-yl)-2-cyano-ethyl]-amide (0.25 g, 0.758 mmol) in toluene:Ethanol:water (10:10:10 mL) is added Na$_2$CO$_3$ (0.16 g, 1.515 mmol) at room temperature. Resulting reaction mixture is degassed with nitrogen for 15 minutes followed by addition of Pd(PPh$_3$)$_4$ (0.087 g, 0.076 mmol). Resulting reaction mixture is heated to 80° C. for 3 hours. Solvent is evaporated in vacuo then diluted with water and extracted with ethyl acetate. Organic layer is dried over sodium sulphate, solvent is evaporated in vacuo and purified by combi-flash chromatography using 50% ethyl acetate in hexane to afford the title compound (0.21 g): $^1$H-NMR (400 MHz, DMSO-d$_6$) δ: 1.19 (s, 9H), 1.53 (s, 3H), 1.60 (S, 3H), 2.98-3.04 (m, 1H), 3.17-3.22 (m, 1H), 4.54-4.58 (m, 0.5H), 4.66-4.70 (m, 1H), 4.78-4.84 (m, 1.5H), 4.89-4.95 (m, 1H), 5.26-5.27 (m, 1H), 6.12 (d, J=9 Hz, 1H), 6.64 (t, J=52.4 Hz, 1H), 7.53-7.64 (m, 2H), 7.76 (d, J=8.2 Hz, 1H), 7.82 (d, J=8.12 Hz, 2H), 8.89 (d, J=1.84 Hz, 1H), 8.86 (d, J=2.08 Hz, 1H). LC-MS (m/z): [M+H]=537.2.

Step 4 Preparation of N-((1S,2R)-2-{4-[6-(1-Amino-2-cyano-ethyl)-pyridin-3-yl]-phenyl}-1-fluoromethyl-2-hydroxy-ethyl)-2,2-difluoro-acetamide

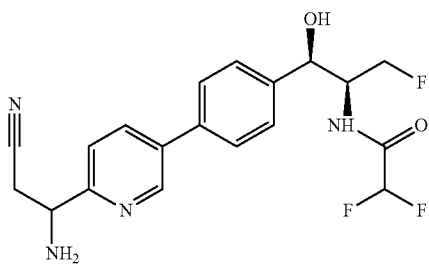 [SMILES: N#CCC(N)c1ccc(-c2ccc([C@@H](O)[C@@H](CF)NC(=O)C(F)F)cc2)cn1]

To a solution of 2-methyl-propane-2-sulfinic acid [2-cyano-1-(5-{4-[(4S,5R)-3-(2,2-difluoro-acetyl)-4-fluoromethyl-2,2-dimethyl-oxazolidin-5-yl]-phenyl}-pyridin-2-yl)-ethyl]-amide (0.21 g, 0.392 mmol) in Ethyl acetate (2 mL) is added HCl in dioxane (2.0 mL) at 0° C. The resulting reaction mixture is stirred at room temperature for 3 hours. Solvent is evaporated in vacuo to get the crude residue and diluted with aqueous ammonia solution and extracted with ethyl acetate. Organic layer is dried over sodium sulphate, concentrated and purified by combi-flash chromatography using 7-8% methanol in CH$_2$Cl$_2$ to afford the title compound (0.032 g): $^1$HNMR (400 MHz, DMSO-d$_6$) δ: 2.85-2.99 (m, 2H), 4.24-4.35 (m, 2.5H), 4.40-4.44 (m, 0.5H), 4.54-4.55 (m, 0.5H), 4.64-4.67 (m, 0.5H), 4.87-4.88 (m, 2H), 5.92 (d, J=4.44 Hz, 1H), 6.20 (t, J=53.8 Hz, 1H), 7.46 (d, J=8.16 Hz, 2H), 7.62 (d, J=8.16 Hz, 1H), 7.71 (d, J=8.22 Hz, 2H), 8.09-8.12 (dd, J1=2.32 Hz, J2=8.2 Hz, 1H), 8.84-8.87 (m, 2H). LC-MS (m/z): [M+H]=393.0.

Example 105

Preparation of N-{(1S,2R)-2-[4-(6-Aminomethyl-pyridazin-3-yl)-phenyl]-1-fluoromethyl-2-hydroxy-ethyl}-2,2-difluoro-acetamide trifluoroacetic acid salt

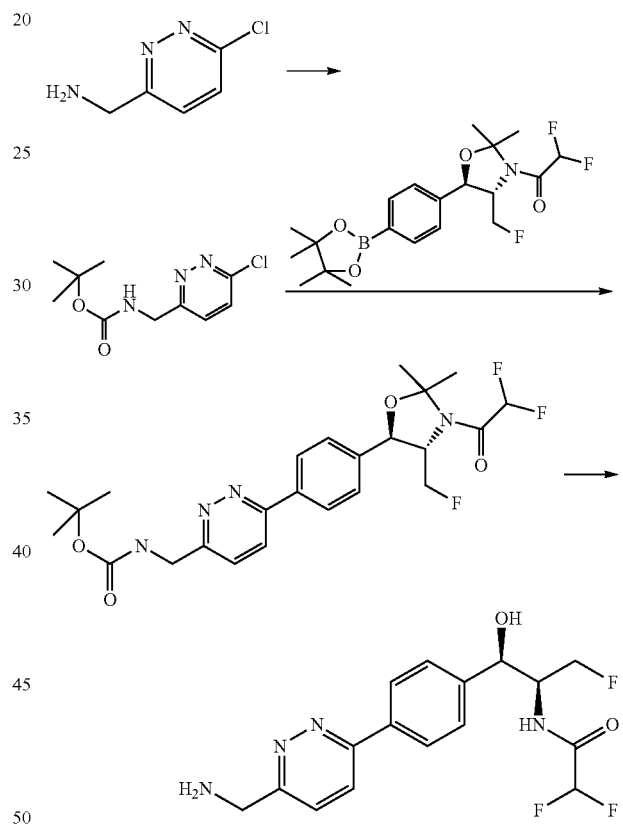

Step 1 Preparation of (6-Chloro-pyridazin-3-ylmethyl)-carbamic acid tert-butyl ester

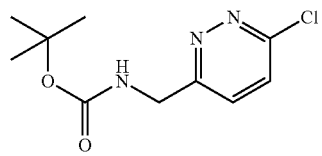 [SMILES: CC(C)(C)OC(=O)NCc1ccc(Cl)nn1]

To a stirred solution of C-(6-Chloro-pyridazin-3-yl)-methylamine hydrochloride salt (0.05 g, 0.279 mmol) in acetonitrile (2 mL) is added triethyl amine (0.08 mL, 0.557 mmol) at room temperature followed by addition of di-tert-butyl dicarbonate (0.076 mmol, 0.334 mmol). Reaction mixture is heated to 60° C. for 2 hours. Solvent is evaporated, and the crude material is purified by combi-flash eluting with 14% methanol in CH$_2$Cl$_2$ to afford the title compound (0.025 g): 1H NMR (400 MHz, DMSO-d$_6$) 1.39 (s, 9H), 4.40 (d, 6.08 Hz, 2H), 7.59 (m, 1H), 7.62 (d, J=9.04 Hz, 1H), 7.89 (d, J=8.88 Hz, 2H). LC-MS (m/z): [M+H]=244.2.

Step 2 Preparation of (6-{4-[(4S,5R)-3-(2,2-Difluoro-acetyl)-4-fluoromethyl-2,2-dimethyl-oxazolidin-5-yl]-phenyl}-pyridazin-3-ylmethyl)-carbamic acid tert-butyl ester

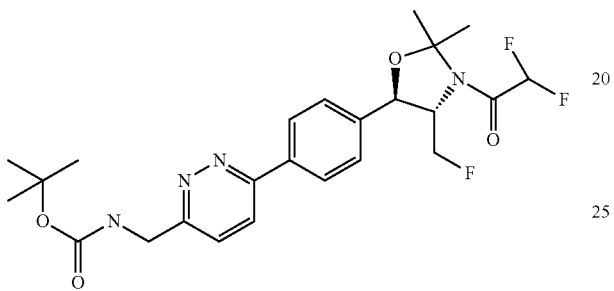

To a stirred solution of 2,2-difluoro-1-{(4S,5R)-4-fluoromethyl-2,2-dimethyl-5-[4-(4,4,5,5-tetramethyl-[1,3,2]dioxaborolan-2-yl)-phenyl]-oxazolidin-3-yl}-ethanone (0.849 g, 2.058 mmol) and (6-Chloro-pyridazin-3-ylmethyl)-carbamic acid tert-butyl ester (0.5 g, 2.058 mmol) in toluene:ethanol:water (20:10:5 mL) is added Na$_2$CO$_3$ (0.436 g, 4.115 mmol) at room temperature. Resulting reaction mixture is degassed with nitrogen for 20 minutes followed by addition of Pd (PPh$_3$)$_4$ (0.237 g, 0.206 mmol). The resulting reaction mixture is heated to 80° C. for 16 h. Solvent is evaporated in vacuo and the crude material is diluted using water and extracted with ethyl acetate. Organic layer is dried over sodium sulphate, concentrated and purified by using Combi-flash eluting with 20% MeOH in DCM to afford the title compound (0.250 g): 1H NMR (400 MHz, DMSO-d$_6$) 1.40 (s, 9H), 1.53 (s, 3H), 1.61 (s, 3H), 3.94 (s, 1H), 4.47 (d, J=6.08 Hz, 2H), 4.58-4.59 (m, 0.5H), 4.70-4.71 (m, 1H), 4.83-4.84 (m, 0.5H), 4.94-4.97 (m, 1H), 5.30 (d, J=3.32 Hz, 1H), 6.65 (t, J=52.32 Hz, 1H), 7.61-7.67 (m, 4H), 8.18 (d, J=8.12 Hz, 2H), 8.24 (d, J=8.84 Hz, 1H). LC-MS (m/z): [M+H]=495.2.

Step 3 Preparation of N-{(1S,2R)-2-[4-(6-Aminomethyl-pyridazin-3-yl)-phenyl]-1-fluoromethyl-2-hydroxy-ethyl}-2,2-difluoro-acetamide trifluoroacetic acid salt

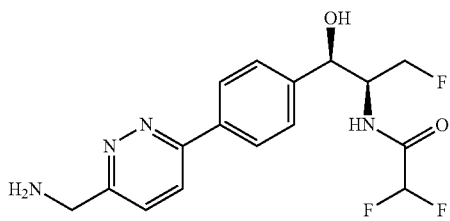 [SMILES: NCc1ccc(-c2ccc([C@@H](O)[C@@H](CF)NC(=O)C(F)F)cc2)nn1]

To a stirred solution of (6-{4-[(4S,5R)-3-(2,2-Difluoro-acetyl)-4-fluoromethyl-2, 2-dimethyl-oxazolidin-5-yl]-phenyl}-pyridazin-3-ylmethyl)-carbamic acid tert-butyl ester (0.25 g, 0.506 mmol) in CH$_2$Cl$_2$ (10 mL) is added trifluoroacetic acid (1.5 mL) at room temperature. Resulting reaction mixture is allowed to stir at room temperature for 5 h. The solvent evaporated in vacuo and the crude material is striped out with CH$_2$Cl$_2$ followed by washing with n-pentane and diethyl ether and dried to afford title compound (0.181 g): 1H NMR (400 MHz, DMSO-d$_6$) 4.32-4.39 (m, 1.5H), 4.46 (m, 2.5H), 4.55-4.58 (m, 0.5H), 4.68-4.71 (m, 0.5H), 4.94 (bs, 1H), 5.99 (bs, 1H), 6.19 (t, J=53.76 Hz, 1H), 7.54 (d, J=8.28 Hz, 2H), 7.85 (d, J=8.92 Hz, 1H), 8.13 (d, J=8.32 Hz, 2H), 8.36 (d, J=10 HZ, 1H), 8.51 (bs, 2H), 8.87 (d, J=8.72 Hz, 1H). LC-MS (m/z): [M+H]=355.

Example 106

Preparation of N-((1R,2S)-1-(4-(6-((S)-1-amino-2-hydroxyethyl)-pyridin-3-yl)phenyl)-3-fluoro-1-hydroxypropan-2-yl)-2,2-difluoroacetamide Step 1 Preparation of (S)-tert-butyl 1-(5-bromopyridin-2-yl)-2-hydroxyethylcarbamate

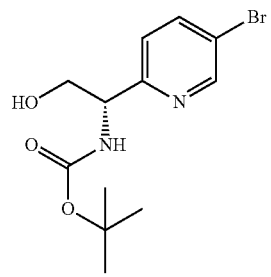 [SMILES: CC(C)(C)OC(=O)N[C@H](CO)c1ccc(Br)cn1]

A solution of (S)-2-amino-2-(5-bromopyridin-2-yl)ethanol (250 mg, 0.99) in CH$_2$Cl$_2$ (10 ml) is treated with di-tert-butyl dicarbonate (237 mg, 1.08 mmol) and triethylamine (0.275 ml, 1.97), and stirred at ambient temperature for 16 hours. The reaction mixture is washed with 10% aqueous citric acid solution (25 ml). The organic phase is dried over anhydrous magnesium sulfate, filtered and concentrated to afford the title compound (262 mg): m/z M+H 317. Retention time 2.50 min.

Step 2 Preparation of tert-butyl (S)-1-(5-(4-((4S,5R)-3-(2,2-difluoroacetyl)-4-(fluoromethyl)-2,2-dimethyloxazolidin-5-yl)phenyl)pyridin-2-yl)-2-hydroxyethylcarbamate

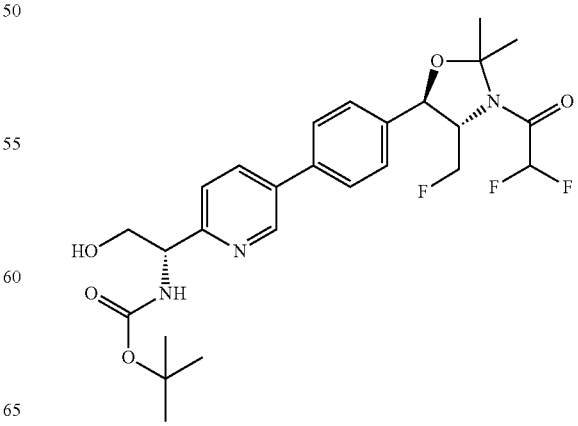

To a solution of 2,2-Difluoro-1-{(4S,5R)-4-fluoromethyl-2,2-dimethyl-5-[4-(4,4,5,5-tetramethyl-[1,3,2]dioxaborolan-2-yl)-phenyl]-oxazolidin-3-yl}-ethanone (339 mg, 0.820 mmol) in a mixture of toluene (5 ml) and ethanol (3 ml) is added (S)-tert-butyl 1-(5-bromopyridin-2-yl)-2-hydroxyethylcarbamate (260 mg, 0.82 mmol), aqueous sodium bicarbonate solution (2M, 3.28 mmol, 1.64 ml), and [1,1'Bis(diphenylphosphino)ferrocene]dichloropalladium (II) (30 mg, 0.04 mmol). The stirred reaction mixture is heated at 80° C. under a blanket of nitrogen for 1 hour. The reaction is concentrated to dryness and partitioned between methylene chloride (25 ml) and water (25 ml). The organic phase is washed with saturated brine (25 ml) and concentrated on to silica gel (1 g). Purification by column chromatography (12 g silica gel, ethyl acetate/heptane 0-100%, 16 cvs) affords the title compound (260 mg): m/z M+H 524.2. Retention time 2.73 min.

Step 3 Preparation of N-((1R,2S)-1-(4-(6-((S)-1-amino-2-hydroxyethyl)-pyridin-3-yl)phenyl)-3-fluoro-1-hydroxypropan-2-yl)-2,2-difluoroacetamide

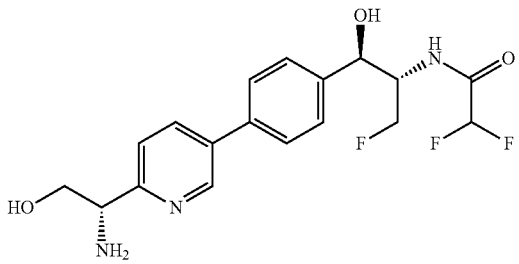 [SMILES: N[C@H](CO)c1ccc(-c2ccc([C@@H](O)[C@@H](CF)NC(=O)C(F)F)cc2)cn1]

To a stirred solution of tert-butyl (S)-1-(5-(4-((4S,5R)-3-(2,2-difluoroacetyl)-4-(fluoromethyl)-2,2-dimethyloxazolidin-5-yl)phenyl)pyridin-2-yl)-2-hydroxyethylcarbamate (260 mg, 0.49 mmol) and methylene chloride (25 mL), cooled to 0° C., is added trifluoroacetic acid (2.5 mL) and water (50 ul). The reaction is allowed to warm to ambient temperature, and is stirred for a further 1 h. Toluene (20 mL) is added and the reaction mixture concentrated under vacuum to give the crude product as a bis trifluoroacetate salt. 400 mg. m/z M+H 384.1. Retention time 1.69 min.

Example 107

Preparation of N-((1R,2S)-1-(4-(6-(2-amino-1-hydroxypropan-2-yl)pyridin-3-yl)phenyl)-3-fluoro-1-hydroxypropan-2-yl)-2,2-difluoroacetamide Step 1 Preparation of tert-butyl 2-(5-bromopyridin-2-yl)-1-hydroxypropan-2-ylcarbamate

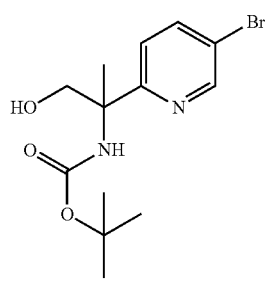 [SMILES: CC(C)(C)OC(=O)NC(C)(CO)c1ccc(Br)cn1]

A solution of 2-amino-2-(5-bromopyridin-2-yl)propan-1-ol (264 mg, 0.99 mmol) in DCM (10 ml) is treated with di-tert-butyl dicarbonate (237 mg, 1.08 mmol) and triethylamine (0.275 ml, 1.97), and stirred at ambient temperature for 16 h. The reaction mixture is washed with 10% aqueous citric acid solution (25 ml). The organic phase is dried over anhydrous magnesium sulfate, filtered and concentrated to afford the title compound (165 mg): m/z M+H 332.1. Retention time 2.61 min.

Step 2 Preparation of tert-butyl 2-(5-(4-((4S,5R)-3-(2,2-difluoroacetyl)-4-(fluoromethyl)-2,2-dimethyloxazolidin-5-yl)phenyl)pyridin-2-yl)-1-hydroxypropan-2-ylcarbamate

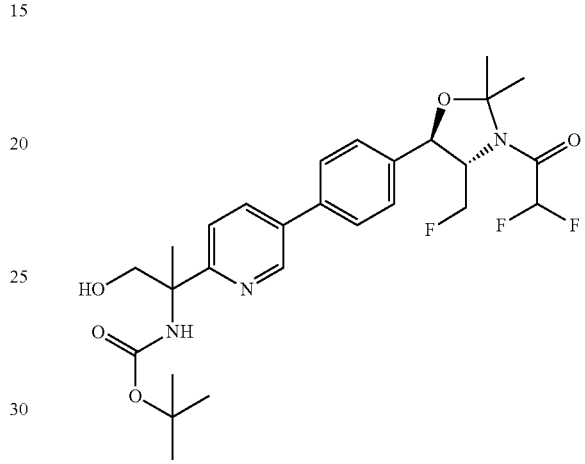

To a solution of 2,2-Difluoro-1-{(4S,5R)-4-fluoromethyl-2,2-dimethyl-5-[4-(4,4,5,5-tetramethyl-[1,3,2]dioxaborolan-2-yl)-phenyl]-oxazolidin-3-yl}-ethanone (200 mg, 0.48 mmol) in a mixture of toluene (3 ml) and ethanol (2 ml) is added tert-butyl 2-(5-bromopyridin-2-yl)-1-hydroxypropan-2-ylcarbamate (160 mg, 0.48 mmol), aqueous sodium bicarbonate solution (2M, 2 mmol, 1 ml), and [1,1'Bis(diphenylphosphino)ferrocene]dichloropalladium (II) (18 mg, 0.024 mmol). The stirred reaction mixture is heated at 80° C. under a blanket of nitrogen for 1 hour. The reaction is concentrated to dryness and partitioned between methylene chloride (25 ml) and water (25 ml). The organic phase is washed with saturated brine (25 ml) and concentrated on to silica gel (1 g). Purification by column chromatography (12 g silica gel, ethyl acetate/heptane 0-100%, 16 cvs) affords the title compound (62 mg): m/z M+H 538.2. Retention time 2.75 min.

Step 3 Preparation of N-((1R,2S)-1-(4-(6-(2-amino-1-hydroxypropan-2-yl)pyridin-3-yl)phenyl)-3-fluoro-1-hydroxypropan-2-yl)-2,2-difluoroacetamide

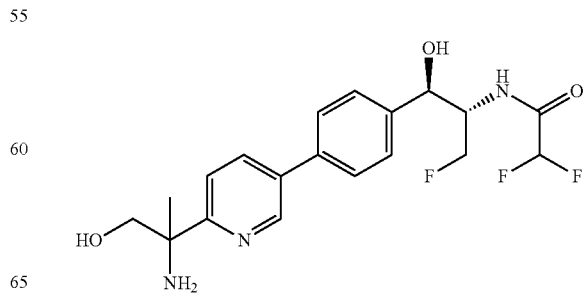

To a stirred solution of tert-butyl 2-(5-(4-((4S,5R)-3-(2,2-difluoroacetyl)-4-(fluoromethyl)-2,2-dimethyloxazolidin-5-yl)phenyl)pyridin-2-yl)-1-hydroxypropan-2-ylcarbamate (62 mg, 0.11 mmol) and methylene chloride (10 mL), cooled to 0° C., is added trifluoroacetic acid (1 mL) and water (20 ul). The reaction is allowed to warm to ambient temperature, and is stirred for a further 1 h. Toluene (10 mL) is added and the reaction mixture concentrated under vacuum to give the crude product as a bis-trifluoroacetate salt. 100 mg. m/z M+H 398.1. Retention time 1.83 min.

Example 108

Preparation of N-((1R,2S)-1-(4-(2-(1-aminoethyl)thiazol-5-yl)phenyl)-3-fluoro-1-hydroxypropan-2-yl)-2,2-dichloroacetamide Step 1 Preparation of tert-butyl 1-(5-bromothiazol-2-yl)ethylcarbamate

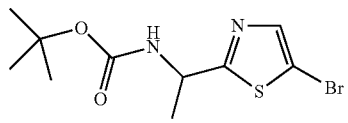 [SMILES: CC(NC(=O)OC(C)(C)C)c1ncc(Br)s1]

Following the procedure previously described in WO2011053542 (p 47-49), but using racemic 2-methyl-2-propanesulfinamide the title compound is obtained (2.06 g): m/z (CI) M+H 311+313.

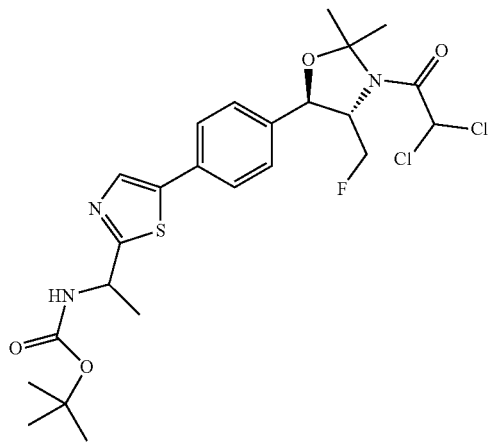 [SMILES: CC(NC(=O)OC(C)(C)C)c1ncc(-c2ccc([C@H]3OC(C)(C)N(C(=O)C(Cl)Cl)[C@@H]3CF)cc2)s1]

Following the general procedure of Example 21—Step 2 and making non-critical variations but using tert-butyl 1-(5-bromothiazol-2-yl)ethylcarbamate the title compound is obtained (1030 mg): m/z (CI) 546 [M+H].

Step 3 Preparation of N-((1R,2S)-1-(4-(2-(1-aminoethyl)thiazol-5-yl)-phenyl)-3-fluoro-1-hydroxypropan-2-yl)-2,2-dichloroacetamide

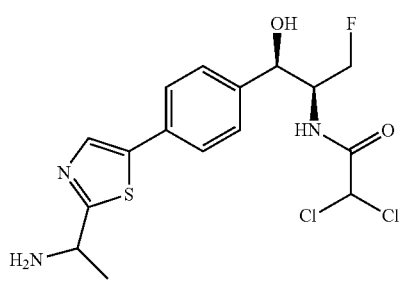 [SMILES: CC(N)c1ncc(-c2ccc([C@@H](O)[C@@H](CF)NC(=O)C(Cl)Cl)cc2)s1]

Following the general procedure of Example 2—Step 2 and making non-critical variations but using tert-butyl 1-(5-(4-((4S,5R)-3-(2,2-dichloroacetyl)-4-(fluoromethyl)-2,2-dimethyloxazolidin-5-yl)phenyl)thiazol-2-yl)ethylcarbamate the title compound is obtained (55 mg): 1H NMR (400 MHz, DMSO-$d_6$) δ: 1.42 (d, 3H), 3.75 (m, 2H), 4.15-4.35 (m, 2.5H), 4.39-4.43 (m, 0.5H), 4.55-4.59 (m, 0.5H), 4.67-4.70 (m, 0.5H), 4.87 (t, 1H), 5.98 (d, 1H), 6.51 (s, 1H), 7.40 (d, 2H), 7.58 (d, 2H), 8.06 (s, 1H), 8.59 (d, 1H); m/z (CI) 406 [M+H].

Example 109

Preparation of 2,2-Difluoro-N-[(1S,2R)-1-fluoromethyl-2-hydroxy-2-(4-{6[(1-methyl-1H-imidazol-2-ylamino)-methyl]-pyridin-3-yl}-phenyl)-ethyl]-acetamide Step 1 Preparation of 2,2-Difluoro-1-{(4S,5R)-4-fluoromethyl-5-[4-(6-hydroxymethyl-pyridin-3-yl)-phenyl]-2,2-dimethyl-oxazolidin-3-yl}-ethanone

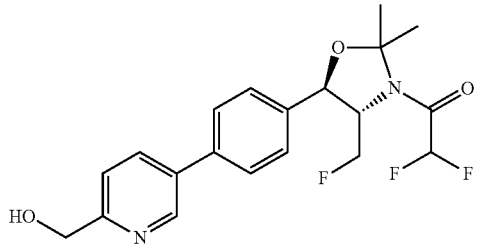 [SMILES: CC1(C)O[C@H](c2ccc(-c3ccc(CO)nc3)cc2)[C@@H](CF)N1C(=O)C(F)F]

To as solution of 2,2-Difluoro-1-{(4S,5R)-4-fluoromethyl-2,2-dimethyl-5-[4-(4,4,5,5-tetramethyl-[1,3,2]dioxaborolan-2-yl)-phenyl]-oxazolidin-3-yl}-ethanone (200 mg, 0.48 mmol) in toluene (3.2 ml) and ethanol (2.4 ml) is added (5-Bromo-pyridin-2-yl)-methanol (91 mg, 0.48 mmol); aqueous sodium bicarbonate solution (1.94 mmol, 2M, 1 ml) and [1,1'Bis(diphenylphosphino)ferrocene]dichloropalladium (II) (18 mg, 0.02 mmol). The reaction is heated at 80° C., under nitrogen, for 45 minutes. The reaction mixture is concentrated under reduced pressure and purified by column chromatography (40 g silica gel, 0-100% ethyl acetate/heptane) to give the title compound (92 mg): $^1$H NMR (400 MHz, CDCl$_3$) 1.61-1.79 (m, 6H), 3.7-3.81 (m, 1H), 4.50-4.88 (m, 5H), 5.24-5.31 (m, 1H), 6.13 (t, 1H), 7.36 (d, 1H), 7.55 (d, 2H), 7.63 (d, 2H), 7.87-7.92 (m, 1H), 8.78-8.82 (m, 1H). m/z M+H 395.

Step 2 Preparation of 1-{(4S,5R)-5-[4-(6-Chloromethyl-pyridin-3-yl)-phenyl]-4-fluoromethyl-2,2-dimethyl-oxazolidin-3-yl}-2,2-difluoro-ethanone

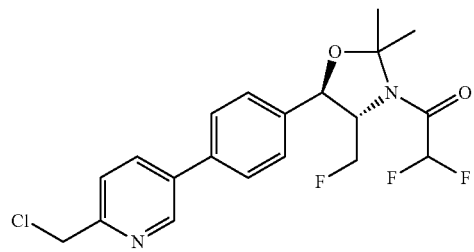 [SMILES: CC1(C)O[C@H](c2ccc(-c3ccc(CCl)nc3)cc2)[C@@H](CF)N1C(=O)C(F)F]

A stirred solution of 2,2-Difluoro-1-{(4S,5R)-4-fluoromethyl-5-[4-(6-hydroxy-methyl-pyridin-3-yl)-phenyl]-2,2-dimethyl-oxazolidin-3-yl}-ethanone (1660 mg, 4.2 mmol) and triethylamine (0.88 ml, 6.31 mmol) in $CH_2Cl_2$ (30 ml) is treated with methanesulfonyl chloride (0.49 ml, 6.31 mmol) and stirred at ambient temperature for 16 hours. The reaction mixture is concentrated to dryness to afford the title compound as a red oil (1.53 g): $^1$H NMR (400 MHz, $CDCl_3$) 1.60-1.77 (m, 6H), 4.53-4.84 (m, 5H), 5.25-5.31 (m, 1H), 6.12 (t, 1H), 7.58 (d, 2H), 7.65 (d, 2H), 7.68 (d, 1H), 8.03-8.07 (m, 1H), 8.86-8.90 (m, 1H). m/z M+H 413.

Step 3 Preparation of 2,2-Difluoro-N-[(1S,2R)-1-fluoromethyl-2-hydroxy-2-(4-{6-[(1-methyl-1H-imidazol-2-ylamino)-methyl]-pyridin-3-yl}-phenyl)-ethyl]-acetamide

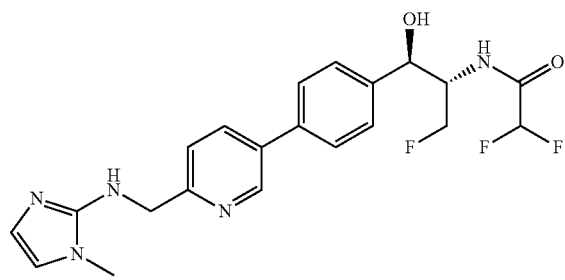 [SMILES: Cn1ccnc1NCc1ccc(-c2ccc([C@@H](O)[C@@H](CF)NC(=O)C(F)F)cc2)cn1]

A solution of 1-{(4S,5R)-5-[4-(6-chloromethyl-pyridin-3-yl)-phenyl]-4-fluoromethyl-2,2-dimethyl-oxazolidin-3-yl}-2,2-difluoro-ethanone (25 mg, 0.06 mmol) and 1-Methyl-1H-imidazol-2-ylamine (30 mg, 0.3 mmol) in dimethyl formamide (2 ml) is heated at 75° C. for 16 h. The reaction mixture is concentrated to dryness, dissolved in $CH_2Cl_2$ (1 ml) and treated with trifluoroacetic acid (0.5 ml) and water (0.1 ml). The mixture is shaken at ambient temperature for 2 hours and then concentrated to dryness. The crude product is purified by preparative HPLC to give the title compound (7 mg): $^1$H NMR (400 MHz, DMSO-$d_6$) 2.50 (s, 3H), 3.51 (s, 2H), 4.24-4.36 (m, 1.5H), 4.37-4.46 (m, 0.5H), 4.51-4.59 (m, 0.5H), 4.63-4.71 (m, 0.5H), 4.87-4.92 (m, 1H), 5.31 (s, 2H), 6.22 (t, 1H), 7.05-7.10 (m, 2H), 7.40-7.52 (m, 3H), 7.66-7.74 (m, 2H), 8.09-8.16 (m, 1H), 8.86 (s, 1H), 9.63-9.69 (m, 1H). m/z M+H 434.

The following Table 1 shows other examples made using this method, with a variety of amines replacing the thiazol-5-ylamine in Example 109, Step 3. Retention times refer to the following HPLC method: Column=Phenomenex Luna C18 4.6×20 mm 5 um, mobile phase A=20 mM NH4OAc in H2O, mobile phase B=ACN, Linear gradient 10% B to 60% in 5 min, 1 mL/min.

TABLE 1

| Example Number | Structure | Name | Retention Time (min) | m/z M + H |
|---|---|---|---|---|
| 110 | 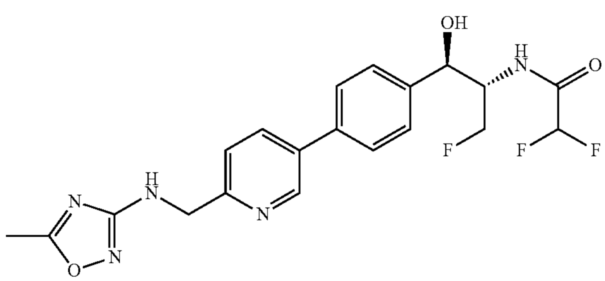 [SMILES: Cc1nc(NCc2ccc(-c3ccc([C@@H](O)[C@@H](CF)NC(=O)C(F)F)cc3)cn2)no1] | 2,2-difluoro-N-{(1R,2S)-3-fluoro-1-hydroxy-1-[4-(6-{[(5-methyl-1,2,4-oxadiazol-3-yl)amino]-methyl}pyridin-3-yl)-phenyl]propan-2-yl}-acetamide | 2.68 | 436 |
| 111 | 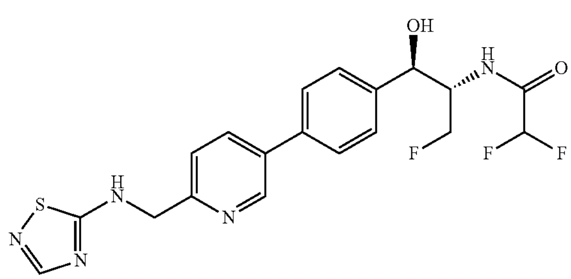 [SMILES: O=C(N[C@H](CF)[C@H](O)c1ccc(-c2ccc(CNc3ncns3)nc2)cc1)C(F)F] | 2,2-difluoro-N-[(1R,2S)-3-fluoro-1-hydroxy-1-(4-{6-[(1,2,4-thiadiazol-5-yl-amino)methyl]pyridin-3-yl}phenyl)propan-2-yl]-acetamide | 2.55 | 438 |

TABLE 1-continued

| Example Number | Name | Retention Time (min) | m/z M + H |
|---|---|---|---|
| 112 | 2,2-difluoro-N-{(1R,2S)-3-fluoro-1-hydroxy-1-[4-(6-{[(2-methyl-2H-tetrazol-5-yl)amino]methyl}pyridin-3-yl)phenyl]propan-2-yl}-acetamide | 2.53 | 436 |
| 113 | 2,2-difluoro-N-{(1R,2S)-3-fluoro-1-hydroxy-1-[4-(6-{[(1-methyl-1H-1,2,4-triazol-3-yl)amino]methyl}-pyridin-3-yl)phenyl]-propan-2-yl}acetamide | 2.12 | 435 |
| 114 | 2,2-difluoro-N-[(1R,2S)-3-fluoro-1-hydroxy-1-(4-{6-[(1,2-oxazol-5-ylamino)-methyl]pyridin-3-yl}-phenyl)propan-2-yl]-acetamide | 2.19 | 421 |
| 115 | 2,2-difluoro-N-[(1R,2S)-3-fluoro-1-hydroxy-1-(4-{6-[(1,3-thiazol-4-ylamino)-methyl]pyridin-3-yl}-phenyl)propan-2-yl]-acetamide | 2.13 | 437 |
| 116 | 2,2-difluoro-N-[(1R,2S)-3-fluoro-1-hydroxy-1-(4-{6-[(1,2,5-thiadiazol-3-yl-amino)methyl]pyridin-3-yl}phenyl)propan-2-yl]-acetamide | 3.24 | 438 |

TABLE 1-continued

| Example Number | Structure | Name | Retention Time (min) | m/z M + H |
|---|---|---|---|---|
| 117 | 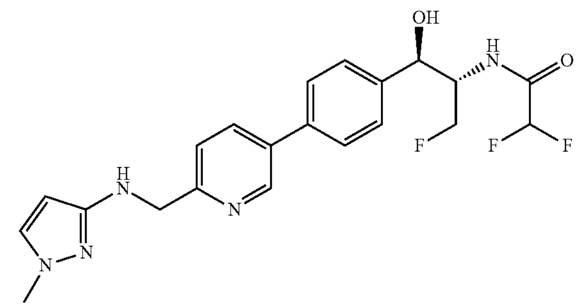 [SMILES: Cn1ccc(NCc2ccc(-c3ccc([C@@H](O)[C@@H](CF)NC(=O)C(F)F)cc3)cn2)n1] | 2,2-difluoro-N-{(1R,2S)-3-fluoro-1-hydroxy-1-[4-(6-{[(1-methyl-1H-pyrazol-3-yl)amino]methyl}pyridin-3-yl)phenyl]propan-2-yl}-acetamide | 2.61 | 434 |
| 118 | 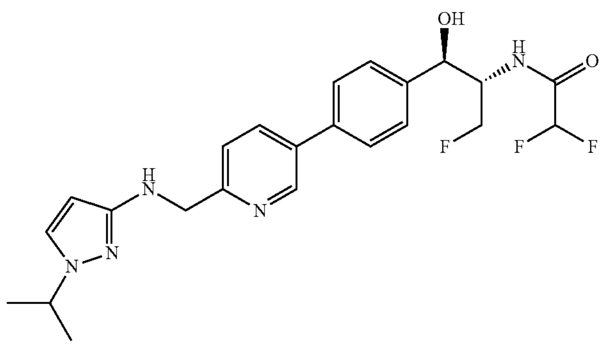 [SMILES: CC(C)n1ccc(NCc2ccc(-c3ccc([C@@H](O)[C@@H](CF)NC(=O)C(F)F)cc3)cn2)n1] | 2,2-difluoro-N-[(1R,2S)-3-fluoro-1-hydroxy-1-{4-[6-({[1-(propan-2-yl)-1H-pyrazol-3-yl]amino}-methyl)pyridin-3-yl]-phenyl}propan-2-yl]-acetamide | 3.28 | 462 |
| 119 | 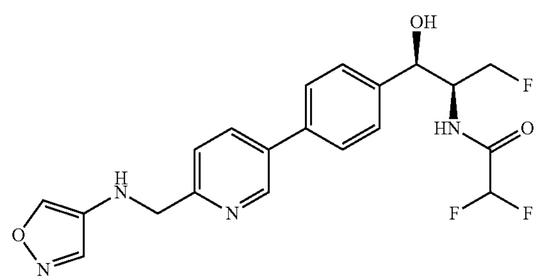 [SMILES: O=C(N[C@H](CF)[C@H](O)c1ccc(-c2ccc(CNc3cnoc3)nc2)cc1)C(F)F] | 2,2-difluoro-N-[(1R,2S)-3-fluoro-1-hydroxy-1-(4-{6-[(1,2-oxazol-4-ylamino)-methyl]pyridin-3-yl}-phenyl)propan-2-yl]-acetamide | 2.82 | 421 |
| 120 | 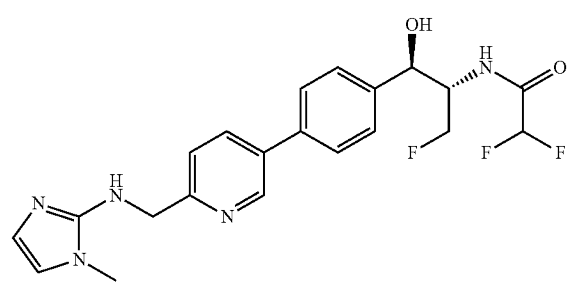 [SMILES: Cn1ccnc1NCc1ccc(-c2ccc([C@@H](O)[C@@H](CF)NC(=O)C(F)F)cc2)cn1] | 2,2-difluoro-N-{(1R,2S)-3-fluoro-1-hydroxy-1-[4-(6-{[(1-methyl-1H-imidazol-2-yl)amino]methyl}pyridin-3-yl)phenyl]propan-2-yl}-acetamide | 1.70 | 434 |
| 121 | 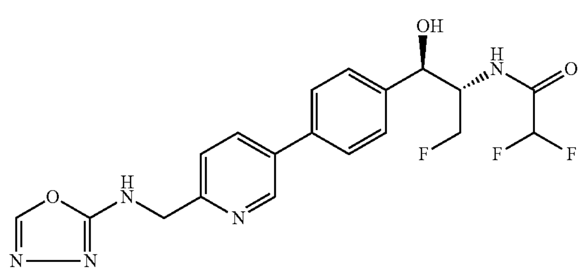 [SMILES: O=C(N[C@H](CF)[C@H](O)c1ccc(-c2ccc(CNc3nnco3)nc2)cc1)C(F)F] | 2,2-difluoro-N-[(1R,2S)-3-fluoro-1-hydroxy-1-(4-{6-[(1,3,4-oxadiazol-2-yl-amino)methyl]pyridin-3-yl}phenyl)propan-2-yl]-acetamide | 1.79 | 422 |

TABLE 1-continued

| Example Number | Structure | Name | Retention Time (min) | m/z M + H |
|---|---|---|---|---|
| 122 | 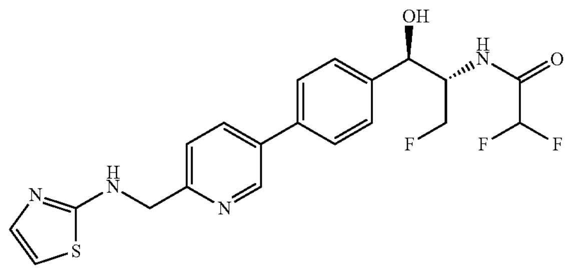 [SMILES: O=C(N[C@H](CF)[C@H](O)c1ccc(-c2ccc(CNc3nccs3)nc2)cc1)C(F)F] | 2,2-difluoro-N-[(1R,2S)-3-fluoro-1-hydroxy-1-(4-{6-[(1,3-thiazol-2-ylamino)-methyl]pyridin-3-yl}-phenyl)propan-2-yl]-acetamide | 1.70 | 437 |
| 123 | 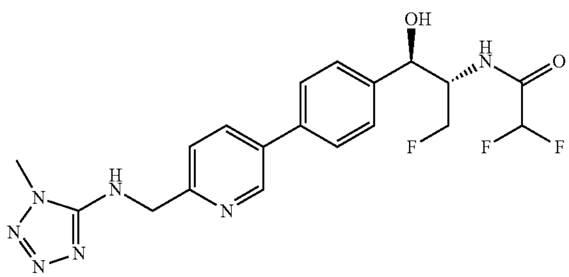 [SMILES: Cn1nnnc1NCc1ccc(-c2ccc([C@@H](O)[C@@H](CF)NC(=O)C(F)F)cc2)cn1] | 2,2-difluoro-N-{(1R,2S)-3-fluoro-1-hydroxy-1-[4-(6-{[(1-methyl-1H-tetrazol-5-yl)amino]methyl}pyridin-3-yl)phenyl]propan-2-yl}-acetamide | 2.17 | 436 |
| 124 | 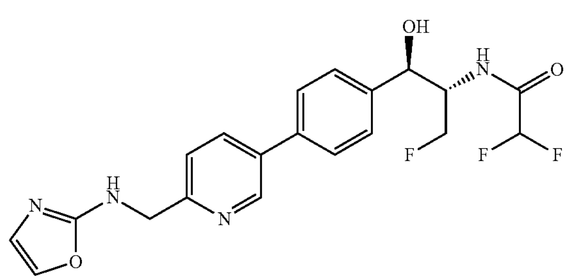 [SMILES: O=C(N[C@H](CF)[C@H](O)c1ccc(-c2ccc(CNc3ncco3)nc2)cc1)C(F)F] | 2,2-difluoro-N-[(1R,2S)-3-fluoro-1-hydroxy-1-(4-{6-[(1,3-oxazol-2-ylamino)-methyl]pyridin-3-yl}-phenyl)propan-2-yl]-acetamide | 2.12 | 421 |
| 125 | 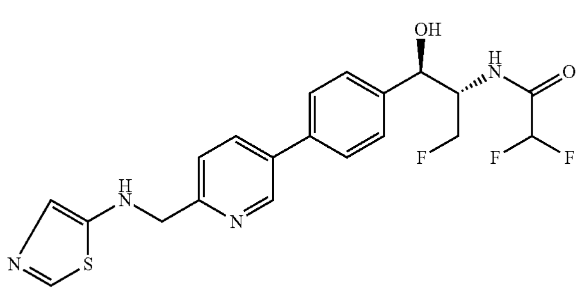 [SMILES: O=C(N[C@H](CF)[C@H](O)c1ccc(-c2ccc(CNc3cncs3)nc2)cc1)C(F)F] | 2,2-difluoro-N-[(1R,2S)-3-fluoro-1-hydroxy-1-(4-{6-[(1,3-thiazol-5-ylamino)-methyl]pyridin-3-yl}-phenyl)propan-2-yl]-acetamide | 2.46 | 437 |

TABLE 1-continued

| Example Number | Structure | Name | Retention Time (min) | m/z M + H |
|---|---|---|---|---|
| 126 | 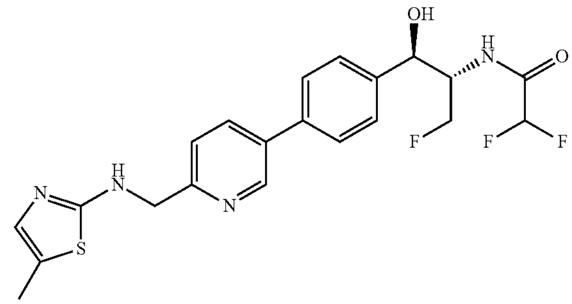 [SMILES: Cc1cnc(NCc2ccc(-c3ccc([C@@H](O)[C@@H](CF)NC(=O)C(F)F)cc3)cn2)s1] | 2,2-difluoro-N-{(1R,2S)-3-fluoro-1-hydroxy-1-[4-(6-{[(5-methyl-1,3-thiazol-2-yl)amino]methyl}pyridin-3-yl)phenyl]propan-2-yl}-acetamide | 2.09 | 451 |
| 127 | 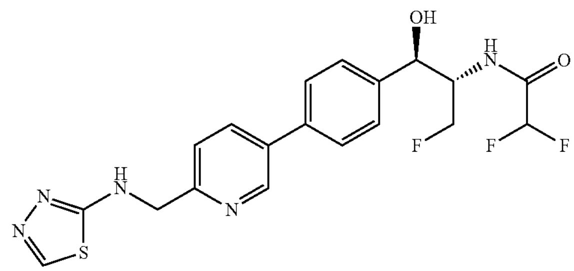 [SMILES: O=C(N[C@H](CF)[C@H](O)c1ccc(-c2ccc(CNc3nncs3)nc2)cc1)C(F)F] | 2,2-difluoro-N-[(1R,2S)-3-fluoro-1-hydroxy-1-(4-{6-[(1,3,4-thiadiazol-2-yl-amino)methyl]pyridin-3-yl}phenyl)propan-2-yl]-acetamide | 2.25 | 438 |

Example 128

Preparation of N-((1R,2S)-1-(4-(6-(2-oxa-5-azaspiro[3.4]octan-5-ylmethyl)pyridin-3-yl)phenyl)-3-fluoro-1-hydroxypropan-2-yl)-2,2-difluoroacetamide Step 1 Preparation of 1-((4S,5R)-5-(4-(6-(2-oxa-5-azaspiro[3.4]octan-5-ylmethyl)pyridin-3-yl)phenyl)-4-(fluoromethyl)-2,2-dimethyloxazolidin-3-yl)-2,2-difluoroethanone

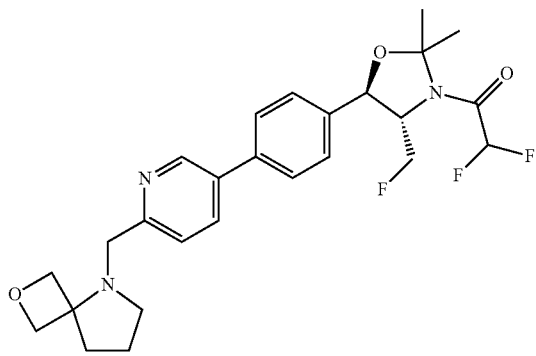 [SMILES: CC1(C)O[C@H](c2ccc(-c3ccc(CN4CCCC45COC5)nc3)cc2)[C@@H](CF)N1C(=O)C(F)F]

A mixture of 2-oxa-5-azaspiro[3.4]octane (0.1 mmol, 15.8 mg), 1-{(4S,5R)-5-[4-(6-Chloromethyl-pyridin-3-yl)-phenyl]-4-fluoromethyl-2,2-dimethyl-oxazolidin-3-yl}-2,2-difluoro-ethanone (Example 99, Step 2, 0.09 mmol, 37 mg) and cesium carbonate (0.25 mmol, 81 mg) and acetonitrile (1 mL) was heated to 55° C. for 5 hours. The crude mixture was filtered on a bed of celite and the cake was washed with CH₂Cl₂ (2 mL). The volatiles were removed. The crude mixtures were used "as is" in step 2.

Step 2 Preparation of N-((1R,2S)-1-(4-(6-(2-oxa-5-azaspiro[3.4]octan-5-ylmethyl)pyridin-3-yl)phenyl)-3-fluoro-1-hydroxypropan-2-yl)-2,2-difluoroacetamide

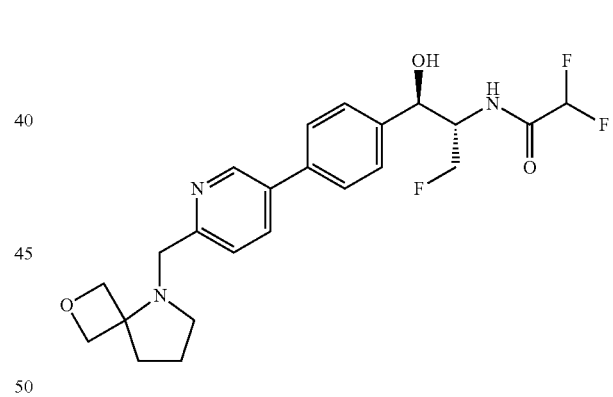

The crude mixture was dissolved in 0.75 mL mixture of TFA/CH₂Cl₂/H₂O (25/10/1) and stirred at RT for 2 hours. 1 mL of MeOH/Toluene (50/50) was then added and the mixture concentrated to dryness. The crude product was purified by preparative HPLC to give the title compound (12 mg). Retention times and MS refer to the following HPLC-MS method: Column=Waters ACQUITY UPLC BEH C8 1.7 um 2.1×50 mm, mobile phase A=0.1% TFA in H2O, mobile phase B=0.1% TFA in ACN, linear gradient 10% B to 100% B in 5 min, 0.8 mL/min RT=3.270 min, MS m/z=450.2 (M+H).

The following Table 2 shows other examples made using this method, with a variety of amines replacing the 2-oxa-5-azaspiro[3.4]octane in step 1 of Example 128. Retention times refer to the following HPLC method: Column=Waters ACQUITY UPLC BEH C8 1.7 um 2.1×50 mm, mobile phase A=0.1% TFA in H2O, mobile phase B=0.1% TFA in ACN, Linear gradient 10% B to 100% in 5 min, 0.8 mL/min.

TABLE 2

| Example Number | Structure | Name | Retention Time (min) | m/z M + H |
|---|---|---|---|---|
| 129 | 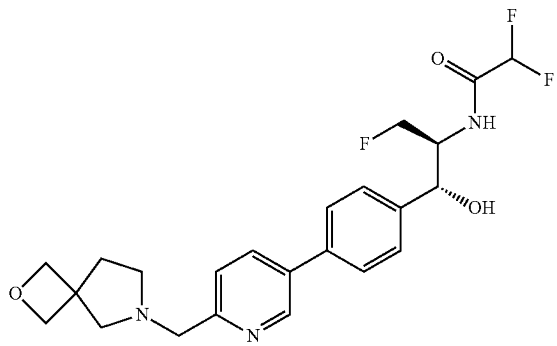 [SMILES: O=C(N[C@H](CF)[C@H](O)c1ccc(-c2ccc(CN3CCC4(COC4)C3)nc2)cc1)C(F)F] | N-((1R,2S)-1-(4-(6-(2-oxa-6-azaspiro-[3.4]octan-6-yl-methyl)pyridin-3-yl)phenyl)-3-fluoro-1-hydroxypropan-2-yl)-2,2-difluoro-acetamide | 2.767 | 450.2 |
| 130 | 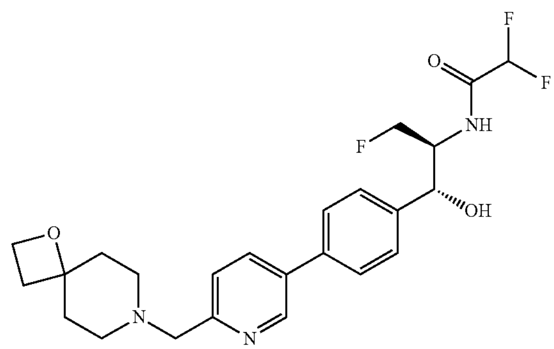 [SMILES: O=C(N[C@H](CF)[C@H](O)c1ccc(-c2ccc(CN3CCC4(CCO4)CC3)nc2)cc1)C(F)F] | N-((1R,2S)-1-(4-(6-(1-oxa-7-azaspiro-[3.5]nonan-7-yl-methyl)pyridin-3-yl)phenyl)-3-fluoro-1-hydroxypropan-2-yl)-2,2-difluoro-acetamide | 2.884 | 464.2 |
| 131 | 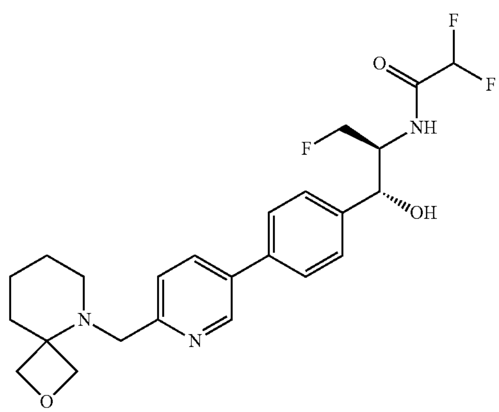 [SMILES: O=C(N[C@H](CF)[C@H](O)c1ccc(-c2ccc(CN3CCCCC34COC4)nc2)cc1)C(F)F] | N-((1R,2S)-1-(4-(6-(2-oxa-5-azaspiro-[3.5]nonan-5-yl-methyl)pyridin-3-yl)phenyl)-3-fluoro-1-hydroxypropan-2-yl)-2,2-difluoro-acetamide | 3.009 | 464.3 |
| 132 | 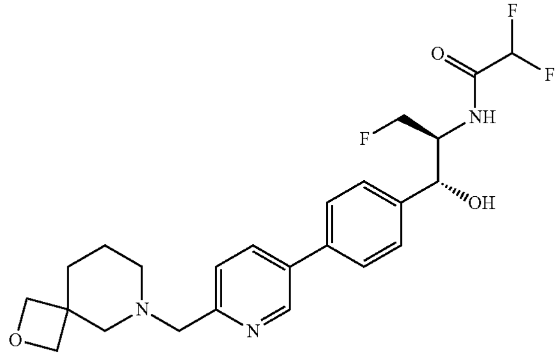 [SMILES: O=C(N[C@H](CF)[C@H](O)c1ccc(-c2ccc(CN3CCCC4(COC4)C3)nc2)cc1)C(F)F] | N-((1R,2S)-1-(4-(6-(2-oxa-6-azaspiro-[3.5]nonan-6-yl-methyl)pyridin-3-yl)phenyl)-3-fluoro-1-hydroxypropan-2-yl)-2,2-difluoro-acetamide | 2.899 | 464.2 |

TABLE 2-continued

| Example Number | Structure | Name | Retention Time (min) | m/z M + H |
|---|---|---|---|---|
| 133 | 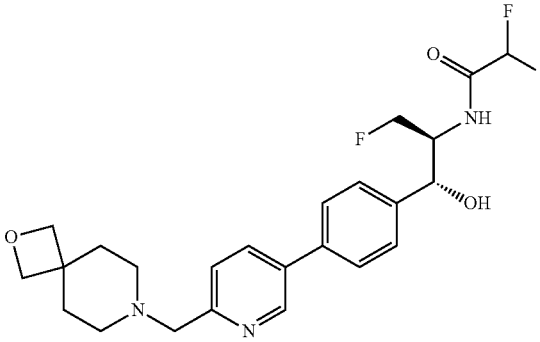 | N-((1R,2S)-1-(4-(6-(2-oxa-7-azaspiro-[3.5]nonan-7-yl-methyl)pyridin-3-yl)phenyl)-3-fluoro-1-hydroxypropan-2-yl)-2,2-difluoro-acetamide | 2.847 | 464.2 |
| 134 | 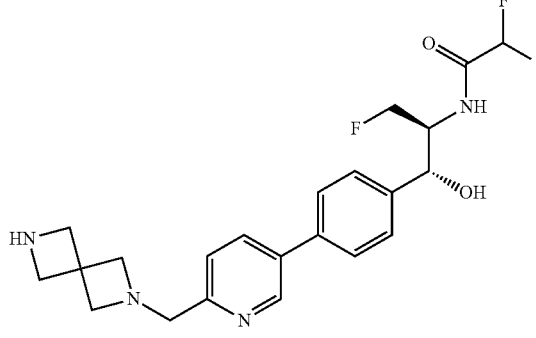 | N-((1R,2S)-1-(4-(6-(2,6-diazaspiro-[3.3]-heptan-2-yl-methyl)-pyridin-3-yl)phenyl)-3-fluoro-1-hydroxy-propan-2-yl)-2,2-difluoro-acetamide | 2.349 | 435.2 |
| 135 | 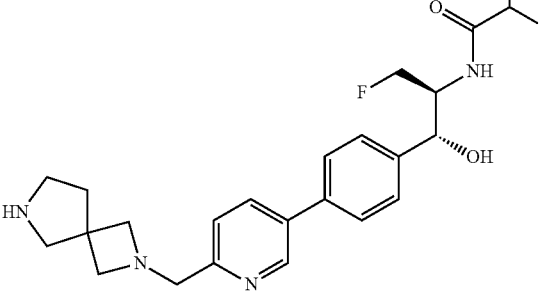 | N-((1R,2S)-1-(4-(6-(2,6-diazaspiro-[3.4]-octan-2-yl-methyl)-pyridin-3-yl)phenyl)-3-fluoro-1-hydroxy-propan-2-yl)-2,2-difluoro-acetamide | 2.335 | 449.2 |
| 136 | 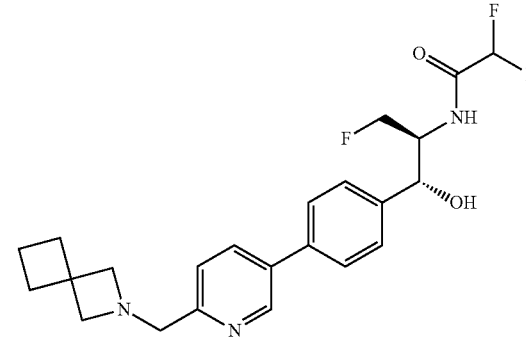 | N-((1R,2S)-1-(4-(6-(2-azaspiro[3.3]-heptan-2-ylmethyl)-pyridin-3-yl)-phenyl)-3-fluoro-1-hydroxy-propan-2-yl)-2,2-difluoro-acetamide | 3.063 | 434.2 |

TABLE 2-continued

| Example Number | Name | Retention Time (min) | m/z M + H |
|---|---|---|---|
| 137 | N-((1R,2S)-1-(4-(6-(2,6-diazaspiro-[3.5]-nonan-6-ylmethyl)-pyridin-3-yl)phenyl)-3-fluoro-1-hydroxy-propan-2-yl)-2,2-difluoro-acetamide | 2.479 | 463.2 |
| 138 | N-((1R,2S)-1-(4-(6-(2,7-diazaspiro-[3.5]-nonan-7-yl-methyl)-pyridin-3-yl)phenyl)-3-fluoro-1-hydroxy-propan-2-yl)-2,2-difluoro-acetamide | 2.518 | 463.3 |
| 139 | N-((1R,2S)-1-(4-(6-(2,6-diazaspiro-[3.5]-nonan-2-yl-methyl)-pyridin-3-yl)phenyl)-3-fluoro-1-hydroxy-propan-2-yl)-2,2-difluoro-acetamide | 2.590 | 463.3 |
| 140 | N-((1R,2S)-1-(4-(6-(2,5-diazaspiro-[3.5]-nonan-2-yl-methyl)-pyridin-3-yl)phenyl)-3-fluoro-1-hydroxy-propan-2-yl)-2,2-difluoro-acetamide | 3.294 | 463.3 |

TABLE 2-continued

| Example Number | Structure | Name | Retention Time (min) | m/z M + H |
|---|---|---|---|---|
| 141 | 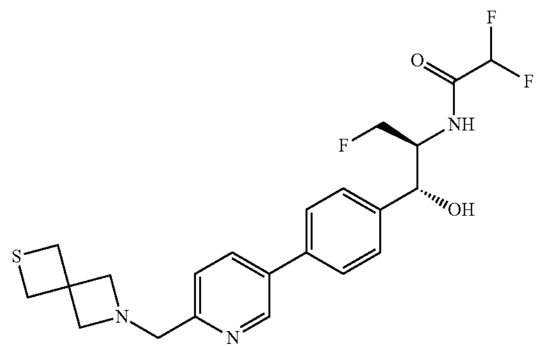 [SMILES: O=C(N[C@H](CF)[C@H](O)c1ccc(-c2ccc(CN3CC4(CSC4)C3)nc2)cc1)C(F)F] | N-((1R,2S)-1-(4-(6-(2-thia-6-azaspiro-[3.3]heptan-6-yl-methyl)pyridin-3-yl)-phenyl)-3-fluoro-1-hydroxypropan-2-yl)-2,2-difluoro-acetamide | 3.180 | 452.2 |
| 142 | 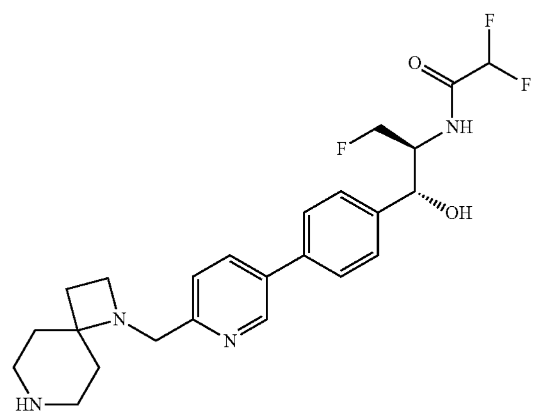 [SMILES: O=C(N[C@H](CF)[C@H](O)c1ccc(-c2ccc(CN3CCC34CCNCC4)nc2)cc1)C(F)F] | N-((1R,2S)-1-(4-(6-(1,7-diazaspiro-[3.5]nonan-1-yl-methyl)pyridin-3-yl)phenyl)-3-fluoro-1-hydroxypropan-2-yl)-2,2-difluoro-acetamide | 2.409 | 463.3 |
| 143 | 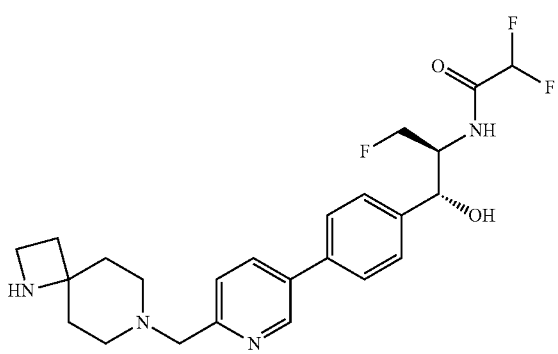 [SMILES: O=C(N[C@H](CF)[C@H](O)c1ccc(-c2ccc(CN3CCC4(CCN4)CC3)nc2)cc1)C(F)F] | N-((1R,2S)-1-(4-(6-(1,7-diazaspiro-[3.5]nonan-7-ylmethyl)-pyridin-3-yl)phenyl)-3-fluoro-1-hydroxy-propan-2-yl)-2,2-difluoro-acetamide | 2.598 | 463.2 |
| 144 | 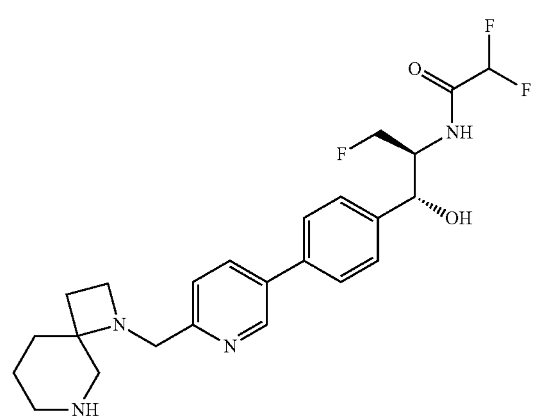 [SMILES: O=C(N[C@H](CF)[C@H](O)c1ccc(-c2ccc(CN3CCC34CCCNC4)nc2)cc1)C(F)F] | N-((1R,2S)-1-(4-(6-(2,6-diazaspiro-[3.5]-nonan-2-yl-methyl)-pyridin-3-yl)phenyl)-3-fluoro-1-hydroxy-propan-2-yl)-2,2-difluoro-acetamide | 2.590 | 463.3 |

TABLE 2-continued

| Example Number | Structure | Name | Retention Time (min) | m/z M + H |
|---|---|---|---|---|
| 145 | 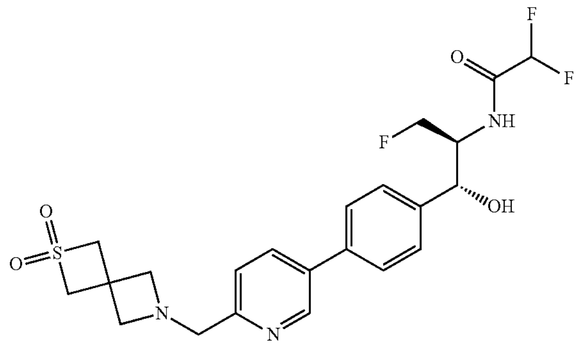 [SMILES: O=C(N[C@H](CF)[C@H](O)c1ccc(-c2ccc(CN3CC4(C3)CS(=O)(=O)C4)nc2)cc1)C(F)F] | N-((1R,2S)-1-(4-(6-((2,2-dioxido-2-thia-6-azaspiro[3.3]-heptan-6-yl)-methyl)pyridin-3-yl)phenyl)-3-fluoro-1-hydroxypropan-2-yl)-2,2-difluoro-acetamide | 1.923 | 484.2 |
| 146 | 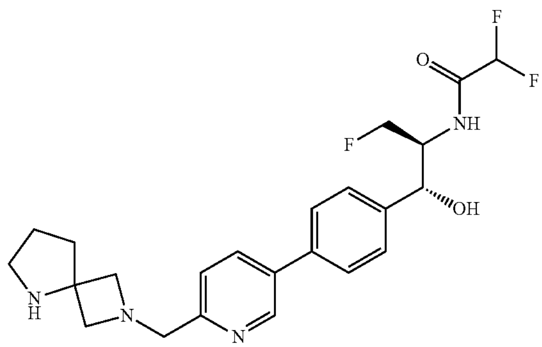 [SMILES: O=C(N[C@H](CF)[C@H](O)c1ccc(-c2ccc(CN3CC4(CCCN4)C3)nc2)cc1)C(F)F] | N-((1R,2S)-1-(4-(6-(2,5-diazaspiro-[3.4]-octan-2-yl-methyl)-pyridin-3-yl)phenyl)-3-fluoro-1-hydroxy-propan-2-yl)-2,2-difluoro-acetamide | 2.337 | 449.3 |
| 147 | 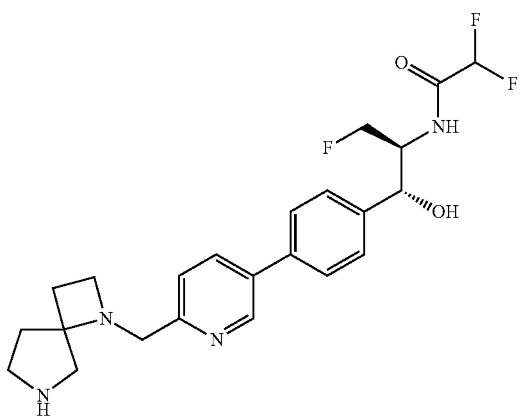 [SMILES: O=C(N[C@H](CF)[C@H](O)c1ccc(-c2ccc(CN3CCC34CCNC4)nc2)cc1)C(F)F] | N-((1R,2S)-1-(4-(6-(1,6-diazaspiro-[3.4]-octan-1-yl-methyl)-pyridin-3-yl)phenyl)-3-fluoro-1-hydroxy-propan-2-yl)-2,2-difluoro-acetamide | 2.392 | 449.4 |
| 148 | 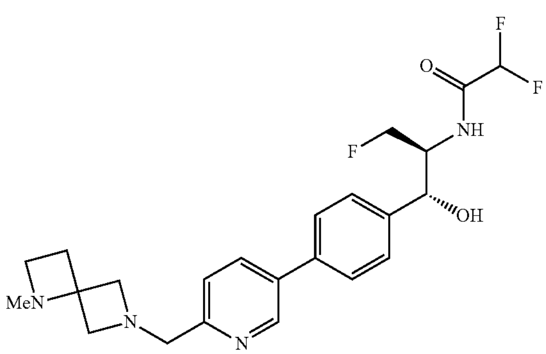 [SMILES: CN1CCC12CN(Cc1ccc(-c3ccc([C@@H](O)[C@@H](CF)NC(=O)C(F)F)cc3)cn1)C2] | 2,2-difluoro-N-((1R,2S)-3-fluoro-1-hydroxy-1-(4-(6-((1-methyl-1,6-diaza-spiro[3.3]heptan-6-yl)methyl)pyridin-3-yl)phenyl)propan-2-yl)acetamide | 2.420 | 449.3 |

TABLE 2-continued

| Example Number | Structure | Name | Retention Time (min) | m/z M + H |
|---|---|---|---|---|
| 149 | 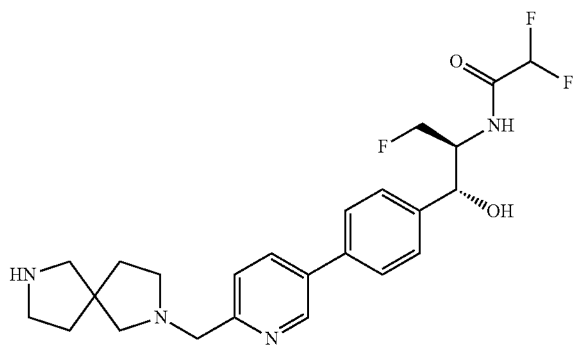 [SMILES: O=C(N[C@H](CF)[C@H](O)c1ccc(-c2ccc(CN3CCC4(CCNC4)C3)nc2)cc1)C(F)F] | N-((1R,2S)-1-(4-(6-(2,7-diazaspiro-[4.4]nonan-2-yl-methyl)pyridin-3-yl)-phenyl)-3-fluoro-1-hydroxypropan-2-yl)-2,2-difluoro-acetamide | 2.507 | 463.3 |
| 150 | 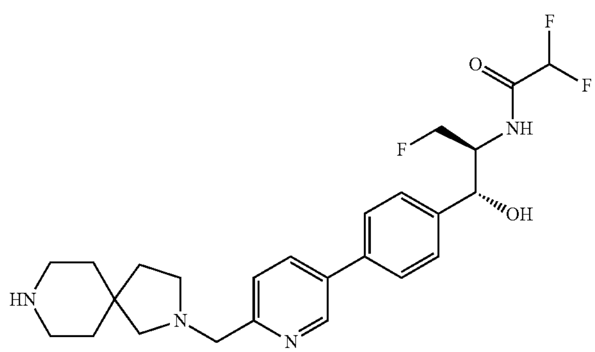 [SMILES: O=C(N[C@H](CF)[C@H](O)c1ccc(-c2ccc(CN3CCC4(CCNCC4)C3)nc2)cc1)C(F)F] | N-((1R,2S)-1-(4-(6-(2,8-diazaspiro-[4.5]-decan-2-yl-methyl)-pyridin-3-yl)phenyl)-3-fluoro-1-hydroxy-propan-2-yl)-2,2-difluoro-acetamide | 2.610 | 477.3 |
| 151 | 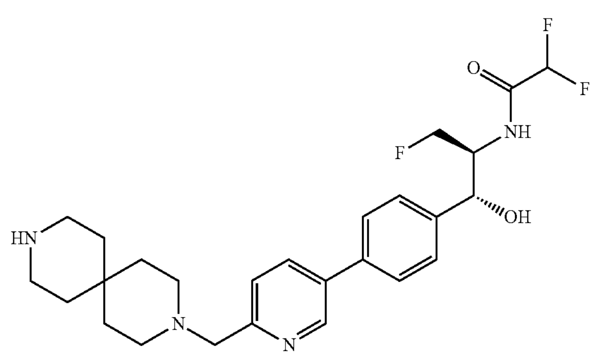 [SMILES: O=C(N[C@H](CF)[C@H](O)c1ccc(-c2ccc(CN3CCC4(CCNCC4)CC3)nc2)cc1)C(F)F] | N-((1R,2S)-1-(4-(6-(3,9-diazaspiro-[5.5]-undecan-3-ylmethyl)-pyridin-3-yl)phenyl)-3-fluoro-1-hydroxy-propan-2-yl)-2,2-difluoro-acetamide | 2.725 | 491.4 |
| 152 | 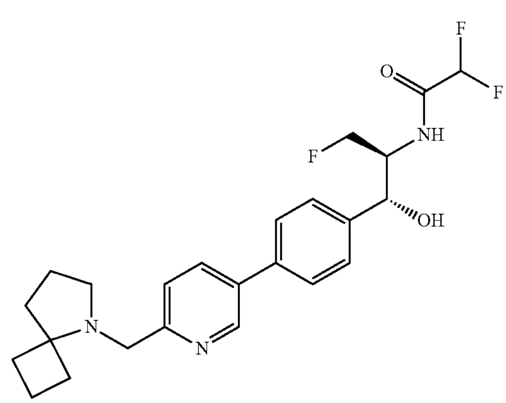 [SMILES: O=C(N[C@H](CF)[C@H](O)c1ccc(-c2ccc(CN3CCCC34CCC4)nc2)cc1)C(F)F] | N-((1R,2S)-1-(4-(6-(5-azaspiro[3.4]-octan-5-ylmethyl)-pyridin-3-yl)-phenyl)-3-fluoro-1-hydroxy-propan-2-yl)-2,2-difluoro-acetamide | 3.515 | 448.2 |

| Example Number | Structure | Name | Retention Time (min) | m/z M + H |
|---|---|---|---|---|
| 153 | 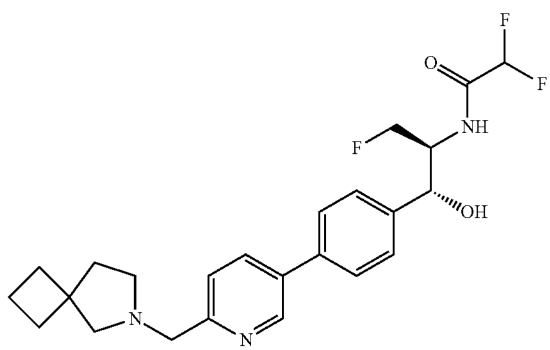 [SMILES: O=C(N[C@H](CF)[C@H](O)c1ccc(-c2ccc(CN3CCC4(CCC4)C3)nc2)cc1)C(F)F] | N-((1R,2S)-1-(4-(6-(6-azaspiro[3.4]-octan-6-ylmethyl)-pyridin-3-yl)-phenyl)-3-fluoro-1-hydroxy-propan-2-yl)-2,2-difluoro-acetamide | 3.615 | 448.2 |
| 154 | 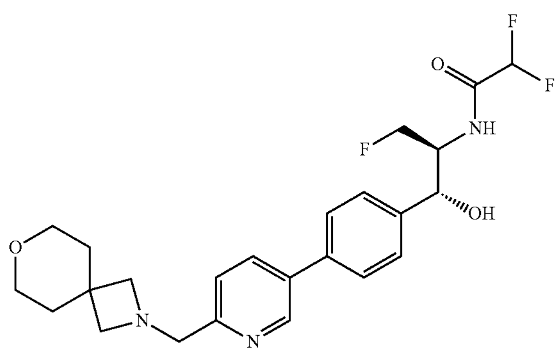 [SMILES: O=C(N[C@H](CF)[C@H](O)c1ccc(-c2ccc(CN3CC4(CCOCC4)C3)nc2)cc1)C(F)F] | N-((1R,2S)-1-(4-(6-(7-oxa-2-azaspiro-[3.5]nonan-2-yl-methyl)pyridin-3-yl)phenyl)-3-fluoro-1-hydroxypropan-2-yl)-2,2-difluoro-acetamide | 3.331 | 464.2 |
| 155 | 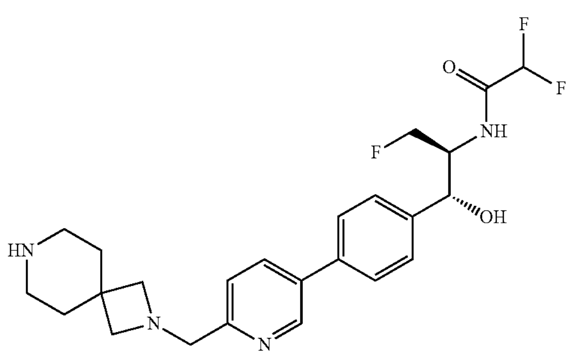 [SMILES: O=C(N[C@H](CF)[C@H](O)c1ccc(-c2ccc(CN3CC4(CCNCC4)C3)nc2)cc1)C(F)F] | N-((1R,2S)-1-(4-(6-(2,7-diazaspiro-[3.5]nonan-2-yl-methyl)pyridin-3-yl)phenyl)-3-fluoro-1-hydroxypropan-2-yl)-2,2-difluoro-acetamide | 2.861 | 463.3 |
| 156 | 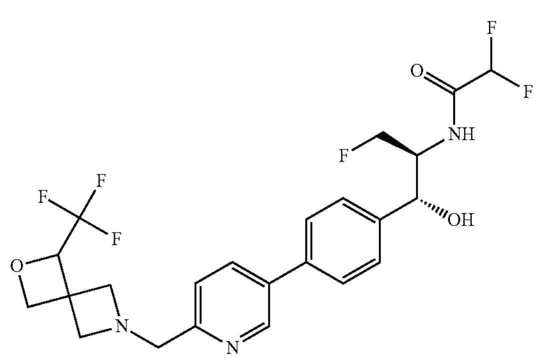 [SMILES: O=C(N[C@H](CF)[C@H](O)c1ccc(-c2ccc(CN3CC4(COC4C(F)(F)F)C3)nc2)cc1)C(F)F] | 2,2-difluoro-N-((1R,2S)-3-fluoro-1-hydroxy-1-(4-(6-((1-(trifluoromethyl)-2-oxa-6-azaspiro-[3.3]-heptan-6-yl)methyl)-pyridin-3-yl)phenyl)-propan-2-yl)-acetamide | 3.627 | 504.1 |

TABLE 2-continued

| Example Number | Structure | Name | Retention Time (min) | m/z M + H |
|---|---|---|---|---|
| 157 | 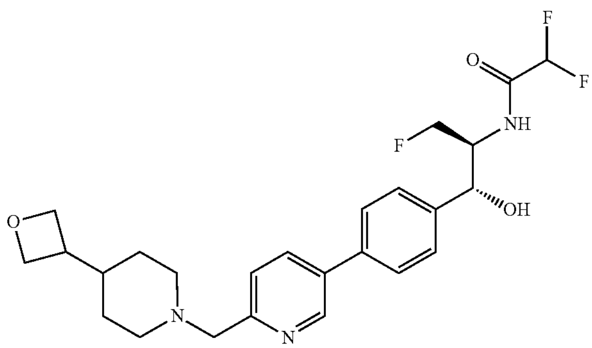 [SMILES: O=C(N[C@H](CF)[C@H](O)c1ccc(-c2ccc(CN3CCC(C4COC4)CC3)nc2)cc1)C(F)F] | 2,2-difluoro-N-((1R,2S)-3-fluoro-1-hydroxy-1-(4-(6-((4-(oxetan-3-yl)-piperidin-1-yl)-methyl)-pyridin-3-yl)phenyl)-propan-2-yl)-acetamide | 3.348 | 478.3 |
| 158 | 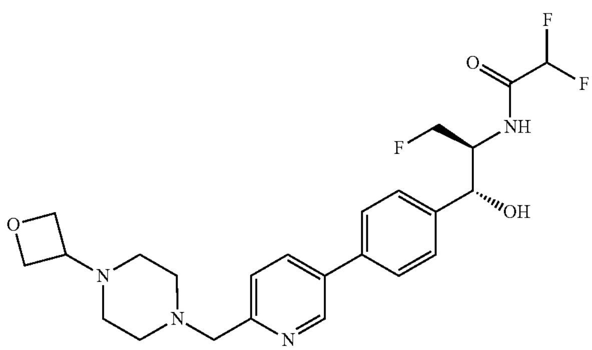 [SMILES: O=C(N[C@H](CF)[C@H](O)c1ccc(-c2ccc(CN3CCN(C4COC4)CC3)nc2)cc1)C(F)F] | 2,2-difluoro-N-((1R,2S)-3-fluoro-1-hydroxy-1-(4-(6-((4-(oxetan-3-yl)-piperazin-1-yl)-methyl)pyridin-3-yl)phenyl)propan-2-yl)-acetamide | 2.984 | 479.2 |
| 159 | 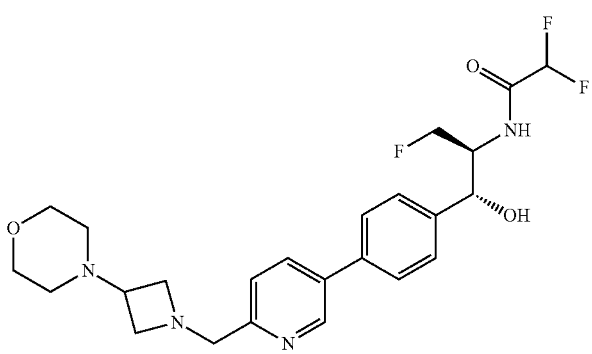 [SMILES: O=C(N[C@H](CF)[C@H](O)c1ccc(-c2ccc(CN3CC(N4CCOCC4)C3)nc2)cc1)C(F)F] | 2,2-difluoro-N-((1R,2S)-3-fluoro-1-hydroxy-1-(4-(6-((3-morpholinoazetidin-1-yl)methyl)pyridin-3-yl)phenyl)propan-2-yl)acetamide | 3.178 | 479.2 |
| 160 | 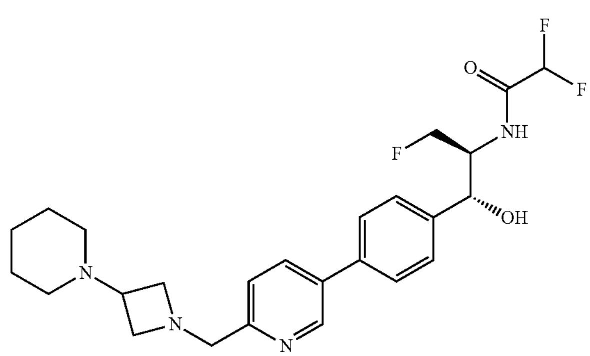 [SMILES: O=C(N[C@H](CF)[C@H](O)c1ccc(-c2ccc(CN3CC(N4CCCCC4)C3)nc2)cc1)C(F)F] | 2,2-difluoro-N-((1R,2S)-3-fluoro-1-hydroxy-1-(4-(6-((3-(piperidin-1-yl)-azetidin-1-yl)-methyl)pyridin-3-yl)phenyl)propan-2-yl)-acetamide | 3.204 | 477.3 |

TABLE 2-continued

| Example Number | Structure | Name | Retention Time (min) | m/z M + H |
|---|---|---|---|---|
| 161 | 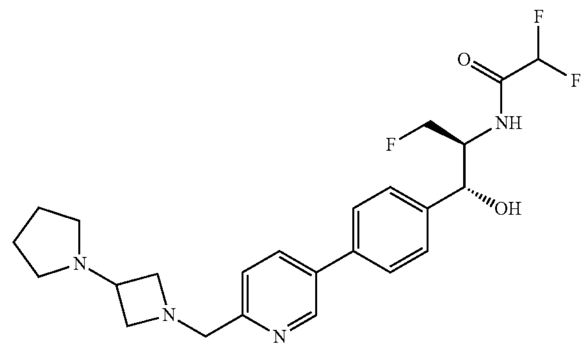 [SMILES: O=C(N[C@H](CF)[C@H](O)c1ccc(-c2ccc(CN3CC(N4CCCC4)C3)nc2)cc1)C(F)F] | 2,2-difluoro-N-((1R,2S)-3-fluoro-1-hydroxy-1-(4-(6-((3-(pyrrolidin-1-yl)-azetidin-1-yl)-methyl)pyridin-3-yl)phenyl)propan-2-yl)-acetamide | 2.849 | 463.3 |

The following compounds of Table 3 can be made using the schemes shown below:

TABLE 3

| No. | R1 | R2 | R3 | R4 | Het | W | X | Y | Z |
|---|---|---|---|---|---|---|---|---|---|
| 162 | H | H | CH$_2$OH | H | Pyridine | OH | F | F | H |
| 163 | H | H | CH$_2$CN | H | Pyridine | OH | F | F | H |
| 164 | H | H | CH$_2$SO$_2$Me | H | Pyridine | OH | F | F | H |
| 165 | H | H | 2-oxazole (see below) | H | Pyridine | OH | F | F | H |
| 166 | H | H | 2-thiazole | H | Pyridine | OH | F | F | H |
| 167 | H | H | 2-imidazole | H | Pyridine | OH | F | F | H |
| 168 | H | H | 1-Methyl-2-imidazole | H | Pyridine | OH | F | F | H |
| 169 | H | H | Et | H | Pyridine | OH | F | F | H |
| 170 | H | H | Cyclopropyl | H | Pyridine | OH | F | F | H |
| 171 | H | H | CH(Me)OH | H | Pyridine | OH | F | F | H |
| 172 | H | H | CH$_2$OMe | H | Pyridine | OH | F | F | H |
| 173 | H | H | CO$_2$H | H | Pyridine | OH | F | F | H |
| 174 | H | H | CH$_2$OH | Me | Pyridine | OH | F | F | H |
| 175 | H | R2=R3=(CH$_2$)$_2$ | | H | Pyridine | OH | F | F | H |
| 176 | H | R2=R3=(CH$_2$)$_2$ | | F | Pyridine | OH | F | F | H |
| 177 | H | R2=R3=(CH$_2$)$_2$ | | OH | Pyridine | OH | F | F | H |
| 178 | H | H | H | H | Pyridazine | OH | F | F | H |
| 179 | H | H | Me | H | Pyridazine | OH | F | F | H |
| 180 | H | H | H | H | Pyrimidine | OH | F | F | H |
| 181 | H | H | Me | H | Pyrimidine | OH | F | F | H |
| 182 | H | H | H | H | Pyrazine | OH | F | F | H |
| 183 | H | H | Me | H | Pyrazine | OH | F | F | H |

For example, the title compound of Example 175 is N-((1R,2S)-1-(4-(6-(azetidin-2-yl)pyridin-3-yl)phenyl)-3-fluoro-1-hydroxypropan-2-yl)-2,2-difluoroacetamide;

Examples 162, 171-174 and 177-183 can be synthesized from commercially available bromopyridines, and so procedures from Example 22—Step 3 can be used in their preparation. Examples 163-170 can be synthesized using the scheme shown below:

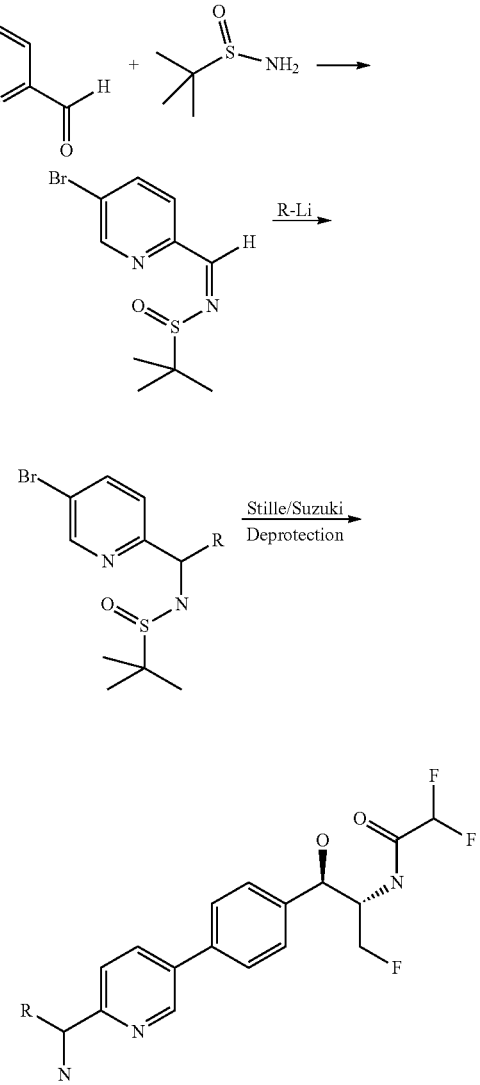

R=CH$_2$CN, CH$_2$SO$_2$CH$_3$, 3-oxazole, 2-thiazole, 2-imidazole, 2-thiazole, 1-methyl-2-imidazole, ethyl, cyclopropyl Examples 175, 176 and 177 can be synthesized using the scheme shown below:

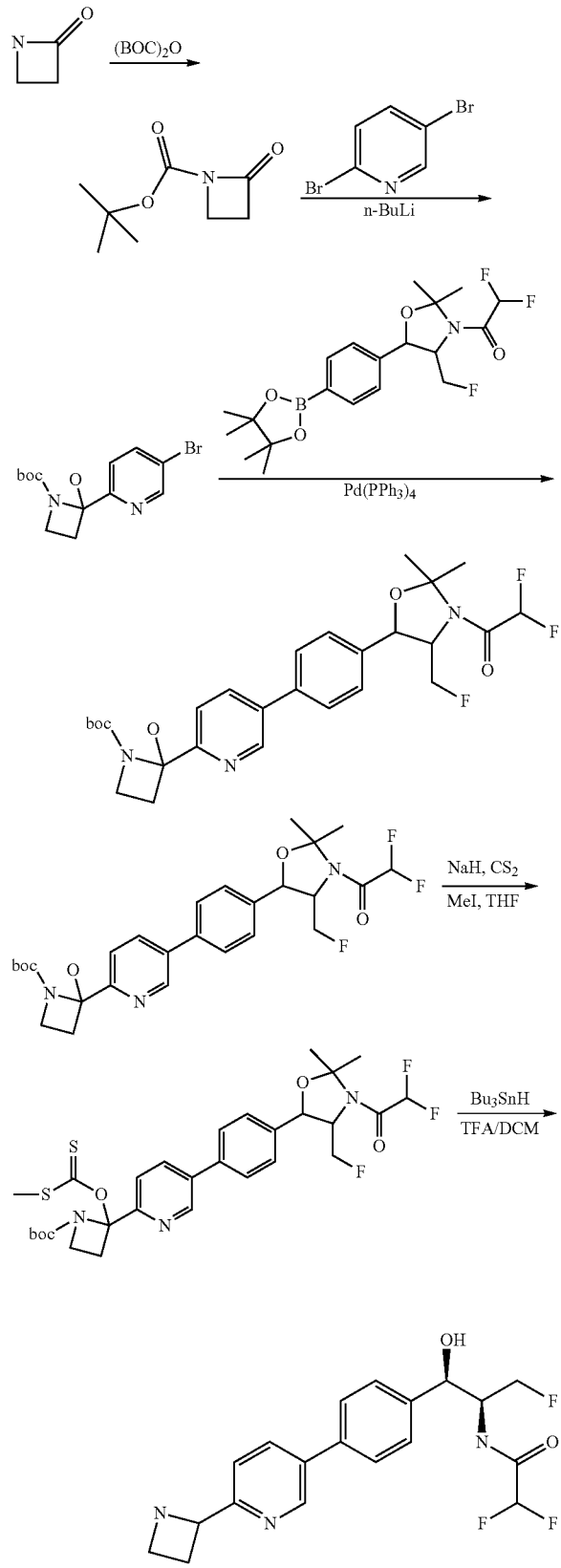

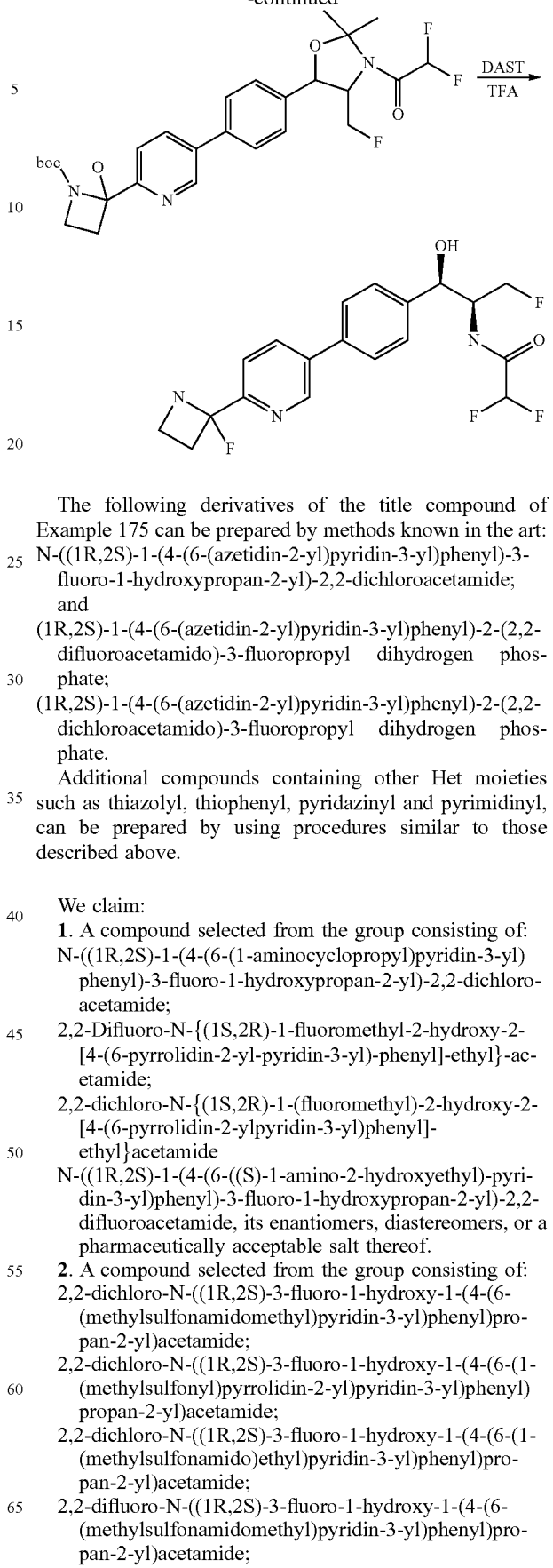

The following derivatives of the title compound of Example 175 can be prepared by methods known in the art:
N-((1R,2S)-1-(4-(6-(azetidin-2-yl)pyridin-3-yl)phenyl)-3-fluoro-1-hydroxypropan-2-yl)-2,2-dichloroacetamide; and
(1R,2S)-1-(4-(6-(azetidin-2-yl)pyridin-3-yl)phenyl)-2-(2,2-difluoroacetamido)-3-fluoropropyl dihydrogen phosphate;
(1R,2S)-1-(4-(6-(azetidin-2-yl)pyridin-3-yl)phenyl)-2-(2,2-dichloroacetamido)-3-fluoropropyl dihydrogen phosphate.

Additional compounds containing other Het moieties such as thiazolyl, thiophenyl, pyridazinyl and pyrimidinyl, can be prepared by using procedures similar to those described above.

We claim:

1. A compound selected from the group consisting of:
N-((1R,2S)-1-(4-(6-(1-aminocyclopropyl)pyridin-3-yl)phenyl)-3-fluoro-1-hydroxypropan-2-yl)-2,2-dichloroacetamide;
2,2-Difluoro-N-{(1S,2R)-1-fluoromethyl-2-hydroxy-2-[4-(6-pyrrolidin-2-yl-pyridin-3-yl)-phenyl]-ethyl}-acetamide;
2,2-dichloro-N-{(1S,2R)-1-(fluoromethyl)-2-hydroxy-2-[4-(6-pyrrolidin-2-ylpyridin-3-yl)phenyl]-ethyl}acetamide
N-((1R,2S)-1-(4-(6-((S)-1-amino-2-hydroxyethyl)-pyridin-3-yl)phenyl)-3-fluoro-1-hydroxypropan-2-yl)-2,2-difluoroacetamide, its enantiomers, diastereomers, or a pharmaceutically acceptable salt thereof.

2. A compound selected from the group consisting of:
2,2-dichloro-N-((1R,2S)-3-fluoro-1-hydroxy-1-(4-(6-(methylsulfonamidomethyl)pyridin-3-yl)phenyl)propan-2-yl)acetamide;
2,2-dichloro-N-((1R,2S)-3-fluoro-1-hydroxy-1-(4-(6-(1-(methylsulfonyl)pyrrolidin-2-yl)pyridin-3-yl)phenyl)propan-2-yl)acetamide;
2,2-dichloro-N-((1R,2S)-3-fluoro-1-hydroxy-1-(4-(6-(1-(methylsulfonamido)ethyl)pyridin-3-yl)phenyl)propan-2-yl)acetamide;
2,2-difluoro-N-((1R,2S)-3-fluoro-1-hydroxy-1-(4-(6-(methylsulfonamidomethyl)pyridin-3-yl)phenyl)propan-2-yl)acetamide;

N-((1R,2S)-1-(4-(6-(2-aminopropan-2-yl)pyridin-3-yl)phenyl)-3-fluoro-1-hydroxypropan-2-yl)-2,2-difluoro-acetamide;

N-((1R,2S)-1-(4-(2-(1-aminoethyl)thiazol-5-yl)phenyl)-3-fluoro-1-hydroxypropan-2-yl)-2,2-difluoroacetamide;

2,2-Difluoro-N-[(1R,2R)-1-fluoromethyl-2-(4-{6-[(3-fluoro-propylamino)-methyl]-pyridin-3-yl}-phenyl)-2-hydroxy-ethyl]-acetamide;

N-((1S,2R)-2-{4-[6-(1-Amino-2,2,2-trifluoro-ethyl)-pyridin-3-yl]-phenyl}-1-fluoromethyl-2-hydroxy-ethyl)-2,2-difluoro-acetamide;

2,2-Difluoro-N-((1S,2R)-1-fluoromethyl-2-hydroxy-2-{4-[6-(1-morpholin-4-yl-ethyl)-pyridin-3-yl]-phenyl}-ethyl)-acetamide;

2,2-Difluoro-N-((1S,2R)-1-fluoromethyl-2-hydroxy-2-{4-[6-(1-methylamino-ethyl)-pyridin-3-yl]-phenyl}-ethyl)-acetamide;

2,2-Difluoro-N-[(1S,2R)-2-(4-{6-[1-(2-fluoro-ethyl-amino)-ethyl]-pyridin-3-yl}-phenyl)-1-fluoromethyl-2-hydroxy-ethyl]-acetamide;

N-((1R,2S)-1-(4-(6-(3-aminooxetan-3-yl)pyridin-3-yl)phenyl)-3-fluoro-1-hydroxypropan-2-yl)-2,2-difluoro-acetamide;

2,2-difluoro-N-((1R,2S)-3-fluoro-1-hydroxy-1-(4-(6-(1-(methylsulfonamido)cyclopropyl)pyridin-3-yl)phenyl)propan-2-yl)acetamide;

N-((1R,2S)-1-(4-(5-(1-aminoethyl)thiophen-2-yl)phenyl)-3-fluoro-1-hydroxypropan-2-yl)-2,2-dichloroacetamide;

2,2-difluoro-N-((1R,2S)-3-fluoro-1-hydroxy-1-(4-(6-((RS)-1-(methylsulfonamido)ethyl)pyridin-3-yl)phenyl)propan-2-yl)acetamide;

2,2-difluoro-N-((1R,2S)-3-fluoro-1-hydroxy-1-(4-(6-(morpholin-3-yl)pyridin-3-yl)phenyl)propan-2-yl)acetamide;

N-((1R,2S)-1-(4-(6-(1-amino-2-methoxyethyl)pyridin-3-yl)phenyl)-3-fluoro-1-hydroxypropan-2-yl)-2,2-difluoroacetamide;

N-((1S,2R)-2-{4-[6-(1-amino-2-cyano-ethyl)-pyridin-3-yl]-phenyl}-1-fluoromethyl-2-hydroxy-ethyl)-2,2-difluoro-acetamide;

N-((1R,2S)-1-(4-(6-(2-amino-1-hydroxypropan-2-yl)pyridin-3-yl)phenyl)-3-fluoro-1-hydroxypropan-2-yl)-2,2-difluoroacetamide;

N-((1R,2S)-1-(4-(2-(1-aminoethyl)thiazol-5-yl)phenyl)-3-fluoro-1-hydroxypropan-2-yl)-2,2-dichloroacetamide;

N-((1R,2S)-1-(4-(6-(1-aminopropyl)pyridin-3-yl)phenyl)-3-fluoro-1-hydroxypropan-2-yl)-2,2-difluoroacetamide;

N-((1R,2S)-1-(4-(6-(amino(cyclopropyl)methyl)pyridin-3-yl)phenyl)-3-fluoro-1-hydroxypropan-2-yl)-2,2-difluoroacetamide;

N-((1R,2S)-1-(4-(6-(1-amino-2-hydroxypropyl)pyridin-3-yl)phenyl)-3-fluoro-1-hydroxypropan-2-yl)-2,2-difluoroacetamide; and N-((1R,2S)-1-(4-(6-(azetidin-2-yl)pyridin-3-yl)phenyl)-3-fluoro-1-hydroxypropan-2-yl)-2,2-difluoroacetamide, its enantiomers, diastereomers, or a pharmaceutically acceptable salt thereof.

3. A pharmaceutical composition comprising a compound of claim 1, enantiomers, diastereomers, or a pharmaceutically acceptable salt thereof, and a pharmaceutically acceptable carrier.

4. A method for controlling or treating infections in livestock by administering to an animal in need of a therapeutically effective amount of a compound of claim 1, enantiomers, diastereomers, or a pharmaceutically acceptable salt thereof.

5. A pharmaceutical composition comprising a compound of claim 2, enantiomers, diastereomers, or a pharmaceutically acceptable salt thereof, and a pharmaceutically acceptable carrier.

6. A method for controlling or treating infections in livestock by administering to an animal in need of a therapeutically effective amount of a compound of claim 2 enantiomers, diastereomers, or a pharmaceutically acceptable salt thereof.

* * * * *